US012104201B2

(12) United States Patent
Cho et al.

(10) Patent No.: US 12,104,201 B2
(45) Date of Patent: Oct. 1, 2024

(54) ENGINEERED GYRI-LIKE MUTEIN APTAMERS, AND RELATED METHODS

(71) Applicant: CROSSLIFE TECHNOLOGIES INC., Carlsbad, CA (US)

(72) Inventors: HyunDae Cho, San Marcos, CA (US); Sharrol T. Bachas, Carlsbad, CA (US)

(73) Assignee: CROSSLIFE TECHNOLOGIES INC., Carlsbad, CA (US)

( * ) Notice: Subject to any disclaimer, the term of this patent is extended or adjusted under 35 U.S.C. 154(b) by 954 days.

(21) Appl. No.: 17/090,792

(22) Filed: Nov. 5, 2020

(65) Prior Publication Data

US 2021/0139958 A1 May 13, 2021

Related U.S. Application Data

(60) Provisional application No. 62/934,668, filed on Nov. 13, 2019.

(51) Int. Cl.
*C12Q 1/6816* (2018.01)
*C12N 15/115* (2010.01)
*C40B 40/06* (2006.01)

(52) U.S. Cl.
CPC .......... *C12Q 1/6816* (2013.01); *C12N 15/115* (2013.01); *C40B 40/06* (2013.01)

(58) Field of Classification Search
CPC ................ C12N 15/115; C12Q 1/6816; C12Q 2525/205; C12Q 2563/107; C40B 40/06
See application file for complete search history.

(56) References Cited

FOREIGN PATENT DOCUMENTS

WO 02094868 A2 11/2002
WO WO20121390951 A1 10/2012

OTHER PUBLICATIONS

Dietrich et al. (Reviews in Molecular Biotechnology, 2002, 82:211-231) (Year: 2002).*
Qi Zhang et al., Monoclonal Antibodies as Therapeutic Agents in Oncology and Antibody Gene Therapy; Cell Research 17(2), pp. 89-99 (2007).
Edward M. Kennedy et al., Gene Editing: a New Toolfor Viral Disease, Annu Rev .Med 68, pp. 401-411 (2017).
Arne Skerra, Alternative binding proteins: Anticalins—harnessing thestructural plasticity of the lipocalin ligand pocket toengineer novel binding activities. the FEBS Journal, 2677-2683 (Mar. 9, 2008).
Rubi Mahato et al., Prodrugs for Improving Tumor Targetability and Efficiency. Adv Drug Deliv Rv, pp. 659-670, Jul. 18, 2011.
Michael S. Packer et al., Methods for the directed evolution of proteins. Nat Rev Genet 16, pp. 379-394, Jul. 2015.
Dewey D. Y. Ryu et al, Recent Progress in Biomolecular Engineering. Biotechnology Progress 16, pp. 2-16, Jan. 15, 2000.
(Continued)

*Primary Examiner* — Jeremy C Flinders
(74) *Attorney, Agent, or Firm* — Procopio, Cory, Hargreaves & Savitch LLP

(57) ABSTRACT

The present invention relates to the field of protein engineering, molecular imaging, and molecular diagnostics. More particularly, provided herein are novel synthetic aptamers produced using the Gyrl-like family of proteins as a scaffold. Methods of obtaining and using the synthetic mutein aptamers are also provided.

42 Claims, 60 Drawing Sheets

Specification includes a Sequence Listing.

(56) References Cited

OTHER PUBLICATIONS

Peter H. Tobin et al., Protein Engineering: a New Frontier for Biological Therapeutics; Current Drug Metabolism 15, pp. 743-756, 2014.
Lisa Urquhart; Top Drugs and Companies by Sales in 2017; Nature Reviews Drug Discovery 17, pp. 232; Mar. 28, 2018.
Dolapo Awoniyi et al, Antibody and Host Inflammatory Biomarker Combinations as Diagnostic Tools for TB Diseas. American Journal of Clinical Pathaology, pp. 126-127; 2018.
"Frédéric Ducancel et al., Molecular engineering of antibodiesfor therapeutic and diagnostic purposes, mAbs 2(4); pp. 445-457, Jul./Aug. 2012".
"Asim Azhar et al., Recent advances in the development of novel protein scaffolds basedtherapeutics, International Journal of Biological Macromolecules, pp. 630-641; Apr. 10, 2017".
"A. Richter, E. Eggenstein et al., Anticalins: Exploiting a non-Ig scaffold with hypervariable loopsfor the engineering of binding proteins, FEBS Letters 588, pp. 213-218, 2014".
"Michaela Gebauer et al., Engineered protein scaffolds as next-generation antibody therapeutics, Curr Opinion in Chemical Biology, pp. 245-255, 2009".
Gert-Jan Kremers et al., Fluorescent proteins at a glance, Journal of Cell Science, pp. 157-160, 2011.
Christian A. Combs et al., Fluorescence Microscopy: a Concise Guide to Current Imaging Methods; Current Protocols in Neuroscience 79, pp. 2.1.1-2.1.25, Apr. 2017.
Christopher Baugh et al., 2.8 AÊ Crystal Structure of the Malachite Green Aptamer, Journal of Molecular Biology 301, pp. 117-128, 2000.
"Elena V. Dolgosheina et al., RNA Mango Aptamer-Fluorophore: a Bright, High-Affinity Complexfor RNA Labeling and Tracking, ACS Chemical Biology 9, pp. 2412-2420, Jun. 23, 2014".
"Hyaeyeong Kim et al., A Fluorogenic RNA-Based Sensor Activated byMetabolite-Induced RNA Dimerization; Cell Chemcical Biology; pp. 1725-1731; Dec. 19, 2019".
Jeremy S. Paige et al., RNA mimics of green fluorescent protein; Science (New York, N.Y), pp. 642-646, Jul. 29, 2011.
"Ljiljana Sjeklo et al., Binding between G Quadruplexes at the HomodimerInterface of the Com RNA Aptamer StronglyActivates Thioflavin T Fluorescence; Cell Chemical Biology; pp. 1159-1168; Apr. 2019".
"Katherine Deigan Warner et al., Structural basis for activity of highly efficient RNA mimics ofgreen fluorescent protein, Nat Struct Mol Biol; pp. 658-663, Aug. 2014".
Robert J. Trachman et al., Structural basis for high-affinity fluorophore binding and activation by RNA Mango, Nat Chem Biol., pp. 807-813, Jul. 2017.
"Lynda Truong et al., From fluorescent proteins to fluorogenicRNAs: Tools for imaging cellularmacromolecules; Protein Science 28; pp. 1374-1386, Mar. 22, 2019".
Farah Bouhedda et al., Light-Up RNA Aptamers and Their CognateFluorogens: From Their Development to Their Applications; International Journal of Molecular Sciences; pp. 24; Dec. 15, 2017.
"Shengnan Xua et al., Fluorogen-activatingproteins:beyondclassicalfluorescent proteins; Acta Pharmaceutica Sinica B; pp. 339-348; Dec. 27, 2017".
Jiayi Dou et al., De novo design of a fluorescence-activating β-barrel; Nature; pp. 485-491; Sep. 2018.
"Andrew Moreno et al., Solution Binding and Structural Analyses Reveal Potential MultidrugResistance Functions for SAV2435 and CTR107 and Other Gyrl-likeProteins; Biochemistry 55; pp. 4850-4863; 2016".
"Sharrol Bachas et al., Structural contributions to multidrug recognition inthe multidrug resistance (MDR) gene regulator, BmrR; Proc Natl Acad Sci USA; pp. 11046-11051; May 23, 2011".
"Feng Wang et al., BrlR from Pseudomonas aeruginosa is a receptorfor both cyclic di-GMP and pyocyanin; Nat Commun; pp. 1-14; 2018".
"Hua Yuan et al., Gyrl-like proteins catalyze cyclopropanoidhydrolysis to confer cellular protection; Nat Commun 8; pp. 1-8; 2017".
"Sharrol Bachas et al.; Charge is Major Determinant of Activation of the Ligand-Responsive Multidrug Resistance Gene Regulator, BmrR; ChemMedChem 11; pp. 1038-1041; 2016".
"Murat Sunbul et al.; SRB-2: a promiscuous rainbow aptamer for live-cellRNA imaging; Nucleic Acids Reasearchm 2018, vol. 46, No. 18; pp. e110, 1-10; Feb. 14, 2018".
"Mary Katherine Johansson et al; Intramolecular Dimers: a New Strategy to FluorescenceQuenching in Dual-Labeled Oligonucleotide Probes; JACS Articles; Journal of the American Chemical Society; pp. 6950-6956; Jan. 23, 2002".
Bernard Juskowiak et al.; Nucleic Acid-Based Fluorescent Probes and Their Analytical Potential; Anal Bional Chem 399; pp. 3157-3176; Oct. 2010.
International Search Report and Written Opinion for PCT/US20/59195 dated Apr. 22, 2021; 13 pages.
Moreno et al; Solution Binding and Structural Analysis Reveal Potential Multidrug Resistance Functions for SAV2435 and CTR107 and Other Gyrl-like Proteins. Biochemistry, Aug. 9, 2016, vol. 55, No. 34, pp. 4850-4863.
Uniprotkb-A0a390wl27, AraC family transcriptional regulator, *Staphylococcus aureus*, Dec. 5, 2018[online]. [Retrived on Mar. 12, 2021; Retrieved from internet: ,URL:https://www.uniprot.org/uniprot/A0A390WL27> entire document.
Newberry Kate J. et al: "Structures of BmrR-Drug Complexes Reveal a Rigid Multidrug Binding Pocket and Transcription Activation through Tyrosine Expulsion", Journal of Biological Chemistry, vol. 283, No. 39, Sep. 1, 2008 (Sep. 1, 2008), pp. 26795-26804, XP093090388, US ISSN: 0021-9258, DOI: 10.1074/jbc.M804191200.
Communication Pursuant to RUle 164(1)EPC for related European Application No. 20888692.9, dated Feb. 12, 2024, 14 pages.

* cited by examiner

*SAV2435 WT*

```
atggagtaccagctgcagcaactggcgagcctgaccctggtgggtatcaaggagacctat
 M   E   Y   Q   L   Q   Q   L   A   S   L   T   L   V   G   I   K   E   T   Y
gaaaacggccgtcaagcgcagcaacacatcgcgggtttctggcagcgttgctaccaagag
 E   N   G   R   Q   A   Q   Q   H   I   A   G   F   W   Q   R   C   Y   Q   E
ggcgttattgcggacctgcagctgaagaacaacggtgatctggcgggtatcctgggcctg
 G   V   I   A   D   L   Q   L   K   N   N   G   D   L   A   G   I   L   G   L
tgcattccggaactggacggtaaaatgagctatatgatcgcggtgaccggcgacaacagc
 C   I   P   E   L   D   G   K   M   S   Y   M   I   A   V   T   G   D   N   S
gcggacatcgcgaagtacgatgtgattaccctggcgagcagcaaatatatggtttttgaa
 A   D   I   A   K   Y   D   V   I   T   L   A   S   S   K   Y   M   V   F   E
gcgcaaggtgcggtgccgaaggcggttcagcaaaaaatggaggaagtgcaccactacatt
 A   Q   G   A   V   P   K   A   V   Q   Q   K   M   E   E   V   H   H   Y   I
caccagtatcaagcgaacaccgttaaaagcgcgccgttctttgagctgtaccaagacggt
 H   Q   Y   Q   A   N   T   V   K   S   A   P   F   F   E   L   Y   Q   D   G
gataccaccagcgagaagtatatcaccgaaatttggatgccggttaaaggcctggaacac
 D   T   T   S   E   K   Y   I   T   E   I   W   M   P   V   K   G   L   E   H
caccaccaccaccac (SEQ ID NO:1)
 H   H   H   H   H   (SEQ ID NO:2)
```

*CTR107 WT*

```
atggacttcgagtgccagtttgtgtgcgagctgaaggaactggcgccggttccggcgctg
 M   D   F   E   C   Q   F   V   C   E   L   K   E   L   A   P   V   P   A   L
ctgatccgtacccaaaccaccatgagcgagctgggtagcctgttcgaagcgggctaccac
 L   I   R   T   Q   T   T   M   S   E   L   G   S   L   F   E   A   G   Y   H
gatattctgcagctgctggcgggtcagggtaagagcccgagcggtccgccgtttgcgcgt
 D   I   L   Q   L   L   A   G   Q   G   K   S   P   S   G   P   P   F   A   R
tattttggtatgagcgcgggcacctttgaggtggagttcggctttccggtggagggtggc
 Y   F   G   M   S   A   G   T   F   E   V   E   F   G   F   P   V   E   G   G
gttgaaggtagcggccgtgtggttaccggtctgaccccgagcggcaaggcggcgagcagc
 V   E   G   S   G   R   V   V   T   G   L   T   P   S   G   K   A   A   S   S
ctgtacatcggtccgtatggcgagattgaagcggtgtacgacgcgctgatgaaatgggtt
 L   Y   I   G   P   Y   G   E   I   E   A   V   Y   D   A   L   M   K   W   V
gacgataacggtttcgatctgagcggcgaggcgtacgaaatctatctggacaacccggcg
 D   D   N   G   F   D   L   S   G   E   A   Y   E   I   Y   L   D   N   P   A
gaaaccgcgccggatcagctgcgtacccgtgttagcctgatgctgcacgagagcctggaa
 E   T   A   P   D   Q   L   R   T   R   V   S   L   M   L   H   E   S   L   E
caccaccaccaccaccac    (SEQ ID NO:3)
```

FIG. 2A

*LIN2189 WT* atgggtagccaccaccaccaccaccacaccgagaagaaaatcgacttcaagaaagaggaa
M G S H H H H H H T E K K I D F K K E E
aagaaattttacgcgccgaagcgtaagccggagcgtattttcgtgccggaaatgaacttt
K K F Y A P K R K P E R I F V P E M N F
ctgatggttgatggtaaaggcgacccggatggcgaggaataccagaaggcggtgcaaagc
L M V D G K G D P D G E E Y Q K A V Q S
ctgtacgcgatcgcgtataccattaaaatgagcaagatgggtgaaacccgtctggacggc
L Y A I A Y T I K M S K M G E T R L D G
tatagcgatttcgtggttccgccgctggagggtttctggtggagcgaaggcaaatttgac
Y S D F V V P P L E G F W W S E G K F D
ctgaaggaccgtgatgcgtggctgtggaccagcatcctgcgtcagccggatttcgtgacc
L K D R D A W L W T S I L R Q P D F V T
gaggaagttctggagtgggcgaaagaagtggcgcgtaagaaaaagccggacgttgatacc
E E V L E W A K E V A R K K K P D V D T
agccgtgtgaagctggttcgttttgaggaaggtgaatgcgtgcagatgatgcacgttggc
S R V K L V R F E E G E C V Q M M H V G
ccgttcagcgaggaggtgcacaccgttgcggaaatgcaccaatttatggagaccgaaggt
P F S E E V H T V A E M H Q F M E T E G
ctgcgtaacgacaccggcgcgatccgtaaacaccacgagatttatctgagcgatccgcgt
L R N D T G A I R K H H E I Y L S D P R
aaggcgaacccggaaaaaatgaagaccattctgcgtctgccggttagc (SEQ ID NO:5)
K A N P E K M K T I L R L P V S (SEQ ID NO:6)

FIG. 2B

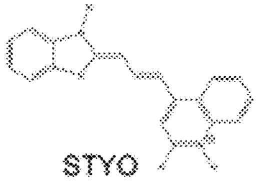
STYO
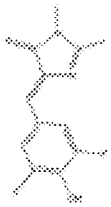
DFHBI
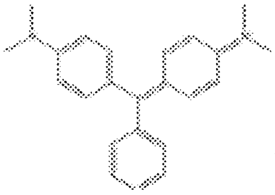
Malachite Green
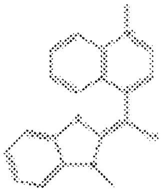
Thiazole Orange
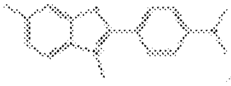
Thioflavin T
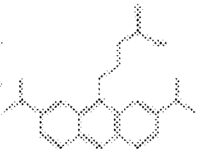
Atto 495
Acridine Orange
Cyanine 5 (CY5)
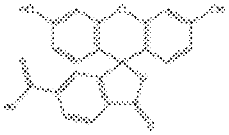
6-Carboxyfluorescein (FAM)
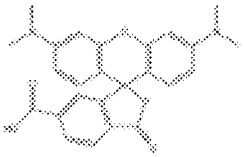
6-Carboxytetramethylrhodamine (TAMRA)
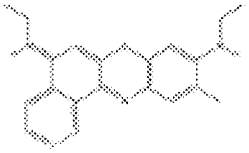
Oxazine 170
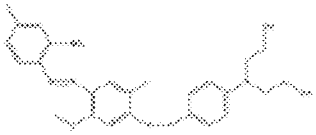
Blackhole Quencher 1 (BHQ1)
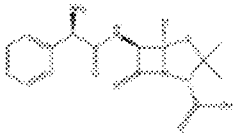
Ampicillin
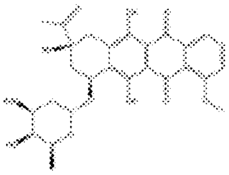
Daunorubicin
FIG. 4

DFHBI ENHANCEMENT BY GYRI-LIKE PROTEINS

MALACHITE GREEN ENHANCEMENT BY GYRI-LIKE PROTEINS pNPP
(colorless)

pNP
(yellow)

Iodonitrotetrazolium
(Colorless)

Iodonitroformazan
(Red)

*SAV2435 N27W* gene and amino acid sequence atg gag tac cag ctg cag caa ctg gcg agc ctg acc ctg gtg ggt atc aag gag acc tat

M E Y Q L Q Q L A S L T L V G I K E T Y gaa aac ggc cgt caa gcg tgg caa cac atc gcg ggt ttc tgg cag cgt tgc tac caa gag

E N G R Q A W Q H I A G F W Q R C Y Q E ggc gtt att gcg gac ctg cag ctg aag aac aac ggt gat ctg gcg ggt atc ctg ggc ctg

G V I A D L Q L K N N G D L A G I L G L tgc att ccg gaa ctg gac ggt aaa atg agc tat atg atc gcg gtg acc ggc gac aac agc

C I P E L D G K M S Y M I A V T G D N S gcg gac atc gcg aag tac gat gtg att acc ctg gcg agc agc aaa tat atg gtt ttt gaa

A D I A K Y D V I T L A S S K Y M V F E gcg caa ggt gcg gtg ccg aag gcg gtt cag caa aaa atg gag gaa gtg cac cac tac att

A Q G A V P K A V Q Q K M E E V H H Y I cac cag tat caa gcg aac acc gtt aaa agc gcg ccg ttc ttt gag ctg tac caa gac ggt

H Q Y Q A N T V K S A P F F E L Y Q D G gat acc acc agc gag aag tat atc acc gaa att tgg atg ccg gtt aaa ggc ctg gaa cac

Figure 19A:
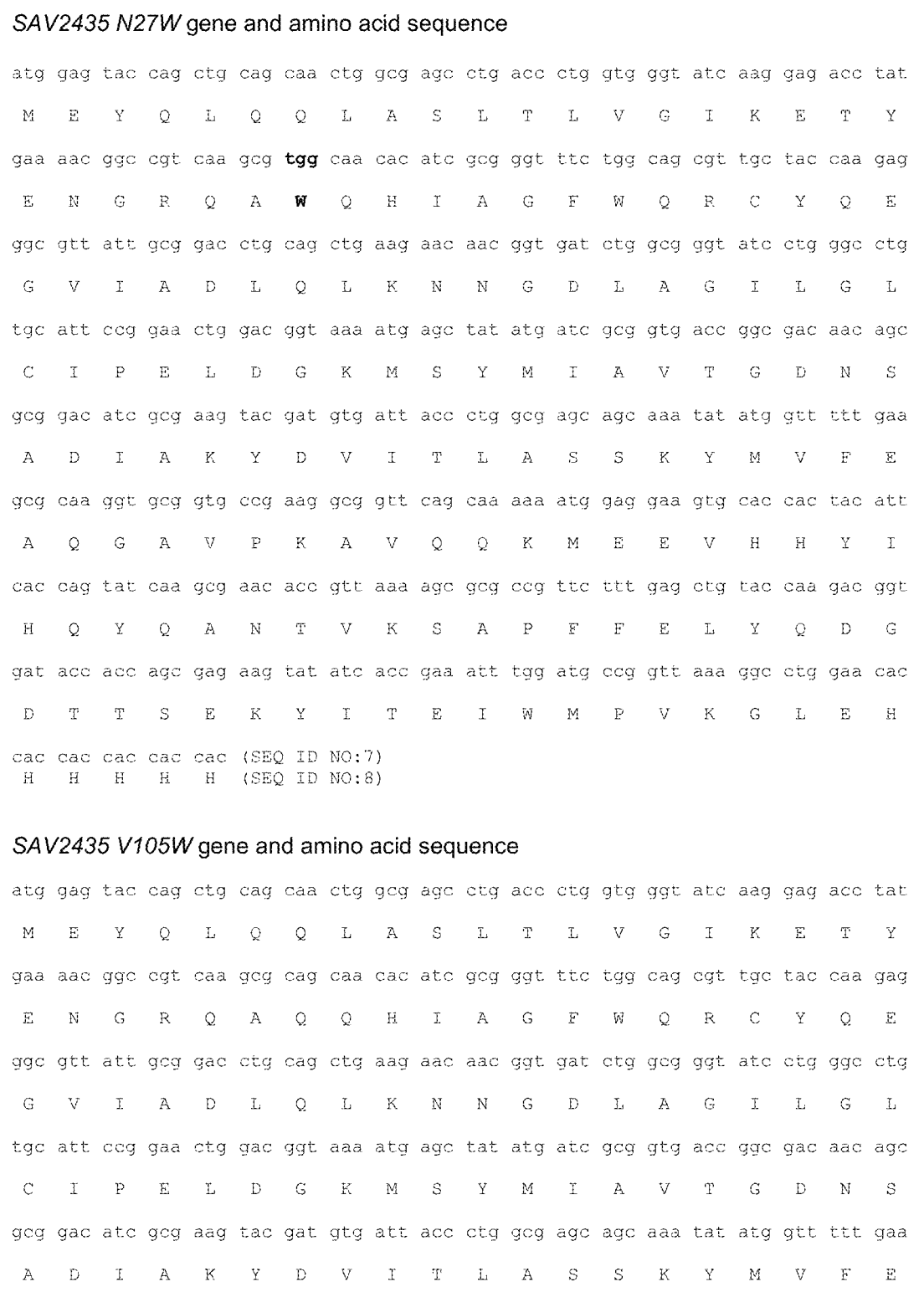

D T T S E K Y I T E I W M P V K G L E H cac cac cac cac cac (SEQ ID NO:7)
H H H H H (SEQ ID NO:8)

*SAV2435 V105W* gene and amino acid sequence atg gag tac cag ctg cag caa ctg gcg agc ctg acc ctg gtg ggt atc aag gag acc tat

M E Y Q L Q Q L A S L T L V G I K E T Y gaa aac ggc cgt caa gcg cag caa cac atc gcg ggt ttc tgg cag cgt tgc tac caa gag

E N G R Q A Q Q H I A G F W Q R C Y Q E ggc gtt att gcg gac ctg cag ctg aag aac aac ggt gat ctg gcg ggt atc ctg ggc ctg

G V I A D L Q L K N N G D L A G I L G L tgc att ccg gaa ctg gac ggt aaa atg agc tat atg atc gcg gtg acc ggc gac aac agc

C I P E L D G K M S Y M I A V T G D N S gcg gac atc gcg aag tac gat gtg att acc ctg gcg agc agc aaa tat atg gtt ttt gaa

A D I A K Y D V I T L A S S K Y M V F E

FIG. 19A gcg caa ggt gcg tgg ccg aag gcg gtt cag caa aaa atg gag gaa gtg cac cac tac att

A Q G A W P K A V Q Q K M E E V H H Y I cac cag tat caa gcg aac acc gtt aaa agc gcg ccg ttc ttt gag ctg tac caa gac ggt

H Q Y Q A N T V K S A P F F E L Y Q D G gat acc acc agc gag aag tat atc acc gaa att tgg atg ccg gtt aaa ggc ctg gaa cac

D T T S E K Y I T E I W M P V K G L E H cac cac cac cac cac (SEQ ID NO:9)
H H H H H (SEQ ID NO:10)

*SAV2435 P106W* gene and amino acid sequence atg gag tac cag ctg cag caa ctg gcg agc ctg acc ctg gtg ggt atc aag gag acc tat

M E Y Q L Q Q L A S L T L V G I K E T Y gaa aac ggc cgt caa gcg cag caa cac atc gcg ggt ttc tgg cag cgt tgc tac caa gag

E N G R Q A Q Q H I A G F W Q R C Y Q E ggc gtt att gcg gac ctg cag ctg aag aac aac ggt gat ctg gcg ggt atc ctg ggc ctg

G V I A D L Q L K N N G D L A G I L G L tgc att ccg gaa ctg gac ggt aaa atg agc tat atg atc gcg gtg acc ggc gac aac agc

C I P E L D G K M S Y M I A V T G D N S gcg gac atc gcg aag tac gat gtg att acc ctg gcg agc agc aaa tat atg gtt ttt gaa

A D I A K Y D V I T L A S S K Y M V F E gcg caa ggt gcg gtg tgg aag gcg gtt cag caa aaa atg gag gaa gtg cac cac tac att

A Q G A V W K A V Q Q K M E E V H H Y I cac cag tat caa gcg aac acc gtt aaa agc gcg ccg ttc ttt gag ctg tac caa gac ggt

H Q Y Q A N T V K S A P F F E L Y Q D G gat acc acc agc gag aag tat atc acc gaa att tgg atg ccg gtt aaa ggc ctg gaa cac

D T T S E K Y I T E I W M P V K G L E H cac cac cac cac cac (SEQ ID NO:11)
H H H H H (SEQ ID NO:12)

*SAV2435 E135Q* gene and amino acid sequence atg gag tac cag ctg cag caa ctg gcg agc ctg acc ctg gtg ggt atc aag gag acc tat

M E Y Q L Q Q L A S L T L V G I K E T Y

FIG. 19B gaa aac ggc cgt caa gcg cag caa cac atc gcg ggt ttc tgg cag cgt tgc tac caa gag
E N G R Q A Q Q H I A G F W Q R C Y Q E
ggc gtt att gcg gac ctg cag ctg aag aac aac ggt gat ctg gcg ggt atc ctg ggc ctg
G V I A D L Q L K N N G D L A G I L G L
tgc att ccg gaa ctg gac ggt aaa atg agc tat atg atc gcg gtg acc ggc gac aac agc
C I P E L D G K M S Y M I A V T G D N S
gcg gac atc gcg aag tac gat gtg att acc ctg gcg agc agc aaa tat atg gtt ttt gaa
A D I A K Y D V I T L A S S K Y M V F E
gcg caa ggt gcg tgg ccg aag gcg gtt cag caa aaa atg gag gaa gtg cac cac tac att
A Q G A W P K A V Q Q K M E E V H H Y I
cac cag tat caa gcg aac acc gtt aaa agc gcg ccg ttc ttt cag ctg tac caa gac ggt
H Q Y Q A N T V K S A P F F Q L Y Q D G
gat acc acc agc gag aag tat atc acc gaa att tgg atg ccg gtt aaa ggc ctg gaa cac
D T T S E K Y I T E I W M P V K G L E H
cac cac cac cac cac (SEQ ID NO:13)
H H H H H (SEQ ID NO:14)

*SAV2435 Y137W* gene and amino acid sequence atg gag tac cag ctg cag caa ctg gcg agc ctg acc ctg gtg ggt atc aag gag acc tat
M E Y Q L Q Q L A S L T L V G I K E T Y
gaa aac ggc cgt caa gcg cag caa cac atc gcg ggt ttc tgg cag cgt tgc tac caa gag
E N G R Q A Q Q H I A G F W Q R C Y Q E
ggc gtt att gcg gac ctg cag ctg aag aac aac ggt gat ctg gcg ggt atc ctg ggc ctg
G V I A D L Q L K N N G D L A G I L G L
tgc att ccg gaa ctg gac ggt aaa atg agc tat atg atc gcg gtg acc ggc gac aac agc
C I P E L D G K M S Y M I A V T G D N S
gcg gac atc gcg aag tac gat gtg att acc ctg gcg agc agc aaa tat atg gtt ttt gaa
A D I A K Y D V I T L A S S K Y M V F E
gcg caa ggt gcg tgg ccg aag gcg gtt cag caa aaa atg gag gaa gtg cac cac tac att
A Q G A W P K A V Q Q K M E E V H H Y I
cac cag tat caa gcg aac acc gtt aaa agc gcg ccg ttc ttt gag ctg tgg caa gac ggt
H Q Y Q A N T V K S A P F F E L W Q D G

FIG. 19C gat acc acc agc gag aag tat atc acc gaa att tgg atg ccg gtt aaa ggc ctg gaa cac

D T T S E K Y I T E I W M P V K G L E H cac cac cac cac cac (SEQ ID NO:15)
H H H H H (SEQ ID NO:16)

*CTR107 E36R* gene and amino acid sequence atg gac ttc gag tgc cag ttt gtg tgc gag ctg aag gaa ctg gcg ccg gtt ccg gcg ctg

M D F E C Q F V C E L K E L A P V P A L ctg atc cgt acc caa acc acc atg agc gag ctg ggt agc ctg ttc aga gcg ggc tac cac

L I R T Q T T M S E L G S L F R A G Y H gat att ctg cag ctg ctg gcg ggt cag ggt aag agc ccg agc ggt ccg ccg ttt gcg cgt

D I L Q L L A G Q G K S P S G P P F A R tat ttt ggt atg agc gcg ggc acc ttt gag gtg gag ttc ggc ttt ccg gtg gag ggt ggc

Y F G M S A G T F E V E F G F P V E G G gtt gaa ggt agc ggc cgt gtg gtt acc ggt ctg acc ccg agc ggc aag gcg gcg agc agc

V E G S G R V V T G L T P S G K A A S S ctg tac atc ggt ccg tat ggc gag att gaa gcg gtg tac gac gcg ctg atg aaa tgg gtt

L Y I G P Y G E I E A V Y D A L M K W V gac gat aac ggt ttc gat ctg agc ggc gag gcg tac gaa atc tat ctg gac aac ccg gcg

D D N G F D L S G E A Y E I Y L D N P A gaa acc gcg ccg gat cag ctg cgt acc cgt gtt agc ctg atg ctg cac gag agc ctg gaa

E T A P D Q L R T R V S L M L H E S L E cac cac cac cac cac cac (SEQ ID NO:17)
H H H H H H (SEQ ID NO:18)

*CTR107 Y106W gene* and amino acid sequence atg gac ttc gag tgc cag ttt gtg tgc gag ctg aag gaa ctg gcg ccg gtt ccg gcg ctg

M D F E C Q F V C E L K E L A P V P A L ctg atc cgt acc caa acc acc atg agc gag ctg ggt agc ctg ttc gaa gcg ggc tac cac

L I R T Q T T M S E L G S L F E A G Y H gat att ctg cag ctg ctg gcg ggt cag ggt aag agc ccg agc ggt ccg ccg ttt gcg cgt

D I L Q L L A G Q G K S P S G P P F A R tat ttt ggt atg agc gcg ggc acc ttt gag gtg gag ttc ggc ttt ccg gtg gag ggt ggc

FIG. 19D

```
Y   F   G   M   S   A   G   T   F   E   V   E   F   G   F   P   V   E   G   G

gtt gaa ggt agc ggc cgt gtg gtt acc ggt ctg acc ccg agc ggc aag gcg gcg agc agc

V   E   G   S   G   R   V   V   T   G   L   T   P   S   G   K   A   A   S   S

ctg tac atc ggt ccg tgg ggc gag att gaa gcg gtg tac gac gcg ctg atg aaa tgg gtt

L   Y   I   G   P   W   G   E   I   E   A   V   Y   D   A   L   M   K   W   V

gac gat aac ggt ttc gat ctg agc ggc gag gcg tac gaa atc tat ctg gac aac ccg gcg

D   D   N   G   F   D   L   S   G   E   A   Y   E   I   Y   L   D   N   P   A

gaa acc gcg ccg gat cag ctg cgt acc cgt gtt agc ctg atg ctg cac gag agc ctg gaa

E   T   A   P   D   Q   L   R   T   R   V   S   L   M   L   H   E   S   L   E

cac cac cac cac cac cac    (SEQ ID NO:19)
 H   H   H   H   H   H     (SEQ ID NO:20)
```

*CTR107 E133Q gene* and amino acid sequence

```
atg gac ttc gag tgc cag ttt gtg tgc gag ctg aag gaa ctg gcg ccg gtt ccg gcg ctg

M   D   F   E   C   Q   F   V   C   E   L   K   E   L   A   P   V   P   A   L

ctg atc cgt acc caa acc acc atg agc gag ctg ggt agc ctg ttc gaa gcg ggc tac cac

L   I   R   T   Q   T   T   M   S   E   L   G   S   L   F   E   A   G   Y   H

gat att ctg cag ctg ctg gcg ggt cag ggt aag agc ccg agc ggt ccg ccg ttt gcg cgt

D   I   L   Q   L   L   A   G   Q   G   K   S   P   S   G   P   P   F   A   R

tat ttt ggt atg agc gcg ggc acc ttt gag gtg gag ttc ggc ttt ccg gtg gag ggt ggc

Y   F   G   M   S   A   G   T   F   E   V   E   F   G   F   P   V   E   G   G

gtt gaa ggt agc ggc cgt gtg gtt acc ggt ctg acc ccg agc ggc aag gcg gcg agc agc

V   E   G   S   G   R   V   V   T   G   L   T   P   S   G   K   A   A   S   S

ctg tac atc ggt ccg tat ggc gag att gaa gcg gtg tac gac gcg ctg atg aaa tgg gtt

L   Y   I   G   P   Y   G   E   I   E   A   V   Y   D   A   L   M   K   W   V

gac gat aac ggt ttc gat ctg agc ggc gag gcg tac caa atc tat ctg gac aac ccg gcg

D   D   N   G   F   D   L   S   G   E   A   Y   Q   I   Y   L   D   N   P   A

gaa acc gcg ccg gat cag ctg cgt acc cgt gtt agc ctg atg ctg cac gag agc ctg gaa

E   T   A   P   D   Q   L   R   T   R   V   S   L   M   L   H   E   S   L   E

cac cac cac cac cac cac (SEQ ID NO:21)
 H   H   H   H   H   H  (SEQ ID NO:22)
```

*CTR107 TRIP (E36R H40Y Y106W) gene* and amino acid sequence

```
atg gac ttc gag tgc cag ttt gtg tgc gag ctg aag gaa ctg gcg ccg gtt ccg gcg ctg
```

FIG. 19E

```
M   D   F   E   C   Q   F   V   C   E   L   K   E   L   A   P   V   P   A   L

ctg atc cgt acc caa acc acc atg agc gag ctg ggt agc ctg ttc aga gcg ggc tac tac

L   I   R   T   Q   T   T   M   S   E   L   G   S   L   F   R   A   G   Y   Y

gat att ctg cag ctg ctg gcg ggt cag ggt aag agc ccg agc ggt ccg ccg ttt gcg cgt

D   I   L   Q   L   L   A   G   Q   G   K   S   P   S   G   P   P   F   A   R

tat ttt ggt atg agc gcg ggc acc ttt gag gtg gag ttc ggc ttt ccg gtg gag ggt ggc

Y   F   G   M   S   A   G   T   F   E   V   E   F   G   F   P   V   E   G   G

gtt gaa ggt agc ggc cgt gtg gtt acc ggt ctg acc ccg agc ggc aag gcg gcg agc agc

V   E   G   S   G   R   V   V   T   G   L   T   P   S   G   K   A   A   S   S

ctg tac atc ggt ccg tgg ggc gag att gaa gcg gtg tac gac gcg ctg atg aaa tgg gtt

L   Y   I   G   P   W   G   E   I   E   A   V   Y   D   A   L   M   K   W   V

gac gat aac ggt ttc gat ctg agc ggc gag gcg tac gaa atc tat ctg gac aac ccg gcg

D   D   N   G   F   D   L   S   G   E   A   Y   E   I   Y   L   D   N   P   A

gaa acc gcg ccg gat cag ctg cgt acc cgt gtt agc ctg atg ctg cac gag agc ctg gaa

E   T   A   P   D   Q   L   R   T   R   V   S   L   M   L   H   E   S   L   E

cac cac cac cac cac cac     (SEQ ID NO:23)
H   H   H   H   H   H       (SEQ ID NO:24)
```

*CTR107 QUAD (E36R H40Y Y106W E133Q) gene* and amino acid sequence

```
atg gac ttc gag tgc cag ttt gtg tgc gag ctg aag gaa ctg gcg ccg gtt ccg gcg ctg

M   D   F   E   C   Q   F   V   C   E   L   K   E   L   A   P   V   P   A   L

ctg atc cgt acc caa acc acc atg agc gag ctg ggt agc ctg ttc aga gcg ggc tac tac

L   I   R   T   Q   T   T   M   S   E   L   G   S   L   F   R   A   G   Y   Y

gat att ctg cag ctg ctg gcg ggt cag ggt aag agc ccg agc ggt ccg ccg ttt gcg cgt

D   I   L   Q   L   L   A   G   Q   G   K   S   P   S   G   P   P   F   A   R

tat ttt ggt atg agc gcg ggc acc ttt gag gtg gag ttc ggc ttt ccg gtg gag ggt ggc

Y   F   G   M   S   A   G   T   F   E   V   E   F   G   F   P   V   E   G   G

gtt gaa ggt agc ggc cgt gtg gtt acc ggt ctg acc ccg agc ggc aag gcg gcg agc agc

V   E   G   S   G   R   V   V   T   G   L   T   P   S   G   K   A   A   S   S

ctg tac atc ggt ccg tgg ggc gag att gaa gcg gtg tac gac gcg ctg atg aaa tgg gtt

L   Y   I   G   P   W   G   E   I   E   A   V   Y   D   A   L   M   K   W   V

gac gat aac ggt ttc gat ctg agc ggc gag gcg tac caa atc tat ctg gac aac ccg gcg
```

FIG. 19F

```
 D   D   N   G   F   D   L   S   G   E   A   Y   Q   I   Y   L   D   N   P   A
gaa acc gcg ccg gat cag ctg cgt acc cgt gtt agc ctg atg ctg cac gag agc ctg gaa
 E   T   A   P   D   Q   L   R   T   R   V   S   L   M   L   H   E   S   L   E
cac cac cac cac cac cac    (SEQ ID NO:25)
 H   H   H   H   H   H     (SEQ ID NO:26)
```

*LIN2189 E157A gene* and amino acid sequence

```
atg ggt agc cac cac cac cac cac cac acc gag aag aaa atc gac ttc aag aaa gag gaa
 M   G   S   H   H   H   H   H   H   T   E   K   K   I   D   F   K   K   E   E
aag aaa ttt tac gcg ccg aag cgt aag ccg gag cgt att ttc gtg ccg gaa atg aac ttt
 K   K   F   Y   A   P   K   R   K   P   E   R   I   F   V   P   E   M   N   F
ctg atg gtt gat ggt aaa ggc gac ccg gat ggc gag gaa tac cag aag gcg gtg caa agc
 L   M   V   D   G   K   G   D   P   D   G   E   E   Y   Q   K   A   V   Q   S
ctg tac gcg atc gcg tat acc att aaa atg agc aag atg ggt gaa acc cgt ctg gac ggc
 L   Y   A   I   A   Y   T   I   K   M   S   K   M   G   E   T   R   L   D   G
tat agc gat ttc gtg gtt ccg ccg ctg gag ggt ttc tgg tgg agc gaa ggc aaa ttt gac
 Y   S   D   F   V   V   P   P   L   E   G   F   W   W   S   E   G   K   F   D
ctg aag gac cgt gat gcg tgg ctg tgg acc agc atc ctg cgt cag ccg gat ttc gtg acc
 L   K   D   R   D   A   W   L   W   T   S   I   L   R   Q   P   D   F   V   T
gag gaa gtt ctg gag tgg gcg aaa gaa gtg gcg cgt aag aaa aag ccg gac gtt gat acc
 E   E   V   L   E   W   A   K   E   V   A   R   K   K   K   P   D   V   D   T
agc cgt gtg aag ctg gtt cgt ttt gag gaa ggt gaa tgc gtg cag atg atg cac gtt ggc
 S   R   V   K   L   V   R   F   E   E   G   E   C   V   Q   M   M   H   V   G
ccg ttc agc gag gcg gtg cac acc gtt gcg gaa atg cac caa ttt atg gag acc gaa ggt
 P   F   S   E   A   V   H   T   V   A   E   M   H   Q   F   M   E   T   E   G
ctg cgt aac gac acc ggc gcg atc cgt aaa cac cac gag att tat ctg agc gat ccg cgt
 L   R   N   D   T   G   A   I   R   K   H   H   E   I   Y   L   S   D   P   R
aag gcg aac ccg gaa aaa atg aag acc att ctg cgt ctg ccg gtt agc (SEQ ID NO:27)
 K   A   N   P   E   K   M   K   T   I   L   R   L   P   V   S  (SEQ ID NO:28)
```

FIG. 19G

*LIN2189 E185L gene* and amino acid sequence atg ggt agc cac cac cac cac cac cac acc gag aag aaa atc gac ttc aag aaa gag gaa

M G S H H H H H H T E K K I D F K K E E aag aaa ttt tac gcg ccg aag cgt aag ccg gag cgt att ttc gtg ccg gaa atg aac ttt

K K F Y A P K R K P E R I F V P E M N F ctg atg gtt gat ggt aaa ggc gac ccg gat ggc gag gaa tac cag aag gcg gtg caa agc

L M V D G K G D P D G E E Y Q K A V Q S ctg tac gcg atc gcg tat acc att aaa atg agc aag atg ggt gaa acc cgt ctg gac ggc

L Y A I A Y T I K M S K M G E T R L D G tat agc gat ttc gtg gtt ccg ccg ctg gag ggt ttc tgg tgg agc gaa ggc aaa ttt gac

Y S D F V V P P L E G F W W S E G K F D ctg aag gac cgt gat gcg tgg ctg tgg acc agc atc ctg cgt cag ccg gat ttc gtg acc

L K D R D A W L W T S I L R Q P D F V T gag gaa gtt ctg gag tgg gcg aaa gaa gtg gcg cgt aag aaa aag ccg gac gtt gat acc

E E V L E W A K E V A R K K K P D V D T agc cgt gtg aag ctg gtt cgt ttt gag gaa ggt gaa tgc gtg cag atg atg cac gtt ggc

S R V K L V R F E E G E C V Q M M H V G ccg ttc agc gag gag gtg cac acc gtt gcg gaa atg cac caa ttt atg gag acc gaa ggt

P F S E E V H T V A E M H Q F M E T E G ctg cgt aac gac acc ggc gcg atc cgt aaa cac cac ctg att tat ctg agc gat ccg cgt

L R N D T G A I R K H H L I Y L S D P R aag gcg aac ccg gaa aaa atg aag acc att ctg cgt ctg ccg gtt agc (SEQ ID NO:29)
K A N P E K M K T I L R L P V S (SEQ ID NO:30)

*LIN2189 DUB (E157A E185L) gene* and amino acid sequence atg ggt agc cac cac cac cac cac cac acc gag aag aaa atc gac ttc aag aaa gag gaa

M G S H H H H H H T E K K I D F K K E E aag aaa ttt tac gcg ccg aag cgt aag ccg gag cgt att ttc gtg ccg gaa atg aac ttt

K K F Y A P K R K P E R I F V P E M N F ctg atg gtt gat ggt aaa ggc gac ccg gat ggc gag gaa tac cag aag gcg gtg caa agc

L M V D G K G D P D G E E Y Q K A V Q S ctg tac gcg atc gcg tat acc att aaa atg agc aag atg ggt gaa acc cgt ctg gac ggc

FIG. 19H

L Y A I A Y T I K M S K M G E T R L D G
tat agc gat ttc gtg gtt ccg ccg ctg gag ggt ttc tgg tgg agc gaa ggc aaa ttt gac

Y S D F V V P P L E G F W W S E G K F D ctg aag gac cgt gat gcg tgg ctg tgg acc agc atc ctg cgt cag ccg gat ttc gtg acc

L K D R D A W L W T S I L R Q P D F V T gag gaa gtt ctg gag tgg gcg aaa gaa gtg gcg cgt aag aaa aag ccg gac gtt gat acc

E E V L E W A K E V A R K K K P D V D T agc cgt gtg aag ctg gtt cgt ttt gag gaa ggt gaa tgc gtg cag atg atg cac gtt ggc

S R V K L V R F E E G E C V Q M M H V G ccg ttc agc gag gcg gtg cac acc gtt gcg gaa atg cac caa ttt atg gag acc gaa ggt

P F S E A V H T V A E M H Q F M E T E G ctg cgt aac gac acc ggc gcg atc cgt aaa cac cac ctg att tat ctg agc gat ccg cgt

L R N D T G A I R K H H L I Y L S D P R aag gcg aac ccg gaa aaa atg aag acc att ctg cgt ctg ccg gtt agc (SEQ ID NO:31)
K A N P E K M K T I L R L P V S (SEQ ID NO:32

FIG. 19I

*SAV2435 WT* binding site combinatorial mutant library

Gene with corresponding amino acid sequence atggagtaccagctgcagcaactggcgagcctgaccctggtgggtatcaaggagacctat

M E Y Q L Q Q L A S L T L V G I K E T Y gaaaacggccgtcaagcgcagcaacacatcgcgggtttctggcagcgttgctaccaagag

E N G R Q A Q Q H I A G F W Q R C Y Q E ggcgttattgcggacctgcagctgaagaacaacggtgatctggcgggtatcctgggcctg

G V I A D L Q L K N N G D L A G I L G L tgcattccggaactggacggtaaaatgagctatatgatcgcggtgaccggcgacaacagc

C I P E L D G K M S Y M I A V T G D N S gcggacatcgcgaagtacgatgtgattaccctggcgagcagcaaatatatggtttttgaa

A D I A K Y D V I T L A S S K Y M V F E gcgcaaggtgcggtgccgaaggcggttcagcaaaaaatggaggaagtgcaccactacatt

A Q G A V P K A V Q Q K M E E V H H Y I caccagtatcaagcgaacaccgttaaaagcgcgccgttctttgagctgtaccaagacggt

H Q Y Q A N T V K S A P F F E L Y Q D G gataccaccagcgagaagtatatcaccgaaatttggatgccggttaaaggcctggaacac

D T T S E K Y I T E I W M P V K G L E H caccaccaccaccac (SEQ ID NO:1)

H H H H H (SEQ ID NO:2)

Targeted binding site residues(bold) with codon numbering

ATGGAGTACCAGCTGCAGCAACTGGCGAGCCTGACCCTGGTGGGTATCAAGGAGACCTATGAAAACGGCCGTCAA
GCGCAG$^{27}$CAACACATC$^{30}$GCG$^{31}$GGTTTCTGG$^{34}$CAGCGTTGCTAC$^{38}$CAAGAGGGCGTTATTGCGGACCTGCAGCTGAAGA
ACAACGGTGATCTGGCGGGTATCCTGGGCCTGTGCATTCCGGAACTGGACGGTAAAATGAGCTATATGATCGCGGTGAC
CGGCGACAACAGCGCGGACATCGCGAAGTACGATGTGATTACCCTGGCGAGCAGCAAATATATGGTTTTTGAA
GCGCAAGGTGCGGTG$^{105}$CCG$^{106}$AAGGCGGTT$^{109}$CAG$^{110}$CAAAAAATG$^{113}$GAGGAAGTGCACCACTACATTCACCAGTAT
CAAGCGAACACCGTTAAAAGCGCGCCGTTCTTTGAG$^{135}$CTGTAC$^{137}$CAAGACGGTGATACC$^{142}$ACCAGCGAGAAGTATA
TCACCGAAATTTGGATGCCGGTTAAAGGCCTGGAACACCACCACCACCACCAC (SEQ ID NO:1)

Targeted amino acids for randomized mutations

Q27,I30,A31,W34,Y38,V105,P106,V109,Q110,M113,E135,Y137,T142

*CTR107 WT* binding site combinatorial mutant library

Gene with corresponding amino acid sequence atggacttcgagtgccagtttgtgtgcgagctgaaggaactggcgccggttccggcgctg

M D F E C Q F V C E L K E L A P V P A L ctgatccgtacccaaaccaccatgagcgagctgggtagcctgttcgaagcgggctaccac

L I R T Q T T M S E L G S L F E A G Y H gatattctgcagctgctggcgggtcagggtaagagcccgagcggtccgccgtttgcgcgt

D I L Q L L A G Q G K S P S G P P F A R tattttggtatgagcgcgggcacctttgaggtggagttcggctttccggtggagggtggc

Y F G M S A G T F E V E F G F P V E G G gttgaaggtagcggccgtgtggttaccggtctgaccccgagcggcaaggcggcgagcagc

V E G S G R V V T G L T P S G K A A S S ctgtacatcggtccgtatggcgagattgaagcggtgtacgacgcgctgatgaaatgggtt

L Y I G P Y G E I E A V Y D A L M K W V gacgataacggtttcgatctgagcggcgaggcgtacgaaatctatctggacaacccggcg

D D N G F D L S G E A Y E I Y L D N P A gaaaccgcgccggatcagctgcgtacccgtgttagcctgatgctgcacgagagcctggaa

E T A P D Q L R T R V S L M L H E S L E

Caccaccaccaccaccac (SEQ ID NO:3)

H H H H H H (SEQ ID NO:4)

FIG. 20A

Targeted binding site residues(bold) with codon numbering
ATGGACTTCGAGTGCCAGTTTGTGTGCGAGCTGAAGGAACTGGCGCCGGTTCCGGCGCTGCTGATCCGTACCCAA
ACCACCATGAGCGAGCTG$^{31}$GGT$^{32}$AGCCTGTTC$^{35}$GAA$^{36}$GCGGGCTAC$^{39}$CAC$^{40}$GATATTCTG$^{43}$CAGCTGCTGGCGGGTC
AGGGTAAGAGCCCGAGCGGTCCGCCGTTTGCGCGTTAT$^{61}$TTTGGTATGAGCGCGGGCACCTTTGAGGTGGAGTTCGGCT
TT$^{75}$CCGGTGGAGGGTGGCGTTGAAGGTAGCGGCCGTGTGGTTACCGGTCTGACCCCGAGCGGCAAGGCGGCGAGCAGC
CTGTACATCGGTCCGTAT$^{106}$GGCGAGATTGAAGCGGTGTACGACGCGCTGATGAAATGGGTTGACGATAACGGTTTC
GATCTGAGCGGCGAGGCGTACGAA$^{133}$ATCTAT$^{135}$CTGGACAAC$^{138}$CCGGCGGAAACCGCGCCGGATCAGCTGCGTACCC
GTGTTAGCCTGATGCTGCACGAGAGCCTGGAACACCACCACCACCACCAC (SEQ ID NO:3)

Targeted amino acids for randomized mutations
L31,G32,F35,E36,Y39,H40,L43,F75,Y106,E133,Y135,N138,

*LIN2189 WT* binding site combinatorial mutant library
Gene with corresponding amino acid sequence
```
atgggtagccaccaccaccaccaccacaccgagaagaaaatcgacttcaagaaagaggaa
 M  G  S  H  H  H  H  H  H  T  E  K  K  I  D  F  K  K  E  E
aagaaattttacgcgccgaagcgtaagccggagcgtatttttcgtgccggaaatgaacttt
 K  K  F  Y  A  P  K  R  K  P  E  R  I  F  V  P  E  M  N  F
ctgatggttgatggtaaaggcgacccggatggcgaggaataccagaaggcggtgcaaagc
 L  M  V  D  G  K  G  D  P  D  G  E  E  Y  Q  K  A  V  Q  S
ctgtacgcgatcgcgtataccattaaaatgagcaagatgggtgaaacccgtctggacggc
 L  Y  A  I  A  Y  T  I  K  M  S  K  M  G  E  T  R  L  D  G
tatagcgatttcgtggttccgccgctggagggttttctggtggagcgaaggcaaatttgac
 Y  S  D  F  V  V  P  P  L  E  G  F  W  S  E  G  K  F  D
ctgaaggaccgtgatgcgtggctgtggaccagcatcctgcgtcagccggatttcgtgacc
 L  K  D  R  D  A  W  L  W  T  S  I  L  R  Q  P  D  F  V  T
gaggaagttctggagtgggcgaaagaagtggcgcgtaagaaaaagccggacgttgatacc
 E  E  V  L  E  W  A  K  E  V  A  R  K  K  K  P  D  V  D  T
agccgtgtgaagctggttcgttttgaggaaggtgaatgcgtgcagatgatgcacgttggc
 S  R  V  K  L  V  R  F  E  E  G  E  C  V  Q  M  M  H  V  G
ccgttcagcgaggcggtgcacaccgttgcggaaatgcaccaatttatggagaccgaaggt
 P  F  S  E  A  V  H  T  V  A  E  M  H  Q  F  M  E  T  G
ctgcgtaacgacaccggcgcgatccgtaaacaccacctgatttatctgagcgatccgcgt
 L  R  N  D  T  G  A  I  R  K  H  H  L  I  Y  L  S  D  P  R
Aaggcgaacccggaaaaaatgaagaccattctgcgtctgccggttagc (SEQ ID NO:5)
 K  A  N  P  E  K  M  K  T  I  L  R  L  P  V  S   (SEQ ID NO:6)
```

Targeted binding site residues(red) with codon numbering
ATGGGTAGCCACCACCACCACCACCACACCGAGAAGAAAATCGACTTCAAGAAAGAGGAAAAGAAATTTTACGCGCCGA
AGCGTAAGCCGGAGCGTATTTTCGTGCCGGAAATGAACTTTCTGATGGTTGATGGTAAAGGCGACCCG$^{41}$GAT$^{42}$GGCGAG
GAATAC$^{46}$CAGAAGGCGGTG$^{50}$CAAAGCCTGTAC$^{54}$GCGATCGCGTAT$^{58}$ACCATTAAAATGAGCAAGATGGGTGAAACCCG
TCTGGACGGCTATAGCGATTTCGTGGTTCCGCCGCTG$^{81}$GAGGGTTTCTGG$^{85}$TGGAGCGAAGGCAAATTTGACCTG$^{93}$AA
GGACCGTGATGCGTGG$^{99}$CTGTGGACCAGCATCCTGCGTCAGCCGGATTTCGTGACCGAGGAAGTTCTGGAGTGGGCGAA
AGAAGTGGCGCGTAAGAAAAAGCCGGACGTTGATACCAGCCGTGTGAAGCTGGTTCGTTTTGAGGAAGGTGAATGCGTG
CAGATGATGCACGTTGGCCCG$^{154}$TTCAGCGAGGCG$^{157}$GTGCACACCGTTGCGGAAATGCACCAATTTATGGAGACCGAA
GGTCTGCGTAACGACACCGGCGCGATCCGTAAACACCACCTG$^{185}$ATTTAT$^{187}$CTGAGCGAT$^{190}$CCG$^{191}$CGT$^{192}$AAGGCG
AACCCGGAAAAAATGAAGACCATTCTGCGTCTGCCGGTTAGC (SEQ ID NO:5)

Targeted amino acids for randomized mutations
P41,D42,Y46,V50,Y54,Y58,L81,W85,L93,W99,F154,A157,L185,Y187,
D190,P191,R192,

FIG. 20B

CTR107 FAM 1 5616 (A) FAM-binding aptamer

MDFECQFVCELKELAPVPALLIRTQTTMSELGSLFEAGYHDILQLLAGQGKSPSGPPFA
RYFGMSAGTFEVEFGFPVEGGVEGSGRVVTGLTPSGKAASSLYIGPWGEIEAVYDALMK
WVDDNGFDLSGEAYQIYLDNPAETAPDQLRTRVSLMLHESLEHHHHHH (SEQ ID
NO:33)

W106, Q133

```
wildtype       1 MDFECQFVCELKELAPVPALLIRTQTTMSELGSLFEAGYHDILQLLAGQG     50
                 ||||||||||||||||||||||||||||||||||||||||||||||||||
variant        1 MDFECQFVCELKELAPVPALLIRTQTTMSELGSLFEAGYHDILQLLAGQG     50

wildtype      51 KSPSGPPFARYFGMSAGTFEVEFGFPVEGGVEGSGRVVTGLTPSGKAASS    100
                 ||||||||||||||||||||||||||||||||||||||||||||||||||
variant       51 KSPSGPPFARYFGMSAGTFEVEFGFPVEGGVEGSGRVVTGLTPSGKAASS    100

wildtype     101 LYIGPYGEIEAVYDALMKWVDDNGFDLSGEAYEIYLDNPAETAPDQLRTR    150
                 |||||.||||||||||||||||||||||||||.|||||||||||||||||
variant      101 LYIGPWGEIEAVYDALMKWVDDNGFDLSGEAYQIYLDNPAETAPDQLRTR    150

wildtype     151 VSLMLHESLEHHHHHH    166
                 ||||||||||||||||
variant      151 VSLMLHESLEHHHHHH    166
```

CTR107 FAM 1 5403 FAM-binding aptamer

MDFECQFVCELKELAPVPALLIRTQTTMSEFPSLFLAGMPDILQLLAGQGKSPSGPPFA
RYFGMSAGTFEVEFGYPVEGGVEGSGRVVTGLTPSGKAASSLYIGPYGEIEAVYDALMK
WVDDNGFDLSGEAYIIPLDEPAETAPDQLRTRVSLMLHESLEHHHHHH (SEQ ID
NO:34)

```
wildtype      1 MDFECQFVCELKELAPVPALLIRTQTTMSELGSLFEAGYHDILQLLAGQG    50
                ||||||||||||||||||||||||||||||..|||.||..||||||||||
variant       1 MDFECQFVCELKELAPVPALLIRTQTTMSEFFSLFLAGHPDILQLLAGQG    50

wildtype     51 KSPSGPPFARYFGMSAGTFEVEFGFPVEGGVEGSGRVVTGLTPSGKAASS   100
                ||||||||||||||||||||||||:|||||||||||||||||||||||||
variant      51 KSPSGPPFARYFGMSAGTFEVEFGYPVEGGVEGSGRVVTGLTPSGKAASS   100

wildtype    101 LYIGPYGEIEAVYDALMKWVDDNGFDLSGEAYEIYLDNPAETAPDQLRTR   150
                ||||||||||||||||||||||||||||||||.|.||.||||||||||||
variant     101 LYIGPYGEIEAVYDALMKWVDDNGFDLSGEAYIIFLDEPAETAPDQLRTR   150

wildtype    151 VSLMLHESLEHHHHHH    166
                ||||||||||||||||
variant     151 VSLMLHESLEHHHHHH    166
```

CTR107 FAM 1 5616 (B) FAM-binding aptamer

MDFECQFVCELKELAPVPALLIRTQTTMSEAKSLHLAGSGDIEQLLAGQGKSPSGPPFA
RYFGMSAGTFEVEFGVPVEGGVEGSGRVVTGLTPSGKAASSLYIGPTGEIEAVYDALMK
WVDDNGFDLSGEAYVIWLDTPAETAPDQLRTRVSLMLHESLEHHHHHH (SEQ ID
NO:35)

A31, K32, H35, L36, S39, G40, E43, V75, T106, V133, W135, T138

```
wildtype      1 MDFECQFVCELKELAPVPALLIRTQTTMSELGSLFEAGYHDILQLLAGQG    50
                ||||||||||||||||||||||||||||||..||..||..||.|||||||
variant       1 MDFECQFVCELKELAPVPALLIRTQTTMSEAKSLHLAGSGDIEQLLAGQG    50

wildtype     51 KSPSGPPFARYFGMSAGTFEVEFGFPVEGGVEGSGRVVTGLTPSGKAASS   100
                ||||||||||||||||||||||||.|||||||||||||||||||||||||
variant      51 KSPSGPPFARYFGMSAGTFEVEFGVPVEGGVEGSGRVVTGLTPSGKAASS   100

wildtype    101 LYIGPYGEIEAVYDALMKWVDDNGFDLSGEAYEIYLDNPAETAPDQLRTR   150
                |||||.||||||||||||||||||||||||||.|.||.||||||||||||
variant     101 LYIGPTGEIEAVYDALMKWVDDNGFDLSGEAYVIWLDTPAETAPDQLRTR   150

wildtype    151 VSLMLHESLEHHHHHH    166
                ||||||||||||||||
variant     151 VSLMLHESLEHHHHHH    166
```

CTR107 FAM 4 5616 FAM-binding aptamer

MDFECQFVCELKELAPVPALLIRTQTTMSEGDSLSLAGRRDIVQLLAGQGKSPSGPPFA
RYFGMSAGTFEVEFGCPVEGGVEGSGRVVTGLTPSGKAASSLYIGPIGEIEAVYDALMK
WVDDNGFDLSGEAYTIHLDAPAETAPDQLRTRVSLMLHESLEHHHHHH (SEQ ID
NO:36)

Figure 22C:
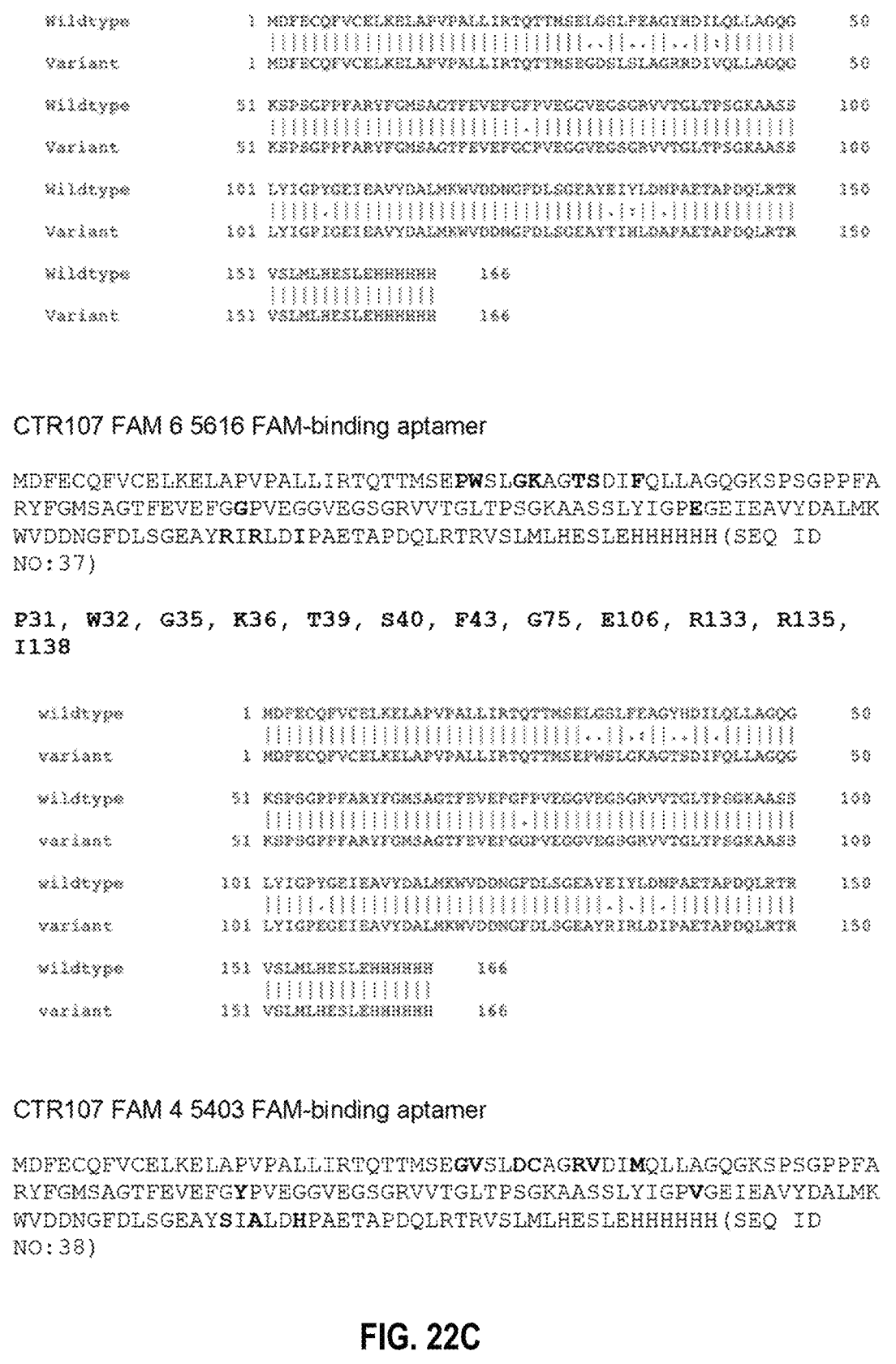

```
Wildtype      1 MDFECQFVCELKELAPVPALLIRTQTTMSELGSLFEAGYHDILQLLAGQG     50
Variant       1 MDFECQFVCELKELAPVPALLIRTQTTMSEGDSLSLAGRHDIVQLLAGQG     50

Wildtype     51 KSPSGPPFARYFGMSAGTFEVEFGFPVEGGVEGSGRVVTGLTPSGKAASS    100
Variant      51 KSPSGPPFARYFGMSAGTFEVEFGCPVEGGVEGSGRVVTGLTPSGKAASS    100

Wildtype    101 LYIGPYGEIEAVYDALMKWVDDNGFDLSGEAYEIYLDNPAETAPDQLRTR    150
Variant     101 LYIGPIGEIEAVYDALMKWVDDNGFDLSGEAYTIHLDAPAETAPDQLRTR    150

Wildtype    151 VSLMLHESLEHHHHHH    166
Variant     151 VSLMLHESLEHHHHHH    166
```

CTR107 FAM 6 5616 FAM-binding aptamer

MDFECQFVCELKELAPVPALLIRTQTTMSEPWSLGKAGTSDIFQLLAGQGKSPSGPPFA
RYFGMSAGTFEVEFGGPVEGGVEGSGRVVTGLTPSGKAASSLYIGPEGEIEAVYDALMK
WVDDNGFDLSGEAYRIRLDIPAETAPDQLRTRVSLMLHESLEHHHHHH (SEQ ID
NO:37)

P31, W32, G35, K36, T39, S40, F43, G75, E106, R133, R135, I138

```
wildtype      1 MDFECQFVCELKELAPVPALLIRTQTTMSELGSLFEAGYHDILQLLAGQG     50
variant       1 MDFECQFVCELKELAPVPALLIRTQTTMSEPWSLGKAGTSDIFQLLAGQG     50

wildtype     51 KSPSGPPFARYFGMSAGTFEVEFGFPVEGGVEGSGRVVTGLTPSGKAASS    100
variant      51 KSPSGPPFARYFGMSAGTFEVEFGGPVEGGVEGSGRVVTGLTPSGKAASS    100

wildtype    101 LYIGPYGEIEAVYDALMKWVDDNGFDLSGEAYEIYLDNPAETAPDQLRTR    150
variant     101 LYIGPEGEIEAVYDALMKWVDDNGFDLSGEAYRIRLDIPAETAPDQLRTR    150

wildtype    151 VSLMLHESLEHHHHHH    166
variant     151 VSLMLHESLEHHHHHH    166
```

CTR107 FAM 4 5403 FAM-binding aptamer

MDFECQFVCELKELAPVPALLIRTQTTMSEGVSLDCAGRVDIMQLLAGQGKSPSGPPFA
RYFGMSAGTFEVEFGYPVEGGVEGSGRVVTGLTPSGKAASSLYIGPVGEIEAVYDALMK
WVDDNGFDLSGEAYSIALDHPAETAPDQLRTRVSLMLHESLEHHHHHH (SEQ ID
NO:38)

```
Wildtype           1 MDFECQFVCELKELAPVPALLIRTQTTMSELGSLFEAGYHDILQLLAGQG     50
                     ||||||||||||||||||||||||||||||..||..||..||:|||||||
Variant            1 MDFECQFVCELKELAPVPALLIRTQTTMSEGVSLDCAGRVDIMQLLAGQG     50

Wildtype          51 KSPSGPPFARYFGMSAGTFEVEFGFPVEGGVEGSGRVVTGLTPSGKAASS    100
                     ||||||||||||||||||||||||:|||||||||||||||||||||||||
Variant           51 KSPSGPPFARYFGMSAGTFEVEFGYPVEGGVEGSGRVVTGLTPSGKAASS    100

Wildtype         101 LYIGPYGEIEAVYDALMKWVDDNGFDLSGEAYEIYLDNPAETAPDQLRTR    150
                     |||||.||||||||||||||||||||||||||.|.||:||||||||||||
Variant          101 LYIGPVGEIEAVYDALMKWVDDNGFDLSGEAYSIALDHPAETAPDQLRTR    150

Wildtype         151 VSLMLHESLEHHHHHH    166
                     ||||||||||||||||
Variant          151 VSLMLHESLEHHHHHH    166
```

CTR107 FAM 6 5403 FAM-binding aptamer

MDFECQFVCELKELAPVPALLIRTQTTMSEILSLILAGKMDIIQLLAGQGKSPSGPPFA RYFGMSAGTFEVEFGFPVEGGVEGSGRVVTGLTPSGKAASSLYIGPLGEIEAVYDALMK WVDDNGFDLSGEAYGIRLDIPAETAPDQLRTRVSLMLHESLEHHHHHH(SEQ ID NO:39)

I31, L32, I35, L36, K39, M40, I43, L106, G133, R135, I138

```
wildtype           1 MDFECQFVCELKELAPVPALLIRTQTTMSELGSLFEAGYHDILQLLAGQG     50
                     ||||||||||||||||||||||||||||||:.||..||..||:|||||||
variant            1 MDFECQFVCELKELAPVPALLIRTQTTMSEILSLILAGKMDIIQLLAGQG     50

wildtype          51 KSPSGPPFARYFGMSAGTFEVEFGFPVEGGVEGSGRVVTGLTPSGKAASS    100
                     ||||||||||||||||||||||||||||||||||||||||||||||||||
variant           51 KSPSGPPFARYFGMSAGTFEVEFGFPVEGGVEGSGRVVTGLTPSGKAASS    100

wildtype         101 LYIGPYGEIEAVYDALMKWVDDNGFDLSGEAYEIYLDNPAETAPDQLRTR    150
                     |||||.||||||||||||||||||||||||||.|.||.||||||||||||
variant          101 LYIGPLGEIEAVYDALMKWVDDNGFDLSGEAYGIRLDIPAETAPDQLRTR    150

wildtype         151 VSLMLHESLEHHHHHH    166
                     ||||||||||||||||
variant          151 VSLMLHESLEHHHHHH    166
```

FIG. 22D

SAV2435 FAM 5 5403 FAM-binding aptamer

MEYQLQQLASLTLVGIKETYENGRQAVQHGHGFFQRCDQEGVIADLQLKNNGDLAGILG
LCIPELDGKMSYMIAVTGDNSADIAKYDVITLASSKYMVFEAQGADSKANTQKGEEVHH
YIHQYQANTVKSAPFFPLVQDGDYTSEKYITEIWMPVKGLEHHHHHH (SEQ ID
NO:40)

**V27, G30, H31, F34, D38, D105, S106, N109, T110, G113,
P135, V137, Y142**

```
Wildtype      1 MEYQLQQLASLTLVGIKETYENGRQAQQHIAGFWQRCYQEGVIADLQLKN     50
                ||||||||||||||||||||||||||.||..||:|||.||||||||||||
Variant       1 MEYQLQQLASLTLVGIKETYENGRQAVQHGHGFFQRCDQEGVIADLQLKN     50

Wildtype     51 NGDLAGILGLCIPELDGKMSYMIAVTGDNSADIAKYDVITLASSKYMVFE    100
                ||||||||||||||||||||||||||||||||||||||||||||||||||
Variant      51 NGDLAGILGLCIPELDGKMSYMIAVTGDNSADIAKYDVITLASSKYMVFE    100

Wildtype    101 AQGAVPKAVQQKMEEVHHYIHQYQANTVKSAPFFELYQDGDTTSEKYITE    150
                ||||..||..||.||||||||||||||||||||||.|.||||.||||||||
Variant     101 AQGADSKANTQKGEEVHHYIHQYQANTVKSAPFFPLVQDGDYTSEKYITE    150

Wildtype    151 IWMPVKGLEHHHHHH    165
                |||||||||||||||
Variant     151 IWMPVKGLEHHHHHH    165
```

SAV2435 CARB 3 5403 Cytarabine-binding aptamer

MEYQLQQLASLTLVGIKETYENGRQAEQHLIGFRQRCLQEGIIADLQLKNNGDLAGILG
LCIPELDGKMSYMIAVTGDNSADIAKYDVITLASSKYMVFEAQGANNKAQSQKCEEVHH
YIHQYQANTVKSAPFFHLKQDGDVTSEKYITEIWMPVKGLEHHHHHH (SEQ ID
NO:41)

```
wildtype      1 MEYQLQQLASLTLVGIKETYENGRQAQQHIAGFWQRCYQEGVIADLQLKN     50
                ||||||||||||||||||||||||||:||:.||.|||.|||:||||||||
mutant        1 MEYQLQQLASLTLVGIKETYENGRQAEQHLIGFRQRCLQEGIIADLQLKN     50

wildtype     51 NGDLAGILGLCIPELDGKMSYMIAVTGDNSADIAKYDVITLASSKYMVFE    100
                ||||||||||||||||||||||||||||||||||||||||||||||||||
mutant       51 NGDLAGILGLCIPELDGKMSYMIAVTGDNSADIAKYDVITLASSKYMVFE    100

wildtype    101 AQGAVFKAVQQKMEEVHHYIHQYQANTVKSAPFFELYQDGDTTSEKYITE    150
                ||||..||..||.|||||||||||||||||||||.|.||||.||||||||
mutant      101 AQGANNKAQSQKCEEVHHYIHQYQANTVKSAPFFHLEQDGDVTSEKYITE    150

wildtype    151 IWMPVKGLEHHHHHH    165
                |||||||||||||||
mutant      151 IWMPVKGLEHHHHHH    165
```

SAV2435 CY5 6 5403 Cy5-binding aptamer

MEYQLQQLASLTLVGIKETYENGRQARQHSNGFIQRCGQEGVIADLQLKNNGDLAGILG
LCIPELDGKMSYMIAVTGDNSADIAKYDVITLASSKYMVFEAQGAKVKAEYQKREEVHH
YIHQYQANTVKSAPFFRLGQDGDSTSEKYITEIWMPVKGLEHHHHHH(SEQ ID
NO:42)

R27, S30, N31, I34, G38, K105, V106, E109, Y110, R113, R135, G137, S142

```
Wildtype      1 MEYQLQQLASLTLVGIKETYENGRQAQQHIAGFWQRCYQEGVIADLQLKN     50
                ||||||||||||||||||||||||||:||..||.|||.||||||||||||
Phage         1 MEYQLQQLASLTLVGIKETYENGRQARQHSNGFIQRCGQEGVIADLQLKN     50

Wildtype     51 NGDLAGILGLCIPELDGKMSYMIAVTGDNSADIAKYDVITLASSKYMVFE    100
                ||||||||||||||||||||||||||||||||||||||||||||||||||
Phage        51 NGDLAGILGLCIPELDGKMSYMIAVTGDNSADIAKYDVITLASSKYMVFE    100

Wildtype    101 AQGAVFKAVQQKMEEVHHYIHQYQANTVKSAPFFELYQDGDTTSEKYITE    150
                ||||..||..||.|||||||||||||||||||||.|.||||:||||||||
Phage       101 AQGAKVKAEYQKREEVHHYIHQYQANTVKSAPFFRLGQDGDSTSEKYITE    150

Wildtype    151 IWMPVKGLEHHHHHH    165
                |||||||||||||||
Phage       151 IWMPVKGLEHHHHHH    165
```

FIG. 24B

SAV2435 CARB 5 5403 Cytarabine-binding aptamer

MEYQLQQLASLTLVGIKETYENGRQAHQHFLGFTQRCRQEGVIADLQLKNNGDLAGILG
LCIPELDGKMSYMIAVTGDNSADIAKYDVITLASSKYMVFEAQGALRKALTQKLEEVHH
YIHQYQANTVKSAPFFILSQDGDQTSEKYITEIWMPVKGLEHHHHHH(SEQ ID
NO:43)

**H27, F30, L31, T34, R38, L105, R106, L109, T110, L113,
I135, S137, Q142**

```
Wildtype          1 MEYQLQQLASLTLVGIKETYENGRQAQQHIAGFWQRCYQEGVIADLQLKN     50
                      ||||||||||||||||||||||||||.||..||.|||.||||||||||||
Variant           1 MEYQLQQLASLTLVGIKETYENGRQAHQHFLGFTQRCRQEGVIADLQLKN     50

Wildtype         51 NGDLAGILGLCIPELDGKMSYMIAVTGDNSADIAKYDVITLASSKYMVFE    100
                      ||||||||||||||||||||||||||||||||||||||||||||||||||
Variant          51 NGDLAGILGLCIPELDGKMSYMIAVTGDNSADIAKYDVITLASSKYMVFE    100

Wildtype        101 AQGAVFKAVQQKMEEVHHYIHQYQANTVKSAPFFELYQDGDTTSEKYITE    150
                      ||||:.||:.||:|||||||||||||||||||||.|.||||.||||||||
Variant         101 AQGALRKALTQKLEEVHHYIHQYQANTVKSAPFFILSQDGDQTSEKYITE    150

Wildtype        151 IWMPVKGLEHHHHHH    165
                      |||||||||||||||
Variant         151 IWMPVKGLEHHHHHH    165
```

SAV2435 CARB 6 5403 Cytarabine-binding aptamer

MEYQLQQLASLTLVGIKETYENGRQAIQHWTGFIQRCMQEGVIADLQLKNNGDLAGILG
LCIPELDGKMSYMIAVTGDNSADIAKYDVITLASSKYMVFEAQGAALKAGFQKCEEVHH
YIHQYQANTVKSAPFFLLSQDGDGTSEKYITEIWMPVKGLEHHHHHH(SEQ ID
NO:44)

**I27, W30, T31, I34, M38, A105, L106, G109, F110, C113,
L135, S137, G142**

```
Wildtype          1 MEYQLQQLASLTLVGIKETYENGRQAQQHIAGFWQRCYQEGVIADLQLKN     50
                      ||||||||||||||||||||||||||.||..||.|||.||||||||||||
Phage             1 MEYQLQQLASLTLVGIKETYENGRQAIQHWTGFIQRCMQEGVIADLQLKN     50

Wildtype         51 NGDLAGILGLCIPELDGKMSYMIAVTGDNSADIAKYDVITLASSKYMVFE    100
                      ||||||||||||||||||||||||||||||||||||||||||||||||||
Phage            51 NGDLAGILGLCIPELDGKMSYMIAVTGDNSADIAKYDVITLASSKYMVFE    100

Wildtype        101 AQGAVFKAVQQKMEEVHHYIHQYQANTVKSAPFFELYQDGDTTSEKYITE    150
                      ||||..||..||.|||||||||||||||||||||.|.||||.||||||||
Phage           101 AQGAALKAGFQKCEEVHHYIHQYQANTVKSAPFFLLSQDGDGTSEKYITE    150

Wildtype        151 IWMPVKGLEHHHHHH    165
                      |||||||||||||||
Phage           151 IWMPVKGLEHHHHHH    165
```

FIG. 24C

SAV2435 CARB 7 5403 Cytarabine-binding aptamer

MEYQLQQLASLTLVGIKETYENGRQATQHKNGFGQRCLQEGVIADLQLKNNGDLAGILG
LCIPELDGKMSYMIAVTGDNSADIAKYDVITLASSKYMVFEAQGAPGKASVQKMEEVHH
YIHQYQANTVKSAPFFSLAQDGDNTSEKYITEIWMPVKGLEHHHHHH(SEQ ID
NO:45)

T27, K30, N31, G34, L38, P105, G106, S109, V110, S135, A137, N142

```
Wildtype        1 MEYQLQQLASLTLVGIKETYENGRQAQQHIAGFWQRCYQEGVIADLQLKN    50
                    ||||||||||||||||||||||||||.||..||.|||.||||||||||||
Phage           1 MEYQLQQLASLTLVGIKETYENGRQATQHKNGFGQRCLQEGVIADLQLKN    50

Wildtype       51 NGDLAGILGLCIPELDGKMSYMIAVTGDNSADIAKYDVITLASSKYMVFE   100
                    ||||||||||||||||||||||||||||||||||||||||||||||||||
Phage          51 NGDLAGILGLCIPELDGKMSYMIAVTGDNSADIAKYDVITLASSKYMVFE   100

Wildtype      101 AQGAVFKAVQQKMEEVHHYIHQYQANTVKSAPFFELYQDGDTTSEKYITE   150
                    ||||..||..||||||||||||||||||||||||.|.||||.||||||||
Phage         101 AQGAPGKASVQKMEEVHHYIHQYQANTVKSAPFFSLAQDGDNTSEKYITE   150

Wildtype      151 IWMPVKGLEHHHHHH    165
                    |||||||||||||||
Phage         151 IWMPVKGLEHHHHHH    165
```

CTR107 CARB 2 5403 Cytarabine-binding aptamer

MDFECQFVCELKELAPVPALLIRTQTTMSEIVSLLPAGSSDILQLLAGQGKSPSGPPFA
RYFGMSAGTFEVEFGAPVEGGVEGSGRVVTGLTPSGKAASSLYIGPCGEIEAVYDALMK
WVDDNGFDLSGEAYSICLDYPAETAPDQLRTRVSLMLHESLEHHHHHH(SEQ ID
NO:46)

I31, V32, L35, P36, S39, S40, A75, C106, S133, C135, Y138

```
wildtype        1 MDFECQFVCELKELAPVPALLIRTQTTMSELGSLFEAGYNDILQLLAGQG    50
                    ||||||||||||||||||||||||||||||:.||..||..||||||||||
variant         1 MDFECQFVCELKELAPVPALLIRTQTTMSEIVSLLPAGSSDILQLLAGQG    50

wildtype       51 KSPSGPPFARYFGMSAGTFEVEFGPPVEGGVEGSGRVVTGLTPSGKAASS   100
                    ||||||||||||||||||||||||.|||||||||||||||||||||||||
variant        51 KSPSGPPFARYFGMSAGTFEVEFGAPVEGGVEGSGRVVTGLTPSGKAASS   100

wildtype      101 LYIGPYGEIEAVYDALMKWVDDNGFDLSGEAYEIYLDNPAETAPDQLRTR   150
                    |||||.||||||||||||||||||||||||||.|.||.||||||||||||
variant       101 LYIGPCGEIEAVYDALMKWVDDNGFDLSGEAYSICLDYPAETAPDQLRTR   150

wildtype      151 VSLMLHESLEHHHHHH    166
                    ||||||||||||||||
variant       151 VSLMLHESLEHHHHHH    166
```

FIG. 24D

CTR107 CARB 3 5403 Cytarabine-binding aptamer

MDFECQFVCYLKELAPVPALLIRTQTTMSEDSSLRYAGKSDIGQLLAGQGKSPSGPPFARYFGMSAGTFEVEFGTPVEGGVEGSGRVVTGLTPSGKAASSLYIGPVGEIEAVYDALMKWVDDNGFDLSGEAYRILLDTPAETAPDQLRTRVSLMLHESLEHHHHHH (SEQ ID NO:47)

D31, S32, R35, Y36, K39, S40, G43, T75, V106, R133, L135, T138

```
Wildtype      1 MDFECQFVCELKELAPVPALLIRTQTTMSELGSLFEAGYHDILQLLAGQG     50
                |||||||||.||||||||||||||||||||..||..||..||.|||||||
Variant       1 MDFECQFVCYLKELAPVPALLIRTQTTMSEDSSLRYAGKSDIGQLLAGQG     50

Wildtype     51 KSPSGPPFARYFGMSAGTFEVEFGPPVEGGVEGSGRVVTGLTPSGKAASS    100
                ||||||||||||||||||||||||.|||||||||||||||||||||||||
Variant      51 KSPSGPPFARYFGMSAGTFEVEFGTPVEGGVEGSGRVVTGLTPSGKAASS    100

Wildtype    101 LYIGPYGEIEAVYDALMKWVDDNGFDLSGEAYEIYLDNPAETAPDQLRTR    150
                |||||.||||||||||||||||||||||||||.|.||.||||||||||||
Variant     101 LYIGPVGEIEAVYDALMKWVDDNGFDLSGEAYRILLDTPAETAPDQLRTR    150

Wildtype    151 VSLMLHESLEHHHHHH    166
                ||||||||||||||||
Variant     151 VSLMLHESLEHHHHHH    166
```

CTR107 CY5 1 5403 Cy5-binding aptamer

MDFECQFVCELKELAPVPALLIRTQTTMSEGVSLDCAGRVDIMQLLAGQGKSPSGPPFARYFGMSAGTFEVEFGYPVEGGVEGSGRVVTGLTPSGKAASSLYIGPVGEIEAVYDALMKWVDDNGFDLSGEAYSIALDHPAETAPDQLRTRVSLMLHESLEHHHHHH (SEQ ID NO:48)

G31, V32, D35, C36, R39, V40, M43, Y75, V106, S133, A135, H138

```
Wildtype      1 MDFECQFVCELKELAPVPALLIRTQTTMSELGSLFEAGYHDILQLLAGQG     50
                ||||||||||||||||||||||||||||||..||..||..||:|||||||
Variant       1 MDFECQFVCELKELAPVPALLIRTQTTMSEGVSLDCAGRVDIMQLLAGQG     50

Wildtype     51 KSPSGPPFARYFGMSAGTFEVEFGPPVEGGVEGSGRVVTGLTPSGKAASS    100
                ||||||||||||||||||||||||:|||||||||||||||||||||||||
Variant      51 KSPSGPPFARYFGMSAGTFEVEFGYPVEGGVEGSGRVVTGLTPSGKAASS    100

Wildtype    101 LYIGPYGEIEAVYDALMKWVDDNGFDLSGEAYEIYLDNPAETAPDQLRTR    150
                |||||.||||||||||||||||||||||||||.|.||:||||||||||||
Variant     101 LYIGPVGEIEAVYDALMKWVDDNGFDLSGEAYSIALDHPAETAPDQLRTR    150

Wildtype    151 VSLMLHESLEHHHHHH    166
                ||||||||||||||||
Variant     151 VSLMLHESLEHHHHHH    166
```

FIG. 24E

CTR107 CY5 2 5403 Cy5-binding aptamer

MDFECQFVCELKELAPVPALLIRTQTTMSEGVSLDCAGRVDIMQLLAGQGKSPSGPPFA
RYFGMNAGTFEVEFGYPVEGGVEGSGRVVTGLTPSGKAASSLHIGPVGEIEAVYDALMK
WVDDNGFDLSGEAYSIALDHPAETAPDQLRTRVSLMLHESLEHHHHHH(SEQ ID
NO:49)

G31, V32, D35, C36, R39, V40, M43, N65, Y75, H102, V106, S133, A135, H138

```
wildtype          1 MDFECQFVCELKELAPVPALLIRTQTTMSELGSLFEAGYHDILQLLAGQG     50
                      ||||||||||||||||||||||||||||||..||..||..||:|||||||
variant           1 MDFECQFVCELKELAPVPALLIRTQTTMSEGVSLDCAGRVDIMQLLAGQG     50

wildtype         51 KSPSGPPFARYFGMSAGTFEVEFGFPVEGGVEGSGRVVTGLTPSGKAASS    100
                      ||||||||||||||:|||||||||:|||||||||||||||||||||||||
variant          51 KSPSGPPFARYFGMNAGTFEVEFGYPVEGGVEGSGRVVTGLTPSGKAASS    100

wildtype        101 LVIGPYGEIEAVYDALMKWVDDNGFDLSGEAYEIYLDNPAETAPDQLRTR    150
                      |:|||.||||||||||||||||||||||||||.|.||:||||||||||||
variant         101 LHIGPVGEIEAVYDALMKWVDDNGFDLSGEAYSIALDHPAETAPDQLRTR    150

wildtype        151 VSLMLHESLEHHHHHH    166
                      ||||||||||||||||
variant         151 VSLMLHESLEHHHHHH    166
```

CTR107 TO1 1 5403 Thiazole Orange-binding aptamer

MDFECQFVCELKELAPVPALLIRTQTTMSERRSLVLAGLLDIYQLLAGQGKSPSGPPFA
RYFGMSAGTFEVEFGIPVEGGVEGSGRVVTGLTPSGKAASSLYIGPIGEIEAVYDALMK
WVDDNGFDLSGEAYDIPLDVPAETAPDQLRTRVSLMLHESLEHHHHHH(SEQ ID
NO:50)

R31, R32, V35, L36, L39, L40, Y43, I75, I106, D133, P135, V138

```
Wildtype          1 MDFECQFVCELKELAPVPALLIRTQTTMSELGSLFEAGYHDILQLLAGQG     50
                      ||||||||||||||||||||||||||||||..||..||..||.|||||||
Variant           1 MDFECQFVCELKELAPVPALLIRTQTTMSERRSLVLAGLLDIYQLLAGQG     50

Wildtype         51 KSPSGPPFARYFGMSAGTFEVEFGFPVEGGVEGSGRVVTGLTPSGKAASS    100
                      ||||||||||||||||||||||||.|||||||||||||||||||||||||
Variant          51 KSPSGPPFARYFGMSAGTFEVEFGIPVEGGVEGSGRVVTGLTPSGKAASS    100

Wildtype        101 LYIGPYGEIEAVYDALMKWVDDNGFDLSGEAYEIYLDNPAETAPDQLRTR    150
                      |||||.||||||||||||||||||||||||||:|.||.||||||||||||
Variant         101 LYIGPIGEIEAVYDALMKWVDDNGFDLSGEAYDIPLDVPAETAPDQLRTR    150

Wildtype        151 VSLMLHESLEHHHHHH    166
                      ||||||||||||||||
Variant         151 VSLMLHESLEHHHHHH    166
```

FIG. 24F

CTR107 TO1 2 5403 Thiazole Orange-binding aptamer

MDFECQFVCELKELAPVPALLIRTQTTMSEYASLPAAGDPDICQLLAGQGKSPSGPPFA
RYFGMSAGTFEVEFGLPVEGGVEGSGRVVTGLTPSGKAASSLYIGPRGEIEAVYDALMK
WVDDNGFDLSGEAYWILLDRPAETAPDQLRTRVSLMLHESLEHHHHHH (SEQ ID
NO:51)

Y31, A32, P35, A36, D39, P40, C43, L75, R106, W133, L135, R138

```
wildtype     1 MDFECQFVCELKELAPVPALLIRTQTTMSELGSLFEAGYHDILQLLAGQG   50
                 ||||||||||||||||||||||||||||||..||..||..||.|||||||
variant      1 MDFECQFVCELKELAPVPALLIRTQTTMSEYASLPAAGDPDICQLLAGQG   50

wildtype    51 KSPSGPPFARYFGMSAGTFEVEFGFPVEGGVEGSGRVVTGLTPSGKAASS  100
                 ||||||||||||||||||||||||.|||||||||||||||||||||||||
variant     51 KSPSGPPFARYFGMSAGTFEVEFGLPVEGGVEGSGRVVTGLTPSGKAASS  100

wildtype   101 LYIGPYGEIEAVYDALMKWVDDNGFDLSGEAYEIYLDNPAETAPDQLRTR  150
                 |||||.||||||||||||||||||||||||||.|.||.||||||||||||
variant    101 LYIGPRGEIEAVYDALMKWVDDNGFDLSGEAYWILLDRPAETAPDQLRTR  150

wildtype   151 VSLMLHESLEHHHHHH   166
                 ||||||||||||||||
variant    151 VSLMLHESLEHHHHHH   166
```

LIN2189 CARB 4 5616 Cytarabine-binding aptamer

MGSHHHHHHTEKKIDFKKEEKKFYAPKRKPERIFVPEMNFLMVDGKGDRLGEEPQKAQQ
SLSAIAGTIKMSKMGETRLDGYSDFVVPPKEGFQWSEGKFDLKDRDAVLWTSILRQPDF
VTEEVLEWAKEVARKKKPDVDTSRVKLVRFEEGECVQMMHVGNFSEFVHTVAEMHQFME
TEGLRNDTGAIRKHHSIVLSSGGKANPEKMKTILRLPVS (SEQ ID NO:52)

```
wildtype           1 MGSHHHHHHTEKKIDFKKEEKKFYAPKRKPERIFVPEMNFLMVDGKGDPD     50
                     ||||||||||||||||||||||||||||||||||||||||||||||||..
variant            1 MGSHHHHHHTEKKIDFKKEEKKFYAPKRKPERIFVPEMNFLMVDGKGDRL     50

wildtype          51 GEEYQKAVQSLYAIAYTIKMSKMGETRLDGYSDFVVPPLEGFWWSEGKFD    100
                     |||.|||.|||.|||.||||||||||||||||||||||.|||.|||||||
variant           51 GEEPQKAQQSLSAIAGTIKMSKMGETRLDGYSDFVVPPKEGFQWSEGKFD    100

wildtype         101 LKDRDAWLWTSILRQPDFVTEEVLEWAKEVARKKKPDVDTSRVKLVRFEE    150
                     ||||||.|||||||||||||||||||||||||||||||||||||||||||
variant          101 LKDRDAVLWTSILRQPDFVTEEVLEWAKEVARKKKPDVDTSRVKLVRFEE    150

wildtype         151 GECVQMMHVGPFSEAVHTVAEMHQFMETEGLRNDTGAIRKHHLIYLSDPR    200
                     ||||||||||.|||.|||||||||||||||||||||||||||.|.||...
variant          151 GECVQMMHVGNFSEFVHTVAEMHQFMETEGLRNDTGAIRKHHSIVLSSGG    200

wildtype         201 KANPEKMKTILRLPVS    216
                     ||||||||||||||||
variant          201 KANPEKMKTILRLPVS    216
```

LIN2189 CARB 1 5616 Cytarabine-binding aptamer

MGSHHHHHHTEKKIDFKKEEKKFYAPKRKPERIFVPEMNFLIVDGKGDSMGEEHQKAAQ
SLSAIADTIKMSKMGETRLDGYSDFVVPPFEGFRWSEGKFDCKDRDALLWTSILRQPDF
VTEEVLEWAKEVARKKKPDVDTSRVKLVRFEEGECVQMMHVGLFSELVHTVAEMHQSME
TEGLRNDTGAIRKHHRIVLSD-MKANPEKMKTILRLPVS (SEQ ID NO:53)

I34, S41, M42, H46, A50, S54, D58, F81, R85, C93, L99, L153, L157, R185, V187, S190, M191

```
Wildtype           1 MGSHHHHHHTEKKIDFKKEEKKFYAPKRKPERIFVPEMNFLMVDGKGDPD     50
                     |||||||||||||||||||||||||||||||||||||||||.||||||..
Variant            1 MGSHHHHHHTEKKIDFKKEEKKFYAPKRKPERIFVPEMNFLIVDGKGDSM     50

Wildtype          51 GEEYQKAVQSLYAIAYTIKMSKMGETRLDGYSDFVVPPLEGFWWSEGKFD    100
                     |||.|||.|||.|||.||||||||||||||||||||||.|||.|||||||
Variant           51 GEEHQKAAQSLSAIADTIKMSKMGETRLDGYSDFVVPPFEGFRWSEGKFD    100

Wildtype         101 LKDRDAWLWTSILRQPDFVTEEVLEWAKEVARKKKPDVDTSRVKLVRFEE    150
                     .|||||.|||||||||||||||||||||||||||||||||||||||||||
Variant          101 CKDRDALLWTSILRQPDFVTEEVLEWAKEVARKKKPDVDTSRVKLVRFEE    150

Wildtype         151 GECVQMMHVGPFSEAVHTVAEMHQFMETEGLRNDTGAIRKHHLIYLSDPR    200
                     ||||||||||.|||.|||||||||.|||||||||||||||||.|.||| .
Variant          151 GECVQMMHVGLFSELVHTVAEMHQSMETEGLRNDTGAIRKHHRIVLSD-M    199

Wildtype         201 KANPEKMKTILRLPVS    216
                     ||||||||||||||||
Variant          200 KANPEKMKTILRLPVS    215
```

FIG. 24H

LIN2189 TO1 2 5403Thiazole Orange-binding aptamer

MGSHHHHHHTEKKIDFKKEEKKFYAPKRKPERIFVPEMNFLMVDGKGDLVGEEIQKAGQ
SLDAIACTIKMSKMGETRLDGYSDFVVPPREGFVWSEGKFDLKDRDAYLWTSILRQPDF
VTEEVLEWAKEVARKKKPDVDTSRVKLVRFEEGECVQMMHVGLFSEFVHTVAEMHQFME
TEGLRNDTGAIRKHHIISLSSHMKANPEKMKTILRLPVS (SEQ ID NO:54)

L41, V42, I46, G50, D54, C58, R81, V85, Y99, L153, F157, I185, S187, S190, H191, M192

```
Wildtype      1 MGSHHHHHHTEKKIDFKKEEKKFYAPKRKPERIFVPEMNFLMVDGKGDPD     50
                ||||||||||||||||||||||||||||||||||||||||||||||||..
Variant       1 MGSHHHHHHTEKKIDFKKEEKKFYAPKRKPERIFVPEMNFLMVDGKGDLV     50

Wildtype     51 GEEYQKAVQSLYAIAYTIKMSKMGETRLDGYSDFVVPPLESFWWSEGKFD    100
                |||.|||.|||.|||.||||||||||||||||||||||.|||.|||||||
Variant      51 GEEIQKAGQSLDAIACTIKMSKMGETRLDGYSDFVVPPREGFVWSEGKFD    100

Wildtype    101 LKDRDAWLWTSILRQPDFVTEEVLEWAKEVARKKKPDVDTSRVKLVRFEE    150
                ||||||:|||||||||||||||||||||||||||||||||||||||||||
Variant     101 LKDRDAYLWTSILRQPDFVTEEVLEWAKEVARKKKPDVDTSRVKLVRFEE    150

Wildtype    151 GECVQMMHVGFFSEAVHTVAEMHQFMETEGLRNDTGAIRKHHLIVLSDPR    200
                ||||||||||.|||.|||||||||||||||||||||||||||:|.||...
Variant     151 GECVQMMHVGLFSEFVHTVAEMHQFMETEGLRNDTGAIRKHHIISLSSHM    200

Wildtype    201 KANPEKMKTILRLPVS    216
                ||||||||||||||||
Variant     201 KANPEKMKTILRLPVS    216
```

FIG. 24I

LIN2189 TO1 1 5403 Thiazole Orange-binding aptamer

MGSHHHHHHTEKKIDFKKEEKKFYAPKRKPERIFVPEMNFLMVDGKGDLAGEEQQKAFQ
SLPAIAYTIKMSKMGETRLDGYSDFVVPPTEGFRWSEGKFDGKDRDAILWTSILRQPDF
VTEEVLEWAKEVARKKKPDVDTSRVKLVRFEEGECVQMMHVGLFSEFVHTVAEMHQFME
TEGLRNDTGAIRKHHFITLSFFCKANPEKMKTILRLPVS (SEQ ID NO:55)

L41, A42, Q46, F50, P54, T81, R85, G93, I99, L153, F157, F185, T187, F190, F191, C192

```
wildtype      1 MGSHHHHHHTEKKIDFKKEEKKFYAPKRKPERIFVPEMNFLMVDGKGDPD    50
                ||||||||||||||||||||||||||||||||||||||||||||||||..
variant       1 MGSHHHHHHTEKKIDFKKEEKKFYAPKRKPERIFVPEMNFLMVDGKGDLA    50

wildtype     51 GEEYQKAVQSLYAIAYTIKMSKMGETRLDGYSDFVVPPLEGFWWSEGKFD   100
                |||.|||.|||.||||||||||||||||||||||||||.|||.|||||||
variant      51 GEEQQKAFQSLPAIAYTIKMSKMGETRLDGYSDFVVPPTEGFRWSEGKFD   100

wildtype    101 LKDRDAWLWTSILRQPDFVTEEVLEWAKEVARKKKPDVDTSRVKLVRFEE   150
                .||||.||||||||||||||||||||||||||||||||||||||||||||
variant     101 GKDRDAILWTSILRQPDFVTEEVLEWAKEVARKKKPDVDTSRVKLVRFEE   150

wildtype    151 GECVQMMHVGFFSEAVHTVAEMHQFMETEGLRNDTGAIRKHHLIVLSDFR   200
                ||||||||||.|||.|||||||||||||||||||||||||||.|.||...
variant     151 GECVQMMHVGLFSEFVHTVAEMHQFMETEGLRNDTGAIRKHHFITLSFFC   200

wildtype    201 KANPEKMKTILRLPVS    216
                ||||||||||||||||
variant     201 KANPEKMKTILRLPVS    216
```

FIG. 24J

LIN2189 CY5 5 5403 CY5-binding aptamer

MGSHHHHHHTEKKIDFKKEEKKFYAPKRKPERIFVPEMNFLMVDGKGDFCGEESQKAWQ
SLEAIAYTIKMSKMGETRLDGYSDFVVPPTEGFRWSEGKFDPKDRDAILWTSILRQPDF
VTEEVLEWAKEVARKKKPDVDTSRVKLVRFEEGECVQMMHVGHFSEGVHTVAEMHQFME
TEGLRNDTGAIRKHHFILLSNFG**KANPEKMKTILRLPVS (SEQ ID NO:56)

F41, C42, S46, W50, E54, T81, R85, P93, I99, H153, G157, F185, L187, N190, F191, G192

```
wildtype    1 MGSHHHHHHTEKKIDFKKEEKKFYAPKRKPERIFVPEMNFLMVDGKGDFD    50
              ||||||||||||||||||||||||||||||||||||||||||||||||..
variant     1 MGSHHHHHHTEKKIDFKKEEKKFYAPKRKPERIFVPEMNFLMVDGKGDFC    50

wildtype   51 GEEYQKAVQSLYAIAYTIKMSKMGETRLDGYSDFVVPPLEGFWWSEGKFD   100
              |||.|||.|||.||||||||||||||||||.|||.|||||||||||||||
variant    51 GEESQKAWQSLEAIAYTIKMSKMGETRLDGYSDFVVPPTEGFRWSEGKFD   100

wildtype  101 LKDRDAWLWTSILRQPDFVTEEVLEWAKEVARKKKPDVDTSRVKLVRFEE   150
              .|||||.|||||||||||||||||||||||||||||||||||||||||||
variant   101 PKDRDAILWTSILRQPDFVTEEVLEWAKEVARKKKPDVDTSRVKLVRFEE   150

wildtype  151 GECVQMMHVGPFSEAVHTVAEMHQFMETEGLRNDTGAIRKHHLIYLSDFR   200
              ||||||||||.|||.||||||||||||||||||||||||||.|.||:..
variant   151 GECVQMMHVGHFSEGVHTVAEMHQFMETEGLRNDTGAIRKHHFILLSNFG   200

wildtype  201 KANPEKMKTILRLPVS   216
              ||||||||||||||||
variant   201 KANPEKMKTILRLPVS   216
```

FIG. 24K

Spike protein LIN2189 3 5403

MGSHHHHHHTEKKIDFKKEEKKFYAPKRKPERIFVPEMNFLMVDGKGDPDGEEYQKAVQ
SLSAIAYTIKMSKMGETRLDGYSDFVVPPSEGFMWSEGKFDAKDRDASLWTSILRQPDF
VTEEVLEWAKEVARKKKPDVDTSRVKLVRFEEGECVQMMHVGPFSEYVHTVAEMHQFME
TEGLRNDTGAIRKHHHISLSCSKKANPEKMKTILRLPVS(SEQ ID NO:57)

S54, S81, M85, A93, S99, Y157, H185, S187, C190, S191, K192

```
wildtype          1 MGSHHHHHHTEKKIDFKKEEKKFYAPKRKPERIFVPEMNFLMVDGKGDPD     50
                      ||||||||||||||||||||||||||||||||||||||||||||||||||
variant           1 MGSHHHHHHTEKKIDFKKEEKKFYAPKRKPERIFVPEMNFLMVDGKGDPD     50

wildtype         51 GEEYQKAVQSLYAIAYTIKMSKMGETRLDGYSDFVVPPLEGFWWSEGKFD    100
                      |||||||||||.||||||||||||||||||||||||||.|||.|||||||
variant          51 GEEYQKAVQSLSAIAYTIKMSKMGETRLDGYSDFVVPPSEGFMWSEGKFD    100

wildtype        101 LKDRDAWLWTSILRQPDFVTEEVLEWAKEVARKKKPDVDTSRVKLVRFEE    150
                    .|||||.|||||||||||||||||||||||||||||||||||||||||||
variant         101 AKDRDASLWTSILRQPDFVTEEVLEWAKEVARKKKPDVDTSRVKLVRFEE    150

wildtype        151 GECVQMMHVGPFSEAVHTVAEMHQFMETEGLRNDTGAIRKHHLIYLSDPK    200
                    ||||||||||||||.|||||||||||||||||||||||||||.|.||..:
variant         151 GECVQMMHVGPFSEYVHTVAEMHQFMETEGLRNDTGAIRKHHHISLSCSK    200

wildtype        201 KANPEKMKTILRLPVS    216
                    ||||||||||||||||
variant         201 KANPEKMKTILRLPVS    216
```

Spike protein SAV2435 1 5403

MEYQLQQLASLTLVGIKETYENGRQAVQHNNGFPQRCEQEGVIADLQLKNNGDLAGILG
LCIPELDGKMSYMIAVTGDNSADIAKYDVITLASSKYMVFEAQGATVKAVHQKHEEVHH
YIHQYQANTVKSAPFFVLYQDGDGTSEKYITEIWMPVKGLEHHHHHH(SEQ ID
NO:58)

V27, N30, N31, P34, E38, T105, V106, H110, H113, V135, G142

```
wildtype          1 MEYQLQQLASLTLVGIKETYENGRQAQQHIAGFWQRCVQEGVIADLQLKN     50
                    ||||||||||||||||||||||||||.||..||.|||.||||||||||||
variant           1 MEYQLQQLASLTLVGIKETYENGRQAVQHNNGFPQRCEQEGVIADLQLKN     50

wildtype         51 NGDLAGILGLCIPELDGKMSYMIAVTGDNSADIAKYDVITLASSKYMVFE    100
                    ||||||||||||||||||||||||||||||||||||||||||||||||||
variant          51 NGDLAGILGLCIPELDGKMSYMIAVTGDNSADIAKYDVITLASSKYMVFE    100

wildtype        101 AQGAVPKAVQQKMEEVHHYIHQYQANTVKSAPFFELYQDGDTTSEKYITE    150
                    ||||..|||.||.|||||||||||||||||||||.||||||.||||||||
variant         101 AQGATVKAVHQKHEEVHHYIHQYQANTVKSAPFFVLYQDGDGTSEKYITE    150

wildtype        151 IWMPVKGLEHHHHHH    165
                    |||||||||||||||
variant         151 IWMPVKGLEHHHHHH    165
```

FIG. 24L

Spike protein SAV2435 3 5403

MEYQLQQLASLTLVGIKETYENGRQANQHTTGFNQRCHQEGVIADLQLKNNGDLAGILG
LCIPELDGKMSYMIAVTGDNSADIAKYDVITLASSKYMVFEAQGATCKASTQKGEEVHH
YIHQYQANTVKSAPFFALFQDGDVTSEKYITEIWMPVKGLEHHHHHH(SEQ ID
NO:59)

N27, T30, T31, N34, H38, T105, C106, S109, T110, G113, A135, F137, V142

```
wildtype           1 MEYQLQQLASLTLVGIKETYENGRQAQQHIAGFWQRCYQEGVIADLQLKN     50
                     ||||||||||||||||||||||||||.||..||.|||:||||||||||||
variant            1 MEYQLQQLASLTLVGIKETYENGRQANQHTTGFNQRCHQEGVIADLQLKN     50

wildtype          51 NGDLAGILGLCIPELDGKMSYMIAVTGDNSADIAKYDVITLASSKYMVFE    100
                     ||||||||||||||||||||||||||||||||||||||||||||||||||
variant           51 NGDLAGILGLCIPELDGKMSYMIAVTGDNSADIAKYDVITLASSKYMVFE    100

wildtype         101 AQGAVFKAVQQKMEEVHHYIHQYQANTVKSAPFFELVQDGDTTSEKYITE    150
                     ||||..||..||.|||||||||||||||||||||.|:||||.||||||||
variant          101 AQGATCKASTQKGEEVHHYIHQYQANTVKSAPFFALFQDGDVTSEKYITE    150

wildtype         151 IWMPVKGLEHHHHHH    165
                     |||||||||||||||
variant          151 IWMPVKGLEHHHHHH    165
```

FIG. 24M

SEQUENCE LISTING

<160> NUMBER OF SEQ ID NOS: 59

<210> SEQ ID NO 1
<211> LENGTH: 495
<212> TYPE: DNA
<213> ORGANISM: Escherichia coli

<400> SEQUENCE: 1
atggagtacc agctgcagca actggcgagc ctgaccctgg tgggtatcaa ggagacctat 60
gaaaacggcc gtcaagcgca gcaacacatc gcgggtttct ggcagcgttg ctaccaagag 120
ggcgttattg cggacctgca gctgaagaac aacggtgatc tggcgggtat cctgggcctg 180
tgcattccgg aactggacgg taaaatgagc tatatgatcg cggtgaccgg cgacaacagc 240
gcggacatcg cgaagtacga tgtgattacc ctggcgagca gcaaatatat ggtttttgaa 300
gcgcaaggtg cggtgccgaa ggcggttcag caaaaaatgg aggaagtgca ccactacatt 360
caccagtatc aagcgaacac cgttaaaagc gcgccgttct ttgagctgta ccaagacggt 420
gataccacca gcgagaagta tatcaccgaa atttggatgc cggttaaagg cctggaacac 480
caccaccacc accac 495

<210> SEQ ID NO 2
<211> LENGTH: 165
<212> TYPE: PRT
<213> ORGANISM: Escherichia coli

<400> SEQUENCE: 2

Met Glu Tyr Gln Leu Gln Gln Leu Ala Ser Leu Thr Leu Val Gly Ile
1 5 10 15

Lys Glu Thr Tyr Glu Asn Gly Arg Gln Ala Gln Gln His Ile Ala Gly
20 25 30

```
Phe Trp Gln Arg Cys Tyr Gln Glu Gly Val Ile Ala Asp Leu Gln Leu
        35                  40                  45

Lys Asn Asn Gly Asp Leu Ala Gly Ile Leu Gly Leu Cys Ile Pro Glu
    50                  55                  60

Leu Asp Gly Lys Met Ser Tyr Met Ile Ala Val Thr Gly Asp Asn Ser
65                  70                  75                  80

Ala Asp Ile Ala Lys Tyr Asp Val Ile Thr Leu Ala Ser Ser Lys Tyr
                85                  90                  95

Met Val Phe Glu Ala Gln Gly Ala Val Pro Lys Ala Val Gln Gln Lys
            100                 105                 110

Met Glu Glu Val His His Tyr Ile His Gln Tyr Gln Ala Asn Thr Val
        115                 120                 125

Lys Ser Ala Pro Phe Phe Glu Leu Tyr Gln Asp Gly Asp Thr Thr Ser
    130                 135                 140

Glu Lys Tyr Ile Thr Glu Ile Trp Met Pro Val Lys Gly Leu Glu His
145                 150                 155                 160

His His His His His
                165


<210> SEQ ID NO 3
<211> LENGTH: 498
<212> TYPE: DNA
<213> ORGANISM: Escherichia coli

<400> SEQUENCE: 3

atggacttcg agtgccagtt tgtgtgcgag ctgaaggaac tggcgccggt tccggcgctg      60

ctgatccgta cccaaaccac catgagcgag ctgggtagcc tgttcgaagc gggctaccac     120

gatattctgc agctgctggc gggtcagggt aagagcccga gcggtccgcc gtttgcgcgt     180

tattttggta tgagcgcggg cacctttgag gtggagttcg gctttccggt ggagggtggc     240

gttgaaggta gcggccgtgt ggttaccggt ctgaccccga gcggcaaggc ggcgagcagc     300

ctgtacatcg gtccgtatgg cgagattgaa gcggtgtacg acgcgctgat gaaatgggtt     360

gacgataacg gtttcgatct gagcggcgag gcgtacgaaa tctatctgga caacccggcg     420

gaaaccgcgc cggatcagct gcgtacccgt gttagcctga tgctgcacga gagcctggaa     480

caccaccacc accaccac                                                   498


<210> SEQ ID NO 4
<211> LENGTH: 166
<212> TYPE: PRT
<213> ORGANISM: Escherichia coli

<400> SEQUENCE: 4

Met Asp Phe Glu Cys Gln Phe Val Cys Glu Leu Lys Glu Leu Ala Pro
1               5                   10                  15

Val Pro Ala Leu Leu Ile Arg Thr Gln Thr Thr Met Ser Glu Leu Gly
            20                  25                  30

Ser Leu Phe Glu Ala Gly Tyr His Asp Ile Leu Gln Leu Leu Ala Gly
        35                  40                  45

Gln Gly Lys Ser Pro Ser Gly Pro Pro Phe Ala Arg Tyr Phe Gly Met
    50                  55                  60

Ser Ala Gly Thr Phe Glu Val Glu Phe Gly Phe Pro Val Glu Gly Gly
65                  70                  75                  80

Val Glu Gly Ser Gly Arg Val Val Thr Gly Leu Thr Pro Ser Gly Lys
                85                  90                  95
```

-continued

```
Ala Ala Ser Ser Leu Tyr Ile Gly Pro Tyr Gly Glu Ile Glu Ala Val
            100                 105                 110

Tyr Asp Ala Leu Met Lys Trp Val Asp Asp Asn Gly Phe Asp Leu Ser
        115                 120                 125

Gly Glu Ala Tyr Glu Ile Tyr Leu Asp Asn Pro Ala Glu Thr Ala Pro
    130                 135                 140

Asp Gln Leu Arg Thr Arg Val Ser Leu Met Leu His Glu Ser Leu Glu
145                 150                 155                 160

His His His His His His
                165


<210> SEQ ID NO 5
<211> LENGTH: 648
<212> TYPE: DNA
<213> ORGANISM: Escherichia coli

<400> SEQUENCE: 5

atgggtagcc accaccacca ccaccacacc gagaagaaaa tcgacttcaa gaaagaggaa      60

aagaaatttt acgcgccgaa gcgtaagccg gagcgtattt tcgtgccgga aatgaacttt     120

ctgatggttg atggtaaagg cgacccggat ggcgaggaat accagaaggc ggtgcaaagc     180

ctgtacgcga tcgcgtatac cattaaaatg agcaagatgg gtgaaacccg tctggacggc     240

tatagcgatt tcgtggttcc gccgctggag ggtttctggt ggagcgaagg caaatttgac     300

ctgaaggacc gtgatgcgtg gctgtggacc agcatcctgc gtcagccgga tttcgtgacc     360

gaggaagttc tggagtgggc gaaagaagtg gcgcgtaaga aaaagccgga cgttgatacc     420

agccgtgtga agctggttcg ttttgaggaa ggtgaatgcg tgcagatgat gcacgttggc     480

ccgttcagcg aggaggtgca caccgttgcg gaaatgcacc aatttatgga gaccgaaggt     540

ctgcgtaacg acaccggcgc gatccgtaaa caccacgaga tttatctgag cgatccgcgt     600

aaggcgaacc cggaaaaaat gaagaccatt ctgcgtctgc cggttagc                  648


<210> SEQ ID NO 6
<211> LENGTH: 216
<212> TYPE: PRT
<213> ORGANISM: Escherichia coli

<400> SEQUENCE: 6

Met Gly Ser His His His His His His Thr Glu Lys Lys Ile Asp Phe
1               5                   10                  15

Lys Lys Glu Glu Lys Lys Phe Tyr Ala Pro Lys Arg Lys Pro Glu Arg
            20                  25                  30

Ile Phe Val Pro Glu Met Asn Phe Leu Met Val Asp Gly Lys Gly Asp
        35                  40                  45

Pro Asp Gly Glu Glu Tyr Gln Lys Ala Val Gln Ser Leu Tyr Ala Ile
    50                  55                  60

Ala Tyr Thr Ile Lys Met Ser Lys Met Gly Glu Thr Arg Leu Asp Gly
65                  70                  75                  80

Tyr Ser Asp Phe Val Val Pro Pro Leu Glu Gly Phe Trp Trp Ser Glu
                85                  90                  95

Gly Lys Phe Asp Leu Lys Asp Arg Asp Ala Trp Leu Trp Thr Ser Ile
            100                 105                 110

Leu Arg Gln Pro Asp Phe Val Thr Glu Glu Val Leu Glu Trp Ala Lys
        115                 120                 125

Glu Val Ala Arg Lys Lys Lys Pro Asp Val Asp Thr Ser Arg Val Lys
```

130 135 140

Leu Val Arg Phe Glu Glu Gly Glu Cys Val Gln Met Met His Val Gly
145 150 155 160

Pro Phe Ser Glu Glu Val His Thr Val Ala Glu Met His Gln Phe Met
165 170 175

Glu Thr Glu Gly Leu Arg Asn Asp Thr Gly Ala Ile Arg Lys His His
180 185 190

Glu Ile Tyr Leu Ser Asp Pro Arg Lys Ala Asn Pro Glu Lys Met Lys
195 200 205

Thr Ile Leu Arg Leu Pro Val Ser
210 215

<210> SEQ ID NO 7
<211> LENGTH: 495
<212> TYPE: DNA
<213> ORGANISM: Escherichia coli

<400> SEQUENCE: 7
atggagtacc agctgcagca actggcgagc ctgaccctgg tgggtatcaa ggagacctat 60
gaaaacggcc gtcaagcgtg gcaacacatc gcgggtttct ggcagcgttg ctaccaagag 120
ggcgttattg cggacctgca gctgaagaac aacggtgatc tggcgggtat cctgggcctg 180
tgcattccgg aactggacgg taaaatgagc tatatgatcg cggtgaccgg cgacaacagc 240
gcggacatcg cgaagtacga tgtgattacc ctggcgagca gcaaatatat ggtttttgaa 300
gcgcaaggtg cggtgccgaa ggcggttcag caaaaaatgg aggaagtgca ccactacatt 360
caccagtatc aagcgaacac cgttaaaagc gcgccgttct ttgagctgta ccaagacggt 420
gataccacca gcgagaagta tatcaccgaa atttggatgc cggttaaagg cctggaacac 480
caccaccacc accac 495

<210> SEQ ID NO 8
<211> LENGTH: 165
<212> TYPE: PRT
<213> ORGANISM: Escherichia coli

<400> SEQUENCE: 8

Met Glu Tyr Gln Leu Gln Gln Leu Ala Ser Leu Thr Leu Val Gly Ile
1 5 10 15

Lys Glu Thr Tyr Glu Asn Gly Arg Gln Ala Trp Gln His Ile Ala Gly
20 25 30

Phe Trp Gln Arg Cys Tyr Gln Glu Gly Val Ile Ala Asp Leu Gln Leu
35 40 45

Lys Asn Asn Gly Asp Leu Ala Gly Ile Leu Gly Leu Cys Ile Pro Glu
50 55 60

Leu Asp Gly Lys Met Ser Tyr Met Ile Ala Val Thr Gly Asp Asn Ser
65 70 75 80

Ala Asp Ile Ala Lys Tyr Asp Val Ile Thr Leu Ala Ser Ser Lys Tyr
85 90 95

Met Val Phe Glu Ala Gln Gly Ala Val Pro Lys Ala Val Gln Gln Lys
100 105 110

Met Glu Glu Val His His Tyr Ile His Gln Tyr Gln Ala Asn Thr Val
115 120 125

Lys Ser Ala Pro Phe Phe Glu Leu Tyr Gln Asp Gly Asp Thr Thr Ser
130 135 140

Glu Lys Tyr Ile Thr Glu Ile Trp Met Pro Val Lys Gly Leu Glu His

-continued 145 150 155 160

His His His His His
165

<210> SEQ ID NO 9
<211> LENGTH: 495
<212> TYPE: DNA
<213> ORGANISM: Escherichia coli

<400> SEQUENCE: 9
atggagtacc agctgcagca actggcgagc ctgaccctgg tgggtatcaa ggagacctat 60
gaaaacggcc gtcaagcgca gcaacacatc gcgggtttct ggcagcgttg ctaccaagag 120
ggcgttattg cggacctgca gctgaagaac aacggtgatc tggcgggtat cctgggcctg 180
tgcattccgg aactggacgg taaaatgagc tatatgatcg cggtgaccgg cgacaacagc 240
gcggacatcg cgaagtacga tgtgattacc ctggcgagca gcaaatatat ggtttttgaa 300
gcgcaaggtg cgtggccgaa ggcggttcag caaaaaatgg aggaagtgca ccactacatt 360
caccagtatc aagcgaacac cgttaaaagc gcgccgttct ttgagctgta ccaagacggt 420
gataccacca gcgagaagta tatcaccgaa atttggatgc cggttaaagg cctggaacac 480
caccaccacc accac 495

<210> SEQ ID NO 10
<211> LENGTH: 165
<212> TYPE: PRT
<213> ORGANISM: Escherichia coli

<400> SEQUENCE: 10

Met Glu Tyr Gln Leu Gln Gln Leu Ala Ser Leu Thr Leu Val Gly Ile
1 5 10 15

Lys Glu Thr Tyr Glu Asn Gly Arg Gln Ala Gln Gln His Ile Ala Gly
20 25 30

Phe Trp Gln Arg Cys Tyr Gln Glu Gly Val Ile Ala Asp Leu Gln Leu
35 40 45

Lys Asn Asn Gly Asp Leu Ala Gly Ile Leu Gly Leu Cys Ile Pro Glu
50 55 60

Leu Asp Gly Lys Met Ser Tyr Met Ile Ala Val Thr Gly Asp Asn Ser
65 70 75 80

Ala Asp Ile Ala Lys Tyr Asp Val Ile Thr Leu Ala Ser Ser Lys Tyr
85 90 95

Met Val Phe Glu Ala Gln Gly Ala Trp Pro Lys Ala Val Gln Gln Lys
100 105 110

Met Glu Glu Val His His Tyr Ile His Gln Tyr Gln Ala Asn Thr Val
115 120 125

Lys Ser Ala Pro Phe Phe Glu Leu Tyr Gln Asp Gly Asp Thr Thr Ser
130 135 140

Glu Lys Tyr Ile Thr Glu Ile Trp Met Pro Val Lys Gly Leu Glu His
145 150 155 160

His His His His His
165

<210> SEQ ID NO 11
<211> LENGTH: 495
<212> TYPE: DNA
<213> ORGANISM: Escherichia coli

<400> SEQUENCE: 11
atggagtacc agctgcagca actggcgagc ctgaccctgg tgggtatcaa ggagacctat 60
gaaaacggcc gtcaagcgca gcaacacatc gcgggtttct ggcagcgttg ctaccaagag 120
ggcgttattg cggacctgca gctgaagaac aacggtgatc tggcgggtat cctgggcctg 180
tgcattccgg aactggacgg taaaatgagc tatatgatcg cggtgaccgg cgacaacagc 240
gcggacatcg cgaagtacga tgtgattacc ctggcgagca gcaaatatat ggtttttgaa 300
gcgcaaggtg cggtgtggaa ggcggttcag caaaaaatgg aggaagtgca ccactacatt 360
caccagtatc aagcgaacac cgttaaaagc gcgccgttct ttgagctgta ccaagacggt 420
gataccacca gcgagaagta tatcaccgaa atttggatgc cggttaaagg cctggaacac 480
caccaccacc accac 495

<210> SEQ ID NO 12
<211> LENGTH: 165
<212> TYPE: PRT
<213> ORGANISM: Escherichia coli

<400> SEQUENCE: 12

Met Glu Tyr Gln Leu Gln Gln Leu Ala Ser Leu Thr Leu Val Gly Ile
1 5 10 15

Lys Glu Thr Tyr Glu Asn Gly Arg Gln Ala Gln Gln His Ile Ala Gly
20 25 30

Phe Trp Gln Arg Cys Tyr Gln Glu Gly Val Ile Ala Asp Leu Gln Leu
35 40 45

Lys Asn Asn Gly Asp Leu Ala Gly Ile Leu Gly Leu Cys Ile Pro Glu
50 55 60

Leu Asp Gly Lys Met Ser Tyr Met Ile Ala Val Thr Gly Asp Asn Ser
65 70 75 80

Ala Asp Ile Ala Lys Tyr Asp Val Ile Thr Leu Ala Ser Ser Lys Tyr
85 90 95

Met Val Phe Glu Ala Gln Gly Ala Val Trp Lys Ala Val Gln Gln Lys
100 105 110

Met Glu Glu Val His His Tyr Ile His Gln Tyr Gln Ala Asn Thr Val
115 120 125

Lys Ser Ala Pro Phe Phe Glu Leu Tyr Gln Asp Gly Asp Thr Thr Ser
130 135 140

Glu Lys Tyr Ile Thr Glu Ile Trp Met Pro Val Lys Gly Leu Glu His
145 150 155 160

His His His His His
165

<210> SEQ ID NO 13
<211> LENGTH: 495
<212> TYPE: DNA
<213> ORGANISM: Escherichia coli

<400> SEQUENCE: 13
atggagtacc agctgcagca actggcgagc ctgaccctgg tgggtatcaa ggagacctat 60
gaaaacggcc gtcaagcgca gcaacacatc gcgggtttct ggcagcgttg ctaccaagag 120
ggcgttattg cggacctgca gctgaagaac aacggtgatc tggcgggtat cctgggcctg 180
tgcattccgg aactggacgg taaaatgagc tatatgatcg cggtgaccgg cgacaacagc 240
gcggacatcg cgaagtacga tgtgattacc ctggcgagca gcaaatatat ggtttttgaa 300
gcgcaaggtg cgtggccgaa ggcggttcag caaaaaatgg aggaagtgca ccactacatt 360
caccagtatc aagcgaacac cgttaaaagc gcgccgttct ttcagctgta ccaagacggt 420
gataccacca gcgagaagta tatcaccgaa atttggatgc cggttaaagg cctggaacac 480
caccaccacc accac 495

<210> SEQ ID NO 14
<211> LENGTH: 165
<212> TYPE: PRT
<213> ORGANISM: Escherichia coli

<400> SEQUENCE: 14

Met Glu Tyr Gln Leu Gln Gln Leu Ala Ser Leu Thr Leu Val Gly Ile
1 5 10 15

Lys Glu Thr Tyr Glu Asn Gly Arg Gln Ala Gln Gln His Ile Ala Gly
20 25 30

Phe Trp Gln Arg Cys Tyr Gln Glu Gly Val Ile Ala Asp Leu Gln Leu
35 40 45

Lys Asn Asn Gly Asp Leu Ala Gly Ile Leu Gly Leu Cys Ile Pro Glu
50 55 60

Leu Asp Gly Lys Met Ser Tyr Met Ile Ala Val Thr Gly Asp Asn Ser
65 70 75 80

Ala Asp Ile Ala Lys Tyr Asp Val Ile Thr Leu Ala Ser Ser Lys Tyr
85 90 95

Met Val Phe Glu Ala Gln Gly Ala Trp Pro Lys Ala Val Gln Gln Lys
100 105 110

Met Glu Glu Val His His Tyr Ile His Gln Tyr Gln Ala Asn Thr Val
115 120 125

Lys Ser Ala Pro Phe Phe Gln Leu Tyr Gln Asp Gly Asp Thr Thr Ser
130 135 140

Glu Lys Tyr Ile Thr Glu Ile Trp Met Pro Val Lys Gly Leu Glu His
145 150 155 160

His His His His His
165

<210> SEQ ID NO 15
<211> LENGTH: 495
<212> TYPE: DNA
<213> ORGANISM: Escherichia coli

<400> SEQUENCE: 15
atggagtacc agctgcagca actggcgagc ctgaccctgg tgggtatcaa ggagacctat 60
gaaaacggcc gtcaagcgca gcaacacatc gcgggtttct ggcagcgttg ctaccaagag 120
ggcgttattg cggacctgca gctgaagaac aacggtgatc tggcgggtat cctgggcctg 180
tgcattccgg aactggacgg taaaatgagc tatatgatcg cggtgaccgg cgacaacagc 240
gcggacatcg cgaagtacga tgtgattacc ctggcgagca gcaaatatat ggtttttgaa 300
gcgcaaggtg cgtggccgaa ggcggttcag caaaaaatgg aggaagtgca ccactacatt 360
caccagtatc aagcgaacac cgttaaaagc gcgccgttct ttgagctgtg gcaagacggt 420
gataccacca gcgagaagta tatcaccgaa atttggatgc cggttaaagg cctggaacac 480
caccaccacc accac 495

<210> SEQ ID NO 16
<211> LENGTH: 165
<212> TYPE: PRT
<213> ORGANISM: Escherichia coli

<400> SEQUENCE: 16

```
Met Glu Tyr Gln Leu Gln Gln Leu Ala Ser Leu Thr Leu Val Gly Ile
1               5                   10                  15

Lys Glu Thr Tyr Glu Asn Gly Arg Gln Ala Gln Gln His Ile Ala Gly
            20                  25                  30

Phe Trp Gln Arg Cys Tyr Gln Glu Gly Val Ile Ala Asp Leu Gln Leu
        35                  40                  45

Lys Asn Asn Gly Asp Leu Ala Gly Ile Leu Gly Leu Cys Ile Pro Glu
    50                  55                  60

Leu Asp Gly Lys Met Ser Tyr Met Ile Ala Val Thr Gly Asp Asn Ser
65                  70                  75                  80

Ala Asp Ile Ala Lys Tyr Asp Val Ile Thr Leu Ala Ser Ser Lys Tyr
                85                  90                  95

Met Val Phe Glu Ala Gln Gly Ala Trp Pro Lys Ala Val Gln Gln Lys
            100                 105                 110

Met Glu Glu Val His His Tyr Ile His Gln Tyr Gln Ala Asn Thr Val
        115                 120                 125

Lys Ser Ala Pro Phe Phe Glu Leu Trp Gln Asp Gly Asp Thr Thr Ser
    130                 135                 140

Glu Lys Tyr Ile Thr Glu Ile Trp Met Pro Val Lys Gly Leu Glu His
145                 150                 155                 160

His His His His His
                165
```

<210> SEQ ID NO 17
<211> LENGTH: 498
<212> TYPE: DNA
<213> ORGANISM: Escherichia coli

<400> SEQUENCE: 17

```
atggacttcg agtgccagtt tgtgtgcgag ctgaaggaac tggcgccggt tccggcgctg     60

ctgatccgta cccaaaccac catgagcgag ctgggtagcc tgttcagagc gggctaccac    120

gatattctgc agctgctggc gggtcagggt aagagcccga gcggtccgcc gtttgcgcgt    180

tattttggta tgagcgcggg cacctttgag gtggagttcg gctttccggt ggagggtggc    240

gttgaaggta gcggccgtgt ggttaccggt ctgaccccga gcggcaaggc ggcgagcagc    300

ctgtacatcg gtccgtatgg cgagattgaa gcggtgtacg acgcgctgat gaaatgggtt    360

gacgataacg gtttcgatct gagcggcgag gcgtacgaaa tctatctgga caacccggcg    420

gaaaccgcgc cggatcagct gcgtacccgt gttagcctga tgctgcacga gagcctggaa    480

caccaccacc accaccac                                                  498
```

<210> SEQ ID NO 18
<211> LENGTH: 166
<212> TYPE: PRT
<213> ORGANISM: Escherichia coli

<400> SEQUENCE: 18

```
Met Asp Phe Glu Cys Gln Phe Val Cys Glu Leu Lys Glu Leu Ala Pro
1               5                   10                  15

Val Pro Ala Leu Leu Ile Arg Thr Gln Thr Thr Met Ser Glu Leu Gly
            20                  25                  30

Ser Leu Phe Arg Ala Gly Tyr His Asp Ile Leu Gln Leu Leu Ala Gly
        35                  40                  45
```

-continued

```
Gln Gly Lys Ser Pro Ser Gly Pro Pro Phe Ala Arg Tyr Phe Gly Met
    50                  55                  60

Ser Ala Gly Thr Phe Glu Val Glu Phe Gly Phe Pro Val Glu Gly Gly
65                  70                  75                  80

Val Glu Gly Ser Gly Arg Val Val Thr Gly Leu Thr Pro Ser Gly Lys
                85                  90                  95

Ala Ala Ser Ser Leu Tyr Ile Gly Pro Tyr Gly Glu Ile Glu Ala Val
            100                 105                 110

Tyr Asp Ala Leu Met Lys Trp Val Asp Asp Asn Gly Phe Asp Leu Ser
        115                 120                 125

Gly Glu Ala Tyr Glu Ile Tyr Leu Asp Asn Pro Ala Glu Thr Ala Pro
    130                 135                 140

Asp Gln Leu Arg Thr Arg Val Ser Leu Met Leu His Glu Ser Leu Glu
145                 150                 155                 160

His His His His His His
                165
```

```
<210> SEQ ID NO 19
<211> LENGTH: 498
<212> TYPE: DNA
<213> ORGANISM: Escherichia coli

<400> SEQUENCE: 19

atggacttcg agtgccagtt tgtgtgcgag ctgaaggaac tggcgccggt tccggcgctg      60

ctgatccgta cccaaaccac catgagcgag ctgggtagcc tgttcgaagc gggctaccac     120

gatattctgc agctgctggc gggtcagggt aagagcccga gcggtccgcc gtttgcgcgt     180

tattttggta tgagcgcggg cacctttgag gtggagttcg gctttccggt ggagggtggc     240

gttgaaggta gcggccgtgt ggttaccggt ctgaccccga gcggcaaggc ggcgagcagc     300

ctgtacatcg gtccgtgggg cgagattgaa gcggtgtacg acgcgctgat gaaatgggtt     360

gacgataacg gtttcgatct gagcggcgag gcgtacgaaa tctatctgga caacccggcg     420

gaaaccgcgc cggatcagct gcgtacccgt gttagcctga tgctgcacga gagcctggaa     480

caccaccacc accaccac                                                   498


<210> SEQ ID NO 20
<211> LENGTH: 166
<212> TYPE: PRT
<213> ORGANISM: Escherichia coli

<400> SEQUENCE: 20

Met Asp Phe Glu Cys Gln Phe Val Cys Glu Leu Lys Glu Leu Ala Pro
1               5                   10                  15

Val Pro Ala Leu Leu Ile Arg Thr Gln Thr Thr Met Ser Glu Leu Gly
            20                  25                  30

Ser Leu Phe Glu Ala Gly Tyr His Asp Ile Leu Gln Leu Leu Ala Gly
        35                  40                  45

Gln Gly Lys Ser Pro Ser Gly Pro Pro Phe Ala Arg Tyr Phe Gly Met
    50                  55                  60

Ser Ala Gly Thr Phe Glu Val Glu Phe Gly Phe Pro Val Glu Gly Gly
65                  70                  75                  80

Val Glu Gly Ser Gly Arg Val Val Thr Gly Leu Thr Pro Ser Gly Lys
                85                  90                  95

Ala Ala Ser Ser Leu Tyr Ile Gly Pro Trp Gly Glu Ile Glu Ala Val
            100                 105                 110
```

-continued

```
Tyr Asp Ala Leu Met Lys Trp Val Asp Asp Asn Gly Phe Asp Leu Ser
        115                 120                 125

Gly Glu Ala Tyr Glu Ile Tyr Leu Asp Asn Pro Ala Glu Thr Ala Pro
    130                 135                 140

Asp Gln Leu Arg Thr Arg Val Ser Leu Met Leu His Glu Ser Leu Glu
145                 150                 155                 160

His His His His His His
                165


<210> SEQ ID NO 21
<211> LENGTH: 498
<212> TYPE: DNA
<213> ORGANISM: Escherichia coli

<400> SEQUENCE: 21

atggacttcg agtgccagtt tgtgtgcgag ctgaaggaac tggcgccggt tccggcgctg      60

ctgatccgta cccaaaccac catgagcgag ctgggtagcc tgttcgaagc gggctaccac     120

gatattctgc agctgctggc gggtcagggt aagagcccga gcggtccgcc gtttgcgcgt     180

tattttggta tgagcgcggg cacctttgag gtggagttcg gctttccggt ggagggtggc     240

gttgaaggta gcggccgtgt ggttaccggt ctgaccccga gcggcaaggc ggcgagcagc     300

ctgtacatcg gtccgtatgg cgagattgaa gcggtgtacg acgcgctgat gaaatgggtt     360

gacgataacg gtttcgatct gagcggcgag gcgtaccaaa tctatctgga caacccggcg     420

gaaaccgcgc cggatcagct gcgtacccgt gttagcctga tgctgcacga gagcctggaa     480

caccaccacc accaccac                                                   498


<210> SEQ ID NO 22
<211> LENGTH: 166
<212> TYPE: PRT
<213> ORGANISM: Escherichia coli

<400> SEQUENCE: 22

Met Asp Phe Glu Cys Gln Phe Val Cys Glu Leu Lys Glu Leu Ala Pro
1               5                   10                  15

Val Pro Ala Leu Leu Ile Arg Thr Gln Thr Thr Met Ser Glu Leu Gly
            20                  25                  30

Ser Leu Phe Glu Ala Gly Tyr His Asp Ile Leu Gln Leu Leu Ala Gly
        35                  40                  45

Gln Gly Lys Ser Pro Ser Gly Pro Pro Phe Ala Arg Tyr Phe Gly Met
    50                  55                  60

Ser Ala Gly Thr Phe Glu Val Glu Phe Gly Phe Pro Val Glu Gly Gly
65                  70                  75                  80

Val Glu Gly Ser Gly Arg Val Val Thr Gly Leu Thr Pro Ser Gly Lys
                85                  90                  95

Ala Ala Ser Ser Leu Tyr Ile Gly Pro Tyr Gly Glu Ile Glu Ala Val
            100                 105                 110

Tyr Asp Ala Leu Met Lys Trp Val Asp Asp Asn Gly Phe Asp Leu Ser
        115                 120                 125

Gly Glu Ala Tyr Gln Ile Tyr Leu Asp Asn Pro Ala Glu Thr Ala Pro
    130                 135                 140

Asp Gln Leu Arg Thr Arg Val Ser Leu Met Leu His Glu Ser Leu Glu
145                 150                 155                 160

His His His His His His
                165
```

-continued

<210> SEQ ID NO 23
<211> LENGTH: 498
<212> TYPE: DNA
<213> ORGANISM: Escherichia coli

<400> SEQUENCE: 23
atggacttcg agtgccagtt tgtgtgcgag ctgaaggaac tggcgccggt tccggcgctg 60
ctgatccgta cccaaaccac catgagcgag ctgggtagcc tgttcagagc gggctactac 120
gatattctgc agctgctggc gggtcagggt aagagcccga gcggtccgcc gtttgcgcgt 180
tattttggta tgagcgcggg cacctttgag gtggagttcg gctttccggt ggagggtggc 240
gttgaaggta gcggccgtgt ggttaccggt ctgaccccga gcggcaaggc ggcgagcagc 300
ctgtacatcg gtccgtgggg cgagattgaa gcggtgtacg acgcgctgat gaaatgggtt 360
gacgataacg gtttcgatct gagcggcgag gcgtacgaaa tctatctgga caacccggcg 420
gaaaccgcgc cggatcagct gcgtacccgt gttagcctga tgctgcacga gagcctggaa 480
caccaccacc accaccac 498

<210> SEQ ID NO 24
<211> LENGTH: 166
<212> TYPE: PRT
<213> ORGANISM: Escherichia coli

<400> SEQUENCE: 24

Met Asp Phe Glu Cys Gln Phe Val Cys Glu Leu Lys Glu Leu Ala Pro
1               5                   10                  15

Val Pro Ala Leu Leu Ile Arg Thr Gln Thr Thr Met Ser Glu Leu Gly
            20                  25                  30

Ser Leu Phe Arg Ala Gly Tyr Tyr Asp Ile Leu Gln Leu Leu Ala Gly
        35                  40                  45

Gln Gly Lys Ser Pro Ser Gly Pro Pro Phe Ala Arg Tyr Phe Gly Met
    50                  55                  60

Ser Ala Gly Thr Phe Glu Val Glu Phe Gly Phe Pro Val Glu Gly Gly
65                  70                  75                  80

Val Glu Gly Ser Gly Arg Val Val Thr Gly Leu Thr Pro Ser Gly Lys
                85                  90                  95

Ala Ala Ser Ser Leu Tyr Ile Gly Pro Trp Gly Glu Ile Glu Ala Val
            100                 105                 110

Tyr Asp Ala Leu Met Lys Trp Val Asp Asp Asn Gly Phe Asp Leu Ser
        115                 120                 125

Gly Glu Ala Tyr Glu Ile Tyr Leu Asp Asn Pro Ala Glu Thr Ala Pro
    130                 135                 140

Asp Gln Leu Arg Thr Arg Val Ser Leu Met Leu His Glu Ser Leu Glu
145                 150                 155                 160

His His His His His His
                165

<210> SEQ ID NO 25
<211> LENGTH: 498
<212> TYPE: DNA
<213> ORGANISM: Escherichia coli

<400> SEQUENCE: 25
atggacttcg agtgccagtt tgtgtgcgag ctgaaggaac tggcgccggt tccggcgctg 60
ctgatccgta cccaaaccac catgagcgag ctgggtagcc tgttcagagc gggctactac 120

```
gatattctgc agctgctggc gggtcagggt aagagcccga gcggtccgcc gtttgcgcgt    180

tattttggta tgagcgcggg cacctttgag gtggagttcg gctttccggt ggagggtggc    240

gttgaaggta gcggccgtgt ggttaccggt ctgaccccga gcggcaaggc ggcgagcagc    300

ctgtacatcg gtccgtgggg cgagattgaa gcggtgtacg acgcgctgat gaaatgggtt    360

gacgataacg gtttcgatct gagcggcgag gcgtaccaaa tctatctgga caacccggcg    420

gaaaccgcgc cggatcagct gcgtacccgt gttagcctga tgctgcacga gagcctggaa    480

caccaccacc accaccac                                                  498


<210> SEQ ID NO 26
<211> LENGTH: 166
<212> TYPE: PRT
<213> ORGANISM: Escherichia coli

<400> SEQUENCE: 26

Met Asp Phe Glu Cys Gln Phe Val Cys Glu Leu Lys Glu Leu Ala Pro
1               5                   10                  15

Val Pro Ala Leu Leu Ile Arg Thr Gln Thr Thr Met Ser Glu Leu Gly
            20                  25                  30

Ser Leu Phe Arg Ala Gly Tyr Tyr Asp Ile Leu Gln Leu Leu Ala Gly
        35                  40                  45

Gln Gly Lys Ser Pro Ser Gly Pro Pro Phe Ala Arg Tyr Phe Gly Met
    50                  55                  60

Ser Ala Gly Thr Phe Glu Val Glu Phe Gly Phe Pro Val Glu Gly Gly
65                  70                  75                  80

Val Glu Gly Ser Gly Arg Val Val Thr Gly Leu Thr Pro Ser Gly Lys
                85                  90                  95

Ala Ala Ser Ser Leu Tyr Ile Gly Pro Trp Gly Glu Ile Glu Ala Val
            100                 105                 110

Tyr Asp Ala Leu Met Lys Trp Val Asp Asp Asn Gly Phe Asp Leu Ser
        115                 120                 125

Gly Glu Ala Tyr Gln Ile Tyr Leu Asp Asn Pro Ala Glu Thr Ala Pro
    130                 135                 140

Asp Gln Leu Arg Thr Arg Val Ser Leu Met Leu His Glu Ser Leu Glu
145                 150                 155                 160

His His His His His His
                165


<210> SEQ ID NO 27
<211> LENGTH: 648
<212> TYPE: DNA
<213> ORGANISM: Escherichia coli

<400> SEQUENCE: 27

atgggtagcc accaccacca ccaccacacc gagaagaaaa tcgacttcaa gaaagaggaa     60

aagaaatttt acgcgccgaa gcgtaagccg gagcgtattt tcgtgccgga aatgaacttt    120

ctgatggttg atggtaaagg cgacccggat ggcgaggaat accagaaggc ggtgcaaagc    180

ctgtacgcga tcgcgtatac cattaaaatg agcaagatgg gtgaaacccg tctggacggc    240

tatagcgatt tcgtggttcc gccgctggag ggtttctggt ggagcgaagg caaatttgac    300

ctgaaggacc gtgatgcgtg gctgtggacc agcatcctgc gtcagccgga tttcgtgacc    360

gaggaagttc tggagtgggc gaaagaagtg gcgcgtaaga aaaagccgga cgttgatacc    420

agccgtgtga agctggttcg ttttgaggaa ggtgaatgcg tgcagatgat gcacgttggc    480
```

-continued

```
ccgttcagcg aggcggtgca caccgttgcg gaaatgcacc aatttatgga gaccgaaggt    540

ctgcgtaacg acaccggcgc gatccgtaaa caccacgaga tttatctgag cgatccgcgt    600

aaggcgaacc cggaaaaaat gaagaccatt ctgcgtctgc cggttagc                 648
```

```
<210> SEQ ID NO 28
<211> LENGTH: 216
<212> TYPE: PRT
<213> ORGANISM: Escherichia coli

<400> SEQUENCE: 28

Met Gly Ser His His His His His His Thr Glu Lys Lys Ile Asp Phe
1               5                   10                  15

Lys Lys Glu Glu Lys Lys Phe Tyr Ala Pro Lys Arg Lys Pro Glu Arg
            20                  25                  30

Ile Phe Val Pro Glu Met Asn Phe Leu Met Val Asp Gly Lys Gly Asp
        35                  40                  45

Pro Asp Gly Glu Glu Tyr Gln Lys Ala Val Gln Ser Leu Tyr Ala Ile
    50                  55                  60

Ala Tyr Thr Ile Lys Met Ser Lys Met Gly Glu Thr Arg Leu Asp Gly
65                  70                  75                  80

Tyr Ser Asp Phe Val Val Pro Pro Leu Glu Gly Phe Trp Trp Ser Glu
                85                  90                  95

Gly Lys Phe Asp Leu Lys Asp Arg Asp Ala Trp Leu Trp Thr Ser Ile
            100                 105                 110

Leu Arg Gln Pro Asp Phe Val Thr Glu Glu Val Leu Glu Trp Ala Lys
        115                 120                 125

Glu Val Ala Arg Lys Lys Lys Pro Asp Val Asp Thr Ser Arg Val Lys
    130                 135                 140

Leu Val Arg Phe Glu Glu Gly Glu Cys Val Gln Met Met His Val Gly
145                 150                 155                 160

Pro Phe Ser Glu Ala Val His Thr Val Ala Glu Met His Gln Phe Met
                165                 170                 175

Glu Thr Glu Gly Leu Arg Asn Asp Thr Gly Ala Ile Arg Lys His His
            180                 185                 190

Glu Ile Tyr Leu Ser Asp Pro Arg Lys Ala Asn Pro Glu Lys Met Lys
        195                 200                 205

Thr Ile Leu Arg Leu Pro Val Ser
    210                 215
```

```
<210> SEQ ID NO 29
<211> LENGTH: 648
<212> TYPE: DNA
<213> ORGANISM: Escherichia coli

<400> SEQUENCE: 29

atgggtagcc accaccacca ccaccacacc gagaagaaaa tcgacttcaa gaaagaggaa     60

aagaaatttt acgcgccgaa gcgtaagccg gagcgtattt tcgtgccgga aatgaacttt    120

ctgatggttg atggtaaagg cgacccggat ggcgaggaat accagaaggc ggtgcaaagc    180

ctgtacgcga tcgcgtatac cattaaaatg agcaagatgg gtgaaacccg tctggacggc    240

tatagcgatt tcgtggttcc gccgctggag ggtttctggt ggagcgaagg caaatttgac    300

ctgaaggacc gtgatgcgtg gctgtggacc agcatcctgc gtcagccgga tttcgtgacc    360

gaggaagttc tggagtgggc gaaagaagtg gcgcgtaaga aaaagccgga cgttgatacc    420

agccgtgtga agctggttcg ttttgaggaa ggtgaatgcg tgcagatgat gcacgttggc    480
```

```
ccgttcagcg aggaggtgca caccgttgcg gaaatgcacc aatttatgga gaccgaaggt    540

ctgcgtaacg acaccggcgc gatccgtaaa caccacctga tttatctgag cgatccgcgt    600

aaggcgaacc cggaaaaaat gaagaccatt ctgcgtctgc cggttagc                 648
```

<210> SEQ ID NO 30
<211> LENGTH: 216
<212> TYPE: PRT
<213> ORGANISM: Escherichia coli

<400> SEQUENCE: 30

```
Met Gly Ser His His His His His His Thr Glu Lys Lys Ile Asp Phe
1               5                   10                  15

Lys Lys Glu Glu Lys Lys Phe Tyr Ala Pro Lys Arg Lys Pro Glu Arg
            20                  25                  30

Ile Phe Val Pro Glu Met Asn Phe Leu Met Val Asp Gly Lys Gly Asp
        35                  40                  45

Pro Asp Gly Glu Glu Tyr Gln Lys Ala Val Gln Ser Leu Tyr Ala Ile
    50                  55                  60

Ala Tyr Thr Ile Lys Met Ser Lys Met Gly Glu Thr Arg Leu Asp Gly
65                  70                  75                  80

Tyr Ser Asp Phe Val Val Pro Pro Leu Glu Gly Phe Trp Trp Ser Glu
                85                  90                  95

Gly Lys Phe Asp Leu Lys Asp Arg Asp Ala Trp Leu Trp Thr Ser Ile
            100                 105                 110

Leu Arg Gln Pro Asp Phe Val Thr Glu Glu Val Leu Glu Trp Ala Lys
        115                 120                 125

Glu Val Ala Arg Lys Lys Lys Pro Asp Val Asp Thr Ser Arg Val Lys
    130                 135                 140

Leu Val Arg Phe Glu Glu Gly Glu Cys Val Gln Met Met His Val Gly
145                 150                 155                 160

Pro Phe Ser Glu Glu Val His Thr Val Ala Glu Met His Gln Phe Met
                165                 170                 175

Glu Thr Glu Gly Leu Arg Asn Asp Thr Gly Ala Ile Arg Lys His His
            180                 185                 190

Leu Ile Tyr Leu Ser Asp Pro Arg Lys Ala Asn Pro Glu Lys Met Lys
        195                 200                 205

Thr Ile Leu Arg Leu Pro Val Ser
    210                 215
```

<210> SEQ ID NO 31
<211> LENGTH: 648
<212> TYPE: DNA
<213> ORGANISM: Escherichia coli

<400> SEQUENCE: 31

```
atgggtagcc accaccacca ccaccacacc gagaagaaaa tcgacttcaa gaaagaggaa     60

aagaaatttt acgcgccgaa gcgtaagccg gagcgtattt tcgtgccgga aatgaacttt    120

ctgatggttg atggtaaagg cgacccggat ggcgaggaat accagaaggc ggtgcaaagc    180

ctgtacgcga tcgcgtatac cattaaaatg agcaagatgg gtgaaacccg tctggacggc    240

tatagcgatt tcgtggttcc gccgctggag ggtttctggt ggagcgaagg caaatttgac    300

ctgaaggacc gtgatgcgtg gctgtggacc agcatcctgc gtcagccgga tttcgtgacc    360

gaggaagttc tggagtgggc gaaagaagtg gcgcgtaaga aaaagccgga cgttgatacc    420
```

-continued

```
agccgtgtga agctggttcg ttttgaggaa ggtgaatgcg tgcagatgat gcacgttggc    480

ccgttcagcg aggcggtgca caccgttgcg gaaatgcacc aatttatgga gaccgaaggt    540

ctgcgtaacg acaccggcgc gatccgtaaa caccacctga tttatctgag cgatccgcgt    600

aaggcgaacc cggaaaaaat gaagaccatt ctgcgtctgc cggttagc                 648


<210> SEQ ID NO 32
<211> LENGTH: 216
<212> TYPE: PRT
<213> ORGANISM: Escherichia coli

<400> SEQUENCE: 32

Met Gly Ser His His His His His His Thr Glu Lys Lys Ile Asp Phe
1               5                   10                  15

Lys Lys Glu Glu Lys Lys Phe Tyr Ala Pro Lys Arg Lys Pro Glu Arg
            20                  25                  30

Ile Phe Val Pro Glu Met Asn Phe Leu Met Val Asp Gly Lys Gly Asp
        35                  40                  45

Pro Asp Gly Glu Glu Tyr Gln Lys Ala Val Gln Ser Leu Tyr Ala Ile
    50                  55                  60

Ala Tyr Thr Ile Lys Met Ser Lys Met Gly Glu Thr Arg Leu Asp Gly
65                  70                  75                  80

Tyr Ser Asp Phe Val Val Pro Pro Leu Glu Gly Phe Trp Trp Ser Glu
                85                  90                  95

Gly Lys Phe Asp Leu Lys Asp Arg Asp Ala Trp Leu Trp Thr Ser Ile
            100                 105                 110

Leu Arg Gln Pro Asp Phe Val Thr Glu Glu Val Leu Glu Trp Ala Lys
        115                 120                 125

Glu Val Ala Arg Lys Lys Lys Pro Asp Val Asp Thr Ser Arg Val Lys
    130                 135                 140

Leu Val Arg Phe Glu Glu Gly Glu Cys Val Gln Met Met His Val Gly
145                 150                 155                 160

Pro Phe Ser Glu Ala Val His Thr Val Ala Glu Met His Gln Phe Met
                165                 170                 175

Glu Thr Glu Gly Leu Arg Asn Asp Thr Gly Ala Ile Arg Lys His His
            180                 185                 190

Leu Ile Tyr Leu Ser Asp Pro Arg Lys Ala Asn Pro Glu Lys Met Lys
        195                 200                 205

Thr Ile Leu Arg Leu Pro Val Ser
    210                 215


<210> SEQ ID NO 33
<211> LENGTH: 166
<212> TYPE: PRT
<213> ORGANISM: Escherichia coli

<400> SEQUENCE: 33

Met Asp Phe Glu Cys Gln Phe Val Cys Glu Leu Lys Glu Leu Ala Pro
1               5                   10                  15

Val Pro Ala Leu Leu Ile Arg Thr Gln Thr Thr Met Ser Glu Leu Gly
            20                  25                  30

Ser Leu Phe Glu Ala Gly Tyr His Asp Ile Leu Gln Leu Leu Ala Gly
        35                  40                  45

Gln Gly Lys Ser Pro Ser Gly Pro Pro Phe Ala Arg Tyr Phe Gly Met
    50                  55                  60

Ser Ala Gly Thr Phe Glu Val Glu Phe Gly Phe Pro Val Glu Gly Gly
```

-continued

```
65                  70                  75                  80

Val Glu Gly Ser Gly Arg Val Val Thr Gly Leu Thr Pro Ser Gly Lys
                85                  90                  95

Ala Ala Ser Ser Leu Tyr Ile Gly Pro Trp Gly Glu Ile Glu Ala Val
            100                 105                 110

Tyr Asp Ala Leu Met Lys Trp Val Asp Asp Asn Gly Phe Asp Leu Ser
        115                 120                 125

Gly Glu Ala Tyr Gln Ile Tyr Leu Asp Asn Pro Ala Glu Thr Ala Pro
    130                 135                 140

Asp Gln Leu Arg Thr Arg Val Ser Leu Met Leu His Glu Ser Leu Glu
145                 150                 155                 160

His His His His His His
                165


<210> SEQ ID NO 34
<211> LENGTH: 166
<212> TYPE: PRT
<213> ORGANISM: Escherichia coli

<400> SEQUENCE: 34

Met Asp Phe Glu Cys Gln Phe Val Cys Glu Leu Lys Glu Leu Ala Pro
1               5                   10                  15

Val Pro Ala Leu Leu Ile Arg Thr Gln Thr Thr Met Ser Glu Phe Pro
            20                  25                  30

Ser Leu Phe Leu Ala Gly Met Pro Asp Ile Leu Gln Leu Leu Ala Gly
        35                  40                  45

Gln Gly Lys Ser Pro Ser Gly Pro Pro Phe Ala Arg Tyr Phe Gly Met
    50                  55                  60

Ser Ala Gly Thr Phe Glu Val Glu Phe Gly Tyr Pro Val Glu Gly Gly
65                  70                  75                  80

Val Glu Gly Ser Gly Arg Val Val Thr Gly Leu Thr Pro Ser Gly Lys
                85                  90                  95

Ala Ala Ser Ser Leu Tyr Ile Gly Pro Tyr Gly Glu Ile Glu Ala Val
            100                 105                 110

Tyr Asp Ala Leu Met Lys Trp Val Asp Asp Asn Gly Phe Asp Leu Ser
        115                 120                 125

Gly Glu Ala Tyr Ile Ile Pro Leu Asp Glu Pro Ala Glu Thr Ala Pro
    130                 135                 140

Asp Gln Leu Arg Thr Arg Val Ser Leu Met Leu His Glu Ser Leu Glu
145                 150                 155                 160

His His His His His His
                165


<210> SEQ ID NO 35
<211> LENGTH: 166
<212> TYPE: PRT
<213> ORGANISM: Escherichia coli

<400> SEQUENCE: 35

Met Asp Phe Glu Cys Gln Phe Val Cys Glu Leu Lys Glu Leu Ala Pro
1               5                   10                  15

Val Pro Ala Leu Leu Ile Arg Thr Gln Thr Thr Met Ser Glu Ala Lys
            20                  25                  30

Ser Leu His Leu Ala Gly Ser Gly Asp Ile Glu Gln Leu Leu Ala Gly
        35                  40                  45

Gln Gly Lys Ser Pro Ser Gly Pro Pro Phe Ala Arg Tyr Phe Gly Met
```

```
    50                  55                  60

Ser Ala Gly Thr Phe Glu Val Glu Phe Gly Val Pro Val Glu Gly Gly
65                  70                  75                  80

Val Glu Gly Ser Gly Arg Val Val Thr Gly Leu Thr Pro Ser Gly Lys
                85                  90                  95

Ala Ala Ser Ser Leu Tyr Ile Gly Pro Thr Gly Glu Ile Glu Ala Val
            100                 105                 110

Tyr Asp Ala Leu Met Lys Trp Val Asp Asp Asn Gly Phe Asp Leu Ser
        115                 120                 125

Gly Glu Ala Tyr Val Ile Trp Leu Asp Thr Pro Ala Glu Thr Ala Pro
    130                 135                 140

Asp Gln Leu Arg Thr Arg Val Ser Leu Met Leu His Glu Ser Leu Glu
145                 150                 155                 160

His His His His His His
                165


<210> SEQ ID NO 36
<211> LENGTH: 166
<212> TYPE: PRT
<213> ORGANISM: Escherichia coli

<400> SEQUENCE: 36

Met Asp Phe Glu Cys Gln Phe Val Cys Glu Leu Lys Glu Leu Ala Pro
1               5                   10                  15

Val Pro Ala Leu Leu Ile Arg Thr Gln Thr Thr Met Ser Glu Gly Asp
            20                  25                  30

Ser Leu Ser Leu Ala Gly Arg Arg Asp Ile Val Gln Leu Leu Ala Gly
        35                  40                  45

Gln Gly Lys Ser Pro Ser Gly Pro Pro Phe Ala Arg Tyr Phe Gly Met
    50                  55                  60

Ser Ala Gly Thr Phe Glu Val Glu Phe Gly Cys Pro Val Glu Gly Gly
65                  70                  75                  80

Val Glu Gly Ser Gly Arg Val Val Thr Gly Leu Thr Pro Ser Gly Lys
                85                  90                  95

Ala Ala Ser Ser Leu Tyr Ile Gly Pro Ile Gly Glu Ile Glu Ala Val
            100                 105                 110

Tyr Asp Ala Leu Met Lys Trp Val Asp Asp Asn Gly Phe Asp Leu Ser
        115                 120                 125

Gly Glu Ala Tyr Thr Ile His Leu Asp Ala Pro Ala Glu Thr Ala Pro
    130                 135                 140

Asp Gln Leu Arg Thr Arg Val Ser Leu Met Leu His Glu Ser Leu Glu
145                 150                 155                 160

His His His His His His
                165


<210> SEQ ID NO 37
<211> LENGTH: 166
<212> TYPE: PRT
<213> ORGANISM: Escherichia coli

<400> SEQUENCE: 37

Met Asp Phe Glu Cys Gln Phe Val Cys Glu Leu Lys Glu Leu Ala Pro
1               5                   10                  15

Val Pro Ala Leu Leu Ile Arg Thr Gln Thr Thr Met Ser Glu Pro Trp
            20                  25                  30

Ser Leu Gly Lys Ala Gly Thr Ser Asp Ile Phe Gln Leu Leu Ala Gly
```

```
        35                  40                  45

Gln Gly Lys Ser Pro Ser Gly Pro Pro Phe Ala Arg Tyr Phe Gly Met
    50                  55                  60

Ser Ala Gly Thr Phe Glu Val Glu Phe Gly Gly Pro Val Glu Gly Gly
65                  70                  75                  80

Val Glu Gly Ser Gly Arg Val Val Thr Gly Leu Thr Pro Ser Gly Lys
                85                  90                  95

Ala Ala Ser Ser Leu Tyr Ile Gly Pro Glu Gly Glu Ile Glu Ala Val
            100                 105                 110

Tyr Asp Ala Leu Met Lys Trp Val Asp Asp Asn Gly Phe Asp Leu Ser
        115                 120                 125

Gly Glu Ala Tyr Arg Ile Arg Leu Asp Ile Pro Ala Glu Thr Ala Pro
    130                 135                 140

Asp Gln Leu Arg Thr Arg Val Ser Leu Met Leu His Glu Ser Leu Glu
145                 150                 155                 160

His His His His His His
                165


<210> SEQ ID NO 38
<211> LENGTH: 166
<212> TYPE: PRT
<213> ORGANISM: Escherichia coli

<400> SEQUENCE: 38

Met Asp Phe Glu Cys Gln Phe Val Cys Glu Leu Lys Glu Leu Ala Pro
1               5                   10                  15

Val Pro Ala Leu Leu Ile Arg Thr Gln Thr Thr Met Ser Glu Gly Val
            20                  25                  30

Ser Leu Asp Cys Ala Gly Arg Val Asp Ile Met Gln Leu Leu Ala Gly
        35                  40                  45

Gln Gly Lys Ser Pro Ser Gly Pro Pro Phe Ala Arg Tyr Phe Gly Met
    50                  55                  60

Ser Ala Gly Thr Phe Glu Val Glu Phe Gly Tyr Pro Val Glu Gly Gly
65                  70                  75                  80

Val Glu Gly Ser Gly Arg Val Val Thr Gly Leu Thr Pro Ser Gly Lys
                85                  90                  95

Ala Ala Ser Ser Leu Tyr Ile Gly Pro Val Gly Glu Ile Glu Ala Val
            100                 105                 110

Tyr Asp Ala Leu Met Lys Trp Val Asp Asp Asn Gly Phe Asp Leu Ser
        115                 120                 125

Gly Glu Ala Tyr Ser Ile Ala Leu Asp His Pro Ala Glu Thr Ala Pro
    130                 135                 140

Asp Gln Leu Arg Thr Arg Val Ser Leu Met Leu His Glu Ser Leu Glu
145                 150                 155                 160

His His His His His His
                165


<210> SEQ ID NO 39
<211> LENGTH: 166
<212> TYPE: PRT
<213> ORGANISM: Escherichia coli

<400> SEQUENCE: 39

Met Asp Phe Glu Cys Gln Phe Val Cys Glu Leu Lys Glu Leu Ala Pro
1               5                   10                  15

Val Pro Ala Leu Leu Ile Arg Thr Gln Thr Thr Met Ser Glu Ile Leu
```

```
            20                  25                  30

Ser Leu Ile Leu Ala Gly Lys Met Asp Ile Ile Gln Leu Leu Ala Gly
        35                  40                  45

Gln Gly Lys Ser Pro Ser Gly Pro Pro Phe Ala Arg Tyr Phe Gly Met
    50                  55                  60

Ser Ala Gly Thr Phe Glu Val Glu Phe Gly Phe Pro Val Glu Gly Gly
65                  70                  75                  80

Val Glu Gly Ser Gly Arg Val Val Thr Gly Leu Thr Pro Ser Gly Lys
                85                  90                  95

Ala Ala Ser Ser Leu Tyr Ile Gly Pro Leu Gly Glu Ile Glu Ala Val
            100                 105                 110

Tyr Asp Ala Leu Met Lys Trp Val Asp Asp Asn Gly Phe Asp Leu Ser
        115                 120                 125

Gly Glu Ala Tyr Gly Ile Arg Leu Asp Ile Pro Ala Glu Thr Ala Pro
    130                 135                 140

Asp Gln Leu Arg Thr Arg Val Ser Leu Met Leu His Glu Ser Leu Glu
145                 150                 155                 160

His His His His His His
                165


<210> SEQ ID NO 40
<211> LENGTH: 165
<212> TYPE: PRT
<213> ORGANISM: Escherichia coli

<400> SEQUENCE: 40

Met Glu Tyr Gln Leu Gln Gln Leu Ala Ser Leu Thr Leu Val Gly Ile
1               5                   10                  15

Lys Glu Thr Tyr Glu Asn Gly Arg Gln Ala Val Gln His Gly His Gly
            20                  25                  30

Phe Phe Gln Arg Cys Asp Gln Glu Gly Val Ile Ala Asp Leu Gln Leu
        35                  40                  45

Lys Asn Asn Gly Asp Leu Ala Gly Ile Leu Gly Leu Cys Ile Pro Glu
    50                  55                  60

Leu Asp Gly Lys Met Ser Tyr Met Ile Ala Val Thr Gly Asp Asn Ser
65                  70                  75                  80

Ala Asp Ile Ala Lys Tyr Asp Val Ile Thr Leu Ala Ser Ser Lys Tyr
                85                  90                  95

Met Val Phe Glu Ala Gln Gly Ala Asp Ser Lys Ala Asn Thr Gln Lys
            100                 105                 110

Gly Glu Glu Val His His Tyr Ile His Gln Tyr Gln Ala Asn Thr Val
        115                 120                 125

Lys Ser Ala Pro Phe Phe Pro Leu Val Gln Asp Gly Asp Tyr Thr Ser
    130                 135                 140

Glu Lys Tyr Ile Thr Glu Ile Trp Met Pro Val Lys Gly Leu Glu His
145                 150                 155                 160

His His His His His
                165


<210> SEQ ID NO 41
<211> LENGTH: 165
<212> TYPE: PRT
<213> ORGANISM: Escherichia coli

<400> SEQUENCE: 41

Met Glu Tyr Gln Leu Gln Gln Leu Ala Ser Leu Thr Leu Val Gly Ile
```

-continued 1 5 10 15

Lys Glu Thr Tyr Glu Asn Gly Arg Gln Ala Glu Gln His Leu Ile Gly
20 25 30

Phe Arg Gln Arg Cys Leu Gln Glu Gly Ile Ile Ala Asp Leu Gln Leu
35 40 45

Lys Asn Asn Gly Asp Leu Ala Gly Ile Leu Gly Leu Cys Ile Pro Glu
50 55 60

Leu Asp Gly Lys Met Ser Tyr Met Ile Ala Val Thr Gly Asp Asn Ser
65 70 75 80

Ala Asp Ile Ala Lys Tyr Asp Val Ile Thr Leu Ala Ser Ser Lys Tyr
85 90 95

Met Val Phe Glu Ala Gln Gly Ala Asn Asn Lys Ala Gln Ser Gln Lys
100 105 110

Cys Glu Glu Val His His Tyr Ile His Gln Tyr Gln Ala Asn Thr Val
115 120 125

Lys Ser Ala Pro Phe Phe His Leu Lys Gln Asp Gly Asp Val Thr Ser
130 135 140

Glu Lys Tyr Ile Thr Glu Ile Trp Met Pro Val Lys Gly Leu Glu His
145 150 155 160

His His His His His
165

<210> SEQ ID NO 42
<211> LENGTH: 165
<212> TYPE: PRT
<213> ORGANISM: Escherichia coli

<400> SEQUENCE: 42

Met Glu Tyr Gln Leu Gln Gln Leu Ala Ser Leu Thr Leu Val Gly Ile
1 5 10 15

Lys Glu Thr Tyr Glu Asn Gly Arg Gln Ala Arg Gln His Ser Asn Gly
20 25 30

Phe Ile Gln Arg Cys Gly Gln Glu Gly Val Ile Ala Asp Leu Gln Leu
35 40 45

Lys Asn Asn Gly Asp Leu Ala Gly Ile Leu Gly Leu Cys Ile Pro Glu
50 55 60

Leu Asp Gly Lys Met Ser Tyr Met Ile Ala Val Thr Gly Asp Asn Ser
65 70 75 80

Ala Asp Ile Ala Lys Tyr Asp Val Ile Thr Leu Ala Ser Ser Lys Tyr
85 90 95

Met Val Phe Glu Ala Gln Gly Ala Lys Val Lys Ala Glu Tyr Gln Lys
100 105 110

Arg Glu Glu Val His His Tyr Ile His Gln Tyr Gln Ala Asn Thr Val
115 120 125

Lys Ser Ala Pro Phe Phe Arg Leu Gly Gln Asp Gly Asp Ser Thr Ser
130 135 140

Glu Lys Tyr Ile Thr Glu Ile Trp Met Pro Val Lys Gly Leu Glu His
145 150 155 160

His His His His His
165

<210> SEQ ID NO 43
<211> LENGTH: 165
<212> TYPE: PRT
<213> ORGANISM: Escherichia coli

<400> SEQUENCE: 43

Met Glu Tyr Gln Leu Gln Gln Leu Ala Ser Leu Thr Leu Val Gly Ile
1               5                   10                  15

Lys Glu Thr Tyr Glu Asn Gly Arg Gln Ala His Gln His Phe Leu Gly
            20                  25                  30

Phe Thr Gln Arg Cys Arg Gln Glu Gly Val Ile Ala Asp Leu Gln Leu
        35                  40                  45

Lys Asn Asn Gly Asp Leu Ala Gly Ile Leu Gly Leu Cys Ile Pro Glu
    50                  55                  60

Leu Asp Gly Lys Met Ser Tyr Met Ile Ala Val Thr Gly Asp Asn Ser
65                  70                  75                  80

Ala Asp Ile Ala Lys Tyr Asp Val Ile Thr Leu Ala Ser Ser Lys Tyr
                85                  90                  95

Met Val Phe Glu Ala Gln Gly Ala Leu Arg Lys Ala Leu Thr Gln Lys
            100                 105                 110

Leu Glu Glu Val His His Tyr Ile His Gln Tyr Gln Ala Asn Thr Val
        115                 120                 125

Lys Ser Ala Pro Phe Phe Ile Leu Ser Gln Asp Gly Asp Gln Thr Ser
    130                 135                 140

Glu Lys Tyr Ile Thr Glu Ile Trp Met Pro Val Lys Gly Leu Glu His
145                 150                 155                 160

His His His His His
                165

<210> SEQ ID NO 44
<211> LENGTH: 165
<212> TYPE: PRT
<213> ORGANISM: Escherichia coli

<400> SEQUENCE: 44

Met Glu Tyr Gln Leu Gln Gln Leu Ala Ser Leu Thr Leu Val Gly Ile
1               5                   10                  15

Lys Glu Thr Tyr Glu Asn Gly Arg Gln Ala Ile Gln His Trp Thr Gly
            20                  25                  30

Phe Ile Gln Arg Cys Met Gln Glu Gly Val Ile Ala Asp Leu Gln Leu
        35                  40                  45

Lys Asn Asn Gly Asp Leu Ala Gly Ile Leu Gly Leu Cys Ile Pro Glu
    50                  55                  60

Leu Asp Gly Lys Met Ser Tyr Met Ile Ala Val Thr Gly Asp Asn Ser
65                  70                  75                  80

Ala Asp Ile Ala Lys Tyr Asp Val Ile Thr Leu Ala Ser Ser Lys Tyr
                85                  90                  95

Met Val Phe Glu Ala Gln Gly Ala Ala Leu Lys Ala Gly Phe Gln Lys
            100                 105                 110

Cys Glu Glu Val His His Tyr Ile His Gln Tyr Gln Ala Asn Thr Val
        115                 120                 125

Lys Ser Ala Pro Phe Phe Leu Leu Ser Gln Asp Gly Asp Gly Thr Ser
    130                 135                 140

Glu Lys Tyr Ile Thr Glu Ile Trp Met Pro Val Lys Gly Leu Glu His
145                 150                 155                 160

His His His His His
                165

<210> SEQ ID NO 45
<211> LENGTH: 165

<212> TYPE: PRT
<213> ORGANISM: Escherichia coli

<400> SEQUENCE: 45

Met Glu Tyr Gln Leu Gln Gln Leu Ala Ser Leu Thr Leu Val Gly Ile
1 5 10 15

Lys Glu Thr Tyr Glu Asn Gly Arg Gln Ala Thr Gln His Lys Asn Gly
20 25 30

Phe Gly Gln Arg Cys Leu Gln Glu Gly Val Ile Ala Asp Leu Gln Leu
35 40 45

Lys Asn Asn Gly Asp Leu Ala Gly Ile Leu Gly Leu Cys Ile Pro Glu
50 55 60

Leu Asp Gly Lys Met Ser Tyr Met Ile Ala Val Thr Gly Asp Asn Ser
65 70 75 80

Ala Asp Ile Ala Lys Tyr Asp Val Ile Thr Leu Ala Ser Ser Lys Tyr
85 90 95

Met Val Phe Glu Ala Gln Gly Ala Pro Gly Lys Ala Ser Val Gln Lys
100 105 110

Met Glu Glu Val His His Tyr Ile His Gln Tyr Gln Ala Asn Thr Val
115 120 125

Lys Ser Ala Pro Phe Phe Ser Leu Ala Gln Asp Gly Asp Asn Thr Ser
130 135 140

Glu Lys Tyr Ile Thr Glu Ile Trp Met Pro Val Lys Gly Leu Glu His
145 150 155 160

His His His His His
165

<210> SEQ ID NO 46
<211> LENGTH: 166
<212> TYPE: PRT
<213> ORGANISM: Escherichia coli

<400> SEQUENCE: 46

Met Asp Phe Glu Cys Gln Phe Val Cys Glu Leu Lys Glu Leu Ala Pro
1 5 10 15

Val Pro Ala Leu Leu Ile Arg Thr Gln Thr Thr Met Ser Glu Ile Val
20 25 30

Ser Leu Leu Pro Ala Gly Ser Ser Asp Ile Leu Gln Leu Leu Ala Gly
35 40 45

Gln Gly Lys Ser Pro Ser Gly Pro Pro Phe Ala Arg Tyr Phe Gly Met
50 55 60

Ser Ala Gly Thr Phe Glu Val Glu Phe Gly Ala Pro Val Glu Gly Gly
65 70 75 80

Val Glu Gly Ser Gly Arg Val Val Thr Gly Leu Thr Pro Ser Gly Lys
85 90 95

Ala Ala Ser Ser Leu Tyr Ile Gly Pro Cys Gly Glu Ile Glu Ala Val
100 105 110

Tyr Asp Ala Leu Met Lys Trp Val Asp Asp Asn Gly Phe Asp Leu Ser
115 120 125

Gly Glu Ala Tyr Ser Ile Cys Leu Asp Tyr Pro Ala Glu Thr Ala Pro
130 135 140

Asp Gln Leu Arg Thr Arg Val Ser Leu Met Leu His Glu Ser Leu Glu
145 150 155 160

His His His His His His
165

<210> SEQ ID NO 47
<211> LENGTH: 166
<212> TYPE: PRT
<213> ORGANISM: Escherichia coli

<400> SEQUENCE: 47

```
Met Asp Phe Glu Cys Gln Phe Val Cys Tyr Leu Lys Glu Leu Ala Pro
1               5                   10                  15

Val Pro Ala Leu Leu Ile Arg Thr Gln Thr Thr Met Ser Glu Asp Ser
            20                  25                  30

Ser Leu Arg Tyr Ala Gly Lys Ser Asp Ile Gly Gln Leu Leu Ala Gly
        35                  40                  45

Gln Gly Lys Ser Pro Ser Gly Pro Pro Phe Ala Arg Tyr Phe Gly Met
    50                  55                  60

Ser Ala Gly Thr Phe Glu Val Glu Phe Gly Thr Pro Val Glu Gly Gly
65                  70                  75                  80

Val Glu Gly Ser Gly Arg Val Val Thr Gly Leu Thr Pro Ser Gly Lys
                85                  90                  95

Ala Ala Ser Ser Leu Tyr Ile Gly Pro Val Gly Glu Ile Glu Ala Val
            100                 105                 110

Tyr Asp Ala Leu Met Lys Trp Val Asp Asp Asn Gly Phe Asp Leu Ser
        115                 120                 125

Gly Glu Ala Tyr Arg Ile Leu Leu Asp Thr Pro Ala Glu Thr Ala Pro
    130                 135                 140

Asp Gln Leu Arg Thr Arg Val Ser Leu Met Leu His Glu Ser Leu Glu
145                 150                 155                 160

His His His His His His
                165
```

<210> SEQ ID NO 48
<211> LENGTH: 166
<212> TYPE: PRT
<213> ORGANISM: Escherichia coli

<400> SEQUENCE: 48

```
Met Asp Phe Glu Cys Gln Phe Val Cys Glu Leu Lys Glu Leu Ala Pro
1               5                   10                  15

Val Pro Ala Leu Leu Ile Arg Thr Gln Thr Thr Met Ser Glu Gly Val
            20                  25                  30

Ser Leu Asp Cys Ala Gly Arg Val Asp Ile Met Gln Leu Leu Ala Gly
        35                  40                  45

Gln Gly Lys Ser Pro Ser Gly Pro Pro Phe Ala Arg Tyr Phe Gly Met
    50                  55                  60

Ser Ala Gly Thr Phe Glu Val Glu Phe Gly Tyr Pro Val Glu Gly Gly
65                  70                  75                  80

Val Glu Gly Ser Gly Arg Val Val Thr Gly Leu Thr Pro Ser Gly Lys
                85                  90                  95

Ala Ala Ser Ser Leu Tyr Ile Gly Pro Val Gly Glu Ile Glu Ala Val
            100                 105                 110

Tyr Asp Ala Leu Met Lys Trp Val Asp Asp Asn Gly Phe Asp Leu Ser
        115                 120                 125

Gly Glu Ala Tyr Ser Ile Ala Leu Asp His Pro Ala Glu Thr Ala Pro
    130                 135                 140

Asp Gln Leu Arg Thr Arg Val Ser Leu Met Leu His Glu Ser Leu Glu
145                 150                 155                 160
```

His His His His His His
165

<210> SEQ ID NO 49
<211> LENGTH: 166
<212> TYPE: PRT
<213> ORGANISM: Escherichia coli

<400> SEQUENCE: 49

Met Asp Phe Glu Cys Gln Phe Val Cys Glu Leu Lys Glu Leu Ala Pro
1 5 10 15

Val Pro Ala Leu Leu Ile Arg Thr Gln Thr Thr Met Ser Glu Gly Val
20 25 30

Ser Leu Asp Cys Ala Gly Arg Val Asp Ile Met Gln Leu Leu Ala Gly
35 40 45

Gln Gly Lys Ser Pro Ser Gly Pro Pro Phe Ala Arg Tyr Phe Gly Met
50 55 60

Asn Ala Gly Thr Phe Glu Val Glu Phe Gly Tyr Pro Val Glu Gly Gly
65 70 75 80

Val Glu Gly Ser Gly Arg Val Val Thr Gly Leu Thr Pro Ser Gly Lys
85 90 95

Ala Ala Ser Ser Leu His Ile Gly Pro Val Gly Glu Ile Glu Ala Val
100 105 110

Tyr Asp Ala Leu Met Lys Trp Val Asp Asp Asn Gly Phe Asp Leu Ser
115 120 125

Gly Glu Ala Tyr Ser Ile Ala Leu Asp His Pro Ala Glu Thr Ala Pro
130 135 140

Asp Gln Leu Arg Thr Arg Val Ser Leu Met Leu His Glu Ser Leu Glu
145 150 155 160

His His His His His His
165

<210> SEQ ID NO 50
<211> LENGTH: 166
<212> TYPE: PRT
<213> ORGANISM: Escherichia coli

<400> SEQUENCE: 50

Met Asp Phe Glu Cys Gln Phe Val Cys Glu Leu Lys Glu Leu Ala Pro
1 5 10 15

Val Pro Ala Leu Leu Ile Arg Thr Gln Thr Thr Met Ser Glu Arg Arg
20 25 30

Ser Leu Val Leu Ala Gly Leu Leu Asp Ile Tyr Gln Leu Leu Ala Gly
35 40 45

Gln Gly Lys Ser Pro Ser Gly Pro Pro Phe Ala Arg Tyr Phe Gly Met
50 55 60

Ser Ala Gly Thr Phe Glu Val Glu Phe Gly Ile Pro Val Glu Gly Gly
65 70 75 80

Val Glu Gly Ser Gly Arg Val Val Thr Gly Leu Thr Pro Ser Gly Lys
85 90 95

Ala Ala Ser Ser Leu Tyr Ile Gly Pro Ile Gly Glu Ile Glu Ala Val
100 105 110

Tyr Asp Ala Leu Met Lys Trp Val Asp Asp Asn Gly Phe Asp Leu Ser
115 120 125

Gly Glu Ala Tyr Asp Ile Pro Leu Asp Val Pro Ala Glu Thr Ala Pro
130 135 140

Asp Gln Leu Arg Thr Arg Val Ser Leu Met Leu His Glu Ser Leu Glu
145 150 155 160

His His His His His His
165

<210> SEQ ID NO 51
<211> LENGTH: 166
<212> TYPE: PRT
<213> ORGANISM: Escherichia coli

<400> SEQUENCE: 51

Met Asp Phe Glu Cys Gln Phe Val Cys Glu Leu Lys Glu Leu Ala Pro
1 5 10 15

Val Pro Ala Leu Leu Ile Arg Thr Gln Thr Thr Met Ser Glu Tyr Ala
20 25 30

Ser Leu Pro Ala Ala Gly Asp Pro Asp Ile Cys Gln Leu Leu Ala Gly
35 40 45

Gln Gly Lys Ser Pro Ser Gly Pro Pro Phe Ala Arg Tyr Phe Gly Met
50 55 60

Ser Ala Gly Thr Phe Glu Val Glu Phe Gly Leu Pro Val Glu Gly Gly
65 70 75 80

Val Glu Gly Ser Gly Arg Val Val Thr Gly Leu Thr Pro Ser Gly Lys
85 90 95

Ala Ala Ser Ser Leu Tyr Ile Gly Pro Arg Gly Glu Ile Glu Ala Val
100 105 110

Tyr Asp Ala Leu Met Lys Trp Val Asp Asp Asn Gly Phe Asp Leu Ser
115 120 125

Gly Glu Ala Tyr Trp Ile Leu Leu Asp Arg Pro Ala Glu Thr Ala Pro
130 135 140

Asp Gln Leu Arg Thr Arg Val Ser Leu Met Leu His Glu Ser Leu Glu
145 150 155 160

His His His His His His
165

<210> SEQ ID NO 52
<211> LENGTH: 216
<212> TYPE: PRT
<213> ORGANISM: Escherichia coli

<400> SEQUENCE: 52

Met Gly Ser His His His His His His Thr Glu Lys Lys Ile Asp Phe
1 5 10 15

Lys Lys Glu Glu Lys Lys Phe Tyr Ala Pro Lys Arg Lys Pro Glu Arg
20 25 30

Ile Phe Val Pro Glu Met Asn Phe Leu Met Val Asp Gly Lys Gly Asp
35 40 45

Arg Leu Gly Glu Glu Pro Gln Lys Ala Gln Gln Ser Leu Ser Ala Ile
50 55 60

Ala Gly Thr Ile Lys Met Ser Lys Met Gly Glu Thr Arg Leu Asp Gly
65 70 75 80

Tyr Ser Asp Phe Val Val Pro Pro Lys Glu Gly Phe Gln Trp Ser Glu
85 90 95

Gly Lys Phe Asp Leu Lys Asp Arg Asp Ala Val Leu Trp Thr Ser Ile
100 105 110

Leu Arg Gln Pro Asp Phe Val Thr Glu Glu Val Leu Glu Trp Ala Lys
115 120 125

```
Glu Val Ala Arg Lys Lys Lys Pro Asp Val Asp Thr Ser Arg Val Lys
    130                 135                 140

Leu Val Arg Phe Glu Glu Gly Glu Cys Val Gln Met Met His Val Gly
145                 150                 155                 160

Asn Phe Ser Glu Phe Val His Thr Val Ala Glu Met His Gln Phe Met
                165                 170                 175

Glu Thr Glu Gly Leu Arg Asn Asp Thr Gly Ala Ile Arg Lys His His
            180                 185                 190

Ser Ile Val Leu Ser Ser Gly Gly Lys Ala Asn Pro Glu Lys Met Lys
        195                 200                 205

Thr Ile Leu Arg Leu Pro Val Ser
    210                 215


<210> SEQ ID NO 53
<211> LENGTH: 215
<212> TYPE: PRT
<213> ORGANISM: Escherichia coli

<400> SEQUENCE: 53

Met Gly Ser His His His His His His Thr Glu Lys Lys Ile Asp Phe
1               5                   10                  15

Lys Lys Glu Glu Lys Lys Phe Tyr Ala Pro Lys Arg Lys Pro Glu Arg
            20                  25                  30

Ile Phe Val Pro Glu Met Asn Phe Leu Ile Val Asp Gly Lys Gly Asp
        35                  40                  45

Ser Met Gly Glu Glu His Gln Lys Ala Ala Gln Ser Leu Ser Ala Ile
    50                  55                  60

Ala Asp Thr Ile Lys Met Ser Lys Met Gly Glu Thr Arg Leu Asp Gly
65                  70                  75                  80

Tyr Ser Asp Phe Val Val Pro Pro Phe Glu Gly Phe Arg Trp Ser Glu
                85                  90                  95

Gly Lys Phe Asp Cys Lys Asp Arg Asp Ala Leu Leu Trp Thr Ser Ile
            100                 105                 110

Leu Arg Gln Pro Asp Phe Val Thr Glu Glu Val Leu Glu Trp Ala Lys
        115                 120                 125

Glu Val Ala Arg Lys Lys Lys Pro Asp Val Asp Thr Ser Arg Val Lys
    130                 135                 140

Leu Val Arg Phe Glu Glu Gly Glu Cys Val Gln Met Met His Val Gly
145                 150                 155                 160

Leu Phe Ser Glu Leu Val His Thr Val Ala Glu Met His Gln Ser Met
                165                 170                 175

Glu Thr Glu Gly Leu Arg Asn Asp Thr Gly Ala Ile Arg Lys His His
            180                 185                 190

Arg Ile Val Leu Ser Asp Met Lys Ala Asn Pro Glu Lys Met Lys Thr
        195                 200                 205

Ile Leu Arg Leu Pro Val Ser
    210                 215


<210> SEQ ID NO 54
<211> LENGTH: 216
<212> TYPE: PRT
<213> ORGANISM: Escherichia coli

<400> SEQUENCE: 54

Met Gly Ser His His His His His His Thr Glu Lys Lys Ile Asp Phe
1               5                   10                  15
```

```
Lys Lys Glu Glu Lys Lys Phe Tyr Ala Pro Lys Arg Lys Pro Glu Arg
            20                  25                  30

Ile Phe Val Pro Glu Met Asn Phe Leu Met Val Asp Gly Lys Gly Asp
        35                  40                  45

Leu Val Gly Glu Glu Ile Gln Lys Ala Gly Gln Ser Leu Asp Ala Ile
    50                  55                  60

Ala Cys Thr Ile Lys Met Ser Lys Met Gly Glu Thr Arg Leu Asp Gly
65                  70                  75                  80

Tyr Ser Asp Phe Val Val Pro Pro Arg Glu Gly Phe Val Trp Ser Glu
                85                  90                  95

Gly Lys Phe Asp Leu Lys Asp Arg Asp Ala Tyr Leu Trp Thr Ser Ile
            100                 105                 110

Leu Arg Gln Pro Asp Phe Val Thr Glu Glu Val Leu Glu Trp Ala Lys
        115                 120                 125

Glu Val Ala Arg Lys Lys Lys Pro Asp Val Asp Thr Ser Arg Val Lys
    130                 135                 140

Leu Val Arg Phe Glu Glu Gly Glu Cys Val Gln Met Met His Val Gly
145                 150                 155                 160

Leu Phe Ser Glu Phe Val His Thr Val Ala Glu Met His Gln Phe Met
                165                 170                 175

Glu Thr Glu Gly Leu Arg Asn Asp Thr Gly Ala Ile Arg Lys His His
            180                 185                 190

Ile Ile Ser Leu Ser Ser His Met Lys Ala Asn Pro Glu Lys Met Lys
        195                 200                 205

Thr Ile Leu Arg Leu Pro Val Ser
    210                 215


<210> SEQ ID NO 55
<211> LENGTH: 216
<212> TYPE: PRT
<213> ORGANISM: Escherichia coli

<400> SEQUENCE: 55

Met Gly Ser His His His His His His Thr Glu Lys Lys Ile Asp Phe
1               5                   10                  15

Lys Lys Glu Glu Lys Lys Phe Tyr Ala Pro Lys Arg Lys Pro Glu Arg
            20                  25                  30

Ile Phe Val Pro Glu Met Asn Phe Leu Met Val Asp Gly Lys Gly Asp
        35                  40                  45

Leu Ala Gly Glu Glu Gln Gln Lys Ala Phe Gln Ser Leu Pro Ala Ile
    50                  55                  60

Ala Tyr Thr Ile Lys Met Ser Lys Met Gly Glu Thr Arg Leu Asp Gly
65                  70                  75                  80

Tyr Ser Asp Phe Val Val Pro Pro Thr Glu Gly Phe Arg Trp Ser Glu
                85                  90                  95

Gly Lys Phe Asp Gly Lys Asp Arg Asp Ala Ile Leu Trp Thr Ser Ile
            100                 105                 110

Leu Arg Gln Pro Asp Phe Val Thr Glu Glu Val Leu Glu Trp Ala Lys
        115                 120                 125

Glu Val Ala Arg Lys Lys Lys Pro Asp Val Asp Thr Ser Arg Val Lys
    130                 135                 140

Leu Val Arg Phe Glu Glu Gly Glu Cys Val Gln Met Met His Val Gly
145                 150                 155                 160

Leu Phe Ser Glu Phe Val His Thr Val Ala Glu Met His Gln Phe Met
                165                 170                 175
```

-continued

```
Glu Thr Glu Gly Leu Arg Asn Asp Thr Gly Ala Ile Arg Lys His His
            180                 185                 190

Phe Ile Thr Leu Ser Phe Phe Cys Lys Ala Asn Pro Glu Lys Met Lys
        195                 200                 205

Thr Ile Leu Arg Leu Pro Val Ser
    210                 215


<210> SEQ ID NO 56
<211> LENGTH: 216
<212> TYPE: PRT
<213> ORGANISM: Escherichia coli

<400> SEQUENCE: 56

Met Gly Ser His His His His His His Thr Glu Lys Lys Ile Asp Phe
1               5                   10                  15

Lys Lys Glu Glu Lys Lys Phe Tyr Ala Pro Lys Arg Lys Pro Glu Arg
            20                  25                  30

Ile Phe Val Pro Glu Met Asn Phe Leu Met Val Asp Gly Lys Gly Asp
        35                  40                  45

Phe Cys Gly Glu Glu Ser Gln Lys Ala Trp Gln Ser Leu Glu Ala Ile
    50                  55                  60

Ala Tyr Thr Ile Lys Met Ser Lys Met Gly Glu Thr Arg Leu Asp Gly
65                  70                  75                  80

Tyr Ser Asp Phe Val Val Pro Pro Thr Glu Gly Phe Arg Trp Ser Glu
                85                  90                  95

Gly Lys Phe Asp Pro Lys Asp Arg Asp Ala Ile Leu Trp Thr Ser Ile
            100                 105                 110

Leu Arg Gln Pro Asp Phe Val Thr Glu Glu Val Leu Glu Trp Ala Lys
        115                 120                 125

Glu Val Ala Arg Lys Lys Lys Pro Asp Val Asp Thr Ser Arg Val Lys
    130                 135                 140

Leu Val Arg Phe Glu Glu Gly Glu Cys Val Gln Met Met His Val Gly
145                 150                 155                 160

His Phe Ser Glu Gly Val His Thr Val Ala Glu Met His Gln Phe Met
                165                 170                 175

Glu Thr Glu Gly Leu Arg Asn Asp Thr Gly Ala Ile Arg Lys His His
            180                 185                 190

Phe Ile Leu Leu Ser Asn Phe Gly Lys Ala Asn Pro Glu Lys Met Lys
        195                 200                 205

Thr Ile Leu Arg Leu Pro Val Ser
    210                 215


<210> SEQ ID NO 57
<211> LENGTH: 216
<212> TYPE: PRT
<213> ORGANISM: Escherichia coli

<400> SEQUENCE: 57

Met Gly Ser His His His His His His Thr Glu Lys Lys Ile Asp Phe
1               5                   10                  15

Lys Lys Glu Glu Lys Lys Phe Tyr Ala Pro Lys Arg Lys Pro Glu Arg
            20                  25                  30

Ile Phe Val Pro Glu Met Asn Phe Leu Met Val Asp Gly Lys Gly Asp
        35                  40                  45

Pro Asp Gly Glu Glu Tyr Gln Lys Ala Val Gln Ser Leu Ser Ala Ile
    50                  55                  60
```

```
Ala Tyr Thr Ile Lys Met Ser Lys Met Gly Glu Thr Arg Leu Asp Gly
65                  70                  75                  80

Tyr Ser Asp Phe Val Val Pro Pro Ser Glu Gly Phe Met Trp Ser Glu
                85                  90                  95

Gly Lys Phe Asp Ala Lys Asp Arg Asp Ala Ser Leu Trp Thr Ser Ile
            100                 105                 110

Leu Arg Gln Pro Asp Phe Val Thr Glu Glu Val Leu Glu Trp Ala Lys
        115                 120                 125

Glu Val Ala Arg Lys Lys Lys Pro Asp Val Asp Thr Ser Arg Val Lys
    130                 135                 140

Leu Val Arg Phe Glu Glu Gly Glu Cys Val Gln Met Met His Val Gly
145                 150                 155                 160

Pro Phe Ser Glu Tyr Val His Thr Val Ala Glu Met His Gln Phe Met
                165                 170                 175

Glu Thr Glu Gly Leu Arg Asn Asp Thr Gly Ala Ile Arg Lys His His
            180                 185                 190

His Ile Ser Leu Ser Cys Ser Lys Lys Ala Asn Pro Glu Lys Met Lys
        195                 200                 205

Thr Ile Leu Arg Leu Pro Val Ser
    210                 215


<210> SEQ ID NO 58
<211> LENGTH: 165
<212> TYPE: PRT
<213> ORGANISM: Escherichia coli

<400> SEQUENCE: 58

Met Glu Tyr Gln Leu Gln Gln Leu Ala Ser Leu Thr Leu Val Gly Ile
1               5                   10                  15

Lys Glu Thr Tyr Glu Asn Gly Arg Gln Ala Val Gln His Asn Asn Gly
            20                  25                  30

Phe Pro Gln Arg Cys Glu Gln Glu Gly Val Ile Ala Asp Leu Gln Leu
        35                  40                  45

Lys Asn Asn Gly Asp Leu Ala Gly Ile Leu Gly Leu Cys Ile Pro Glu
    50                  55                  60

Leu Asp Gly Lys Met Ser Tyr Met Ile Ala Val Thr Gly Asp Asn Ser
65                  70                  75                  80

Ala Asp Ile Ala Lys Tyr Asp Val Ile Thr Leu Ala Ser Ser Lys Tyr
                85                  90                  95

Met Val Phe Glu Ala Gln Gly Ala Thr Val Lys Ala Val His Gln Lys
            100                 105                 110

His Glu Glu Val His His Tyr Ile His Gln Tyr Gln Ala Asn Thr Val
        115                 120                 125

Lys Ser Ala Pro Phe Phe Val Leu Tyr Gln Asp Gly Asp Gly Thr Ser
    130                 135                 140

Glu Lys Tyr Ile Thr Glu Ile Trp Met Pro Val Lys Gly Leu Glu His
145                 150                 155                 160

His His His His His
                165


<210> SEQ ID NO 59
<211> LENGTH: 165
<212> TYPE: PRT
<213> ORGANISM: Escherichia coli

<400> SEQUENCE: 59
```

-continued

```
Met Glu Tyr Gln Leu Gln Gln Leu Ala Ser Leu Thr Leu Val Gly Ile
1               5                   10                  15

Lys Glu Thr Tyr Glu Asn Gly Arg Gln Ala Asn Gln His Thr Thr Gly
            20                  25                  30

Phe Asn Gln Arg Cys His Gln Glu Gly Val Ile Ala Asp Leu Gln Leu
        35                  40                  45

Lys Asn Asn Gly Asp Leu Ala Gly Ile Leu Gly Leu Cys Ile Pro Glu
    50                  55                  60

Leu Asp Gly Lys Met Ser Tyr Met Ile Ala Val Thr Gly Asp Asn Ser
65                  70                  75                  80

Ala Asp Ile Ala Lys Tyr Asp Val Ile Thr Leu Ala Ser Ser Lys Tyr
                85                  90                  95

Met Val Phe Glu Ala Gln Gly Ala Thr Cys Lys Ala Ser Thr Gln Lys
            100                 105                 110

Gly Glu Glu Val His His Tyr Ile His Gln Tyr Gln Ala Asn Thr Val
        115                 120                 125

Lys Ser Ala Pro Phe Phe Ala Leu Phe Gln Asp Gly Asp Val Thr Ser
    130                 135                 140

Glu Lys Tyr Ile Thr Glu Ile Trp Met Pro Val Lys Gly Leu Glu His
145                 150                 155                 160

His His His His His
                165
```

ENGINEERED GYRI-LIKE MUTEIN APTAMERS, AND RELATED METHODS

CROSS-REFERENCE

The present application claims priority to U.S. Provisional Application No. 62/934,668, filed on Nov. 13, 2019, which is hereby incorporated by reference therein.

SEQUENCE LISTING

The instant application contains a Sequence Listing which has been submitted electronically in ASCII format and is hereby incorporated by reference in its entirety. Said ASCII copy, created on Nov. 4, 2020, is named 128617-001WO_SL.txt and is 81,184 bytes in size.

FIELD OF INVENTION

The present invention pertains to the field of protein engineering, molecular imaging, molecular diagnostics, and biopharmaceutics.

BACKGROUND

Biomolecular engineering coupled with directed evolution methods have provided important tools for the biotechnological and biopharmaceutical fields. The ability to improve function or select for novel function has yielded important variants of specialized antibodies, gene editing tools, antibody alternatives, prodrug and drug delivery technologies that have transformed industry, research, and medicine. The challenges in biomolecular engineering are finding a suitable protein, RNA, or in some cases DNA aptamer from a large library of randomized variants and also a robust method of accurate selection. Nevertheless, biomolecular engineering is progressively becoming more successful due to the growing number of protein domains being identified from comparative genomics and improved methods of nucleic acid synthesis and modification.

Protein engineering has afforded numerous biotechnological tools. Using biochemistry and molecular biology techniques several groundbreaking inventions capitalize on natural function of biological macromolecules by engineering them towards useful biotechnological applications. It is now possible to identify important tools such as engineered antibodies that bind target molecules of interest, genome synthesis and genome modifying tools, therapeutic proteins, and engineered enzymes with broad functionality. Modern developments in biotechnological tools along with the demand for versatile proteins for multiple applications continue to drive the field of protein engineering.

Engineered antibodies play a pivotal role in research, diagnostics, and therapeutics. The natural ability of monoclonal antibodies to recognize a wide range of antigens that include nucleic acids, proteins, sugars, metals and small molecules with reasonable affinity makes them the premier molecule for biological recognition in biotechnology. In the past decade, a majority of the best-selling, most effective drugs have been innovations and engineering of monoclonal antibodies. Furthermore, antibodies have become crucial components of cellular imaging, molecular diagnostic technology for detecting biomarkers, and novel mechanisms of targeted drug delivery. Even though antibodies have been so transformative to research and biotechnology, their complexity and high effective cost of manufacturing and maintenance continue to hamper their efficient use as tools in biotechnology and medicine.

Advances in research and bioengineering has allowed for the creation of aptamer variants that work similar to monoclonal antibiodies. These aptamers are able to recognize target molecules of interest with high affinity and sensitivity. In the case of small molecule recognition, aptamers have overcome the challenge of designing a biological recognition motif especially when antibody screening has failed. Aptamers display favorable properties such as small size, higher yields from production, cost-effectiveness, low cross-reactivity, longer shelf life, and the ability to work in non-physiological conditions. To date, aptamers that have been designed for use in biotechnological and medical applications include Anticalins, DARPins, Advimers, TALENs, Zn-finger nucleases, Knottins, ect. Anticalins and DARPins are versatile enough that they can be designed to replace antibodies in many applications. In fact, several of these technologies are currently being investigated in late stage clinical trials.

Fluorescent proteins GFP, RFP, YFP and their engineered variants have provided molecular technology that has revolutionized cellular imaging by providing vast and detailed information on physiological processes. Using such technology the expression of endogenous proteins can be monitored spatially and temporally, in addition to tracking cellular localization or biological interactions. Over the past 20 years fluorescence imaging has been a pioneering method to study biological pathways in cancer, developmental biology, neuroscience and pharmacology. The creation of brighter and more photostable variants of natural fluorescent protein was a key step in the development of powerful cellular imaging technologies used currently to image biological specimen. The cellular resolution of these variants is powerful enough that single molecule biophysical studies can be conducted as low as the nanometer scale. These variants were created by mutagenesis and screening for mutants with higher photostability and improved quantum yields. Even though fluorescent proteins and their photostable variants had profound effects on the development on cellular imaging technologies, the chemical process of fluorophore maturation and protein folding still presents several limitations. If fluorescent proteins that do not rely on fluorophore chemical maturation or proteins with improved protein folding could be designed then fluorescence imaging technologies could be created to overcome the limitations of natural fluorescent proteins and their engineered derivatives.

Recent advancements have demonstrated synthetic ways of creating engineered fluorescent modules that work similarly to natural fluorescent proteins. These modules work by a mechanism of fluorescent enhancement where a non-fluorescent aptamer and non-fluorescent or weakly fluorescent fluorophore bind together and the complex then becomes fluorescent. Such modules provide a switch-activated fluorescent system where fluorescence is not dependent on folding or chemical maturation, but solely on the association of two components. The first of such modules was a RNA-based fluorescent aptamer that was selected to bind to the non-fluorescent dye malachite green and activate its fluorescence. The malachite green aptamer provided the basis for the discovery of improved and less cytotoxic modules that work in a similar fashion. These modules are also RNA aptamers, which were selected to binding to chemical analogs of GFP, RFP, and YFP fluorophores called spinach, corn, and mango, respectively. Together, these RNA aptamers represent synthetic mimics of natural fluorescent proteins and all work through the same mechanism of fluorescence enhancement. In all cases the weakly fluorescent fluorophore is trapped in an aromatic environment formed by G-quadruplex secondary structure in the RNA aptamers. This ligand-binding interaction is driven by the hydrophobic effect and severely limits the rotational freedom of chemical moieties in the fluorophore, thus causing higher absorption and emission of light. To date, these fluorescent RNAs have been utilized as fluorogenic reporters in cellular imaging technology to study mRNA expression, protein synthesis, mRNA localization, splicing or even as RNA-based biosensors. However, RNA-based fluorescent aptamers also present limitations because they can mainly be used to study processes involving RNA, in addition to poor in vivo folding of RNA quadruplex structures that limits fluorophore binding and fluorescence activation.

Synthetic fluorescent proteins that work similarly to fluorogenic RNAs can selectively identified or be rationally designed. Over the past decade several Fluorogen-activating proteins (FAPs) have been designed using antibody binding technology. These FAPs are capable of binding to weak fluorophores like Malachite Green, Dimethyl Indole red and Thiazole Orange and thereby activate their fluorescence. More recently, computational studies have shown that a de novo β-barrel designed to binding fluorophore analog of GFP can be used as a fluorescence enhancement aptamer. This aptamer works similarly to GFP, even though the types of fluorophore interactions are significantly different between the natural occurring and synthetic β-barrels. In fact, the synthetic GFP β-barrel also works in vivo, although it is 35-fold weaker than engineered GFP. However, there is room for considerable improvement of fluorescence enhancement through mutational screening and computational design.

Rationally design β-barrel fluorescent proteins and FAPs demonstrated important principles that can be applied to the design of other fluorescence enhancing proteins. The important interactions were specific hydrogen bonds with polar groups on fluorophores that are further stabilized by a mostly hydrophobic environment. These restricting interactions reduce the degrees of freedom for rotation of fluorgens and stimulate fluorescence through such interactions. For fluorescent RNA aptamers, fluorescence-enhancing interactions were solely through aromatic interactions with minor contributions from polar interactions. Building on these principles it is highly likely that proteins which contain multispecific binding sites with a mixture of aromatic and polar residues could serve as important templates for the design of strong fluorescence enhancement aptamers.

There is a continuously expanding need for rapid, highly specific methods of detecting and quantifying chemical, biochemical and biological substances as analytes in research and diagnostic mixtures. Of particular value are methods for measuring small quantities of nucleic acids, peptides, saccharides, pharmaceuticals, metabolites, microorganisms and other materials of diagnostic value. Examples of such materials include narcotics and poisons, drugs administered for therapeutic purposes, hormones, pathogenic microorganisms and viruses, peptides, e.g., antibodies and enzymes, and nucleic acids, particularly those implicated in disease states.

There is a need in the art for improved enzymes or proteins for use in molecular imaging, and molecular diagnostics.

SUMMARY

The present invention relates to the field of protein engineering, molecular imaging, and molecular diagnostics. More particularly, provided herein are novel methods to design synthetic non-native variant aptamers using the Gyrl-like family of proteins as a scaffold, whereby the non-native variant proteins are also referred to as GYRAPTs or GYRYZYMEs. Also provided herein are non-native variant GYRAPTs or GYRYZYME aptamers that can bind numerous target organic molecules. In particular embodiments, the invention Gyrl-like variant GYRAPTs or GYRYZYME aptamers are useful as on/off bioswitches, and are far less complex than current switches and do not require the use of proteases. In other embodiments, the invention dual on/off bioswitches utilizing Gyrl-like variant GYRAPTs or GYRYZYME aptamers can be used for monitoring complex biological processes in real time in vivo and in vitro.

Gyrl-like proteins are widely distributed in prokaryotes and eukaryotes, and recognized as small-molecule binding proteins. The Gyrl-like family of proteins (PFAM PF06445) represents a multispecific binding scaffold that contains the necessary properties to create versatile aptamers. This large family contains proteins with a small ligand-binding domain (~15 kDa) that is defined by a symmetric duplication of a sheet-helix-sheet-sheet motif. Even though the family is partially characterized, some Gyrl-like proteins have been shown to extensively bind a wide range of small molecules that include organic dyes, antibiotics, anticancer drugs, detergents, and quaternary amines. The best-characterized member is BmrR, a bacterial transcription factor that acts as a drug sensor and activator of multidrug resistance pathways. BmrR can bind a wide range of chemical structures that significantly differ in chemical and physical properties. Although the mechanism of promiscuous ligand recognition by BmrR is understood, it is not a suitable template for aptamer design because of its multidomain complexity. Nevertheless, there exist multiple small, single domain Gyrl-like proteins, some of which are partially characterized, that are ideal candidates for versatile aptamer design. These include SAV2435 from *S. aureus*, CTR107 from *C. tepidium*, and LIN2189 from *L. innocua* (FIG. 1). All three have been structurally characterized and contain binding elements that are similar to the BmrR promiscuous ligand-binding domain. Their small size and stable tertiary fold allow for the generation of mutant libraries that can be easily screened for binding to target molecules. SAV2435 and CTR107 can bind organic dyes, while LIN2189 is an enzyme that can hydrolyze cyclopropanoid antibiotics, but its degree of promiscuity is unknown. The variability of the binding site of all three proteins provides suitable starting templates to screen for small molecule-binding aptamers that can function is broad-scale applications.

This invention describes materials and a simplified method for identifying recombinant aptamers, termed GYRAPTs, that bind to various organic molecules designed from the Gyrl-like family of proteins. Here we describe a collection of recombinant engineered GYRAPTS that can bind to organic molecules using our designed screening assays. Furthermore, this invention discusses protocols for creating specific organic molecule-binding GYRAPTS through rational mutagenesis or through mutant library screening. In addition, we describe methods of creating promiscuous enzymes, called GYRYZYMEs, that can enzymatically modify the chemical structures of organic molecules. This invention demonstrates a method of creating drug-binding aptamers that can be used to improve drug properties and drug action. Because of the versatility of our inventions a wide range of biotechnological tools can be created. Using publicly available bioinformatics data, a strategy for randomizing the binding site of Gyrl-like proteins to achieve favorable target binding after initial screens is described. Moreover, this invention shows how different Gyrl proteins can induce varying effect on the fluorescent properties of different fluorophores and outlines a strategy of initially screening multiple Gyrl-like proteins for desired function followed by mutagenesis and selection. The invention will lead to the development of aptamers that can bind any target organic molecule of interest, including therapeutic drugs. Moreover, the invention will lead to molecular fluorescent switches that controlled shut on or shut off properties that can be applied to a wide range of biotechnological applications. A molecular switch of this kind can be used in a wide range of applications such as biosensor design, molecular diagnostic tools, cellular imaging technology, and in therapeutics. Overall, the experimental approach listed in this invention demonstrates the identification of versatile aptamers that can operate in broad functionality in conjunction with organic dyes.

The invention methods provide a detailed protocol for creating fluorescent enhancement modules by engineering the natural ability of selected Gyrl-like proteins to bind and activate or shut-off fluorescent compounds. In other embodiments, the invention methods provided herein further improve the fluorescence enhancing or quenching properties of Gyrl-like proteins using rational protein engineering or through protein mutant library screening. The invention methods and non-native variant aptamers can be used as versatile biotechnological tools for molecular imaging or molecular diagnostics purposes.

Additionally, the invention methods provide an efficient strategy and protocol for screening various Gyrl-like protein family members for desired aptamer function, all of which demonstrate different binding capabilities for target organic compounds. The invention methods provided herein demonstrate how novel and useful non-native variant aptamers can be isolated from rational design and screening of mutants. Accordingly, provided herein are novel and versatile non-native variant aptamer enzymes (e.g., GYRYZYMEs) are produced through mutation and screening of Gryl-like proteins. Using the invention methods provided herein, additional high affinity GYRAPTS or GYRYZYMEs can be readily isolated. The invention non-native variant aptamers are useful in several broad-scale applications in biotechnology and medicine.

Accordingly, provided herein are the following items:

1. A non-native variant aptamer comprising any combination of one up to all 13 of variant amino acids, relative to wild-type SAV2435, among all variant-positions in the polypeptide set forth in FIG. 20/SEQ ID NO:2; wherein the variant positions correspond to amino acid positions 27, 30, 31, 34, 38, 105, 106, 109, 110, 113, 135, 137 and 142 of SEQ ID NO:1.
2. The non-native variant aptamer of item 1, wherein the variant aptamer comprises a variant amino acid at a number of variant-positions set forth in FIG. 20/SEQ ID NO:2 compared to wild-type SAV2435, wherein the number of variant-positions is selected from the group consisting of: 1, 2, 3, 4, 5, 6, 7, 8, 9, 10, 11, 12, and 13.
3. The non-native variant aptamer of items 1-2, wherein the variant aptamer is capable of one or more functions selected from: fluorescence enhancement of a dye; or fluorescence quenching of a dye; binding to a target-molecule; or enzymatic activity.
4. The non-native variant aptamer of items 1-3, wherein the variant aptamer is capable of fluorescence enhancement of a dye, and wherein the dye is selected from the group consisting of: SYTO9, DHMBI, Malachite Green, Thiazole Orange, Thioflavin T, Atto495, and Acridine Orange.
5. The non-native variant aptamer of items 1-3, wherein the variant aptamer is capable of fluorescence quenching of a dye, wherein the dye is selected from the group consisting of 5(6)-Carboxfluorescein, 5-Carboxytetramethylrhodamine, and oxazine.
6. The non-native variant aptamer of items 1-3, wherein the variant aptamer is capable of binding to a target-molecule selected from the group consisting of: small-molecules, proteins, oligonucleotides, oligosaccharides, lipids, peptides, and polymers.
7. The non-native variant aptamer of items 1-3, wherein the variant aptamer is capable of binding to a molecule selected from the group consisting of: FAM, CY5, Thiazole-orange, Cytarabine, SARS-Cov-2 spike protein, SYTO9, DHMBI, Malachite Green, Thiazole Orange, Thioflavin T, Atto495, Acridine Orange, 5(6)-Carboxfluorescein, 5-Carboxytetramethylrhodamine, and oxazine.
8. The non-native variant aptamer of items 1-7, wherein the variant aptamer is selected from the group consisting of: SAV2435 N27W (SEQ ID NO:8); SAV2435 V105W (SEQ ID NO:10); SAV2435 P106W (SEQ ID NO:12); SAV2435 E135Q (SEQ ID NO:14); SAV2435 Y137W (SEQ ID NO:16); and SEQ ID NOs:40-45 and SEQ ID NOs:58-59.
9. A non-native variant aptamer comprising any combination of one up to all 12 of variant amino acids, relative to wild-type CTR107, among all variant-positions in the polypeptide set forth in FIG. 20/SEQ ID NO:4; wherein the variant positions correspond to amino acid positions 31, 32, 35, 36, 39, 40, 43, 75, 106, 133, 135 and 138 of SEQ ID NO:4.
10. The non-native variant aptamer of item 9, wherein the variant aptamer comprises a variant amino acid at a number of variant-positions set forth in FIG. 20/SEQ ID NO:4 compared to wild-type CTR107, wherein the number of variant-positions is selected from the group consisting of: 1, 2, 3, 4, 5, 6, 7, 8, 9, 10, 11, and 12.
11. The non-native variant aptamer of items 9-10, wherein the variant aptamer is capable of one or more functions selected from: fluorescence enhancement of a dye; or fluorescence quenching of a dye; binding to an organic molecule; or enzymatic activity.
12. The non-native variant aptamer of items 9-11, wherein the variant aptamer is capable of fluorescence enhancement of a dye, and wherein the dye is selected from the group consisting of: SYTO9, DHMBI, Malachite Green, Thiazole Orange, Thioflavin T, Atto495, and Acridine Orange.
13. The non-native variant aptamer of items 9-11, wherein the variant aptamer is capable of fluorescence quenching of a dye, wherein the dye is selected from the group consisting of 5(6)-Carboxfluorescein, 5-Carboxytetramethylrhodamine, and oxazine.
14. The non-native variant aptamer of items 9-11, wherein the variant aptamer is capable of binding to an organic molecule selected from the group consisting of: small-molecules, proteins, oligonucleotides, oligosaccharides, lipids, peptides, and polymers.
15. The non-native variant aptamer of items 9-11, wherein the variant aptamer is capable of binding to a molecule selected from the group consisting of: FAM, CY5, Thiazole-orange, Cytarabine, SARS-Cov-2 spike protein, SYTO9, DHMBI, Malachite Green, Thiazole Orange, Thioflavin T, Atto495, Acridine Orange5(6)-Carboxfluorescein, 5-Carboxytetramethylrhodamine, and oxazin.

16. The non-native variant aptamer of items 9-15, wherein the variant aptamer is selected from the group consisting of: CTR107 E36R (SEQ ID NO:18); CTR107 Y106W (SEQ ID NO:20); CTR107 E133Q (SEQ ID NO:22); CTR107 E36R (SEQ ID NO:18); CTR107 TRIP E36R H40Y Y106W (SEQ ID NO:24); CTR107 QUAD E36R H40Y Y106W E133Q (SEQ ID NO:26); and SEQ ID NOs:33-39 and SEQ ID NOs:46-50.
17. A non-native variant aptamer comprising any combination of one up to all 17 of variant amino acids, relative to wild-type LIN2189, among all variant-positions in the polypeptide set forth in FIG. 20/SEQ ID NO:6; wherein the variant positions correspond to amino acid positions 41, 42, 46, 50, 54, 58, 81, 85, 93, 99, 154, 157, 185, 187, 190, 191 and 192 of SEQ ID NO:6.
18. The non-native variant aptamer of item 17, wherein the variant aptamer comprises a variant amino acid at a number of variant-positions set forth in FIG. 20/SEQ ID NO:6 compared to wild-type LIN2189, wherein the number of variant-positions is selected from the group consisting of: 1, 2, 3, 4, 5, 6, 7, 8, 9, 10, 11, 12, 13, 14, 15, 16 and 17.
19. The non-native variant aptamer of item 17-18, wherein the variant aptamer is capable of one or more functions selected from: fluorescence enhancement of a dye; or fluorescence quenching of a dye; binding to an organic molecule; or enzymatic activity.
20. The non-native variant aptamer of items 17-19, wherein the variant aptamer is capable of fluorescence enhancement of a dye, and wherein the dye is selected from the group consisting of: SYTO9, DHMBI, Malachite Green, Thiazole Orange, Thioflavin T, Atto495, and Acridine Orange.
21. The non-native variant aptamer of items 17-19, wherein the variant aptamer is capable of fluorescence quenching of a dye, wherein the dye is selected from the group consisting of 5(6)-Carboxfluorescein, 5-Carboxytetramethylrhodamine, and oxazine.
22. The non-native variant aptamer of item 19, wherein the variant aptamer is capable of binding to an organic molecule selected from the group consisting of: small-molecules, proteins, oligonucleotides, oligosaccharides, lipids, peptides, and polymers.
23. The non-native variant aptamer of items 17-19, wherein the variant aptamer is capable of binding to a molecule selected from the group consisting of: FAM, CY5, Thiazole-orange, Cytarabine, SARS-Cov-2 spike protein, SYTO9, DHMBI, Malachite Green, Thiazole Orange, Thioflavin T, Atto495, Acridine Orange, 5(6)-Carboxfluorescein, 5-Carboxytetramethylrhodamine, and oxazine.
24. The non-native variant aptamer of item 17-23, wherein the variant aptamer is selected from the group consisting of: LIN2189 E157A (SEQ ID NO:28); LIN2189 E185L (SEQ ID NO:30); and LIN2189 DUB E157A, E185L (SEQ ID NO:32); and SEQ ID NOs: 52-57.
25. An engineered non-native aptamer selected from the group consisting of:

SAV2435 N27W (SEQ ID NO:8); SAV2435 V105W (SEQ ID NO:10); SAV2435 P106W (SEQ ID NO12); SAV2435 E135Q (SEQ ID NO:14); SAV2435 Y137W (SEQ ID NO:16); CTR107 E36R (SEQ ID NO:18); CTR107 Y106W (SEQ ID NO:20); CTR107 E133Q (SEQ ID NO:22); CTR107 TRIP (E36R, H40Y, Y106W)(SEQ ID NO:24); CTR107 QUAD (E36R, H40Y, Y106W, E133Q) (SEQ ID NO:26); LIN2189 E157A (SEQ ID NO:28); LIN2189 E185L (SEQ ID NO:30); and LIN2189 DUB (E157A, E185L)(SEQ ID NO:32); and SEQ ID NOs:33-59.

26. A fluorescence-on/off bioswitch system comprising:
    a first Gyrl-like aptamer; and
    a fluorogenic dye.
27. The bioswitch system of item 26, wherein the dye is selected from the group consisting of: 5(6)-Carboxfluorescein (FAM), 5-Carboxytetramethylrhodamine (TAMRA), oxazine), SYTO9, DHMBI, Malachite Green, Thiazole Orange, Thioflavin T, Atto495, and Acridine Orange.
28. The bioswitch system of items 26-27, wherein the Gyrl-like aptamer is a non-native variant Gyrl-like aptamer that is thermostable and/or pH-stable.
29. The bioswitch system of items 26-28, further comprising a second Gyrl-like aptamer.
30. The bioswitch system of item 26-29, wherein the dye is Atto495; and the first and second aptamers are selected from the group consisting of: CTR107 E133Q and SAV2435 N27W; CTR107 E133Q and SAV2435 Y137W; CTR107 E133Q and CTR107 Y106W; CTR107 E133Q and LIN2189 E157A-E185L double mutant; SAV2435 E135Q and SAV2435 N27W; SAV2435 E135Q and SAV2435 Y137W; SAV2435 E135Q and CTR107 Y106W; and SAV2435 E135Q and LIN2189 E157A-E185L double mutant.
31. The bioswitch system of item 26-29, wherein the dye is Acridine Orange; and the first aptamer is selected from the group consisting of any one or more of: SAV2435 E135Q, SAV2435 V105W, SAV2435 P106W, CTR107 WT and CTR107 E133Q; and second aptamer is selected from the group consisting of any one or more of: SAV2435 WT, SAV2435 N27W, SAV2435 Y137W, CTR107 Y106W.
32. The bioswitch system of item 26-29, wherein the dye is Acridine Orange; and the first and second aptamers are selected from the group consisting of: SAV2435 E135Q and SAV2435 WT, SAV2435 E135Q and SAV2435 N27W, SAV2435 E135Q and SAV2435 Y137W, SAV2435 E135Q and CTR107 Y106W, SAV2435 V105W and SAV2435 WT, SAV2435 V105W and SAV2435 N27W, SAV2435 V105W and SAV2435 Y137W, SAV2435 V105W and CTR107 Y106W, SAV2435 P106W and SAV2435 WT, SAV2435 P106W and SAV2435 N27W, SAV2435 P106W and SAV2435 Y137W, SAV2435 P106W and CTR107 Y106W, CTR107 WT and SAV2435 WT, CTR107 WT and SAV2435 N27W, CTR107 WT and SAV2435 Y137W, CTR107 WT and CTR107 Y106W, CTR107 E133Q and SAV2435 WT, CTR107 E133Q and SAV2435 N27W, CTR107 E133Q and SAV2435 Y137W, and CTR107 E133Q and CTR107 Y106W.
33. A method of detecting a biological signal, said method comprising providing to a biological sample a molecular probe having a fluorophore label; and contacting the molecular probe with a Gyrl-like protein.
34. The method of item 33, wherein upon contact with the Gyrl-like protein, fluorescence of the molecular probe is either increased or decreased.
35. The method of items 33-34, wherein the Gyrl-like protein utilized is a Gyrl-like variant protein.

36. The method of item 33-35, wherein the fluorescence is increased by an amount selected from at least: 2-fold, 3-fold, 4-fold, 5-fold, 10-fold, 15-fold, 20-fold, 30-fold, 40-fold, 50-fold, 60-fold, 70-fold, 80-fold, 90-fold, 100-fold, 200-fold, 300-fold, 400-fold, 500-fold, 600-fold, 700-fold, 800-fold, 900-fold, 1000-fold, or more.
37. The method of item 33-35, wherein the fluorescence is decreased by an amount selected from at least: 2-fold, 3-fold, 4-fold, 5-fold, 10-fold, 15-fold, 20-fold, 30-fold, 40-fold, 50-fold, 60-fold, 70-fold, 80-fold, 90-fold, 100-fold, 200-fold, 300-fold, 400-fold, 500-fold, 600-fold, 700-fold, 800-fold, 900-fold, 1000-fold, or more.
38. The method of items 33-37, wherein the fluorophore is DFHBI or Malechite Green and the Gyrl-like protein is selected from the group consisting of: SAV2435 and CTR107.
39. The method of items 33-37, wherein the fluorophore is Thiazole Orange and the Gyrl-like protein is selected from the group consisting of: SAV2435 WT, SAV2435 V105W, SAV2435 P106W, CTR107 Y106W, SEQ ID NOs:50-51, and SEQ ID NOs:54-55.
40. The method of items 33-37, wherein the fluorophore is Thioflavin T and the Gyrl-like protein is selected from the group consisting of: CTR107 WT and LIN2189 WT.
41. The method of items 33-37, wherein the fluorophore is Atto495 and the Gyrl-like protein is selected from the group consisting of: CTR107 E133Q, SAV2435 E135Q, SAV2435 N27W, SAV2435 Y137W, CTR107 Y106W, and LIN2189 E157A-E185L double mutant.
42. The method of items 33-37, wherein the fluorophore is Acridine Orange and the Gyrl-like protein is selected from the group consisting of: SAV2435 E135Q, SAV2435 V105W, SAV2435 P106W, CTR107 WT, CTR107 E133Q, SAV2435 WT, SAV2435 N27W, SAV2435 Y137W, and CTR107 Y106W.
43. The method of items 33-37, wherein the fluorophore is Cyanine 5 and the Gyrl-like protein is selected from the group consisting of: CTR107 WT, SAV2435 WT, CTR107 E133N, CTR107 Y106W, LIN2189, LIN2189 E157A, LIN2189 E185L, SEQ ID NO:42, SEQ ID NO:48; SEQ ID NO:49 and SEQ ID NO:56.
44. The method of items 33-37, wherein the fluorophore is 5(6)-Carboxyfluorescein (FAM) and the Gyrl-like protein is selected from the group consisting of: CTR107 WT, LIN2189 WT, CTR107 E36R, CTR107 Y106W, CTR107 E133Q, CTR107 E36R Y106W E133Q (triple mutant), LIN2189 E157A E185L (aka LIN2189 DUB; double mutant), and SEQ ID NOs:33-40.
45. The method of items 33-37, wherein the fluorophore is 5-Carboxytetramethylrhodamine (TAMRA) and the Gyrl-like protein is selected from the group consisting of: CTR107 WT, and LIN2189 E157A E185L (aka LIN2189 DUB; double mutant).
46. The method of items 33-37, wherein the fluorophore is Oxazine 170 and the Gyrl-like protein is selected from the group consisting of: SAV2435 WT, CTR107 WT, SAV2435 V105W, SAV2435 P106W, SAV2435 N27W, SAV2435 E135Q, and CTR107 Y106W.
47. The method of items 33-37, wherein the fluorophore is iodonitrotetrazolium and the Gyrl-like protein is selected from the group consisting of: CTR107 E133Q, CTR107 E36R H40Y Y106W E133Q quadruple mutant (QUAD), and CTR107 E36R H40Y V105W (TRIP).
48. The method of item 33-47, wherein the molecular probe further comprises a quencher moiety, wherein the quencher moiety is in operative proximity with a fluorophore such that fluorescence of the fluorophore is quenched.
49. A method of identifying a non-native variant aptamer that has a desired biological property, said method comprising:

providing a test-molecule for analysis;

contacting the test-molecule with at least one of the non-native variant aptamers of items 1-25; and selecting the non-native variant aptamer that has one or more desired biological properties.

50. The method of item 49, wherein the desired biological properties are selected from: binding to a biological target or target-molecule; fluorescence-enhancing; fluorescence-quenching; or enzymatic activity.
51. The method of item 50, wherein the biological target is selected from the group consisting of: FAM, CY5, Thiazole-orange, Cytarabine, SARS-Cov-2 spike protein, SYTO9, DHMBI, Malachite Green, Thiazole Orange, Thioflavin T, Atto495, Acridine Orange, 5(6)-Carboxfluorescein, 5-Carboxytetramethylrhodamine, and oxazine.
52. The method of items 50-51, wherein the biological target is selected from the group consisting of a: protein, peptide, nucleic acid, enzyme, ion channel, receptor, tumor antigens, and disease-related antigens.
53. The method of items 49-50, wherein the test molecule is Cytarabine or SARS-Cov-2.
54. The method of items 53, wherein the test molecule is Cytarabine and the non-native variant aptamer is selected from the group consisting of: SEQ ID NO:41; SEQ ID NOs:43-47; and SEQ ID NOs:52-53.
55. The method of items 53, wherein the test molecule is SARS-Cov-2 spike protein and the non-native variant aptamer is selected from the group consisting of: SEQ ID NOs:57-59.
56. A library of non-native SAV2435 variant aptamers comprising non-native variant aptamers having any combination of one up to all 13 of variant amino acids, relative to wild-type SAV2435, among all variant-positions in the polypeptide set forth in FIG. 20/SEQ ID NO:1; wherein the variant positions correspond to amino acid positions 27, 30, 31, 34, 38, 105, 106, 109, 110, 113, 135, 137 and 142 of SEQ ID NO:1.
57. A library of non-native CTR107 variant aptamers comprising non-native variant aptamers having any combination of one up to all 12 of variant amino acids, relative to wild-type CTR107, among all variant-positions in the polypeptide set forth in FIG. 20/SEQ ID NO:2; wherein the variant positions correspond to amino acid positions 31, 32, 35, 36, 39, 40, 43, 75, 106, 133, 135 and 138 of SEQ ID NO:2.
58. A library of non-native LIN2189 variant aptamers comprising non-native variant aptamers having any combination of one up to all 17 of variant amino acids, relative to wild-type LIN2189, among all variant-positions in the polypeptide set forth in FIG. 20/SEQ ID NO:3; wherein the variant positions correspond to amino acid positions 41, 42, 46, 50, 54, 58, 81, 85, 93, 99, 154, 157, 185, 187, 190, 191 and 192 of SEQ ID NO:3.

BRIEF DESCRIPTION OF THE DRAWINGS

FIG. 2A-2B. Recombinant engineered gene sequences and expressed protein sequences for Gyrl-like proteins FIG. 2A SAV2435, FIG. 2A CTR107, and FIG. 2B LIN2189. Bold letter shows engineered modifications added for cloning, higher expression, and affinity chromatography.

FIG. 3A shows the affinity chromatography results after loading and eluting SAV2435 according to the procedure described in the materials and methods. FIG. 3B shows a denaturing polyacrylamide gel electrophoresis analysis of the affinity chromatography fractions. SAV2435 was obtained in high purity matching its molecular weight of 18 kDa.

FIG. 4. Chemical structures of compounds used in examples 1-13.

FIG. 5A Bar graph comparing the SYTO9 fluorescence enhancement by wildtype Gyrl-like proteins. FIG. 5B Bar graph comparing the SYTO9 fluorescence enhancement by selected Gyrl-like variants. Black bars represent data collected under the green channel and grey bars represents data collected under the red channel. Each bar is the mean of data collected in duplicate experiments and error bars represent the standard deviation of averaged results. Fold changes in fluorescence by aptamers are displayed above each bar. FIG. 5C Thermostable fluorescence module formed by SYTO9 and CTR107 E133Q. Left panel are samples heated to 95° C. for 10 mins then imaged under UV light. Right panel are samples cooled for 10 mins after heating. FIG. 5D Plot of fluorescence enhancement of SYTO9 vs. CTR107 WT protein concentration. X-axis is displayed on a log scale. Each point represents the mean of duplicate experiments and the error bars are the standard deviation of averaged results. Data were fitted to the hill equation by nonlinear regression analysis.

FIG. 6A Bar graph comparing DFHBI fluorescence enhancement by wildtype Gyrl-like proteins. FIG. 6B Bar graph comparing Malachite Green fluorescence enhancement by wildtype Gyrl-like proteins. Black bars represent data collected under the green channel and grey bars represent data collected under the red channel. Values for each bar are the mean of data collected in duplicate experiments and error bars represent the standard deviation of averaged results. Fold changes in fluorescence by aptamers are displayed above each bar.

FIG. 19A-19I Gene and protein sequences of rational designed mutant aptamers used in example 1-17. Mutations are show as bold font.

FIG. 20A-20B. Combinatorial mutant binding-site library designed for Gyrl-like protein FIG. 20A SAV2435 and CTR107 and FIG. 20B LIN2189 used for versatile organic molecule-binding aptamer screening and discovery. Binding site residues are shown as bold font FIG. 21A-21C Structures of FIG. 21A SAV2435, FIG. 21B CTR107 and FIG. 21C LIN2189 binding sites displaying residues targeted for the design of combinatorial mutant library.

FIG. 22A-22D. Sequences of FAM binding CTR107 aptamers identified in phage display mutant library protocol.

FIG. 24A-24M. Sequences of FAM-binding aptamers, Cytarabine-binding aptamers, Cy5-binding aptamers, Thiazole Orange-binding aptamers, and SARS-CoV-2 spike protein-binding aptamers identified in phage display mutant library protocol for Gyrl-like proteins (SAV2435, CTR107, LIN2189).

DETAILED DESCRIPTION

Figure 18:
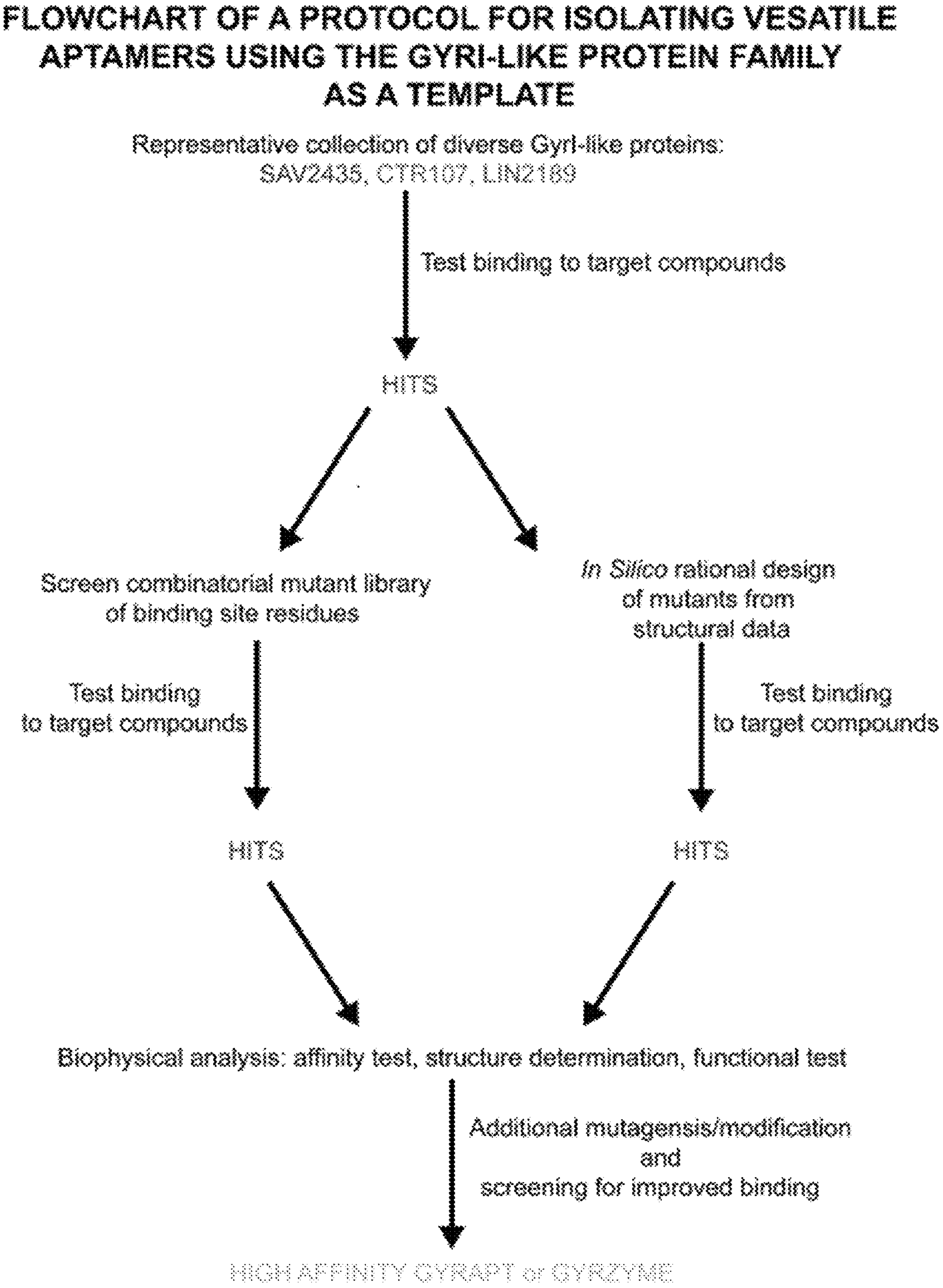
FIG. 18. A detailed protocol for screening and identifying high-affinity GYRAPTs or GYRYZYMEs from selected wildtype Gyrl-like proteins.
Figure 21A:
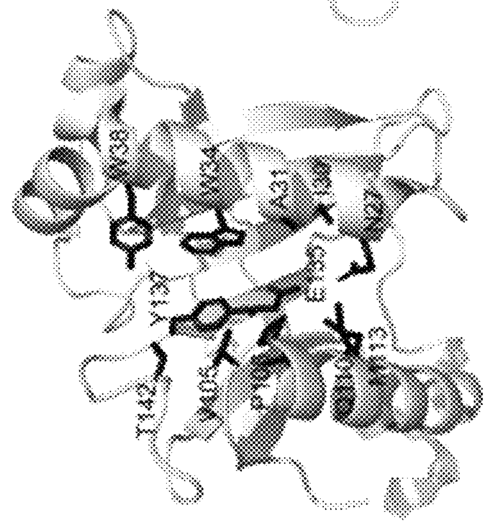
Figure 21B:
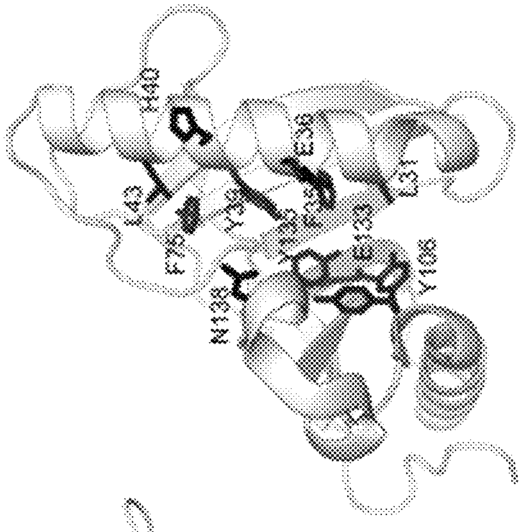
Figure 21C:
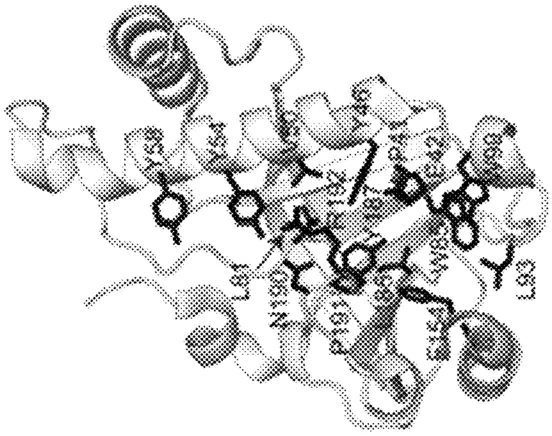

The invention methods and aptamers provided herein take advantage of a novel mechanism of generating fluorescence-activating aptamers, fluorescence-quenching aptamers, organic molecule-binding aptamers and synthetic enzymes, using the Gyrl-like protein family as a template for selection. Gyrl-like proteins have the natural property of multispecificity for their functions in multidrug resistance. In accordance with the present invention, we have identified and provide multiple Gyrl-like protein variant aptamers that can function in a wide range of biotechnological applications through protein engineering. The invention methods provide the framework for transforming Gyrl-like proteins into organic molecule binding-aptamers that can be accomplished through screening family members followed by mutagenesis and selection to generate high-affinity and versatile aptamers (FIG. 16). In particular embodiments, In vitro evolution methodology can be used to convert Gyrl-like proteins into invention variant aptamers with desired binding properties of interest. The invention methods provide the advantage of a less complex method of aptamer selection because Gyrl-like proteins are already preselected to bind to target molecule, therefore, a less rigorous screening process is required for aptamer success. In accordance with the present invention, we have demonstrated that desired aptamer functions can be drastically improved with rationally designed mutants. In accordance with the present invention, those of skill in the art will recognize that Gyrl-like proteins can be mutated and screened for high performance aptamers. In another embodiment, using the invention methods provided herein, one of skill in the art can use publicly available crystal structures of Gyrl-like proteins for the rational design of invention aptamer variants capable of high affinity binding to small molecules of interests. This particular embodiment also significantly reduces the time and effort needed for screening mutant libraries that span the entire protein because the binding residues are known from crystal structures or structural homology. The invention methods provided herein demonstrate that screening 3 proteins from the vast number of Gyrl-like sequences that are available produced multiple invention non-native variant aptamers with improved function (FIG. 18). Schematically, the invention methods increase the likelihood of identifying and designing non-native variant aptamers for target molecules compared to other traditional methods (FIG. 18). In one embodiment of the invention method, numerous organic molecule-binding non-native variant aptamers called GYRAPTS can be generated. In another embodiment of the invention methods, enzymatic GYRI-like non-native variant aptamer proteins called GYRYZMEs are identified and isolated through screening and mutagenesis.

The favorable properties of Gyrl-like proteins allow for the design of novel and useful tools for biotechnology and medicine. Non-native Gyrl-like variant aptamers can be engineered to produce cellular imaging tools with similar properties as engineered fluorescent proteins. In this capacity, the small size, high stability and rapid folding of Gyrl-like proteins allows for a better fluorescence alternative to current technology. Strategies that could provide improved invention non-native variant apatmers include more photostable fluorescent modules and the ability to turn on and off fluorescence at experimenter's discretion. Moreover, the stability of the Gyrl-like protein will help create functional fluorescent non-native variant aptamers that can advantageously work in a wide range of experimental conditions such as high/low pH and high temperature as demonstrated with CTR107 and SAV2435 variants. In particular embodiments, these invention variant-aptamers would be powerful for monitoring the production, trafficking, localization of biomarkers in cancer, metabolism, development, and other physiological pathways. In other embodiments, invention fluorescent non-native variant aptamers from Gyrl-like proteins can also be used for other purposes, such as for example, molecular switches for signal detection in lateral flow devices or ELISA assays. Utilizing the invention variant aptamers provided herein, molecular biology tools can be created for fluorescent fusion protein tagging which can be used to screen protein properties such as folding or enzyme kinetics. Overall, the fluorescence enhancing ability of Gyrl proteins provide a versatile toolbox for the creation of various types of invention non-native variant aptamers for broad-scale applications.

Accordingly, provided herein are non-native SAV2435 variant aptamers comprising any combination of one up to all 13 of variant amino acids, relative to wild-type SAV2435, among all variant-positions in the polypeptide set forth in FIG. 20/SEQ ID NO:1; wherein the variant positions correspond to amino acid positions 27, 30, 31, 34, 38, 105, 106, 109, 110, 113, 135, 137 and 142 of SEQ ID NO:1. In particular embodiments, the SAV2435 variant aptamer comprises a variant amino acid at a number of variant-positions set forth in FIG. 20/SEQ ID NO:2 compared to wild-type SAV2435, wherein the number of variant-positions is selected from the group consisting of: 1, 2, 3, 4, 5, 6, 7, 8, 9, 10, 11, 12, and 13. In other embodiments, the non-native SAV2435 variant aptamer is capable of one or more functions selected from: target-molecule-binding, fluorescence enhancement of a dye; or fluorescence quenching of a dye; binding to an organic molecule; or enzymatic activity. In particular embodiments, the SAV2435 variant aptamer is capable of fluorescence enhancement of a dye, wherein the dye is selected from the group consisting of: SYTO9, DHMBI, Malachite Green, Thiazole Orange, Thioflavin T, Atto495, and Acridine Orange. In other embodiments, the SAV2435 variant aptamer is capable of fluorescence quenching of a dye, wherein the dye is selected from the group consisting of 5(6)-Carboxfluorescein, 5-Carboxytetramethylrhodamine, and oxazine. In yet other embodiments, the SAV2435 variant aptamer is capable of binding to an organic molecule selected from the group consisting of: small-molecules, proteins, oligonucleotides, oligosaccharides, lipids, peptides, and polymers. In further embodiments, the non-native variant aptamer is capable of binding to a molecule selected from the group consisting of: FAM, CY5, Thiazole-orange, Cytarabine, SARS-Cov-2 spike protein, SYTO9, DHMBI, Malachite Green, Thiazole Orange, Thioflavin T, Atto495, Acridine Orange, 5(6)-Carboxfluorescein, 5-Carboxytetramethylrhodamine, and oxazine.

In particular embodiments, the non-native variant SAV2435 aptamer is selected from the group consisting of: SAV2435 N27W (SEQ ID NO:8); SAV2435 V105W (SEQ ID NO:10); SAV2435 P106W (SEQ ID NO:12); SAV2435 E135Q (SEQ ID NO:14); SAV2435 Y137W (SEQ ID NO:16); and SEQ ID NOs:40-45 and SEQ ID NOs:58-59.

Also provided herein are non-native CTR107 variant aptamers comprising any combination of one up to all 12 of variant amino acids, relative to wild-type CTR107, among all variant-positions in the polypeptide set forth in FIG. 20/SEQ ID NO:4; wherein the variant positions correspond to amino acid positions 31, 32, 35, 36, 39, 40, 43, 75, 106, 133, 135 and 138 of SEQ ID NO:2. In particular embodiments, the CTR107 variant aptamer comprises a variant amino acid at a number of variant-positions set forth in FIG. 20/SEQ ID NO:2 compared to wild-type CTR107, wherein the number of variant-positions is selected from the group consisting of: 1, 2, 3, 4, 5, 6, 7, 8, 9, 10, 11, and 12. In certain embodiments, the CTR107 variant aptamer is capable of one or more functions selected from: fluorescence enhancement of a dye; or fluorescence quenching of a dye; binding to an organic molecule; or enzymatic activity. In particular embodiments, the CTR107 variant aptamer is capable of fluorescence enhancement of a dye, and wherein the dye is selected from the group consisting of: SYTO9, DHMBI, Malachite Green, Thiazole Orange, Thioflavin T, Atto495, and Acridine Orange. In other embodiments, the CTR107 variant aptamer is capable of fluorescence quenching of a dye, wherein the dye is selected from the group consisting of 5(6)-Carboxfluorescein, 5-Carboxytetramethylrhodamine, and oxazine. In certain embodiments, the CTR107 variant aptamer is capable of binding to an organic molecule selected from the group consisting of: small-molecules, proteins, oligonucleotides, oligosaccharides, lipids, peptides, and polymers. In yet further embodiments, the CTR107 variant aptamer is capable of binding to a molecule selected from the group consisting of: FAM, CY5, Thiazole-orange, Cytarabine, SARS-Cov-2 spike protein, SYTO9, DHMBI, Malachite Green, Thiazole Orange, Thioflavin T, Atto495, Acridine Orange5(6)-Carboxfluorescein, 5-Carboxytetramethylrhodamine, and oxazin. In a particular embodiment, the invention variant aptamer is CTR107 TRIP (E36R, H40Y, V105W); wherein the variant aptamer can convert Iodonitrotetrazolium to its formazan product.

In particular embodiments, the non-native variant CTR107 aptamer is selected from the group consisting of: CTR107 E36R (SEQ ID NO:18); CTR107 Y106W (SEQ ID NO:20); CTR107 E133Q (SEQ ID NO:22); CTR107 E36R (SEQ ID NO:18); CTR107 TRIP E36R H40Y Y106W (SEQ ID NO:24); CTR107 QUAD E36R H40Y Y106W E133Q (SEQ ID NO:26); and SEQ ID NOs:33-39 and SEQ ID NOs:46-50.

Also provided herein are non-native LIN2189 variant aptamers comprising any combination of one up to all 17 of variant amino acids, relative to wild-type LIN2189, among all variant-positions in the polypeptide set forth in FIG. 20/SEQ ID NO:6; wherein the variant positions correspond to amino acid positions 41, 42, 46, 50, 54, 58, 81, 85, 93, 99, 154, 157, 185, 187, 190, 191 and 192 of SEQ ID NO:3. In particular embodiments, the LIN2189 variant aptamer comprises a variant amino acid at a number of variant-positions set forth in FIG. 20/SEQ ID NO:3 compared to wild-type LIN2189, wherein the number of variant-positions is selected from the group consisting of: 1, 2, 3, 4, 5, 6, 7, 8, 9, 10, 11, 12, 13, 14, 15, 16 and 17. In certain embodiments, the LIN2189 variant aptamer is capable of one or more functions selected from: fluorescence enhancement of a dye; or fluorescence quenching of a dye; binding to an organic molecule; or enzymatic activity. In other embodiments, the LIN2189 variant aptamer is capable of fluorescence enhancement of a dye, and wherein the dye is selected from the group consisting of: SYTO9, DHMBI, Malachite Green, Thiazole Orange, Thioflavin T, Atto495, and Acridine Orange. In particular embodiments, the LIN2189 variant aptamer is capable of fluorescence quenching of a dye, wherein the dye is selected from the group consisting of 5(6)-Carboxfluorescein, 5-Carboxytetramethylrhodamine, and oxazine. In other embodiments, the LIN2189 variant aptamer is capable of binding to an organic molecule selected from the group consisting of: small-molecules, proteins, oligonucleotides, oligosaccharides, lipids, peptides, and polymers. In certain embodiments, the LIN2189 variant aptamer is capable of binding to a molecule selected from the group consisting of: FAM, CY5, Thiazole-orange, Cytarabine, SARS-Cov-2 spike protein, SYTO9, DHMBI, Malachite Green, Thiazole Orange, Thioflavin T, Atto495, Acridine Orange, 5(6)-Carboxfluorescein, 5-Carboxytetramethylrhodamine, and oxazine. In a particular embodiment, the invention LIN2189 variant aptamer is LIN2189 DUB (E157A, L185E), wherein the variant aptamer can enzymatically terminate fluorescence of dye substrates and/or can hydrolyze p-Nitrophenylphosphate to produce p-Nitrophenol.

In particular embodiments, the non-native variant LIN2189 aptamer is selected from the group consisting of: LIN2189 E157A (SEQ ID NO:28); LIN2189 E185L (SEQ ID NO:30); and LIN2189 DUB E157A, E185L (SEQ ID NO:32); and SEQ ID NOs:52-57.

Also provided herein are engineered non-native variant aptamers selected from the group consisting of: SAV2435 N27W (SEQ ID NO:8); SAV2435 V105W (SEQ ID NO:10); SAV2435 P106W (SEQ ID NO12); SAV2435 E135Q (SEQ ID NO:14); SAV2435 Y137W (SEQ ID NO:16); CTR107 E36R (SEQ ID NO:18); CTR107 Y106W (SEQ ID NO:20); CTR107 E133Q (SEQ ID NO:22); CTR107 TRIP (E36R, H40Y, Y106W) (SEQ ID NO:24); CTR107 QUAD (E36R, H40Y, Y106W, E133Q)(SEQ ID NO:26); LIN2189 E157A (SEQ ID NO:28); LIN2189 E185L (SEQ ID NO:30); and LIN2189 DUB (E157A, E185L)(SEQ ID NO:32); and SEQ ID NOs:33-59.

Aptamers that mimic the function of antibodies are crucial to biotechnological developments. Accordingly, provided herein is an invention method for generating target-molecule-binding non-native variant aptamers that can replace, for example, antibodies, and the like, in various applications. Exemplary target-molecules for binding include, small-molecules, proteins, oligonucleotides, oligosaccharides, lipids, peptides, polymers, tumor antigens, and other cell surface proteins or moieties implicated in treating human disease.

Antibodies are commonly used in lateral flow devices for molecular diagnostics purposes as a tool for binding to dyes such as FAM or CY5. In accordance with the present invention methods, provided herein are various non-native variant aptamer GYRAPTs that bind to FAM and CY5. The invention methods provide a proof-of-principle for developing non-native variant aptamer GYRAPTS that can bind to target small molecules of interests. These target molecules to which the invention non-native variant aptamers bind, can be drug compounds, organic dyes, fluorophores, enzymatic substrates, haptens such as biologically relevant oligosaccharides, and naturally occurring biomarkers. Utilizing the invention methods and non-native variant aptamers provided herein, various tools can be developed including fluorescence imaging technology, drug-delivery modules, biopharmaceutical drugs, biosensors, bioswitches, synthetic biotechnological enzymes, and the like.

To create broad and versatile invention non-native variant aptamers for binding to any desired organic molecules for biotechnological and biopharmaceutical applications, provided herein are invention methods and mutagenesis schemes for mutating or modifying selected Gyrl-like proteins (FIG. 18). The invention methods utilize initial screens of Gyrl-like wildtype proteins to identify which candidate serves as the best template for non-native variant aptamer engineering. Subsequently, several rounds of rational or random mutagenesis followed by screening are utilized to identify invention non-native variant aptamers with desired improved functions. Next, biophysical analysis and structure determination provide further information and data to further tune aptamers to desired function (FIG. 18).

Accordingly, the invention methods provided herein can be used to engineer high affinity GYRAPTs or GYRYZYMEs products. The invention methods have provided multiple proof-of-principles by designing and improving the function of aptamers that bind to various small molecules through rational design and screening (FIG. 18, 19). Using the invention methods, we have synthesized mutant libraries of the binding site of Gyrl-like proteins SAV2435, CTR107, LIN2189 (FIG. 20, 21). These invention combinatorial mutant libraries serve as a collection of invention non-native variant aptamers that can be selected for binding to any target organic molecule of interest (FIG. 20, 21). Using these libraries and the invention methods provided herein, invention non-native variant aptamers for various applications can be selected and isolated for use herein or by those of skill in the art. Combined, our invention methods provide a broad-scale approach to design and identify invention non-native variant aptamers that bind to any desired organic molecule, which invention variant aptamers can be incorporated in a multitude of biotechnological and biopharmaceutical applications.

Also provided herein is a fluorescence-on/off bioswitch system comprising:

a first Gyrl-like aptamer; and a fluorogenic dye.

In another embodiment, the bioswitch system further comprising a second Gyrl-like aptamer. In yet another embodiment, either one or both of the Gyrl-like aptamers is a non-native variant Gyrl-like aptamer. In other embodiments, the non-variant Gyrl-like aptamer is thermostable and/or pH-stable.

The invention fluorescence-on/off bioswitch system typically further comprises a dual-labeled molecular probe, as described herein. Accordingly, the present invention provide a further novel mechanism of reversible and controllable fluorescence-switch activation by Gyrl-like variant aptamer proteins. Accordingly, provided herein are invention methods of fluorescence-switch activation of dual-labeled probes (e.g., nucleic acids, linkers, and the like) without the need of complementary nucleic acids, in the case of an oligonucleotide probe. This invention method comprises providing a dual-labelled fluorescence-switch-activation module (aka a dual-labeled molecular probe), wherein the quencher moiety is in operative proximity with a fluorophore such that the fluorophore is quenched; and contacting the fluorescence-switch-activation module with a Gyrl-like protein.

As used herein the term “bioswitch” or “Molecular Switch,” “fluorescence-on/off bioswitch system” or “on/off switch” means a construct that provides a signal upon binding of a ligand. In particular embodiments for example, the signal may be the quenching of a fluorescent signal caused by a conformational change in the sensor construct upon binding a ligand. In other embodiments, the signal of the invention bioswitch system may be quenched in the unbound state and upon ligand binding, the quencher may be moved distal to the fluorophore so that a signal is then detected.

Those of skill in the art will recognize that additional Gyrl-like switch-activation modules can be produced herein for numerous other fluorophore-quencher pairs using the invention methods described herein. These switches are useful in a wide range of biotechnological applications.

As used herein, a “fluorescence-switch-activation module” refers to an linker molecule (e.g., an oligonucleotide or other moiety) that is dual-labelled with a fluorophore on one end and its respective quencher (e.g., from the fluorophore-quencher pair) on the other end, such that while in its ground state the fluorescence-switch-activation module remains quenched. The “fluorescence-switch-activation module” is also known in the art as a dual labeled probe; see U.S. Pat. No. 7,635,598; which is incorporated herein by reference in its entirety for all purposes). In particular embodiments, inducible fluorescent dual labeled probes that include both a fluorophore and a quencher attached by a “linker” are exemplified in the art by an array of dual labeled nucleic acid probes. In particular embodiments, the quencher moiety is in operative proximity with a fluorophore on a probe, such that in can produce a fluorescent signal that is of use in numerous assays with research and diagnostic applications.

In particular embodiments of the bioswitch system, the dye is selected from the group consisting of: 5(6)-Carboxfluorescein (FAM), 5-Carboxytetramethylrhodamine (TAMRA), oxazine), SYTO9, DHMBI, Malachite Green, Thiazole Orange, Thioflavin T, Atto495, and Acridine Orange.

Suitable fluorophore-quencher pairs for use herein in the present invention are well-known in the art, and include for example those shown in Table 1, among others described herein.

TABLE 1

Quencher Dyes BHQ-1 BODIPY 493/503 Alexa 488 FAM Oregon Green TET JOE Cal Fluor® Orange 560™ BHQ-2 Alexa 546 TAMRA BODIPY 581/591 Rhodamine Red-X Cy3.5 Alexa 594 Cal Fluor® Red 610™

In a particular embodiment, the dye is Atto495; and the first and second aptamers are selected from the group consisting of: CTR107 E133Q and SAV2435 N27W; CTR107 E133Q and SAV2435 Y137W; CTR107 E133Q and CTR107 Y106W; CTR107 E133Q and LIN2189 E157A-E185L double mutant; SAV2435 E135Q and SAV2435 N27W; SAV2435 E135Q and SAV2435 Y137W; SAV2435 E135Q and CTR107 Y106W; and SAV2435 E135Q and LIN2189 E157A-E185L double mutant.

In particular embodiments of the bioswitch system, the dye is Acridine Orange; and the first aptamer is selected from the group consisting of any one or more of: SAV2435 E135Q, SAV2435 V105W, SAV2435 P106W, CTR107 WT and CTR107 E133Q; and second aptamer is selected from the group consisting of any one or more of: SAV2435 WT, SAV2435 N27W, SAV2435 Y137W, CTR107 Y106W.

In yet a further embodiment of the bioswitch system, the dye is Acridine Orange; and the first and second aptamers are selected from the group consisting of: SAV2435 E135Q and SAV2435 WT, SAV2435 E135Q and SAV2435 N27W, SAV2435 E135Q and SAV2435 Y137W, SAV2435 E135Q and CTR107 Y106W, SAV2435 V105W and SAV2435 WT, SAV2435 V105W and SAV2435 N27W, SAV2435 V105W and SAV2435 Y137W, SAV2435 V105W and CTR107 Y106W, SAV2435 P106W and SAV2435 WT, SAV2435 P106W and SAV2435 N27W, SAV2435 P106W and SAV2435 Y137W, SAV2435 P106W and CTR107 Y106W, CTR107 WT and SAV2435 WT, CTR107 WT and SAV2435 N27W, CTR107 WT and SAV2435 Y137W, CTR107 WT and CTR107 Y106W, CTR107 E133Q and SAV2435 WT, CTR107 E133Q and SAV2435 N27W, CTR107 E133Q and SAV2435 Y137W, and CTR107 E133Q and CTR107 Y106W.

In certain embodiments, the addition of the Gyrl-like variant aptamer increases fluorescence by an amount selected from at least: 2-fold, 3-fold, 4-fold, 5-fold, 10-fold, 15-fold, 20-fold, 30-fold, 40-fold, 50-fold, 60-fold, 70-fold, 80-fold, 90-fold, 100-fold, 200-fold, 300-fold, 400-fold, 500-fold, 600-fold, 700-fold, 800-fold, 900-fold, 1000-fold, or more. In particular embodiments, the Gyrl-like protein utilized is an invention Gyrl-like variant protein.

Also provided herein, is a method of identifying a non-native variant aptamer that has a desired biological property, said method comprising:

providing a test-molecule for analysis;

contacting the test-molecule with at least one of the non-native variant aptamers of claims 1-25; and selecting the non-native variant aptamer that has one or more desired biological properties.

More particularly, provided herein are invention methods for the rational design of versatile non-native variant aptamers using the Gyrl-like protein family as a template. These invention non-native variant aptamers are capable of binding a wide repertoire of organic molecules that differ in chemical and physical properties. Invention variant aptamers can be generalized into various classes based on their applications.

In particular embodiments, fluorescence enhancing-aptamers are provided herein that are capable of binding otherwise weak fluorophores and stimulate enhanced fluorescence. In other embodiments, fluorescence quenching invention non-native variant aptamers are able to bind to strong fluorophores and shut off fluorescence acting in a switch-like fashion. Drug-binding aptamers bind to therapeutic compounds and improve drug function and drug action. Enzymatic aptamers are capable of modifying various organic molecules to produce useful products. The invention specifically describes how a collection of these aptamers can be utilized as reporters in biosensors and bioswitches, pharmaceutical products, with broad application to biotechnology and cellular imaging technologies. The invention further demonstrates the first example of how multispecific Gyrl-like proteins can be systematically evolved for specific and improved function using mutagenesis strategies.

As used herein, the phrase “desired property” refers to any biological property known in the art to be exhibited by proteins, peptides or small molecules. Exemplary desired properties include, for example, binding-affinity, increased quenching ability, decreased quenching ability, viral coat protein binding (e.g., ligand for SARS-CoV2 Spike protein), binding to a dye, binding to a quencher, and the like. In particular embodiments, the desired biological properties are selected from: binding to a biological target; fluorescence-enhancing; fluorescence-quenching; or enzymatically active.

As used herein, the phrase “biological target” refers to anything within a living organism to which some other entity (like an endogenous ligand, drug or and invention non-native variant aptamer) is directed and/or binds, resulting in a change in its behavior or function. Examples of common classes of biological targets are proteins and nucleic acids. The definition is context-dependent, and can refer to the biological target of a pharmacologically active drug compound, the receptor target of a hormone (like insulin), or some other target of an external stimulus. In particular embodiments, biological targets are most typically proteins such as enzymes, ion channels, and receptors.

In certain embodiments, the biological target is selected from the group consisting of: FAM, CY5, Thiazole-orange, Cytarabine, SARS-Cov-2 spike protein, SYTO9, DHMBI, Malachite Green, Thiazole Orange, Thioflavin T, Atto495, Acridine Orange, 5(6)-Carboxfluorescein, 5-Carboxytetramethylrhodamine, and oxazine. In other embodiments, the biological target is selected from the group consisting of a: protein, peptide, nucleic acid, enzyme, ion channel, receptor, tumor antigens, and disease-related antigens. In a particular embodiment, the test molecule is Cytarabine and the non-native variant aptamer is selected from the group consisting of: SEQ ID NO:41; SEQ ID NOs:43-47; and SEQ ID NOs:52-53. In yet another embodiment, the test molecule is SARS-Cov-2 spike protein and the non-native variant aptamer is selected from the group consisting of: SEQ ID NOs:57-59.

Also provided herein is a library of non-native SAV2435 variant aptamers comprising non-native variant aptamers having any combination of one up to all 13 of variant amino acids, relative to wild-type SAV2435, among all variant-positions in the polypeptide set forth in FIG. 20/SEQ ID NO:1; wherein the variant positions correspond to amino acid positions 27, 30, 31, 34, 38, 105, 106, 109, 110, 113, 135, 137 and 142 of SEQ ID NO:1.

Also provided herein is a library of non-native CTR107 variant aptamers comprising non-native variant aptamers having any combination of one up to all 12 of variant amino acids, relative to wild-type CTR107, among all variant-positions in the polypeptide set forth in FIG. 20/SEQ ID NO:2; wherein the variant positions correspond to amino acid positions 31, 32, 35, 36, 39, 40, 43, 75, 106, 133, 135 and 138 of SEQ ID NO:2.

Also provided herein is a library of non-native LIN2189 variant aptamers comprising non-native variant aptamers having any combination of one up to all 17 of variant amino acids, relative to wild-type LIN2189, among all variant-positions in the polypeptide set forth in FIG. 20/SEQ ID NO:3; wherein the variant positions correspond to amino acid positions 41, 42, 46, 50, 54, 58, 81, 85, 93, 99, 154, 157, 185, 187, 190, 191 and 192 of SEQ ID NO:3.

A key step in aptamer design is finding a versatile starting template that can be engineered for a wide use of applications. In many successful aptamer screens the initial macromolecule does not display affinity for target molecule, but tolerable variations of surface or binding site residues result in hits that display moderate affinityl[2,13]. Affinity can be further increased with additional mutations and selection. Provided herein in accordance with the present invention, is a highly versatile library of non-native variant aptamers that is an important tool and that provides the ability to select aptamers having multispecific binding properties that can be selectively targeted to a wide range of molecules. The invention libraries allow for rapid creation and selection of specific aptamers for any target molecule. The invention mutant libraries of multispecific aptamers represent a collection of predisposed universal binding partners and a means for selection that identifies suitable aptamers for a variety of desired target molecule. The invention variant aptamers are contemplated herein to provide an effective replacement of antibodies in many applications. Moreover, in other embodiments, the invention variant aptamers provide new tools for molecular diagnostics, cellular imagining, and therapeutics.

It is contemplated herein particular non-native variant aptamers provided in invention libraries that bind to, for example, SARS-CoV2 Spike Protein, cytarabine, or any other druggable target, can be used in a respective therapeutic composition to treat the respective disease related to that target.

As used herein, the phrase “druggable target” refers to a protein, peptide, or nucleic acid, or other biologically active moiety, with activity that can be modulated by a drug, such as an invention non-native variant aptamer provided herein. Exemplary druggable targets for use herein, include the molecular targets of approved drugs, totaling more than 890 human and pathogen-derived biomolecules (also referred to herein as “biological targets”) through which 1,578 US FDA-approved drugs currently act. These biomolecules include 667 human-genome-derived proteins targeted by drugs for human disease; which are set forth in Santos et al., Nature Reviews Drug Discovery, Volume 16, pages 19-34 (2017); which is incorporated herein by reference in its entirety for all purposes.

Also provided herein is a method of detecting a biological signal, said method comprising providing to a biological sample a molecular probe having a fluorophore label (e.g., FIGS. 10A and 10B); and contacting the molecular probe with a Gyrl-like protein. In another embodiment, the molecular probe further comprises a quencher moiety, wherein the quencher moiety is in operative proximity with a fluorophore such that fluorescence of the fluorophore is quenched.

FAs used herein, the phrase “biological signal” refers to any evidence that a change in a biological property has occurred. Exemplary biological properties can be either physical or chemical; and include for example, fluorescence, pH, ionic strength or bond strength, absorption, albedo, area, brittleness, boiling point, capacitance, color, concentration, density, dielectric constant, charge, electrical conductivity, electrical impedance, electric field, potential, radiation, flow rate, Fluidity, frequency, inductance, inherent impedance, strength, irradiance, brightness, gloss, flexibility, magnetic field, magnetic flux, quality, momentum, melting point, permeability, dielectric constant, pressure, radiation, solubility, specific heat, strength, Temperature, tension, heat transfer coefficient, flow rate, speed, viscosity, volume, Surface area, shape and wave impedance, and the like.

In particular embodiments of the invention methods, upon contact with the Gyrl-like protein, fluorescence of the molecular probe is either increased or decreased. In certain embodiments, the Gyrl-like protein utilized is a Gyrl-like variant protein. In particular embodiments, the fluorescence is increased by an amount selected from at least: 2-fold, 3-fold, 4-fold, 5-fold, 10-fold, 15-fold, 20-fold, 30-fold, 40-fold, 50-fold, 60-fold, 70-fold, 80-fold, 90-fold, 100-fold, 200-fold, 300-fold, 400-fold, 500-fold, 600-fold, 700-fold, 800-fold, 900-fold, 1000-fold, or more. In other embodiments, the fluorescence is decreased by an amount selected from at least: 2-fold, 3-fold, 4-fold, 5-fold, 10-fold, 15-fold, 20-fold, 30-fold, 40-fold, 50-fold, 60-fold, 70-fold, 80-fold, 90-fold, 100-fold, 200-fold, 300-fold, 400-fold, 500-fold, 600-fold, 700-fold, 800-fold, 900-fold, 1000-fold, or more.

In a particular embodiment of this invention method, the fluorophore is DFHBI or Malechite Green and the Gyrl-like protein is selected from the group consisting of: SAV2435 and CTR107. In another embodiment of this invention method, the fluorophore is Thiazole Orange and the Gyrl-like protein is selected from the group consisting of: SAV2435 WT, SAV2435 V105W, SAV2435 P106W, CTR107 Y106W, SEQ ID NOs:50-51, and SEQ ID NOs: 54-55. In another embodiment of this invention method, the fluorophore is Thioflavin T and the Gyrl-like protein is selected from the group consisting of: CTR107 WT and LIN2189 WT. In yet another embodiment of this invention method, the fluorophore is Atto495 and the Gyrl-like protein is selected from the group consisting of: CTR107 E133Q, SAV2435 E135Q, SAV2435 N27W, SAV2435 Y137W, CTR107 Y106W, and LIN2189 E157A-E185L double mutant. In a further embodiment of this invention method, the fluorophore is Acridine Orange and the Gyrl-like protein is selected from the group consisting of: SAV2435 E135Q, SAV2435 V105W, SAV2435 P106W, CTR107 WT, CTR107 E133Q, SAV2435 WT, SAV2435 N27W, SAV2435 Y137W, and CTR107 Y106W. In another embodiment, the fluorophore is Cyanine 5 and the Gyrl-like protein is selected from the group consisting of: CTR107 WT, SAV2435 WT, CTR107 E133N, CTR107 Y106W, LIN2189, LIN2189 E157A, LIN2189 E185L, SEQ ID NO:42, SEQ ID NO:48; SEQ ID NO:49 and SEQ ID NO:56. In a further embodiment, the fluorophore is 5(6)-Carboxyfluorescein (FAM) and the Gyrl-like protein is selected from the group consisting of: CTR107 WT, LIN2189 WT, CTR107 E36R, CTR107 Y106W, CTR107 E133Q, CTR107 E36R Y106W E133Q (triple mutant), LIN2189 E157A E185L (aka LIN2189 DUB; double mutant), and SEQ ID NOs:33-40. In a further embodiment, the fluorophore is 5-Carboxytetramethylrhodamine (TAMRA) and the Gyrl-like protein is selected from the group consisting of: CTR107 WT, and LIN2189 E157A E185L (aka LIN2189 DUB; double mutant). In yet a further embodiment, the fluorophore is Oxazine 170 and the Gyrl-like protein is selected from the group consisting of: SAV2435 WT, CTR107 WT, SAV2435 V105W, SAV2435 P106W, SAV2435 N27W, SAV2435 E135Q, and CTR107 Y106W. In another embodiment, the fluorophore is iodonitrotetrazolium and the Gyrl-like protein is selected from the group consisting of: CTR107 E133Q, CTR107 E36R H40Y Y106W E133Q quadruple mutant (QUAD), and CTR107 E36R H40Y V105W (TRIP).

Probes

In certain embodiments, the dual labeled "molecular probe," also referred to herein as "probe," that is useful in the present invention systems and methods typically include both a fluorophore and a quencher that quenches fluorescence emission from the fluorophore. In other embodiments and methods contemplated herein, only an unquenched fluorophore is used on the molecular probe. Inducible fluorescent dual labeled probes that include both a fluorophore and a quencher attached by a "linker" are exemplified in the art by an array of dual labeled nucleic acid probes. The nucleic acid probes are of use in conjunction with a variety of nucleic acid amplification/quantification strategies including, for example, 5-nuclease assay, Strand Displacement Amplification (SDA), Nucleic Acid Sequence-Based Amplification (NASBA), Rolling Circle Amplification (RCA), as well as for direct detection of targets in solution phase or solid phase (e.g., array) assays.

In particular embodiments, the probes for use in practicing the methods of the present invention include a quencher that is a substrate for an enzyme or is reactive with a product of an enzymatic reaction, The structure of the quencher is altered by the enzyme or enzyme product, reducing or eliminating its ability to quench fluorescence from the fluorophore. An exemplary probe design is shown below:

F-L-Q in which F is a fluorophore, 0 is a quencher and Lis a linker moiety joining the fluorophore and quencher. In this embodiment, the linker can be any molecule or moiety.

The components are linked together by the reaction of reactive functional groups of complementary reactivity. Thus, in another exemplary embodiment, the probes of the invention have the formula:

$F—X\text{-}L\text{-}X^1\text{-}Q$ in which X and $X^1$ are linking members that are formed by the reaction of a reactive group of the fluorophore with a reactive group of complementary reactivity of the linker, and a reactive group of the quencher with a reactive group of complementary reactivity of the linker, respectively. Exemplary identities for X and $X^1$ are moieties that are essentially stable under physiologically relevant conditions, e.g., $NR^{10}$, O, S, $C(O)NR^{10}$, $OC(O)NR^{10}$, C(O), $P(O)O_2O^-$, in which $R^{10}$ is selected from a bond, substituted or unsubstituted alkyl and substituted or unsubstituted heteroalkyl moieties. Other linking members will be apparent to those of skill in the art.

In other exemplary embodiments dual enzymatic activities are queried using one probe. In such exemplary embodiments a probe having the one or more of the following structures is useful:

$F^1—X^1\text{-}L\text{-}X^2\text{-}Q\text{-}X^3\text{-}L^2\text{-}X^4—F^2$ and $—X^1\text{-}L^1\text{-}X^2—F—X^3\text{-}L^2\text{-}X^4\text{-}Q$ wherein $X^2$, $X^3$, $X^4$ are linking members as X and $X^1$ above, $F^1$ and $F^2$ are flourophores, Q is a quencher, and $L^1$ and $L^2$ are linker moieties as above.

Fluorophores

In particular embodiments, probes for use in the present invention methods and systems can be prepared with substantially any fluorophore that is a donor for a selected quencher. There is a great deal of practical guidance available in the literature for selecting appropriate donor-acceptor pairs for particular probes, as exemplified by the following references: Pesce et al., Eds., FLUORESCENCE SPECTROSCOPY (Marcel Dekker, New York, 1971); White et al., FLUORESCENCE ANALYSIS: A PRACTICAL APPROACH (Marcel Dekker, New York, 1970); and the like. The literature also includes references providing exhaustive lists of fluorescent molecules and their relevant optical properties for choosing reporter-quencher pairs (see, for example, Berlman, HANDBOOK OF FLUORESCENCE SPECTRA OF AROMATIC MOLECULES, 2nd Edition (Academic Press, New York, 1971); Griffiths, COLOUR AND CONSTITUTION OF ORGANIC MOLECULES (Academic Press, New York, 1976); and the like. Further, there is extensive guidance in the literature for derivatizing reporter and quencher molecules for covalent attachment via common reactive functional groups, which are components of a linker, as exemplified by the following references: Haugland (supra); Ullman et al., U.S. Pat. No. 3,996,345; Khanna et al., U.S. Pat. No. 4,351,760. Thus, it is well within the abilities of those of skill in the art to choose an energy exchange pair for a particular application and to conjugate the members of this pair to a linker.

TABLE 2 Suitable moieties that can be selected as donors or acceptors in donor-acceptor energy transfer pairs 4-acetamido-4'-isothiocyanatostilbene-2,2'disulfonic acid acridine and derivatives: acridine acridine isothiocyanate 5-(2'-aminoethyl)aminonaphthalene-1-sulfonic acid (EDANS) 4-amino-N-[3-vinylsulfonyl)phenyl]naphthalimide-3,5 disulfonate N-(4-anilino-1-naphthyl)maleimide anthranilamide BODIPY Brilliant Yellow coumarin and derivatives: coumarin 7-amino-4-methylcoumarin (AMC, Coumarin 120) 7-amino-4-trifluoromethylcouluarin (Coumaran 151) xanthene dyes cyanosine 4',6-diaminidino-2-phenylindole (DAPI) 5',5"-dibromopyrogallol-sulfonaphthalein (Bromopyrogallol Red) 7-diethylamino-3-(4'-isothiocyanatophenyl)-4-methylcoumarin diethylenetriamine pentaacetate 4,4'-diisothiocyanatodihydro-stilbene-2,2'-disulfonic acid 4,4'-diisothiocyanatostilbene-2,2'-disulfonic acid 5-[diN-methylamino]naphthalene-1-sulfonyl chloride (DNS, dansylchloride) 4-(4'-diN-methylaminophenylazo)benzoic acid (DABCYL) 4-diN-methylaminophenylazophenyl-4'-isothiocyanate (DABITC) eosin and derivatives: eosin eosin isothiocyanate erythrosin and derivatives: erythrosin B erythrosin isothiocyanate ethidium fluorescein and derivatives: 5-carboxyfluorescein (FAM) 5-(4,6-dichlorotriazin-2-yl)aminofluorescein (DTAF) 2',7'-dimethoxy-4'5'-dichloro-6-carboxyfluorescein (JOE) fluorescein fluorescein isothiocyanate QFITC (XRITC) fluorescamine IR144 IR1446 Malachite Green isothiocyanate 4-methylumbelliferone ortho cresolphthalein nitrotyrosine pararosaniline Phenol Red B-phycoerythrin o-phthaldialdehyde pyrene and derivatives: pyrene pyrene butyrate succinimidyl 1-pyrene butyrate quantum dots Reactive Red 4 (Cibacron™ Brilliant Red 3B-A) rhodamine and derivatives: 6-carboxy-X-rhodamine (ROX) 6-carboxyrhodam ine (R6G) lissamine rhodamine B sulfonyl chloride rhodamine (Rhod) rhodamine B rhodamine 123 rhodamine X isothiocyanate sulforhodamine B sulforhodamine 101 sulfonyl chloride derivative of sulforhodamine 101 (Texas Red) N,N,N',N'-tetramethyl-6-carboxyrhodamine (TAMRA) tetramethyl rhodamine tetramethyl rhodamine isothiocyanate (TRITC) riboflavin rosolic acid terbium chelate derivatives Quenchers In particular embodiments, quenchers for use in the invention systems and methods include, among others, those that undergo a reaction that diminishes their ability to quench fluorescence from the fluorophore component of the probe.

In a particular embodiment, an exemplary quencher includes an azo bond within its framework. An array of azo-based quenchers has been engineered to efficiently block the emission of most fluorophores (see, for example, U.S. Pat. No. 6,699,975). The azo-based quenchers serve as substrates for a bacterial azoreductase. Upon reduction of the azo bond, the quenching ability is disrupted and the fluorescence of the neighboring fluorophore(s) restored (Scheme 1).

In a particular embodiment, the quencher includes a diazo bond that covalently links two members that are independently selected from substituted or unsubstituted aryl, substituted or unsubstituted heteroaryl, and substituted or unsubstituted unsaturated alkyl.

Exemplary quenchers according to the Black Hole Quencher ("BHQ") format that are of use in the present invention include quenchers having the formulae:

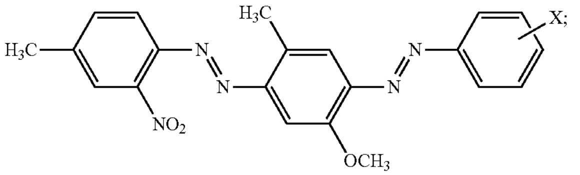

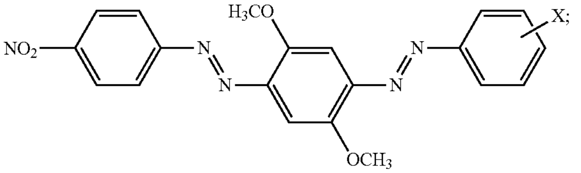

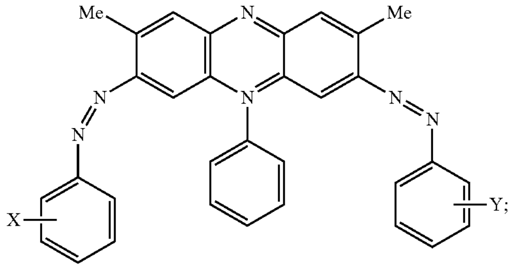

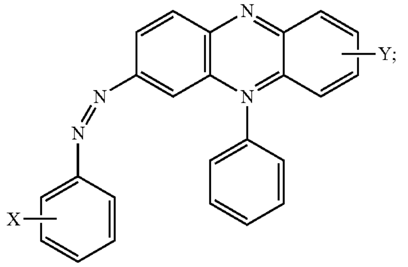

and

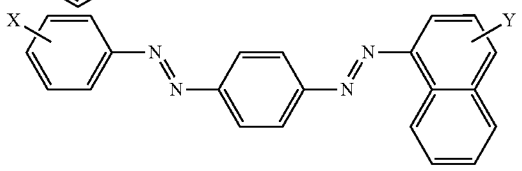

wherein, X and Y represent members independently selected from H, a reactive functional group, a bond to a carrier molecule (e.g., a targeting moiety), a linker bound to a carrier molecule, a solid support, a linker attached to a solid support, a bond to a fluorophore, and a linker bound to a fluorophore. At least one member selected from X and Y preferably is other than H.

In another embodiment, the quencher is a quinone, such as an anthraquinone. An exemplary anthraquinone quencher has the formula:

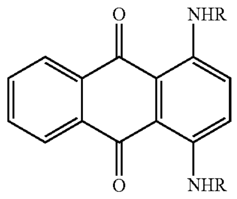

in which the "R" groups are selected from substituted or unsubstituted alkyl, substituted or unsubstituted aryl and substituted or unsubstituted heteroaryl moieties. The reduction of quinones by quinone reductases is known in the art.

The Linkers

Probes of the present invention include a linker moiety to which both the fluorophore and quencher are joined. The linker can be selected from any desirable structure for a particular application and it is well within the abilities of one of skill in the art to select and appropriate linker moiety. The only practical restriction on the linker structure is that it is generally preferred that the linker be of a length and conformation that allows the quencher and the fluorophore to come within operative proximity prior to the reaction of the quencher with the enzyme or enzyme reaction product.

Exemplary linkers are selected from substituted or unsubstituted alkyl, a substituted or unsubstituted heteroalkyl, a substituted or unsubstituted aryl, substituted or unsubstituted heterocycloalkyl or a substituted or unsubstituted heteroaryl moiety. The linker groups can be hydrophilic (e.g., tetraethylene glycol, hexaethylene glycol, polyethylene glycol) or they can be hydrophobic (e.g., hexane, decane, etc.). Certain exemplary linkers include substituted or unsubstituted C6-C30 alkyl groups, polyols (e.g., glycerol), polyethers (e.g., poly(ethyleneglycol)), polyamines, amino acids (e.g., polyaminoacids), saccharides (e.g., polysaccharides), and species that include quaternary amines, phosphate and phosphate ester moieties and combinations thereof.

In yet a further embodiment, a linker group used in the probes of the invention is provided with a group that can be cleaved to release the probe from a species to which it is bound, e.g., solid support, antibody, enzyme, or to release a moiety that is a component of the probe, e.g., the fluorophore, quencher, drug moiety, targeting moiety, carrier molecule and the like from the linker component. Many cleaveable groups are known in the art. See, for example, Jung et al., *Biochem. Biophys. Acta,* 761: 152-162 (1983); Joshi et al., *J. Biol. Chem.,* 265: 14518-14525 (1990); Zarling et al., *J. Immunol.,* 124: 913-920 (1980); Bouizar et al., *Eur. J. Biochem.,* 155: 141-147 (1986); Park et al., *J. Biol. Chem.,* 261: 205-210 (1986); Browning et al., *J. Immunol.,* 143: 1859-1867 (1989); each of which are incorporated herein by reference in their entirety for all purposes. Moreover a broad range of cleavable, bifunctional (both homo- and hetero-bifunctional) linker arms is commercially available from suppliers such as Pierce. Exemplary cleaveable groups are those cleaved by light, e.g., nitrobenzyl derivatives, phenacyl groups, benzoin esters; hydrolysis, e.g., esters, carbonates; changes in pH, etc.

In an exemplary embodiment, the linker imparts water-solubility to the probe and has the formula:

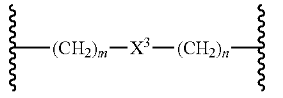

wherein $X^3$ is a member selected from $CH_2$, $NR^{10}$, O, S, $C(O)NR^{10}$, $OC(O)NR^{10}$, $P(O)O_2O^-$, O, $^+N(R^{10})_2$, $NR^{10}$, $OC(O)NR^{10}$, $C(O)NR^{10}$, and $O(CH_2CH_2)_s$, in which s is an integer from 1 to 10. $R^{10}$ is H, substituted or unsubstituted alkyl, or substituted or unsubstituted heteroalkyl. The water-solubility of probes that include this linker arm is greater than an otherwise identical probe that does not include "X".

The linker may also be the bond that is cleaved by the enzymatic reaction, for example, an azo bond. In an exemplary embodiment, the cleavage of the azo bond converts a non-fluorescent compound into a fluorescent species by separating a fluorescent (or "profluorescent") component of a molecule from a second component of the molecule that quenches the fluorescence of the component. An example of the cleavage of a non-fluorescent, azo-containing compound, leading to production of a fluorescent species is set forth below.

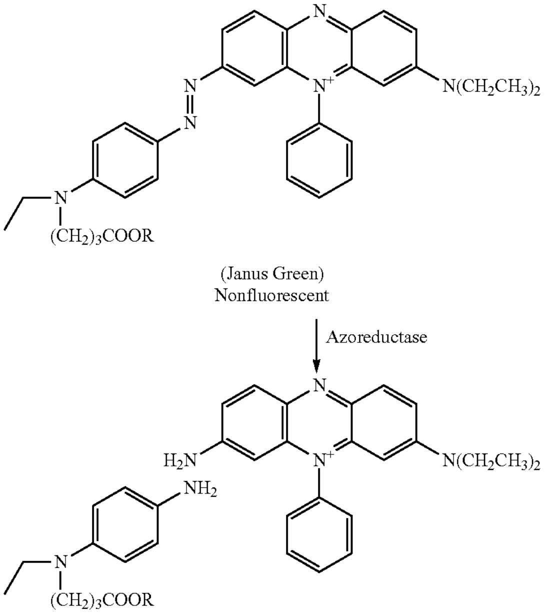

(Janus Green)
Nonfluorescent

MethylViolet 3-RAX
Fluorescent

In the example above, the azo bond is cleaved by the action of a reductase. The invention also encompasses embodiments in which a bond is cleaved by another enzyme or a chemical reductant, e.g., ascorbic acid. As will be appreciated by those of skill in the art, the aryl rings of the moieties set forth above are optionally substituted with one or more substituents for aryl or heteroaryl moieties as set forth herein.

Reactive Functional Groups

The molecular probes used in the invention are assembled by reaction of complementary reactive functional groups on the linker, fluorophore and quencher moieties. Typically, the linking member that is the reaction product formed from the two reactive functional groups is stable under physiologically relevant conditions. Exemplary compounds of the invention, particularly those probes that are designed to be conjugated to another species, bear a reactive functional group, which can be located at any position on the probe molecule through which the probe is conjugated to the other species.

Reactive groups and classes of reactions useful in practicing the present invention are generally those that are well known in the art of bioconjugate chemistry. Currently favored classes of reactions are those proceeding under relatively mild conditions. These include, but are not limited to nucleophilic substitutions (e.g., reactions of amines and alcohols with acyl halides, active esters), electrophilic substitutions (e.g., enamine reactions) and additions to carbon-carbon and carbon-heteroatom multiple bonds (e.g., Michael reaction, Diels-Alder addition).

In certain embodiments of the invention systems and methods, useful reactive functional groups include, for example:

(a) carboxyl groups and derivatives thereof including, but not limited to activated esters, e.g., N-hydroxysuccinimide esters, N-hydroxybenztriazole esters, acid halides, acyl imidazoles, thioesters, p-nitrophenyl esters, alkyl, alkenyl, alkynyl and aromatic esters, activating groups used in peptide synthesis and acid halides;

(b) hydroxyl groups, which can be converted to esters, sulfonates, phosphoramidates, ethers, aldehydes, etc.

(c) haloalkyl groups, wherein the halide can be displaced with a nucleophilic group such as, for example, an amine, a carboxylate anion, thiol anion, carbanion, or an alkoxide ion, thereby resulting in the covalent attachment of a new group at the site of the halogen atom;

(d) dienophile groups, which are capable of participating in Diels-Alder reactions such as, for example, maleimido groups;

(e) aldehyde or ketone groups, allowing derivatization via formation of carbonyl derivatives, e.g., imines, hydrazones, semicarbazones or oximes, or via such mechanisms as Grignard addition or alkyllithium addition;

(f) sulfonyl halide groups for reaction with amines, for example, to form sulfonamides;

(g) thiol groups, which can be converted to disulfides or reacted with acyl halides, for example;

(h) amine or sulfhydryl groups, which can be, for example, acylated, alkylated or oxidized;

(i) alkenes, which can undergo, for example, cycloadditions, acylation, Michael addition, and the like;

(j) epoxides, which can react with, for example, amines and hydroxyl compounds; and (k) phosphoramidites and other standard functional groups useful in nucleic acid synthesis.

The reactive functional groups can be chosen such that they do not participate in, or interfere with, the reactions necessary to assemble or utilize the probe or a conjugate thereof. Alternatively, a reactive functional group can be protected from participating in a selected reaction by the presence of a protecting group. Those of skill in the art understand how to protect a particular functional group such that it does not interfere with a chosen set of reaction conditions. For examples of useful protecting groups, see, for example, Greene et al., PROTECTIVE GROUPS IN ORGANIC SYNTHESIS, John Wiley & Sons, New York, 1991.

In addition to those embodiments in which a molecular probe used in the invention is attached directly to another species, e.g., carrier molecule, solid support, targeting moiety, the probe can also be attached by indirect means. In an exemplary embodiment, a ligand molecule (e.g., biotin) is generally covalently bound to the probe species. The ligand then binds to another molecule (e.g., streptavidin) molecule, which is covalently bound to a species that is a target species for an analysis. Other assay formats that rely on the indirect binding of two or more assay components are known to those of skill in the art.

The probes, or enzymes reactive towards the probes, can be immobilized on substantially any polymer, biomolecule, or solid or semi-solid material having any useful configuration. Moreover, any conjugate comprising one or more probe (or enzyme) can be similarly immobilized. When the support is a solid or semi-solid, examples of preferred types of supports for immobilization of the nucleic acid probe include, but are not limited to, controlled pore glass, glass plates, polystyrene, avidin coated polystyrene beads, cellulose, nylon, acrylamide gel and activated dextran. These solid supports are preferred because of their chemical stability, ease of functionalization and well-defined surface area. Solid supports such as, controlled pore glass (CPG, 500 Å, 1000 Å) and non-swelling high crosslinked polystyrene (1000 Å) are particularly preferred.

A large number of solid supports appropriate for practicing the present invention are available commercially and include, for example, peptide synthesis resins, both with and without attached amino acids and/or peptides (e.g., alkoxybenzyl alcohol resin, aminomethyl resin, aminopolystyrene resin, benzhydrylamine resin, etc. (Bachem)), functionalized controlled pore glass (Biosearch Technologies, Inc.), ion exchange media (Aldrich), functionalized membranes (e.g., —COOH membranes; Asahi Chemical Co., Asahi Glass Co., and Tokuyama Soda Co.), and the like.

Moreover, for applications in which an appropriate solid support is not commercially available, a wide variety of reaction types are available for the functionalization of a solid support surface. For example, supports constructed of a plastic such as polypropylene, can be surface derivatized by chromic acid oxidation, and subsequently converted to hydroxylated or aminomethylated surfaces. The functionalized support is then reacted with a xanthene dye of the invention of complementary reactivity, such as a xanthene dye of the invention active ester, acid chloride or sulfonate ester, for example. Supports made from highly crosslinked divinylbenzene can be surface derivatized by chloromethylation and subsequent functional group manipulation. Additionally, functionalized substrates can be made from etched, reduced polytetrafluoroethylene.

When the support is constructed of a siliceous material, such as glass, the surface can be derivatized by reacting the surface Si—OH, SiO—H, and/or Si—Si groups with a functionalizing reagent.

In an exemplary embodiment, wherein the substrate is made from glass, the covalent bonding of the reactive group to the glass surface is achieved by conversion of groups on the substrate's surface by a silicon-modifying reagent such as:

$$(R^aO)_3\text{—Si—}R^b\text{—}X_a$$

where $R^a$ is an alkyl group, such as methyl or ethyl, $R^b$ is a linking group between silicon and reactive group $X^a$. Silane derivatives having halogens or other leaving groups other than alkoxy groups are also useful in the present invention. Exemplary linking groups include those that include substituted or unsubstituted alkyl and substituted or unsubstituted heteroalkyl groups.

In another preferred embodiment, the reagent used to functionalize the solid support provides for more than one reactive group per each reagent molecule. Using reagents, such as the compound below, each reactive site on the substrate surface is, in essence, "amplified" to two or more functional groups:

$$(R^aO)_3—Si—R^b—(X^a)_n$$

where $R^a$ is an alkyl group (e.g., methyl, ethyl), $R^b$ is a linking group between silicon and $X^a$, $X^a$ is a reactive group or a protected reactive group, and n is an integer between 2 and 50, more preferably between 2 and 20. The amplification of a molecular probe used in the invention by its attachment to a silicon-containing substrate is intended to be exemplary of the general concept of amplification. This amplification strategy is equally applicable to other aspects of the invention in which a molecular probe used in the invention is attached to another molecule or solid support.

A number of siloxane functionalizing reagents can be used, for example:

1. Hydroxyalkyl siloxanes (Silylate surface, functionalize with diborane, and $H_2O_2$ to oxidize to the alcohol)
   a. allyl trichlorosilane→→3-hydroxypropyl
   b. 7-oct-1-enyl trichlorchlorosilane→→8-hydroxyoctyl;
2. Diol (dihydroxyalkyl) siloxanes (silylate surface and hydrolyze to diol)
   a. (glycidyl trimethoxysilane→(2,3-dihydroxypropyloxy) propyl;
3. Aminoalkyl siloxanes (amines requiring no intermediate functionalizing step);
   a. 3-aminopropyl trimethoxysilane→aminopropyl
4. Dimeric secondary aminoalkyl siloxanes
   a. bis(3-trimethoxysilylpropyl)amine→bis(silyloxylpropyl)amine.

It will be apparent to those of skill in the art that an array of similarly useful functionalizing chemistries is available when support components other than siloxanes are used. Thus, for example alkyl thiols (e.g., self-assembled monolayers), functionalized as discussed above in the context of siloxane-modifying reagents, can be attached to metal films and subsequently reacted with a xanthene dye of the invention to produce the immobilized compound of the invention.

Exemplary groups of use for $R^b$ in the above described embodiments of the present invention include, but are not limited to, substituted or unsubstituted alkyl (e.g., substituted or unsubstituted arylalkyl, alkylamino, alkoxy), substituted or unsubstituted aryl (e.g., substituted or unsubstituted arylalkyl, aryloxy and aryloxyalkyl), acyl (e.g., acylamino, acyloxy), mercapto, saturated or unsaturated cyclic hydrocarbyl, substituted or unsubstituted heteroaryl (e.g., substituted or unsubstituted heteroarylalkyl), substituted or unsubstituted heterocycloalkyl, and combinations thereof.

In another exemplary embodiment, a species conjugated to a molecular probe used in the invention is immobilized within a matrix, such as an acrylamide matrix, e.g., "acrydite" (see, Rehman et al., *Nucleic Acids Research,* 27: 649-655 (1999)).

Irreversibly Internalized Probes

In another embodiment, the invention uses molecular probes that include a group, typically a lipophilic group, that facilitates the internalization of the molecular probe into a cell. The facilitating group is preferably linked to the remainder of the molecular probe used in the invention systems and methods through a bond that is cleaved by normal cellular processes, e.g., esterases, lipases, etc. Alternatively, the group can be cleaved by a change in pH, such as that which occurs on going from an extracellular environment to an endocytotic vacuole (e.g., pH 7 to pH 4). The facilitating group can also be cleaved by an intracellular process that is induced. An exemplary probe and its differing states are set forth in the example below.

Protected Azo R Substrate

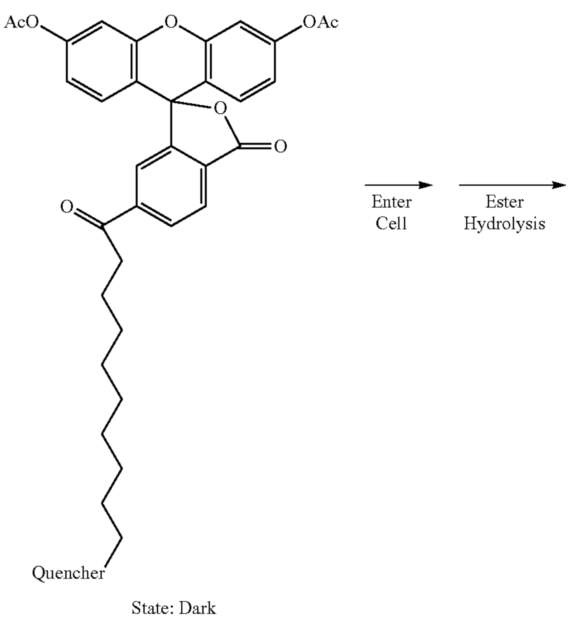

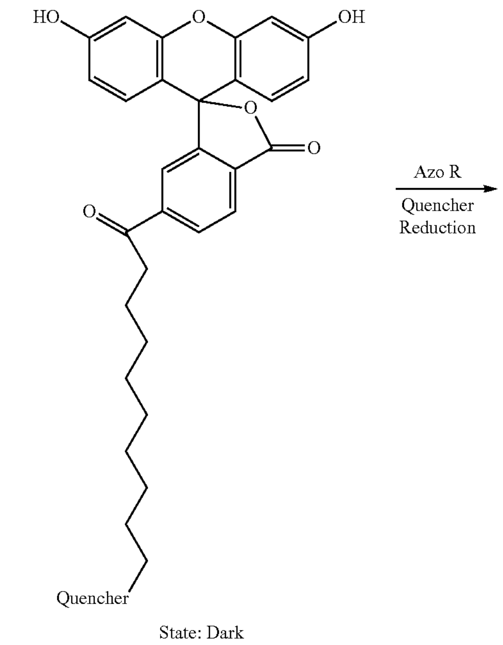

-continued

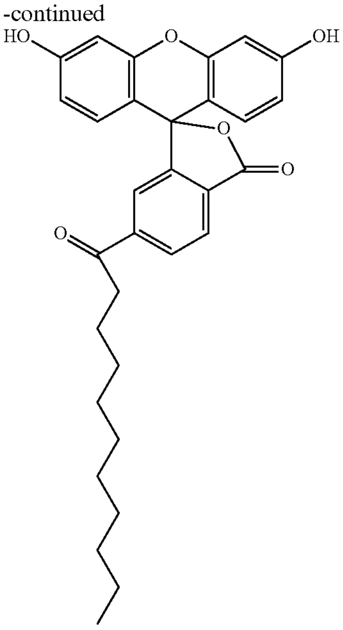

State: Fluorescent

-continued

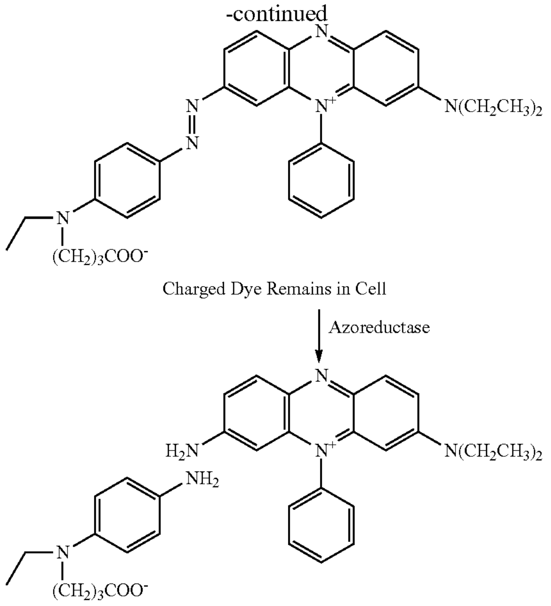

MethylViolet 3-RAX
Fluorescent

In the example above, the probe penetrates the cell wall, becoming internalized in the cell. The acetyl esters are hydrolyzed by intracellular components, trapping the negatively charged probe within the cell. The azo bond of the probe is subsequently cleaved, leaving behind a moiety (not shown) that does not efficiently quench the fluorophore, thereby producing a fluorescent product. The presence of the product in the cell can be confirmed by microscopic or spectroscopic methods, confocal microscopy, cell sorting, etc.

In another exemplary embodiment, as shown below, a side-chain carboxylic acid ester is cleaved, trapping the molecular probe within the cell and the azo bond is cleaved, producing a fluorescent signal.

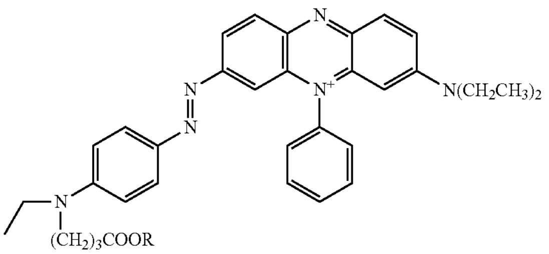

(Janus Green)
Nonfluorescent

Neutral Dye enters Cell

As will be appreciated by those of skill in the art, the molecular probes useful in a variety of embodiments of the present invention are not limited to the cleavable groups or the number of cleavable groups shown in the examples above. Moreover, probes based upon an array of combinations of aryl, conjugated, unsaturated alkyl or heteroaryl groups linked by an azo, or other cleavable bond are within the scope of the present invention. The alkyl, aryl and heteroaryl moieties are optionally substituted with one or more substituent, such as those described in the definition section herein.

Microarrays

The present invention also provides microarray systems comprising an invention xxx of various formats that are of use in performing an assay of the invention. In an exemplary microarray, a molecular probe used in the invention, or a species to which a molecular probe used in the invention is conjugated is immobilized and used to interrogate an assay sample for the presence of an enzyme or other species that reacts with the quencher of the probe, disrupting its ability to quench fluorescence from a fluorophore. In another exemplary format, the enzyme or a species to which the enzyme is attached is immobilized.

Moreover, the invention provides methods of interrogating microarrays using probes or methods of the invention. In an exemplary embodiment, the enzyme is conjugated to a targeting moiety that binds to an immobilized analyte. The analyte and targeting moiety are contacted under conditions appropriate for them to interact, immobilizing the targeting agent-enzyme construct on the microarray. Following any necessary subsequent steps, e.g., washing, buffer change, etc., the probe is added to the microarray. Regions of fluorescence confirm the presence of the analyte. The assay can be run in a somewhat different, but analogous manner, when the targeting moiety is conjugated to the probe. In this case, the microarray is contacted with the enzyme, giving rise to fluorescence in those regions where the analyte is immobilized.

The microarrays of the invention are better understood by reference to nucleic acid microarrays. Nucleic acid microarrays consisting of a multitude of immobilized nucleic acids are revolutionary tools for the generation of genomic information, see, Debouck et al., in supplement to *Nature Genetics,* 21:48-50 (1999). The discussion that follows focuses on the use of a xanthene dye of the invention in conjunction with nucleic acid microarrays. This focus is intended to be illustrative and does not limit the scope of materials with which this aspect of the present invention can be practiced.

Exemplary microarrays comprise n regions of identical or different species (e.g., nucleic acid sequences, bioactive agents). In a preferred embodiment, n is a number from 2 to 100, more preferably, from 10 to 1,000, and more preferably from 100 to 10,000. In a still further preferred embodiment, the n regions are patterned on a substrate as n distinct locations in a manner that allows the identity of each of the n locations to be ascertained.

Methods of preparing microarrays are well known in the art. See, for example, Lehrach, et al., HYBRIDIZATION FINGERPRINTING IN GENOME MAPPING AND SEQUENCING, GENOME ANALYSIS, Vol. 1, Davies et al, Eds., Cold Springs Harbor Press, pp. 39-81 (1990); Pirrung et al., U.S. Pat. No. 5,143,854, issued 1992; each of which are incorporated herein by reference in their entirety for all purposes.

II. EXAMPLES

The experimental data which follows were collected using the materials and methods described below.

Materials and Methods

Cloning, Expression, and Purification of Gyrl-Like Proteins

Genes corresponding to the polypeptide sequence for the engineered recombinant Gyrl proteins SAV2435, LIN2189, CTR107 (FIG. 2) were designed and purchased from Genscript (Piscataway, NJ). All genes were engineered with affinity purification 6×-histags and an initiator starting amino acid sequence for robust protein production. All genes were cloned into a pET28B vector between the NcoI and XhoI restriction sites and transformed into BL21 T7 express competent cells (New England Biolabs, Ipswich, MA).

Figure 1C:
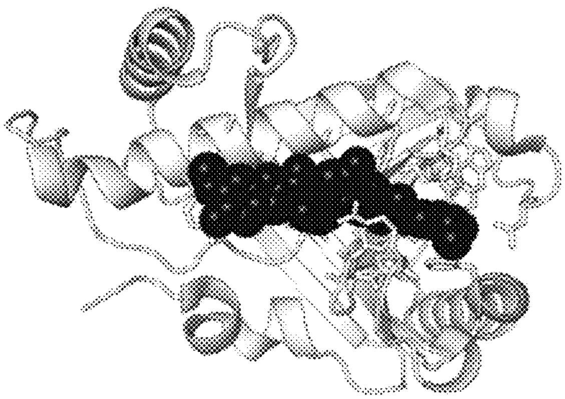
FIG. 1A-FIG. 1C. The crystal structure of selected Gyrl-like proteins FIG. 1A SAV2435 bound to the organic dye Rhodamine6G (PDB_CODE=5KAU), FIG. 1B CTR107 (PDB_CODE=5KAX) bound to the organic dye Rhodamine6G, and FIG. 1C LIN2189 (PDB_CODE=5X5M) bound to Yatakemycin. Ligands are shown as black spheres while interacting residues in Gyrl-like protein binding pockets are shown as white sticks.
Figure 1B:
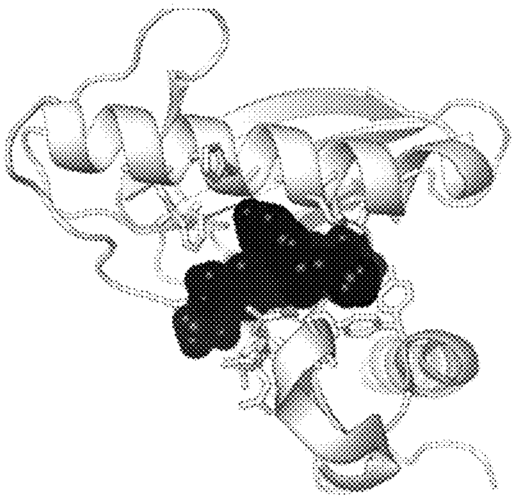
Figure 1A:
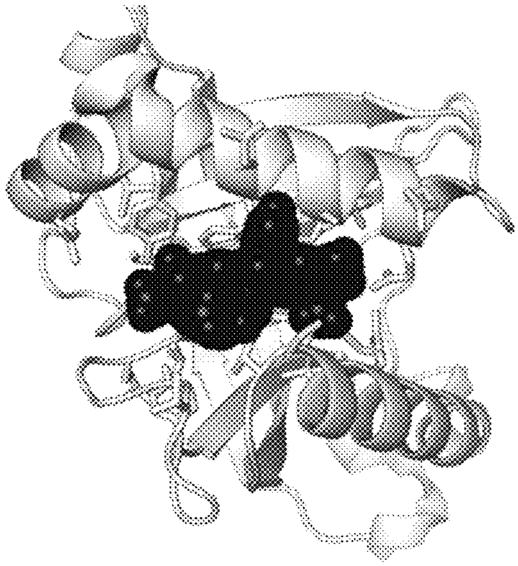
Figure 3A:
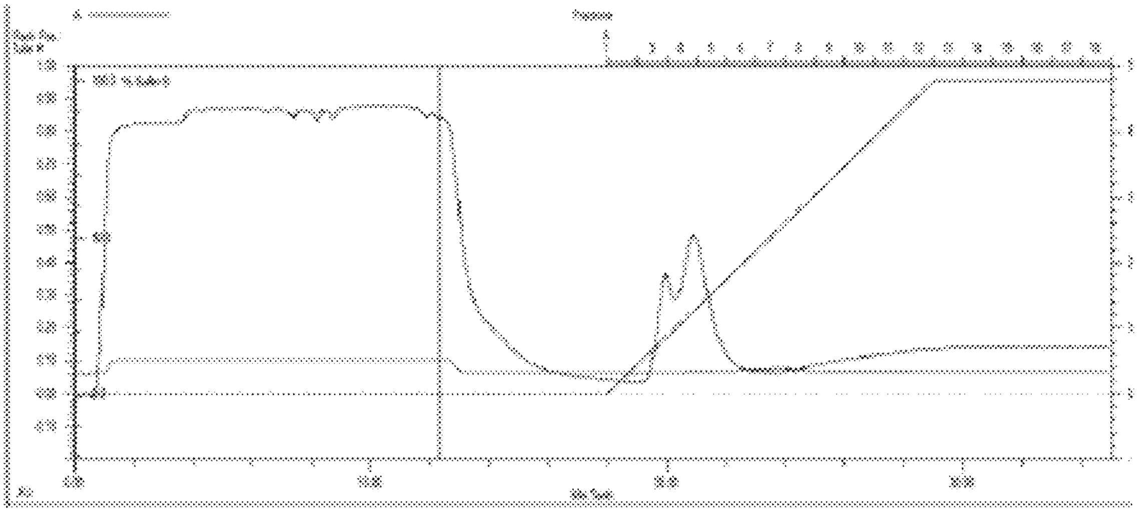
FIG. 3A-3B. An example of the purification process used to obtain Gyrl-like proteins in this experimental design.
Figure 3B:
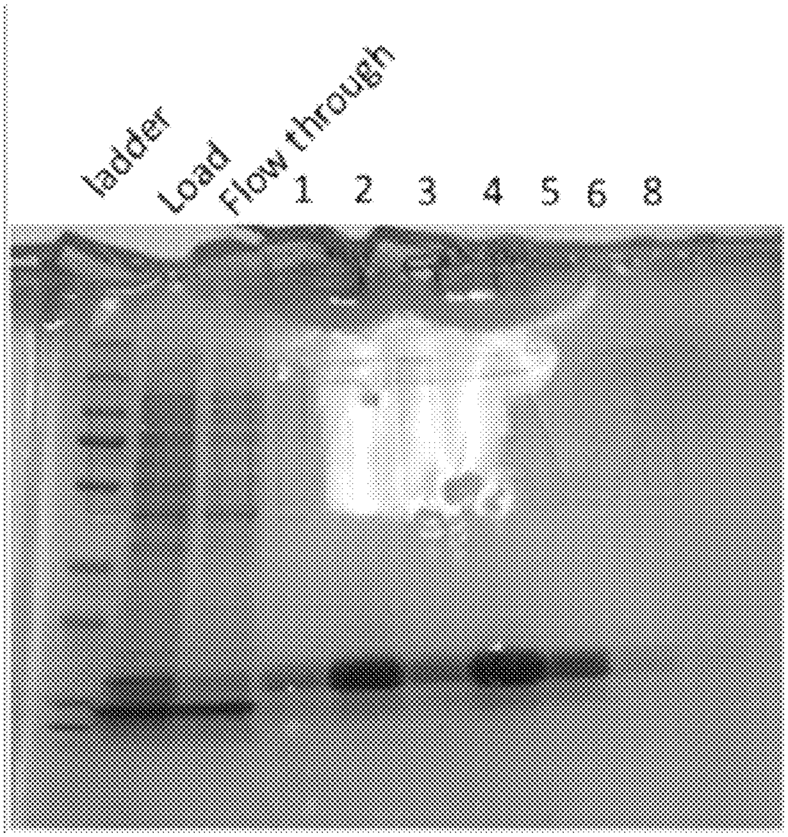

Cells transformed with Gyrl-like protein genes in plasmid were grown in LB media and expressed for 4 hrs by adding 0.5 mM IPTG (Millipore-Sigma, St. Louis, MO) to cells after reaching an $OD_{600}$ of 0.6. Cells were harvested by centrifugation and lysed in lysis buffer (20 mM TRIS-HCl pH 8.0, 300 mM NaCl, 1 mM $MgCl_2$, 15 mM Imidazole, 5% Glycerol, 1 mg/ml Lysozyme, 0.2% Tween20, 0.1% Polyethyleneimine v/v) by incubating for 1 hr followed by 10 cycles of sonication for 30 seconds with 45 second wait between each cycle at a power of 12 W. Supernatants were collected by centrifugation at 14000 RPM and next loaded on Ni-NTA superflow cartridges (Qiagen, Valencia, CA) with equilibration buffer (20 mM TRIS-HCl pH 8.0, 300 mM NaCl, 1 mM $MgCl_2$, 15 mM Imidazole, 5% Glycerol), washed with equilibration buffer and eluted in elution buffer (20 mM TRIS-HCl pH 8.0, 300 mM NaCl, 1 mM $MgCl_2$, 250 mM Imidazole, 5% Glycerol). Proteins were concentrated and stored in storage buffer (20 mM TRIS-HCl pH 8.0, 150 mM NaCl, 1 mM $MgCl_2$, 50% Glycerol) at −20° C. Example of purified proteins is shown in FIG. 3. Variants of SAV2435, CTR107, LIN2189 were created using the Q5 site-directed mutagenesis kit from New England Biolabs (Ipswich, MA). Mutants were purified using the same protocol as wildtype proteins.

Fluorescence Binding Assay

To investigate recombinant Gyrl-like proteins binding to dyes, a fluorescence based assay that monitors changes in the intrinsic fluorescence of organic dies upon the titration of protein was developed. Fluorescence measurements were conducted using a Qubit3 fluorometer (ThermoFisher, Waltham, MA) in fluorescence buffer (20 mM TRIS-HCl pH 8.0, 50 mM KCl, 1 mM $MgCl_2$). Experiments were conducted in 200 μL reaction volumes and data collected in duplicate measurement. Data represents the mean of independent experiments with standard deviation calculated to denote error. In titration experiments proteins were diluted to a final concentration in fluorescence buffer containing dye and thoroughly mixed before data collection. In each experiment a blank measurement of fluorescence buffer only was used to correct experimental data. All dyes used were purchased from Millipore-Sigma (St. Louis, MO). Dyes were dissolved in fluorescence buffer prior to use. Oligonucleotides labeled with dyes were purchased from Integrated DNA Technologies (Coralville, IA). Plots were fitted to the Hill equation when fluorescence was used to determine binding affinity. Fluorescence enhancement was calculated at the ratio of fluorescence increase form protein-dye complex vs. free dye in solution.

Absorption Test

A GeneQuant 1300 spectrophotometer was used to collect absorption data.

Absorption experiments were conducted in fluorescence buffer in 200 μL volumes.

In Vivo Drug-Binding Aptamer Screening

In in vivo experiments, *E. coli* cells transformed with plasmids containing Gyrl-like proteins SAV2435 WT, CTR107 WT, and LIN2189 or control protein were grown to $OD_{600}$ of 0.3 units using 50 μg/ml kanamycin for selection. Cells were grown for 2 hours in the presence of 1 mM IPTG followed by the addition of various concentrations of ampicillin. Samples were grown for 24 hrs then the $OD_{600}$ was monitored using a GeneQuant 1300 spectrophotometer.

100 μl of cells were plated on agar plates contain 100 μg/ml ampicillin and 1 mM IPTG and allowed to grow overnight for colony formation.

Ex Vivo Drug-Metabolizing Aptamer Screening

80 μg/ml of Gyrl-like protein was added to varying concentrations of ampicillin in fluorescence buffer and incubated at 37° C. for 2 hours in an attempt to inactivate the drug. Next, log-phase grown cells were added to the ampicillin-protein mixture and incubated for 24 hrs. The absorbance of samples was then monitored at $OD_{600}$ to determine cell density.

Mutant Library Design

The program PyMOL (Schrodinger, New York, NY) was used to analyze the structural and biophysical properties of SAV2435 (PDB_CODE=5KAU), LIN2189 (PDB_CODE=5KAX), and CTR107 (PDB_CODE=5X5M) binding sites. Residues that were reasoned to make molecular interactions with bound ligands were annotated and selected for random mutagenesis. Mutant libraries were then designed from the wildtype genes of SAV2435, LIN2189, CTR107 through the NNK mutagenesis process. Combinatorial mutant libraries of binding site residues were purchased from Genewiz (La Jolla, CA).

Results

Example 1: Proof of Fluorescence Enhancement Properties by Gyrl-Like Proteins To demonstrate the versatility of Gyrl-like proteins we designed fluorescence enhancing aptamers that can bind weak fluorophores or non-fluorescent fluorophores and activate their fluorescence. To create fluorescence-enhancing modules it is important to select fluorogenic dyes that display a broad range of fluorescence enhancement along with high photostability. One such dye is SYTO9 which is commonly used as a stain for nucleic acids in cellular imaging or for signal detection in real-time polymerase chain reaction (FIG. 4). SYTO9 exhibits low fluorescence at its emission max of 503 nm in the absence of nucleic acids. When intercalated between nucleobases in the major groove of DNA, a strong enhancement of fluorescence is observed.

Figure 5A:
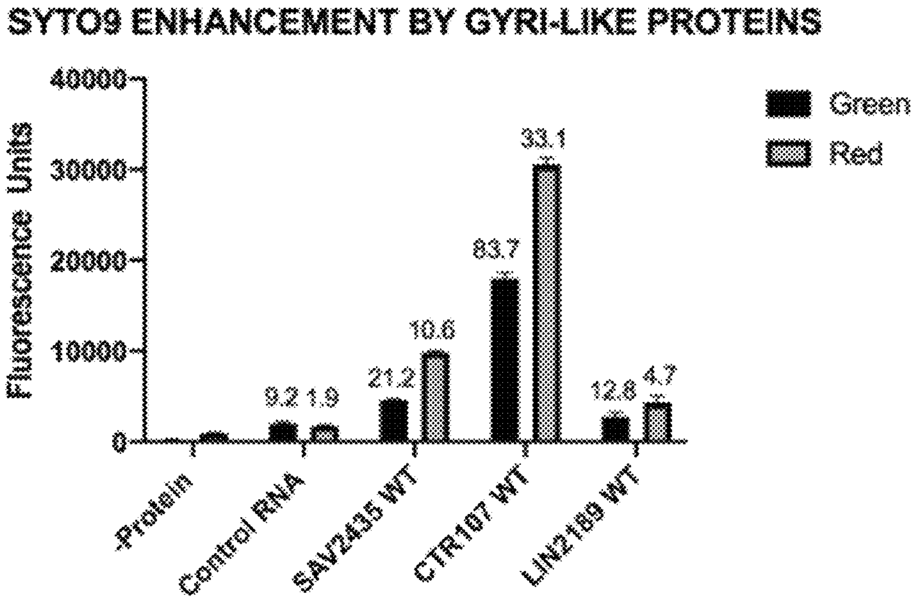
FIG. 5A-5D.

Because of the strong aromatic nature and multi-specificity of Gyrl-like protein it is likely that SYTO9, and other compounds that fluoresce using a similar mechanism, can be activated by upon molecular binding. To test this hypothesis, we conducted fluorescence enhancement assays using 3 selected Gyrl proteins, SAV2435, CTR107, and LIN2189 with SYTO9 (FIG. 5A). SYTO9 displays weak fluorescence in buffer at a concentration of 1 μM when excited at 470 nm and emission simultaneously monitored between 510-580 nm (green channel) and 665-720 nm (red channel) (FIG. 4A). When a 40-mer control RNA is added to SYTO9 near 9-fold and 2-fold increases in fluorescence emission are observed under the green and red channel, respectively. Addition of Gyrl-like proteins to the solution containing SYTO9 resulted in variable results. 10 μM of SAV2534 mixed with SYTO9 caused a modest 21-fold and 11-fold enhancement at the green and red channel, respectively (FIG. 5A). Addition of 10 μM of CTR107 with SYTO9 caused a strong 84-fold and 33-fold enhancement (FIG. 5A). Unlike CTR107 and SAV2435 which both displayed high fluorescence enhancement properties, The Gyrl-like protein LIN2189 showed a small enhancement under the red and green channel similar to the control 40-mer RNA. Because all three binding pockets contain binding sites that vary in physical and chemical properties such effects are expected. These results emphasize the importance of screening multiple Gyrl-like proteins to identify the best fluorescence enhancers of target fluorophores. Overall, these data demonstrate the first evidence that the Gyrl-like protein scaffold can be used as a general template for fluorescence enhancement of weak or non-fluorescent fluorophores.

Example 2: Improving SYTO9 Fluorescence Enhancement by Gyrl-Like Proteins Through Rational Design The Gyrl-like proteins SAV2435 and CTR107 demonstrate the ability to activate non-fluorescent or weakly fluorescent dyes as seen in example 1. To further improve the fluorescence enhancing properties of these proteins targeted mutations in the binding site are required. In accordance with the present invention, crystal structures for SAV2435, CTR107, and LIN2189, were analyzed to determine the residues that form the binding site where various fluorophores will interact. Next, at these binding sites identified herein, the rational design of mutations provides aptamers with improved dye binding activity. More particularly, superimposition of the structure of BmrR with SAV2435 and CTR107 shows that the only similarity is a conserved glutamate. This glutamate is important in cation selectivity by BmrR. In accordance with the present invention, mutations of this conserved glutamate in CTR107 (E133) and SAV2434 (E135) were constructed to remove cation selectivity, and analyzed for their ability to bind uncharged and negatively charged dyes in different orientation.

Figure 5B:
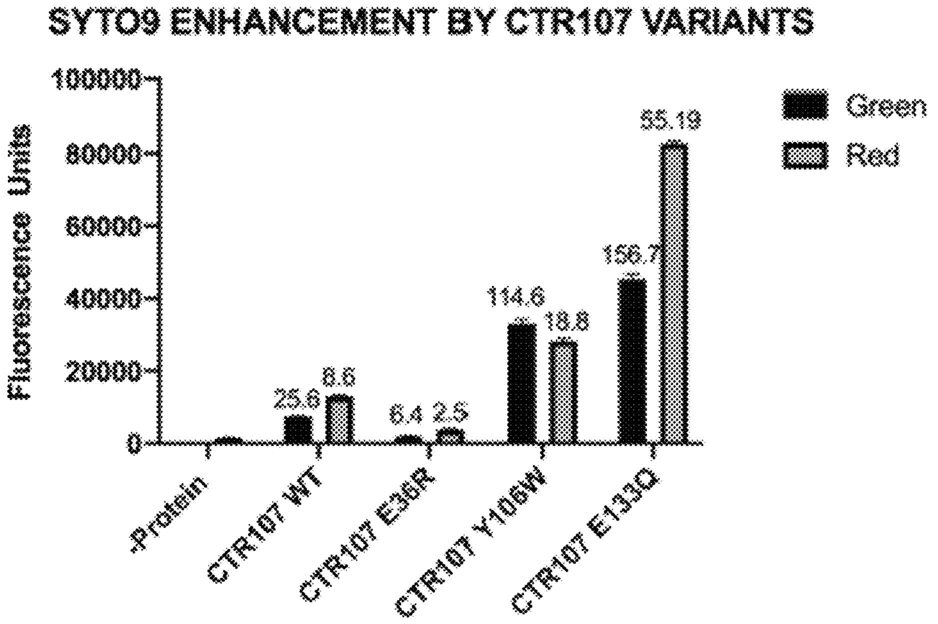

Three mutants were constructed, CTR107 E36R, CTR107 Y106W, and CTR107 E133Q, by site-directed mutagenesis and tested their ability to enhance the fluorescence of SYTO9 (FIG. 5B). Mutant enhancement data was compared to recombinant wildtype CTR107 with 500 nM SYTO9 to determine the effects of mutating target binding site residues. CTR107 E36R displayed weaker enhancement than wildtype which indicates a loss of fluorescence enhancement through this mutation (FIG. 5B). CTR107 Y106W showed a promising 115-fold and 19-fold increase under the green and red channel, respectively. In the case of CTR107 E133Q we observed a significant 157-fold and 55-fold increases in fluorescence under the green and red channel, respectively (FIG. 5B). In both CTR106 Y106W and CTR107 E133Q aptamers, SYTO9 is likely able to bind in an orientation that is more favorable than recombinant CTR107, thereby producing higher fluorescence enhancement.

Figure 5C:
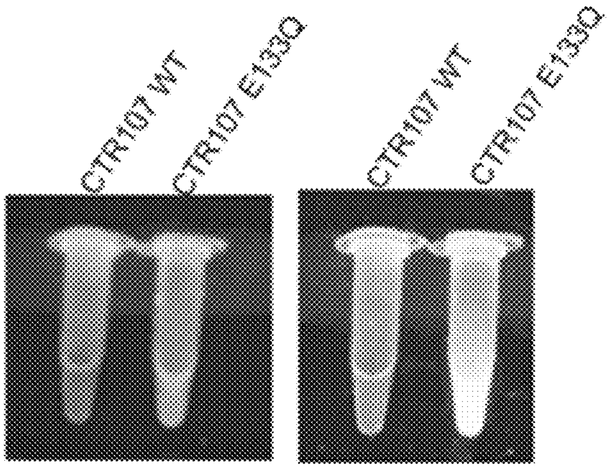
Figure 5D:
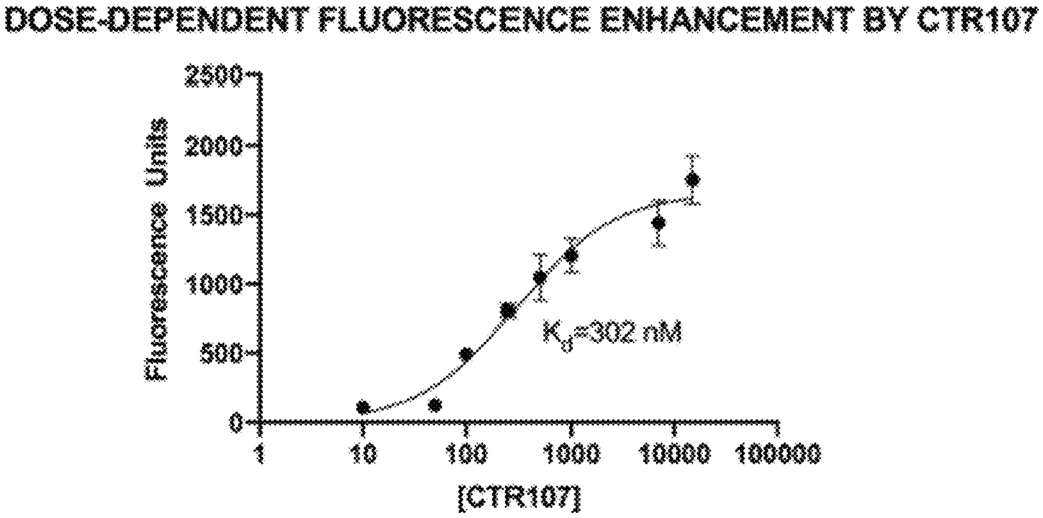

Gyrl-like proteins are stable in solution and at high temperatures. We tested the reversibility of the CTR107 E133Q aptamer bound to SYTO9. We heated samples to 90° C. for 10 mins which would typically denature proteins (FIG. 5C). We analyzed the UV fluorescence of heated samples of recombinant CTR107 and CTR107 E133Q which both showed strong increases in SYTO fluorescence. After cooling to room temperature samples were then analyzed using UV light (FIG. 5C). Only the CTR107 E133Q samples were able to full regain its fluorescence activation, highlighting the stability of interaction with SYTO and the thermostability of Gyrl-like proteins (FIG. 5C). This invention demonstrates a reversible thermostable biomolecular fluorescent switch, a first of its kind. Fluorescence enhancement by CTR107 and variants is dose dependent (FIG. 5D). We estimate the dissociation constant of wildtype CTR107 for SYTO9 is 302 nM. It is expected that stronger enhancers will have a dissociation constant that is similar in value or much tighter. Those of skill in the art will readily understand that rational engineering can be conducted to increase fluorescence activation by Gyrl-like proteins. Furthermore, these results demonstrate that brighter aptamers can be generated from combinatorial mutant libraries of Gyrl-like proteins. Accordingly, provided herein are methods for creating higher affinity and brighter aptamers through mutation of Gyrl-like protein binding sites.

Example 3: Fluorescent Activation of Common Fluorophores Used in Biotechnology DFHBI and Malachite Green are two weak fluorophores that fluorescent aptamers have been designed through in vitro evolution or rational computational design (FIG. 3). DFHBI is a stable, high-quantum yield derivative of the chromophore of naturally occurring GFP. Malachite Green is a triphenylmethane dye that displays no fluorescence in the absence of a binding aptamer. We tested whether both fluorophores would bind with modest affinity to the multi-specific pockets of Gyrl-like proteins, thereby inducing fluorescence enhancement through aromatic interactions or direct hydrogen bonding networks. We explored the ability of SAV2435, CTR107, and LIN2189 to activate DFHBI and Malachite Green in fluorescence enhancement assays (FIG. 6).

Figure 6A:
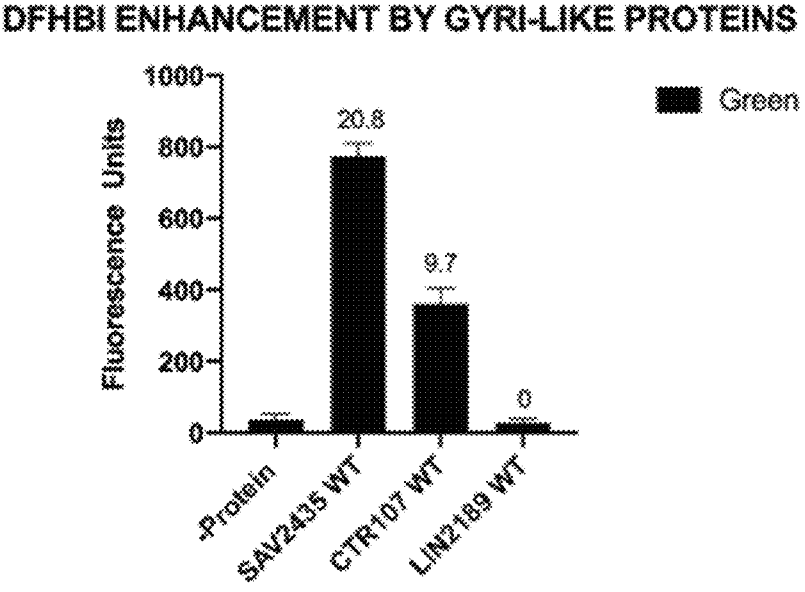
FIG. 6A-6B.

DFHBI displays excitation and emission maximas at 447 nM and 501 nM respectively. In the absence of protein, 500 nM DFHBI showed near background fluorescence under green and red channels. Similar to SYTO9 results, all three Gyrl-like proteins displayed variable enhancement results when added to DFHBI. SAV2435 showed the highest enhancement of all Gyrl-like proteins tested under the green channel (FIG. 5). Addition of 10 μM SAV2435 to 500 nM DFHBI resulted in a 20-fold increase in fluorescence. CTR107 when added at 10 μM induced a 10-fold increase in DFHBI fluorescence (FIG. 6A). Similar to SYTO9, LIN2189 had no effect on fluorescence (FIG. 6A).

Figure 6B:
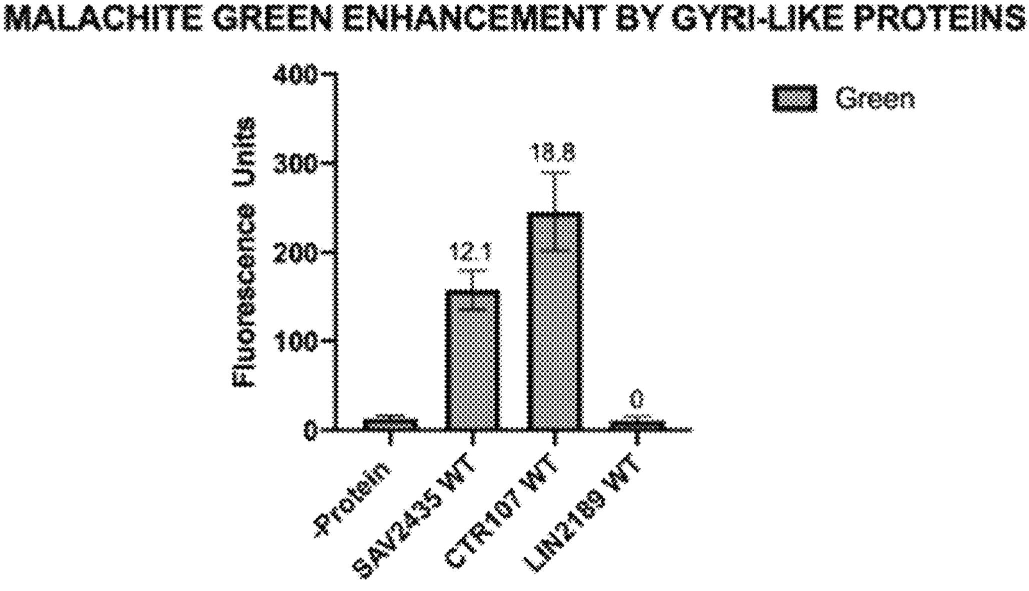

Malachite Green fluoresces in the far-red regions when stimulated by binding aptamers, therefore we monitored its fluorescence emission at 665-720 nm after exciting at 635 nm. In the absence of protein 500 nM Malachite Green shows weak fluorescence under the red channel (FIG. 6B). Addition of 10 μM SAV2435 resulted in a 10-fold increase in Malachite Green fluorescence. Addition of 10 μM of CTR107 produced the highest enhancement and resulted in an 18-fold increase in fluorescence intensity (FIG. 6B). LIN2189 showed no effect on fluorescence enhancement.

Together, these results indicate that the fluorescence enhancement properties of Gyrl-like proteins can be tuned to a wide range of fluorophores. These data represent the first instance of fluorescence activation of fluorophores DFHBI and Malachite Green by Gyrl-like proteins. The variable effects observed demonstrate that the diverse ligand-binding site of Gyrl-like proteins can induce different effects on each fluorophore. As observed SAV2435 was more robust for DFHBI and CTR107 was more robust for Malachite Green. To design high affinity aptamers in accordance with the present invention, mutagenesis of the ligand-binding site is conducted by either rational design or through combinatorial NNK libraries followed by selection for variant aptamers that display tighter binding or higher fluorescence intensities. The enhancement properties displayed for DFHBI and Malachite green is a general mechanism that can be applied to numerous other weakly fluorescent dyes. Moreover, invention Gyrl-like proteins can be selected to bind to and enhance the fluorescence of a broad range of fluorescent molecules.

Example 4: Strong Fluorescence Activation of Thiazole Orange with Useful Applications to Biotechnology The observed enhancement of Malachite Green and DFHBI fluorescence by recombinant wildtype SAV2435 and CTR107 proteins are not useful for biotechnology and cellular imaging and further engineering was required to improve fluorescence activation. In accordance with the present invention, bright fluorescent switches have been created for cellular imaging and for fluorescent signal detection for in vitro diagnostics. To identify more efficient fluorescent enhancing aptamers we explored fluorescence enhancement of Thiazole Orange, a promising weakly fluorescent dye that is nontoxic to cells (FIG. 3). Previous studies have shown engineered protein and RNA aptamers that can strongly activate the fluorescence of Thiazole Orange derivatives. The mango RNA aptamer binds Thiazole Orange covalently attached to a biotin linker using a G-quadruplex similarly to DFHBI. In the dye RNA-complex, the aromatic environment formed by G-quadruplexes is important for the mechanism of fluorescence enhancement.

Figure 7A:
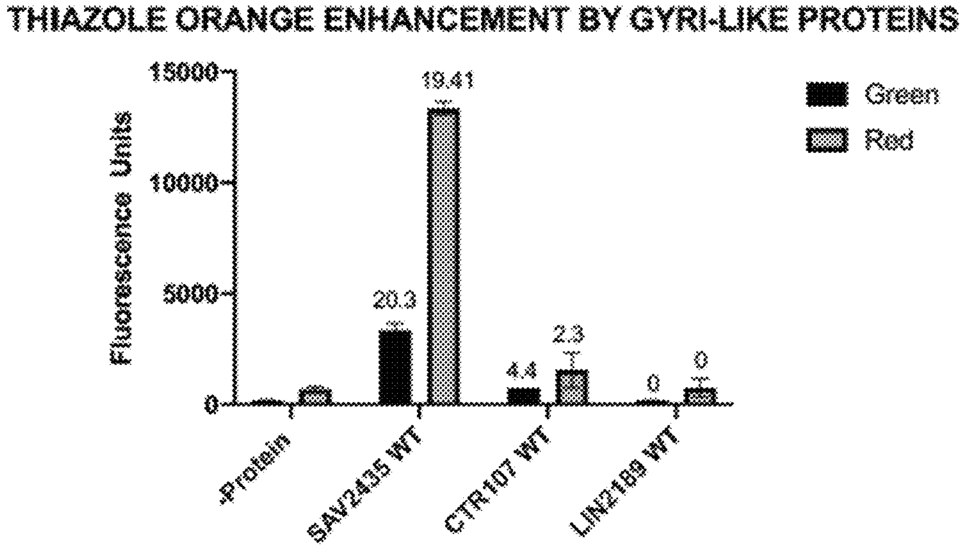
FIG. 7A Bar graph comparing the Thiazole Orange fluorescence enhancement by selected wildtype Gyrl-like proteins.

In accordance with the present invention, we tested whether Gyrl-like proteins could mimic such a mechanism using their multispecific aromatic binding pockets and enhance Thiazole Orange fluorescence. We conducted fluorescence activation assays with Thiazole Orange and MDR proteins SAV2435, LIN2189, and CTR107 to determine the extent of fluorescence activation by Gyrl-like proteins (FIG. 7A). In experiments with 1 μM Thiazole Orange and saturating concentrations of Gyrl-like proteins only SAV2435 WT demonstrated significant enhancement. SAV2435 shows a strong 50-fold increase in thiazole orange fluorescence under the green channel while only small 5-fold increase is observed under the red channel (FIG. 7A). Thiazole orange has an excitation maxima at 505 nm and emission maxima at 535 nm, respectively. Instruments that can focus excitation and emission spectrums at these wavelengths will produce more profound fluorescence enhancement when SAV2435 is bound to Thiazole Orange. Lin1289 and CTR107 showed no effects on Thiazole Orange fluorescence (FIG. 7A).

Figure 7B:
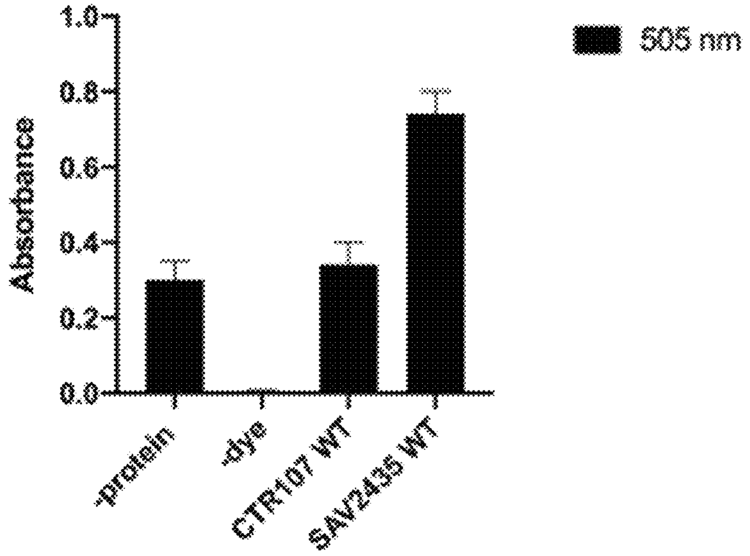
FIG. 7B Effects of Gyrl-like proteins on the absorbance of light by Thiazole Orange.

We further analyzed the mechanism of fluorescence enhancement by conducting absorption experiments on Thiazole Orange in the presence or absence of Gyrl-like proteins (FIG. 7B). Thiazole Orange shows a strong absorption peak of 0.3 units at 505 nM. Addition of CTR107 did not affect the intensity of the Thiazole Orange peak at 505 nm. When SAV2435 was added the Thiazole Orange peak at 505 nm increased significantly to 0.7 units (FIG. 7B). These results strongly demonstrate that SAV2435 increases the excitation of Thiazole Orange dye and this partly contributes to the overall fluorescence activation mechanism. The 20-fold fluorescence increase and the specificity for SAV2435 amongst Gyrl-like proteins makes this aptamer-fluorophore pair an attractive candidate for biotechnological developments. Thus, in accordance with present invention, methods are provided herein comprising mutational analysis of the SAV2435 binding site coupled with fluorescence screening to identify and select brighter aptamer variants.

Example 5: Improving Thiazole Orange Fluorescence Enhancement Through Rational Design of Gyrl-Like Proteins In Example 1, variants of the CTR107 are provided that produce significantly brighter fluorescence enhancing aptamers for SYTO9. Using the same rational design approach, we evaluated the effects of improving Thiazole Orange fluorescence enhancement with mutants of CTR107 and SAV2435. Thus, in accordance with present invention, methods are provided herein comprising mutational analysis of the SAV2435 binding site coupled with fluorescence screening to identify and select brighter aptamer variants.

This example demonstrates the invention methods of improving fluorescence activation by Gyrl-like variant aptamer proteins through mutagenesis and screening with fluorescence enhancement assays.

Figure 7C:
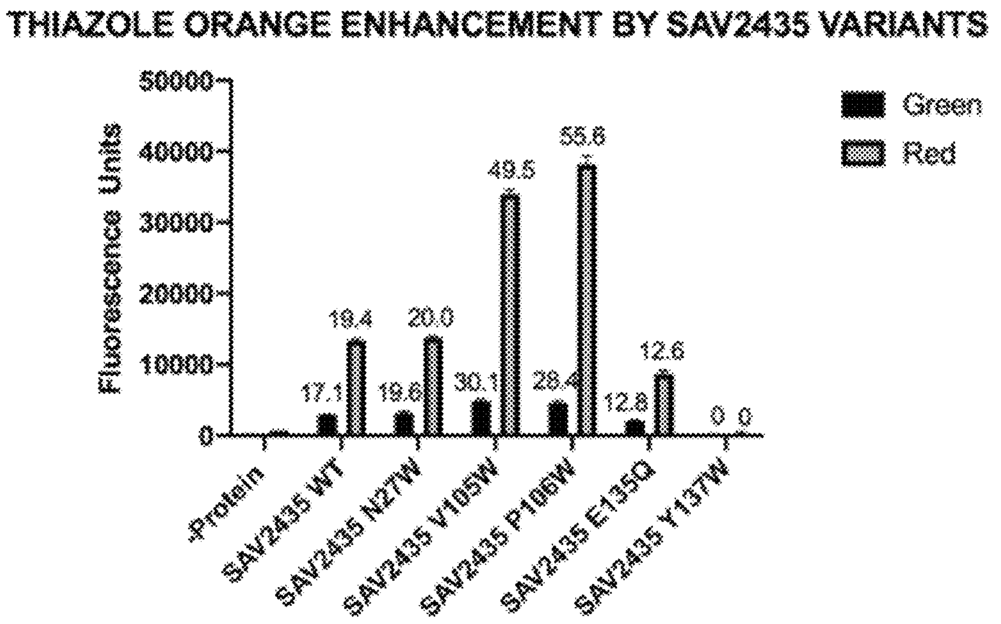
FIG. 7C Bar graph comparing the Thiazole Orange fluorescence enhancement by rationally designed SAV2435 variants.

For SAV2435 WT, the enhancement was significantly higher than CTR107 WT which highlights features of the SAV2435 binding site that are unique for Thiazole Orange fluorescence activation. Using the structure of SAV2435 as a guide, we highlighted an important tryptophan (W34) that is believed to be important in the mechanism of fluorescence enhancement. We evaluated whether mutating other binding site residues to tryptophan would synergistically increase the enhancement of fluorescence. We targeted 5 residues and created binding site variants that would create a "tryptophan sandwich" with W34 where Thiazole Orange can stably bind and activate fluorescence. Of these mutants V105W and P106W, which both are positioned directly across from W34 in the crystal structure, produced increased enhancement compared to wildtype (FIG. 7C). In both cases, 3-fold higher enhancement is seen relative to wildtype and an overall 50-fold enhancement is observed compared to dye alone under the red channel (FIG. 7C). It is likely that the observed enhancement with SAV2435 variants is higher than measured by our instrumentation. Monitoring fluorescence with instrumentation at wavelengths corresponding to the peak emission for Thiazole Orange will show higher enhancement by SAV2435 variants.

Figure 7D:
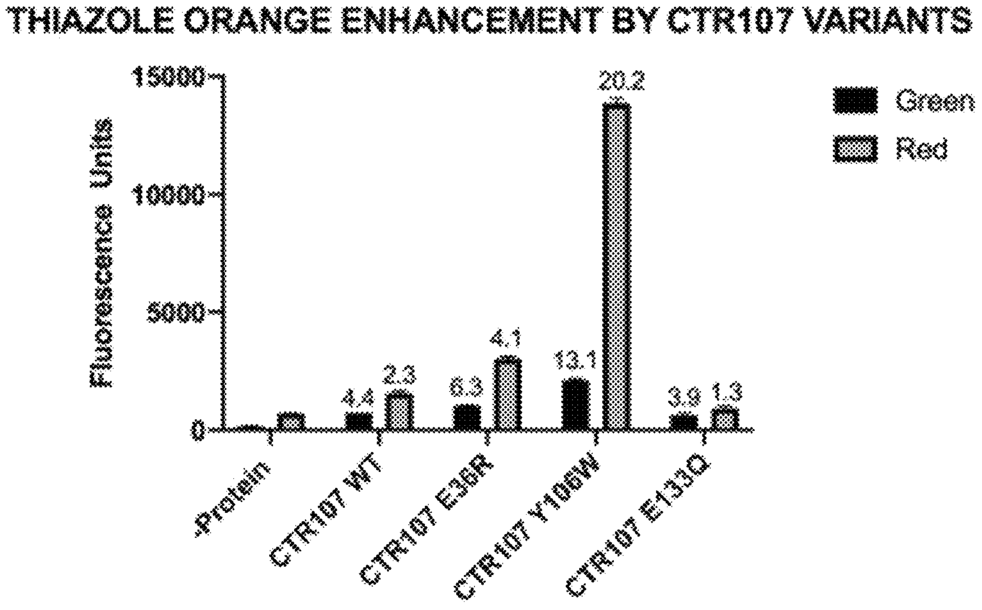
FIG. 7D Bar graph comparing the Thiazole Orange fluorescence enhancement by rationally designed CTR107 variants.

CTR107 WT displayed no enhancement of Thiazole Orange Fluorescence (FIG. 7A). Because our rational tryptophan designs showed enhanced fluorescence by SAV2435 we evaluated whether similar CTR107 variants might also activate its fluorescence enhancement. Variant CTR107 Y106W showed a 13-fold and 20-fold enhancement under the green and red channel, respectively (FIG. 7D). Other CTR107 variants showed no effects on Thiazole Orange fluorescence (FIG. 7D). These results demonstrate a protocol for creating fluorescence activation aptamers from non-activating Gyrl-like proteins. Thus, in accordance with present invention, methods are provided herein for isolating brighter fluorescence activating or enhancing aptamers comprising mutational analysis of a Gyrl-like protein binding site coupled with fluorescence screening to identify and select brighter aptamer variants having fluorescence-enhancing activity. The use of the invention mutant libraries will facilitate isolating brighter fluorescence activating aptamers.

Figure 7E:
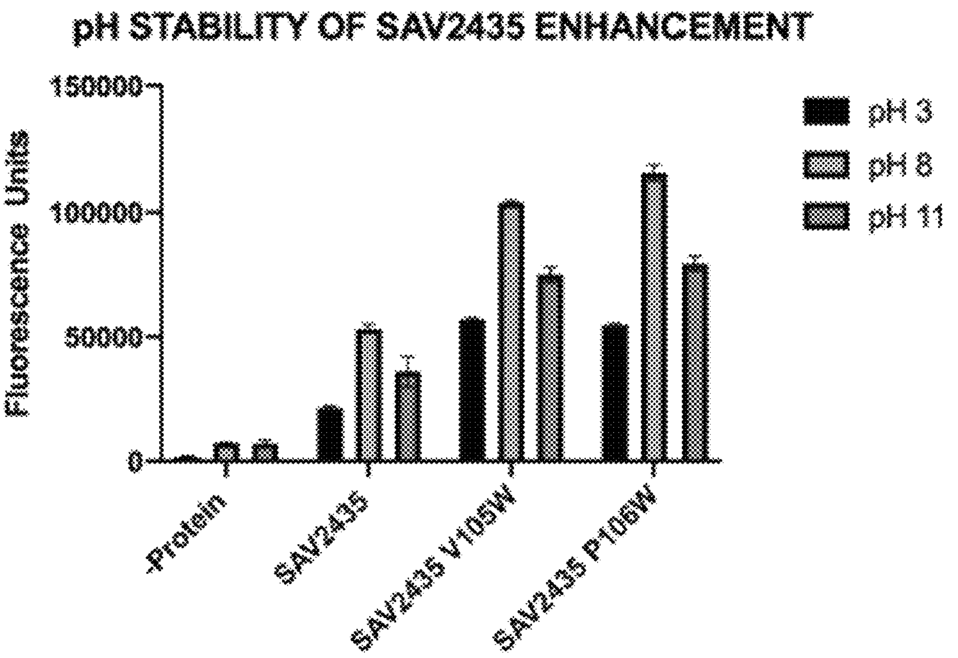
FIG. 7E pH stability of fluorescence module formed by Thiazole Orange and SAV2435 variants. Black bars represent data collected under the green channel and grey bars represents data collected under the red channel. Each bar is the mean of data collected in duplicate experiments and error bars represent the standard deviation of averaged results. Fold changes in fluorescence by aptamers are displayed above each bar.

Because Gyrl-like proteins display strong stability under a wide range of conditions, it is contemplated herein that fluorescence enhancement aptamers designed from this family will work in broad environments. Design of fluorescence switches that work in broad pH environments can be important tools for biotechnology. We tested the pH stability of fluorescence-enhancing SAV2435 variants in acidic (pH 3) and basic conditions (pH 11) (FIG. 7E). We observed a 2-fold decrease in fluorescence under acidic conditions for SAV2435 WT, SAV2435 V105W and SAV2435 P106W. Under basic conditions all three aptamers were slightly more stable than acidic (FIG. 7E). It is believed that typical proteins would denature and unfold under acidic and basic pHs, but the invention Thiazole Orange enhancing aptamers provided herein still unexpectedly displayed high functionality even after being subjected to these extreme environments (FIG. 7E). Thus, in accordance with the present invention, provided herein are pH-stable fluorescence activating aptamer modules, comprising SAV2435 WT, SAV2435 V105W, SAV2435 P106W, CTR107 Y106W, and the like.

Figure 7F:
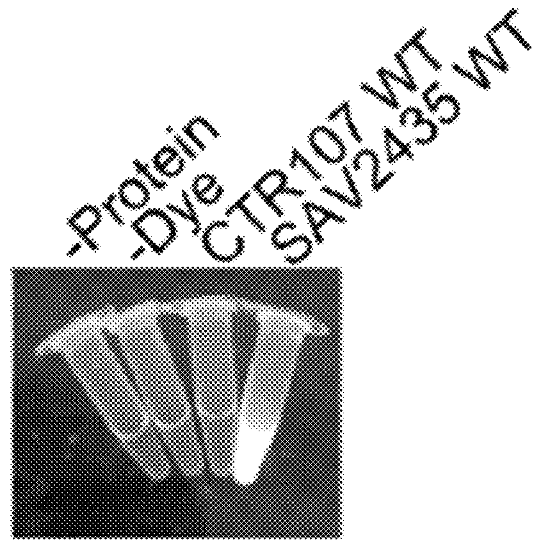
FIG. 7F UV fluorescence enhancement by SAV2435.
Figure 7G:
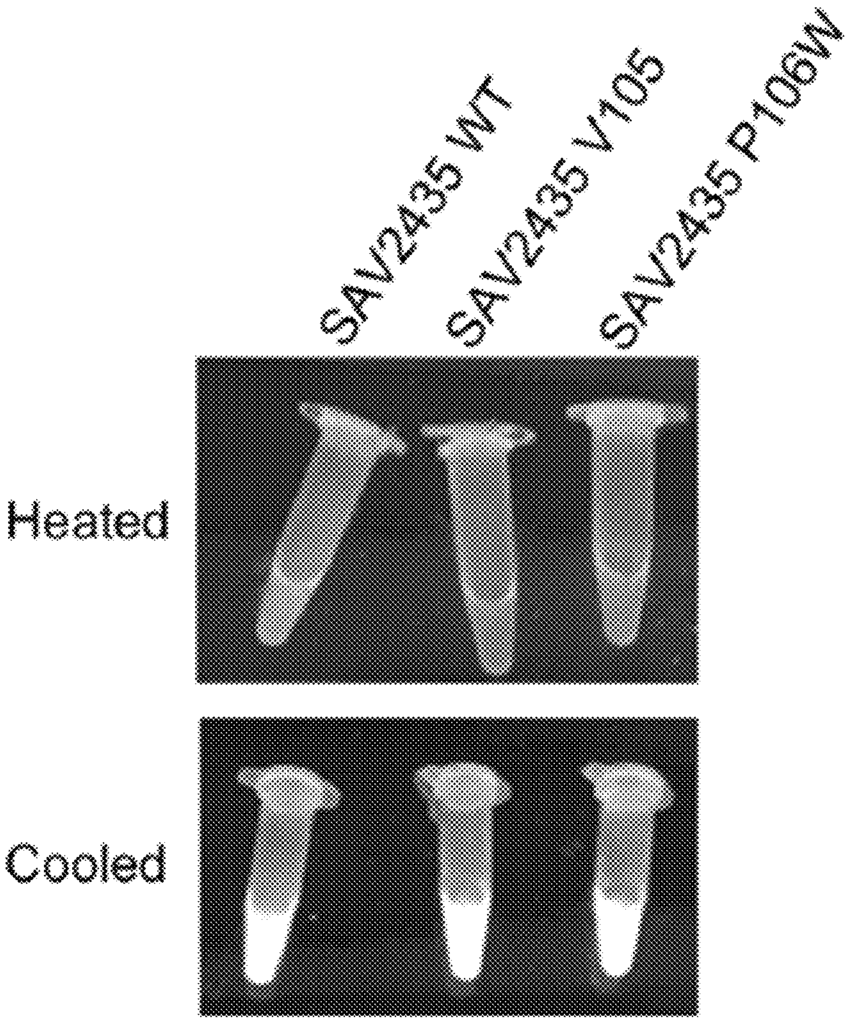
FIG. 7G Thermostability and reversibility of enhancement module formed by Thiazole Orange and SAV2435 variants.

The brightness of SAV2435 bound Thiazole Orange complex can be observed under ultraviolet light (UV) irradiation (FIG. 7F). Normally, Thiazole orange in the absence of enhancing aptamer displays no UV fluorescence. SAV2435 WT protein displays no UV fluorescence in the absence of dye (FIG. 7F). In control experiments no fluorescence is observed when non-enhancing CTR107 WT was added to Thiazole Orange (FIG. 7F). When SAV2435 is added to Thiazole Orange we observe a strong and bright fluorescence from the aptamer dye complex when excited with UV light (FIG. 7F). Accordingly, provided herein in accordance with the present invention, are UV fluorescence-enhancing aptamers comprising engineered non-native variants of SAV2435 WT.

We further used UV fluorescence to confirm the thermostability of fluorescence-enhancing SAV2435 aptamer variants. Heating at 95° C. is sufficient to denature proteins and disrupt ligand-bound complexes. We observed that heating all SAV2435 variants resulted in a loss of Thiazole Orange fluorescence enhancement. Upon cooling for 5 minutes, quite surprisingly fluorescence enhancement is rapidly observed to return from the reformed complex between the invention SAV2435 aptamer variants and Thiazole Orange. Thermostability is an important property of proteins used in biotechnology. The invention Gyrl-like, engineered, non-native, variant aptamer proteins are thermostable and their functions are reversible under various temperature changes. Accordingly, provided herein are reversible and thermostable fluorescence enhancement protein switches, comprising SAV2435 WT, SAV2435 V105W, SAV2435 P106W, and the like. Those of skill in the art will readily understand that further mutational analysis and fluorescence screening will lead to the development of improved fluorescence enhancement aptamers.

Figure 8:
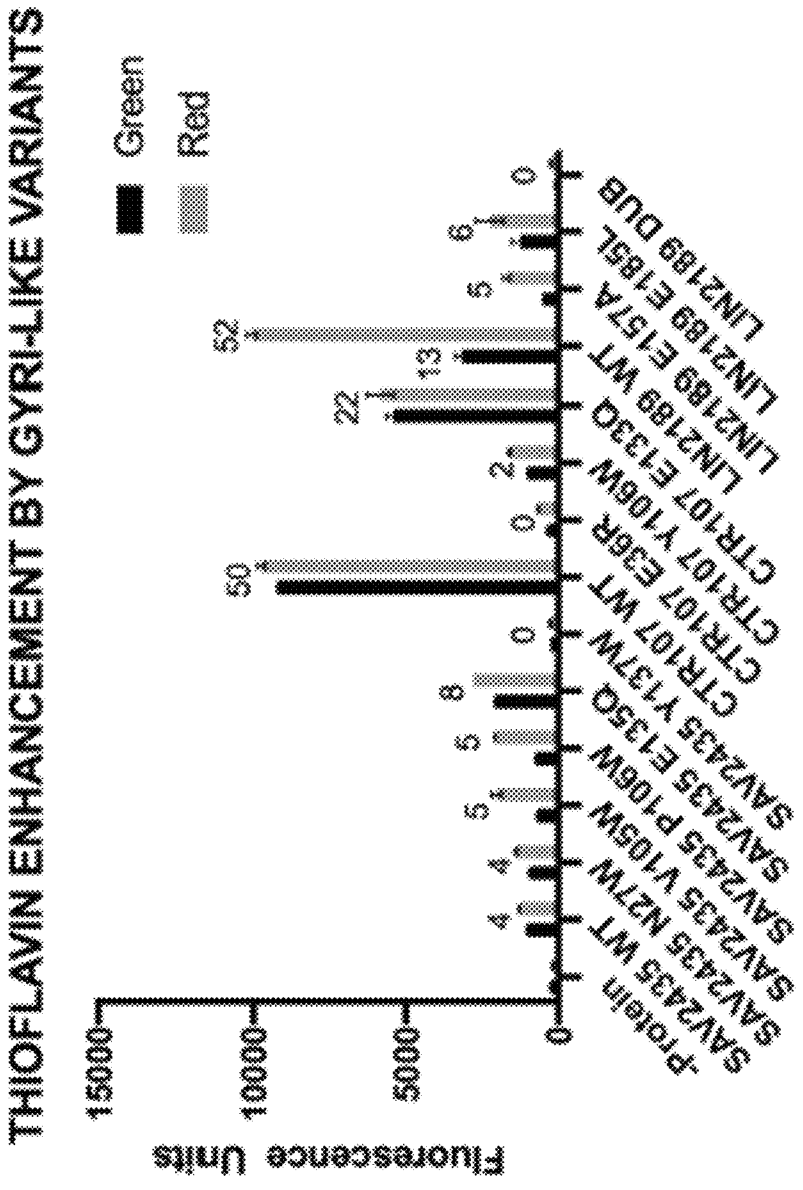
FIG. 8. Bar graph comparing the Thioflavin T fluorescence enhancement by Gyrl-like protein variants. Black bars represent data collected under the green channel and grey bars represents data collected under the red channel. Each bar is the mean of data collected in duplicate experiments and error bars represent the standard deviation of averaged results. Fold changes in fluorescence by aptamers are displayed above each bar.

Example 6: Enhancement of Thioflavin T Fluorescence by Gyrl-Like Protein Aptamer Variants Thioflavin T is a benzothiazole dye that has also been used in many fluorescence applications. Thioflavin T exhibits low background fluorescence but when bound to amyloid fibers or aggregated proteins display strong enhancement of fluorescence. Recently, it has been shown that Thioflavin T binds to a RNA aptamer and exhibits strong fluorescence[20]. The Corn aptamer is able to bind to two Thioflavin T molecules at a homodimer interface formed by G-quadruplexes. We tested whether Gyrl-like proteins could function as fluorescence enhancement aptamers of Thioflavin T. Thioflavin T has excitation and emission maxima of 450 and 527 nM, respectively. We probed the fluorescence enhancing properties of SAV2435, CTR107 and LIN2189 variants on Thioflavin T (FIG. 8). Of these Gyrl-like variants, only CTR107 WT and LIN2189 WT showed significant enhancement. For CTR107 WT the enhancement was 50-fold under both green and red channel. LIN2189 wildtype showed a 13-fold enhancement under the green channel and a 50-fold enhancement under the red channel. The differences in enhancement for CTR107 WT and LIN2189 WT is likely due to variable binding interactions between Thiazole Orange and each binding site. All other variants display either a small 4-6 fold increase or no increase in Thioflavin T fluorescence. The lack of multispecific enhancement demonstrates that the mechanism of enhancement is specific to the binding site interactions with Thioflavin T. The results provided herein that single mutations can completely disrupt or enhance fluorescence activation would lead those of skill in the art to readily understand that mutagenesis can be used to tune invention aptamers to a desired fluorophore enhancement and affinity. Thus, in accordance with present invention, methods are provided herein comprising combinatorial mutational analysis of the Thioflavin T binding site coupled with fluorescence screening to identify and select brighter Thioflavin T enhancing variant aptamers.

Example 7: Fluorescence Enhancement of Acridine Dye Analogs by Gyrl-Like Protein Aptamer Variants We further demonstrate the broad specificity of fluorescence enhancement by Gyrl-like proteins by assessing fluorescence enhancement of acridine analogs. Acridine Orange and Atto 495 are cell-permeable fluorescent dyes used for various fluorescence imaging purposes. Without enhancing aptamer, high concentrations of Acridine and Atto495 are required for visualization under fluorescence microscopy. Previous studies have reported broad RNA aptamers that can enhance dyes Acridine Orange, Atto495 and other similar analogs. These RNA aptamer produce noticeably bright fluorescence enhancement in vivo and require much lower concentrations of dye for visualization. We assessed whether invention Gyrl-like aptamer proteins could enhance Acridine Orange and Atto495 using the same mechanism as RNA Aptamers.

Figure 9A:
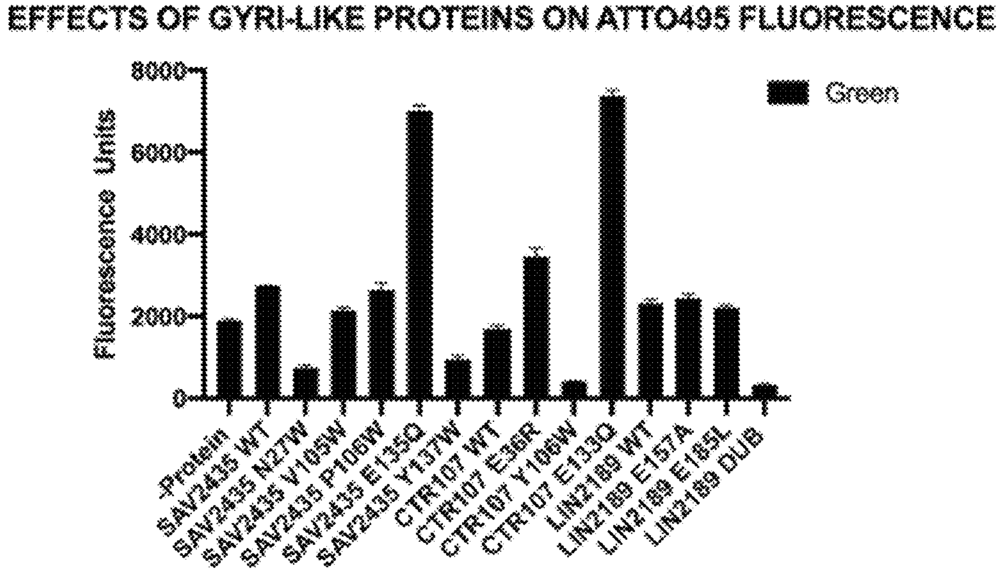
FIG. 9A Bar graph comparing the Atto495 fluorescence enhancement by Gyrl-like protein variants.

In most cases Gyrl-like variants produce very small enhancement when added to 500 nM Atto495 (FIG. 9A). Only variants CTR107 E133Q and SAV2435 E135Q showed a near 4-fold increase in fluorescence enhancement (FIG. 9A). This value is similar to that observed for Atto495 enhancement by SRB-2 RNA aptamer. The chemical structure of Atto495 explains why mutation of conserved glutamate in SAV2435 and CTR107 resulted in increased fluorescence by Atto495 (FIG. 4). The carboxyl tail of Atto495 is presumed to form unfavorable interactions with the side chain of conserved glutamates buried in each pocket. Mutation to glutamine removes repulsive interactions and promotes more favorable binding. We observed fluorescence quenching with aptamers SAV2435 N27W, SAV2435 Y137W, CTR107 Y106W and LIN2189 E157A-E185L double mutant (FIG. 9A). In all cases a 4-fold decrease in fluorescence is observed when each variant is added to Atto495.

These results are indicative of the first (invention) dual fluorescence on/off bioswitch system (e.g., turn-on fluorescence and turn-off fluorescence) mediated by Gyrl-like proteins. For example, the following combinations can work together to both turn-on and turn-off (e.g., activate and quench) the intrinsic fluorescence of Atto495 dye: CTR107 E133Q and SAV2435 N27W; CTR107 E133Q and SAV2435 Y137W; CTR107 E133Q and CTR107 Y106W; CTR107 E133Q and LIN2189 E157A-E185L double mutant; SAV2435 E135Q and SAV2435 N27W; SAV2435 E135Q and SAV2435 Y137W; SAV2435 E135Q and CTR107 Y106W; SAV2435 E135Q and LIN2189 E157A-E185L double mutant; and the like.

Figure 9B:
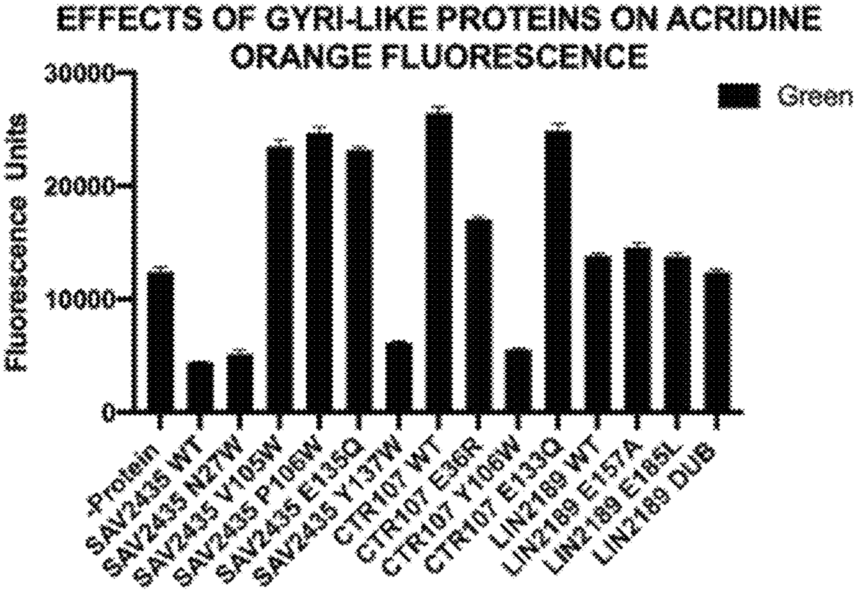
FIG. 9B Bar graph comparing the Acridine Orange fluorescence enhancement by Gyrl-like protein variants. Black bars represent data collected under the green channel and grey bars represents data collected under the red channel. Each bar is the mean of data collected in duplicate experiments and error bars represent the standard deviation of averaged results. Fold changes in fluorescence by aptamers are displayed above each bar.

Acridine Orange is a positively charged dye that is similar in overall structure to Atto495 without the carboxy tail. We assessed the effects of Gyrl-like proteins on Acridine Orange fluorescence (FIG. 9B). Gyrl-like variants showed either a 2-fold increase or decrease in Acridine Orange fluorescence or no effect at all. Variants SAV2435 E135Q, SAV2435 V105W, SAV2435 P106W, CTR107 WT and CTR107 E133Q all doubled the fluorescence intensity of 500 nM Acridine Orange. Variants SAV2435 WT, SAV2435 N27W, SAV2435 Y137W, CTR107 Y106W all showed a 2-3 fold quenching effect on Acridine Orange fluorescence. The dual enhancing-quenching effects seen in this invention by respective Gyrl-like engineered, non-native, variant aptamer proteins demonstrate that various types of fluorescence modules can be created.

For example, the following combinations can work together to both turn-on and turn-off (e.g., activate and quench) the intrinsic fluorescence of Acridine Orange dye: any one of the fluorescence-enhancing aptamers selected from the group consisting of: SAV2435 E135Q, SAV2435 V105W, SAV2435 P106W, CTR107 WT and CTR107 E133Q; in combination with any one of the fluorescence-quenching aptamers selected from the group consisting of: SAV2435 WT, SAV2435 N27W, SAV2435 Y137W, CTR107 Y106W. Accordingly, exemplary specific fluorescence on/off combinations of the invention for modulating the intrinsic fluorescence of Acridine Orange dye include, for example, SAV2435 E135Q and SAV2435 WT, SAV2435 E135Q and SAV2435 N27W, SAV2435 E135Q and SAV2435 Y137W, SAV2435 E135Q and CTR107 Y106W, SAV2435 V105W and SAV2435 WT, SAV2435 V105W and SAV2435 N27W, SAV2435 V105W and SAV2435 Y137W, SAV2435 V105W and CTR107 Y106W, SAV2435 P106W and SAV2435 WT, SAV2435 P106W and SAV2435 N27W, SAV2435 P106W and SAV2435 Y137W, SAV2435 P106W and CTR107 Y106W, CTR107 WT and SAV2435 WT, CTR107 WT and SAV2435 N27W, CTR107 WT and SAV2435 Y137W, CTR107 WT and CTR107 Y106W, CTR107 E133Q and SAV2435 WT, CTR107 E133Q and SAV2435 N27W, CTR107 E133Q and SAV2435 Y137W, CTR107 E133Q and CTR107 Y106W, and the like.

As used herein, the phrase "modulating the intrinsic fluorescence" refers to either activating (increasing) or quenching (also referred to herein as shutting off, lowering or reducing fluorescence) fluorescence by the respective dye.

The ability to produce modest enhancement would lead those of skill in the art to readily understand that further mutational analysis and selection of Gyrl-like proteins will produce brighter fluorescence enhancing aptamers of Atto495 and Acridine Orange. The enhancing effects by Gyrl-like proteins on Atto495 indicates that similar Acridine analogs can be used as fluorescence substrates for aptamer design. This mechanism of fluorescence quenching can also be used as a powerful tool for fluorescence imaging and aptamer design for Acridine analogs. The on/off dual fluorescence (e.g., turning-on/enhancement and turning-off/quenching) can be used to create important molecular switches for a wide range of applications.

Figure 10A:
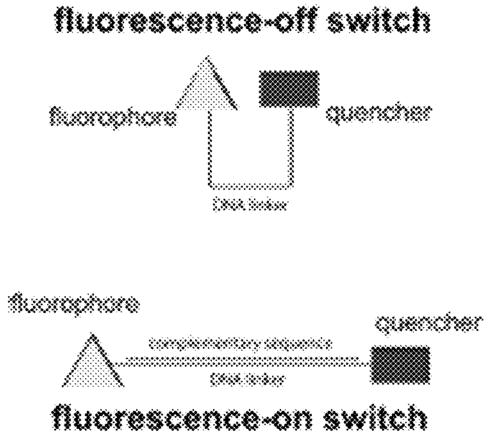
FIG. 10A Schematic diagram of fluorescence switches formed by ground state fluorophore quencher pairs tethered together by a short oligonucleotide and their activation by complementary nucleic acids FIG. 10B hypothetical activation of fluorescence switches formed by ground state fluorophore quencher pairs when bound by Gyrl-like proteins.

Example 8: Design of Fluorescent Switch Activated by Gyrl-Like Protein Aptamers In accordance with the present invention, the determination that Gyrl-like proteins can bind fluorescent dyes permits for the creation of molecular fluorescence activated switches with low background fluorescence. Those of skill in the art will recognize that these invention dual on/off switch tools can be expanded to create sensitive cellular imaging or diagnostic technologies. For example, it has been found that the use of short single-stranded nucleic acids labeled with a fluorophore and a quencher at each end functions as a fluorescence switch. In the ground state the labeled oligonucleotide remains in a fluorescence-off state due to contact quenching mechanisms (FIG. 10A). When a complementary nucleic acid strand is added quenching is disrupted and bright fluorescence is observed. These Fluorophore/quencher labeled oligonucleotides have been used as probes in qPCR or as response switches in various assays.

Figure 10B:
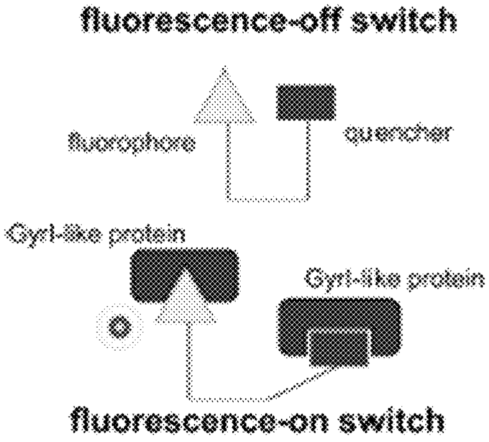
FIG. 10C Bar graph comparing the fluorescence activation of a CY5-DNA-BHQ1 switch by Gyrl-like protein variants. Black bars represent data collected under the green channel and grey bars represents data collected under the red channel. Each bar is the mean of data collected in duplicate experiments and error bars represent the standard deviation of averaged results. Fold changes in fluorescence by aptamers are displayed above each bar.
Figure 10C:
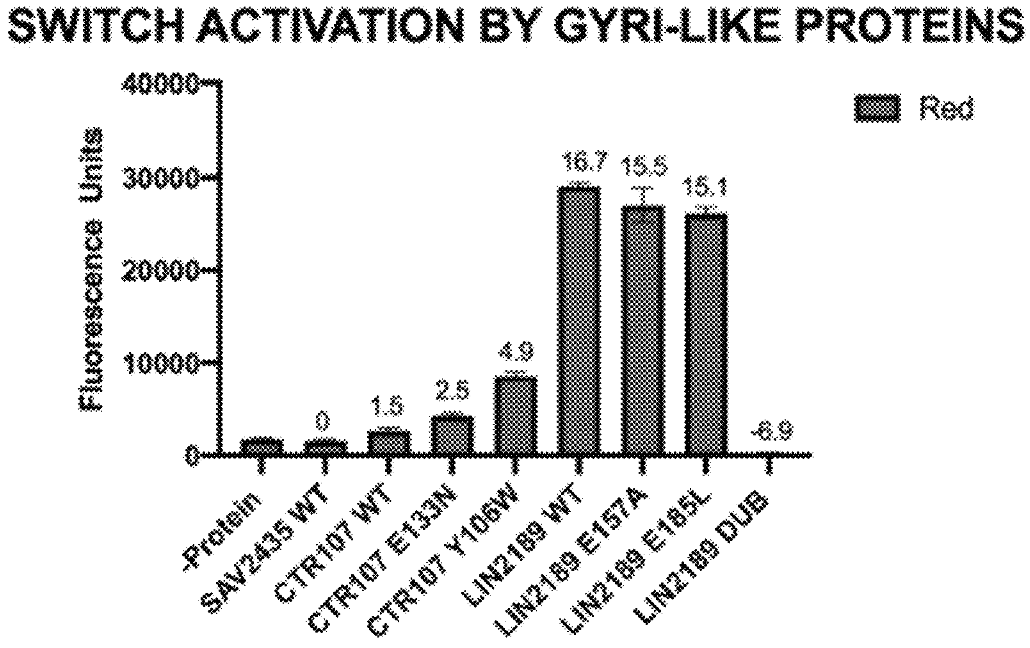

In accordance with the present invention, because it has been found that Gyrl-like proteins can bind to multiple aromatic substrates, we constructed Gyrl-like variant aptamer proteins and assessed whether they could be used as molecular switches by competitively binding to either a fluorophore or quencher, thereby reversibly controlling fluorescence activation and inactivation (i.e., quenching) (FIG. 10B). We designed and purchased a short oligonucleotide (CY5-oligo-BHQ1) probe labeled with Cyanine 5 (CY5) at the 5'-end and a blackhole quencher 1 (BHQ1) molecule at the 3'-end and assessed whether Gyrl-like variant aptamers could activate fluorescence in a switch-like fashion. In fluorescence activation assays, only low fluorescence activation was observed when saturating concentrations of CTR107 WT and SAV2435 were added to 100 nM CY5-oligo-BHQ1 (FIG. 10C). Mutants CTR107 E133N and CTR107 Y106W also showed a small 2-5 fold effect on fluorescence switch activation (FIG. 10C).

However, when either LIN2189 WT, LIN2189 E157A and/or LIN2189 E185L were added to the dual labelled CY5-oligo-BHQ1 (fluorophore/quencher), they each showed dramatic fluorescence-switch activation, resulting in a 15-17-fold CY5 fluorescence increase. Fluorescence enhancement is likely due to interactions between LIN2189 variant aptamers with CY5 or BHQ1 which would disrupt the contact quenching complex formed by the pair in the ground state (FIG. 10B).

Accordingly, the present invention demonstrates a further novel mechanism of reversible and controllable fluorescence-switch activation by Gyrl-like variant proteins. Accordingly, provided herein are invention methods of fluorescence-switch activation of dual-labeled probes (e.g., nucleic acids, linkers, and the like) without the need of complementary nucleic acids, in the case of an oligonucleotide probe. This invention method comprises providing a dual-labelled fluorescence-switch-activation module (aka a dual-labeled probe), wherein the quencher moiety is in operative proximity with a fluorophore such that the fluorophore is quenched; and contacting the fluorescence-switch-activation module with a Gyrl-like protein.

Those of skill in the art will recognize that, in this particular embodiment, further CY5 fluorescence-enhancements can be obtained by screening for additional LIN2189 non-native, variant aptamers from the invention LIN2189 WT mutagenesis library; and that additional Gyrl-like switch-activation modules can be produced herein for numerous other fluorophore-quencher pairs using the invention methods described herein. These switches are useful in a wide range of biotech applications.

Figure 11A:
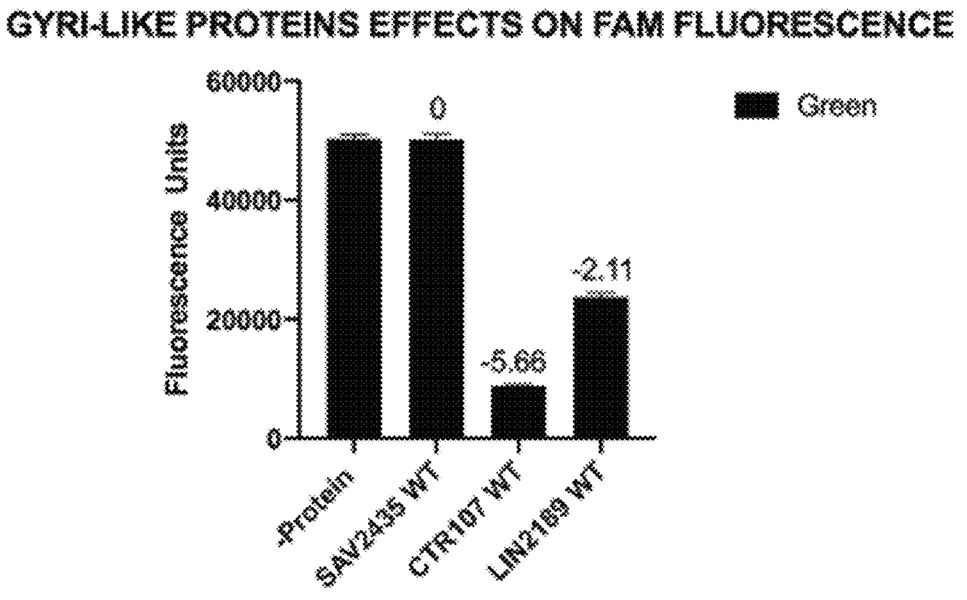
FIG. 11A A Bar graph comparing the 5-(6)Carboxyfluorescein fluorescence quenching by wildtype Gyrl-like protein.

Example 9: Design of Fluorescent Dye-Binding Aptamers from the Gyrl-Like Family with Biotechnological Applications The fluorescence enhancing or quenching properties of Gyrl-like proteins can be used as a tool for identifying aptamers for target organic compounds. Building on Examples 1-8 we designed a protocol for identifying aptamers that bind to fluorescent dyes 5(6)-Carboxyfluorescein (FAM) and 5-Carboxytetramethylrhodamine (TAMRA) (FIG. 4). Both dyes are similar in structure and fluorescence in the green and red regions, respectively. The binding of FAM and TAMRA by Gyrl-like variant aptamers will result in enhancement or quenching of fluorescence. The invention method starts with screening our 3-selected wildtype Gyrl-like proteins to determine which can alter the fluorescence of FAM in solution (FIG. 11A). In fluorescence assays only CTR107 WT (6-fold) and LIN2189 WT (2-fold) caused a decrease in 1 μM FAM fluorescence at saturating concentrations while SAV2435 WT showed no effect. This step indicates that CTR107 and LIN2189 are good templates to design FAM binding aptamers that can be analyzed by fluorescence methods.

Figure 11B:
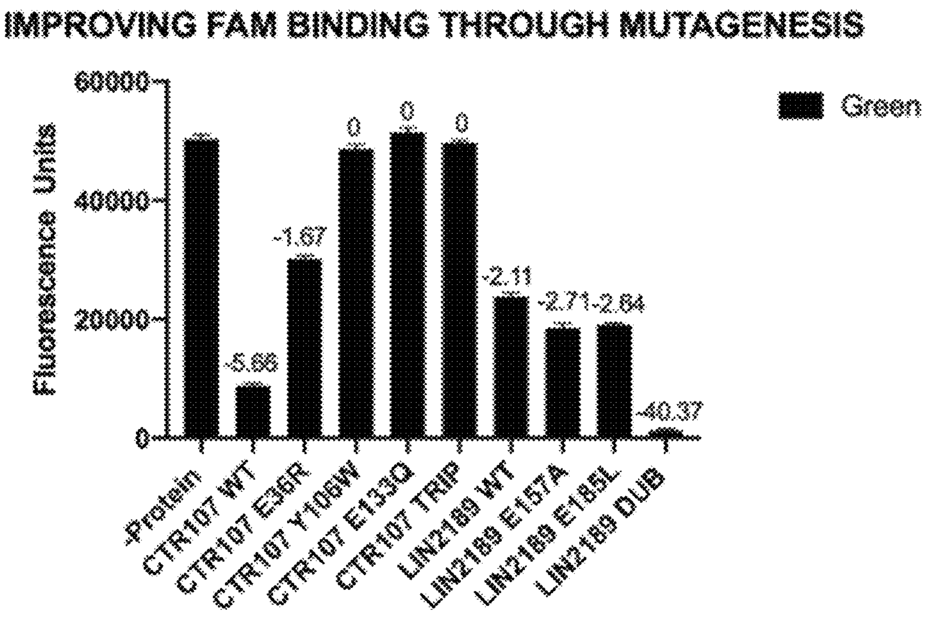
FIG. 11B Bar Graph comparing the 5-(6)Carboxyfluorescein fluorescence quenching by Gyrl-like protein variants.

To further isolate improved FAM-binding aptamers we next analyzed the fluorescence decrease caused by Gyrl-like non-native variant aptamers of CTR107 and LIN2189. We designed rational mutants that were believed to complement FAM binding based on the crystal structure of CTR107 WT bound to Rhodamine6G. We assessed whether substitutions E36R, Y106W, and E133Q would enhance the binding of FAM in the CTR107 pocket. We also assessed whether a triple mutant having all 3 of the E36R, H40Y, and Y106W mutations could synergistically improve FAM binding. In fluorescence assays, all CTR107 variant aptamers tested cause loss of quenching properties (FIG. 11B). This could be a result of loss of FAM binding by these variants or preserved binding with a disruption in the fluorescence quenching mechanism. For LIN2189, we designed mutants based on the crystal structure bound to its substrate Yatekamycin and its catalytic mechanism. Mutations E157A and E185L are sufficient to knockout catalysis without compromising ligand binding. We assessed whether single mutations or double mutations at both amino acid positions (LIN2189 DUB) would create non-catalytic and tight binding aptamers.

We observed that single variants LIN2189 E157A and E185L cause no changes in fluorescence quenching compared to LIN2189 WT (FIG. 11B). However, the double mutant, LIN2189 DUB, unexpectedly induced a near 40-fold decrease in the overall fluorescence of FAM (FIG. 11B). This strong decrease is indicative of strong binding by LIN2189 DUB. In accordance with the present invention, we have identified FAM binding variant aptamers using CTR107 and LIN2189 as a starting template. The sharp decrease in fluorescence of FAM upon binding to invention variant aptamers can be used to create molecular switches, biosensors or molecular diagnostics technologies. Those of skill in the art will recognize that additional higher affinity aptamers can also be isolated by using the invention mutant library creation followed by screening for binding. These invention aptamers can be used in a wide range of innovative technologies ranging from cellular imaging to molecular diagnostics.

Figure 11C:
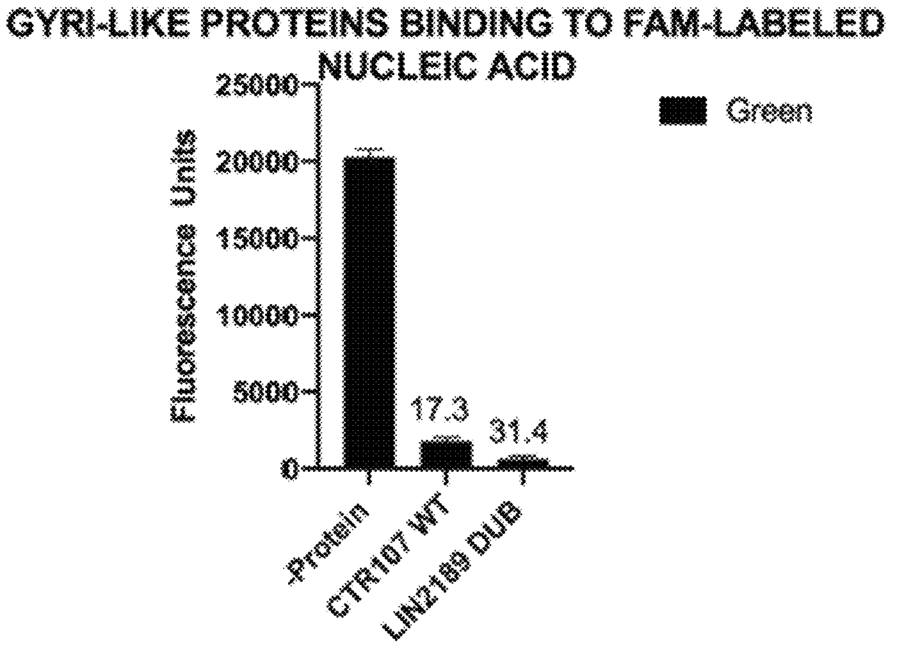
FIG. 11C Bar graph comparing the fluorescence quenching properties of Gyrl-like variants on 5-(6)Carboxyfluorescein-labeled nucleic acid.

FAM and other similar compounds are often used as labels for nucleic acids. Many biotechnology applications such as lateral flow devices and quantitative PCR use labeled oligonucleotides of this kind for sensitive signal detection. We tested the ability of our most potent quenching Gyrl-like aptamer variants to bind to a FAM-labeled oligonucleotide (FAM-PNA) (FIG. 11C). In fluorescence assays we observe that both CTR107 WT and LIN2189 DUB were able to efficiently quench FAM-PNA. In the case of CTR107 WT the quenching was a 17.3-fold decrease, which is drastically more potent than quenching with FAM only (FIG. 11C). LIN2189 DUB had a 31-fold reduction in fluorescence on FAM-PNA and is comparable to the 40-fold reduction seen with non-DNA labeled FAM. Accordingly, provided herein is a method to induce a fluorescence decrease from a fluorophore-labeled nucleic acid. Also provided herein are invention methods of binding and localizing proteins to the 5' or 3' end of nucleic acids. Internal labeled nucleic acids can also be used to localize Gyrl-like proteins to specific base positions. The invention methods also provide powerful tools using fluorophore-labeled nucleic acid that can be applied in biosensors, bioswitches, and molecular diagnostics.

Figure 11D:
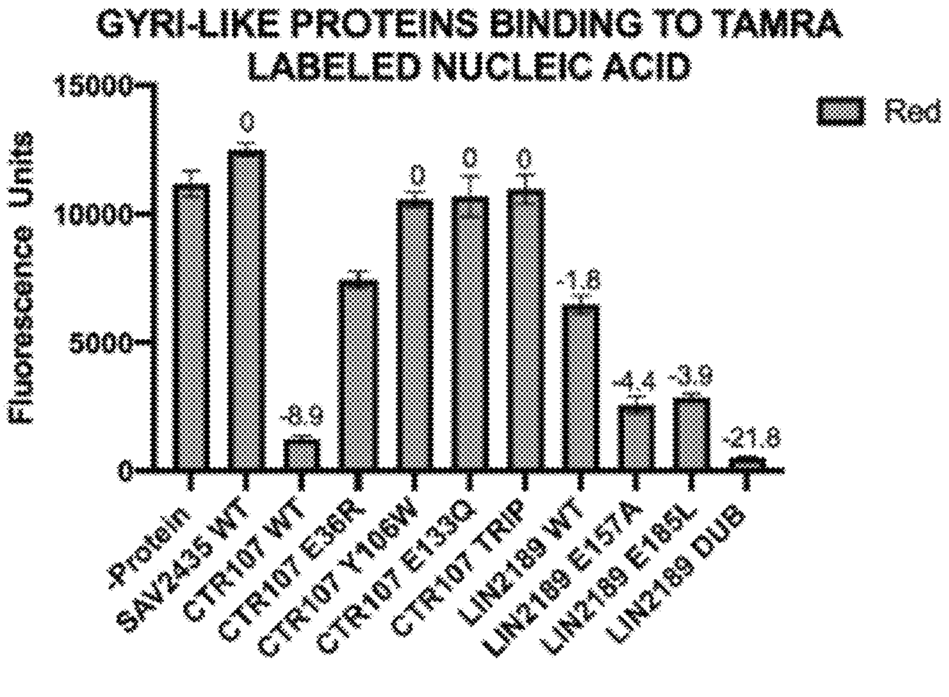
FIG. 11D Bar graph comparing the fluorescence quenching properties of Gyrl-like variants on 5-Tetramethyrhodamine-labeled nucleic acid. Black bars represent data collected under the green channel and grey bars represents data collected under the red channel. Each bar is the mean of data collected in duplicate experiments and error bars represent the standard deviation of averaged results. Fold changes in fluorescence by aptamers are displayed above each bar.

We further tested the versatility of Gyrl-like variants by probing their binding to other dyes. In these experiments, we explored Gyrl-like variants binding and quenching the fluorescence of 1 μM TAMRA-labeled DNA (TAMRA-DNA). TAMRA has an excitation and emission maxima of 546 nm and 579 nm, respectively (FIG. 11D). In this analysis, we monitor fluorescence under the red channel. Similar to FAM binding studies, we only observed strong quenching from CTR107 WT and LIN2189 DUB. CTR107 WT showed a 9-fold quenching effect on TAM-DNA while LIN2189 has 22-fold reduction in fluorescence (FIG. 11D). These results demonstrate the versatility of dye binding by Gyrl-like aptamers.

Figure 11E:
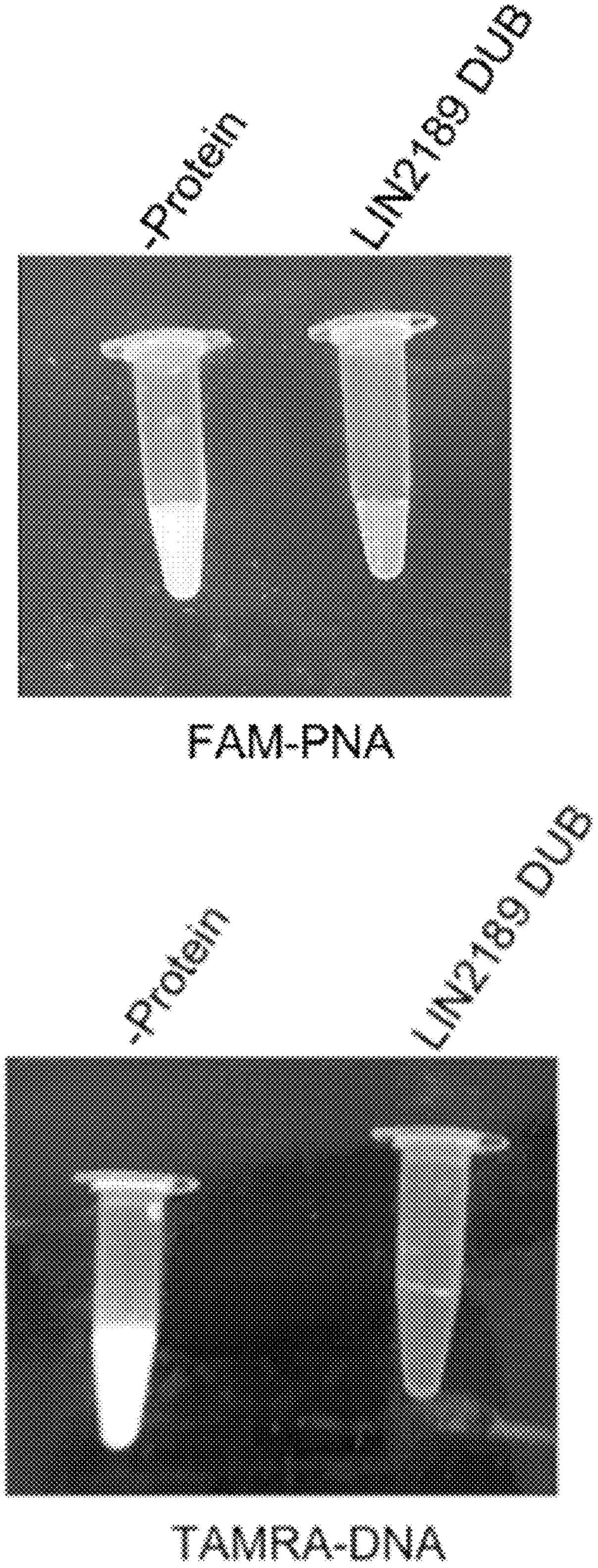
FIG. 11E Potent UV fluorescence quenching by LIN2189 of 5-(6)Carboxyfluorescein-labeled and 5-Tetramethyrhodamine-labeled nucleic acids templates.

Both FAM and TAMRA dyes display bright green and orange fluorescence when illuminated with UV light, respectively. We tested whether the potent quencher LIN2189 WT can shut off (quench) UV fluorescence of FAM-PNA and TAMRA-DNA in solution. At 1 μM, LIN2189 WT was able to completely shut of both the green fluorescence from FAM and red fluorescence from TAMRA observed in the absence of protein (FIG. 11E). In accordance with present invention, it has been found that LIN2189 WT is a potent UV fluorescence-quenching switch that can be utilized in many applications. Using FAM and TAMRA as tag selective DNA binders, invention variant aptamers can be created from the Gyrl-like family of proteins. Those of skill in the art will recognize that several other dye-aptamer pairs can be created using this protocol. These tools can be implemented in technologies such as biosensors, bio-switches, and molecular diagnostics devices.

Figure 12A:
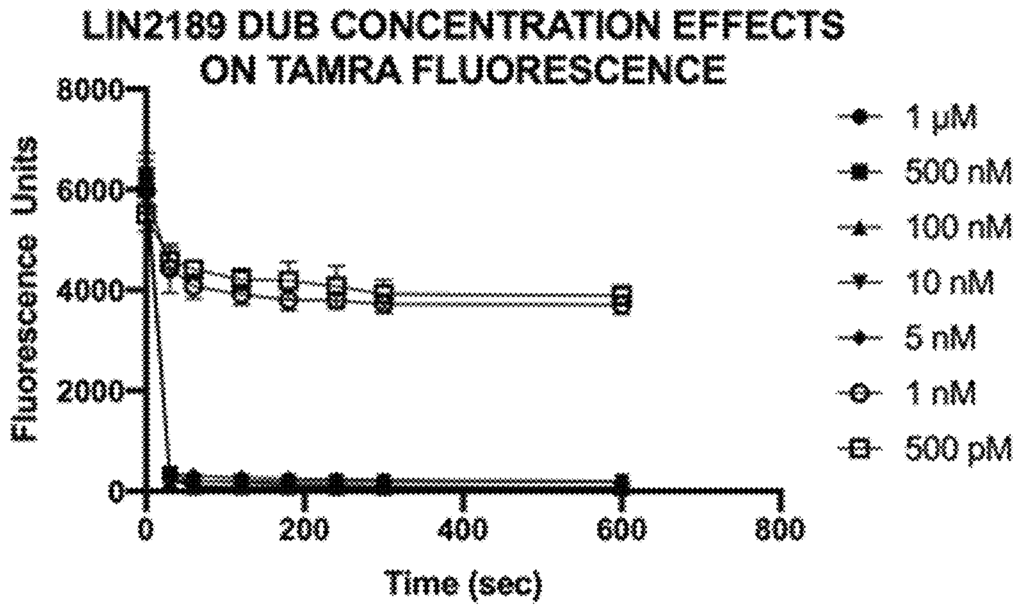
FIG. 12A Enzymatic fluorescence quenching of 5-Tetramethyrhodamine-labeled nucleic acid by LIN2189 DUB at different protein concentrations.
Figure 12B:
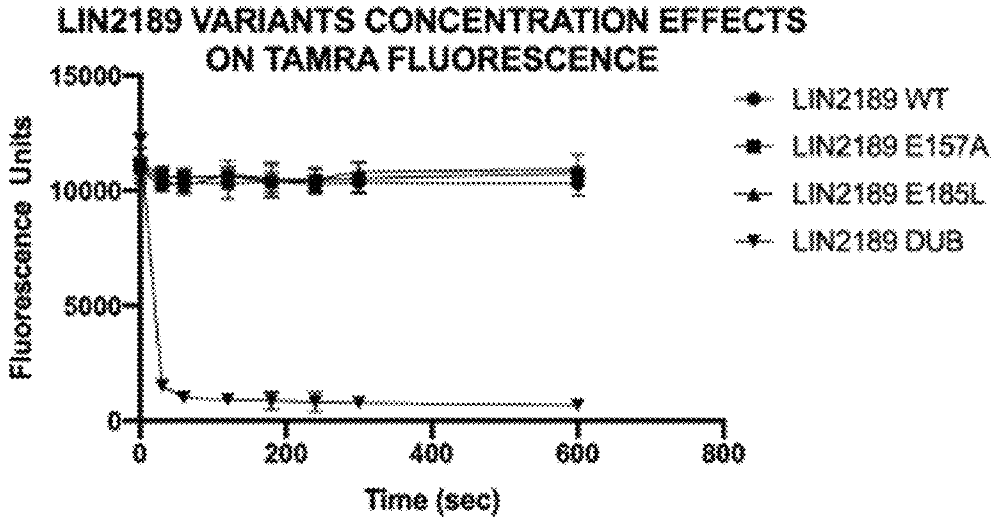
FIG. 12B Comparison of enzymatic LIN2189 DUB quenching of 5-Tetramethyrhodamine-labeled nucleic acid with other non-enzymatic LIN2189 variants. Each point is the mean of data collected in duplicate experiments and error bars represent the standard deviation of averaged results.
Figure 12C:
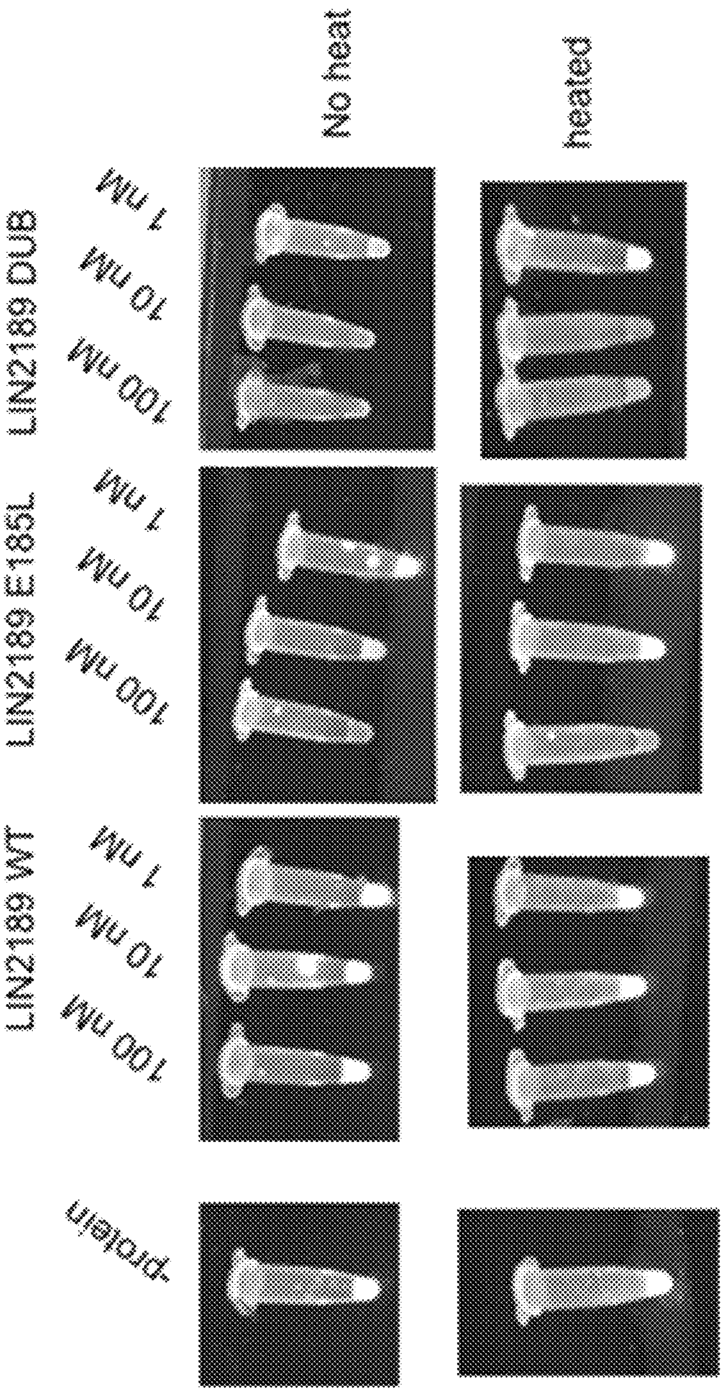
FIG. 12C Comparison of 5-Tetramethyrhodamine-labeled nucleic acid UV fluorescence quenching by enzymatic LIN2189 DUB with non-enzymatic LIN2189 variants. Heated samples were incubated at 95° C. for 10 minutes then rapidly imaged.

Example 10: Design of a Sensitive Fluorescence-Quenching Enzyme (GYRYZYME) from the Gyrl-Like Family of Proteins The invention LIN2189 DUB is a potent quencher of dye fluorescence as seen in example 9. Since LIN2189 WT is an enzyme that is involved in cyclopropanoid hydrolysis, we assessed whether that fluorescence quenching could be a result of LIN2189 DUB binding to fluorophores and disrupting fluorescence or through catalytic modification of fluorophores that perturbs fluorescence mechanism. To determine the mechanism and sensitivity of LIN2189 DUB fluorescence quenching we analyzed its ability to alter TAMRA-DNA fluorescence at various protein concentrations and at different time points (FIG. 12A). LIN2189 DUB is able to completely shut off 100 nM TAMRA fluorescence in 1 minute of incubation time within a concentration range between 5 nM and 1 μM. At 1 nM and 500 μM fluorescence quenching activity is reduced and only a 2-fold reduction in fluorescence is observed in up to 5 minutes incubation time. The non-stoichiometric quenching by LIN2189 DUB strongly indicates that catalysis is the mechanism of fluorescence decrease.

To further confirm the enzymatic properties of LIN2189 DUB fluorescence quenching we compared other LIN2189 variants at non-stoichiometric concentrations with 100 nM TAMRA-DNA. In example 10, all variants cause a decrease in FAM or TAMRA fluorescence at excess concentrations, which can be accounted for due to dye binding by these proteins. At a fixed concentration of 5 nM LIN2189 WT, LIN2189 E157A, and LIN2189 L185E all displayed no effects on TAMRA fluorescence (FIG. 12A). At this concentration LIN2189 DUB is able to efficiently shut off (i.e., quench) TAMRA fluorescence. The difference in LIN2189 variant activities provides strong evidence that LIN2189 DUB is an enzyme capable of acting on multiple substrate dyes.

We used UV fluorescence to further explore the enzymatic functions of LIN2189 DUB in TAMRA fluorescence quenching. 100 nM of TAMRA shows intense fluorescence under UV irradiation. Addition of 1-100 nM of LIN2189 WT did not affect the UV fluorescence of TAMRA. LIN2189 E185L was able to shut off/quench TAMRA fluorescence at 100 nM but was ineffective at 1 nM and 10 nM. In the case of LIN2189 DUB, fluorescence was efficiently quenched at 100 nM and 10 nM with approximately 70% quenching at 1 nM. We further subjected samples to heating at 90° C. for 5 minutes and immediately imaged under UV light to determine if fluorescence quenching is reversible. Heated samples showed no recovery of fluorescence at 100 nM and 10 nM with only partial recovery at 1 nM for LIN2189 DUB. Together these results strongly suggest that fluorescence quenching is irreversible and that enzymatic modification of dye is the mechanism of fluorescence loss.

In accordance with the present invention, we have created a versatile enzyme that is capable of rapid and efficient quenching of fluorescent dyes. The invention LIN2189 DUB is capable of shutting off (quenching) the fluorescence of multiple dyes irreversibly in a switch-off-like manner. Moreover, the broad catalytic properties of LIN2189 DUB provides experimental proof that invention enzymatic Gyrl-like aptamers (referred to herein as GYRYZYMEs) can be produced by mutagenesis, in accordance with the present invention. It is contemplated herein that the special properties of LIN2189 DUB can be incorporated in a wide range of biotechnological applications. Those of skill in the art will recognize that using this protocol of mutagenesis and selection, additional synthetic enzymes for various applications can be created.

Example 11: Sensitive Fluorescence Quenching of Acridine Analogs

Figure 13A:
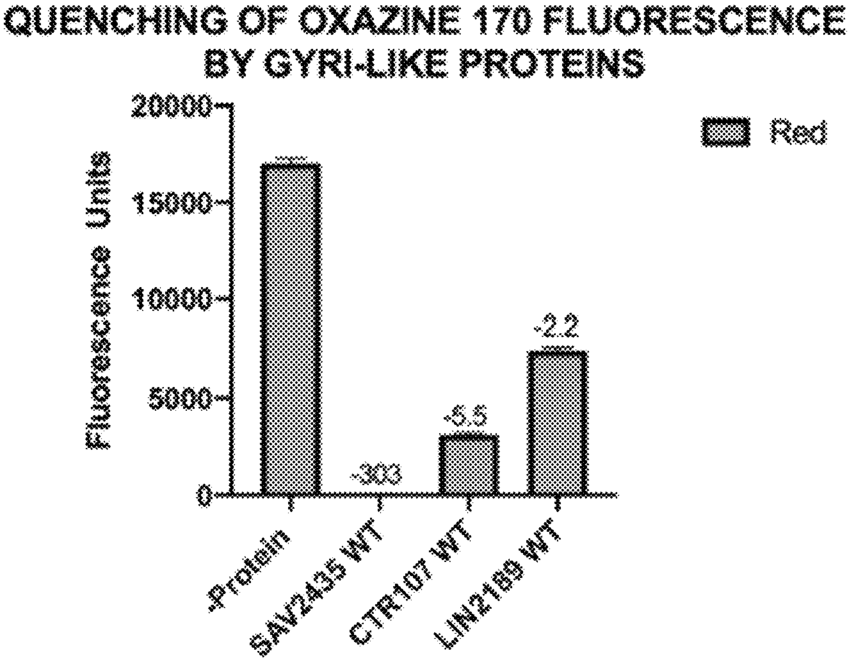
FIG. 13A Bar graph comparing the Oxazine 170 fluorescence quenching by wildtype Gyrl-like protein.

In example 8, we provided proof of fluorescence turn-off (i.e., quenching) by Gyrl-like protein aptamers with Acridine dye analogs (FIG. 4, FIG. 9). The decrease in fluorescence was only a modest 4-fold reduction, which is not potent nor sensitive enough for biosensor or bioswitch development. We further explored other Acridine-like dye analogs to isolate more sensitive and potent quenching modules from the Gyrl-like protein family. Oxazine 170 is a far-red fluorescence dye with excitation and emission maxima at 615 and 642 nM, respectively. Using our fluorescence assay we monitored changes in 500 nM Oxazine 170 fluorescence with saturating concentration of wildtype Gyrl-like proteins under the red channel (FIG. 13A). Only SAV2425 WT and CTR107 WT displayed strong quenching effects. CTR107 WT showed a 6-fold reduction in Oxazine 170 flourescence, while SAV2534 WT displayed a remarkable 303-fold decrease (FIG. 13A). The 303-fold decrease caused by SAV2435 WT is equivalent to a near 100% shut-off of fluorescence by Oxazine 170 (FIG. 13A). The strong decrease by SAV2435 WT is the most potent quenching aptamer discovered from Gyrl-like protein to date.

Figure 13B:
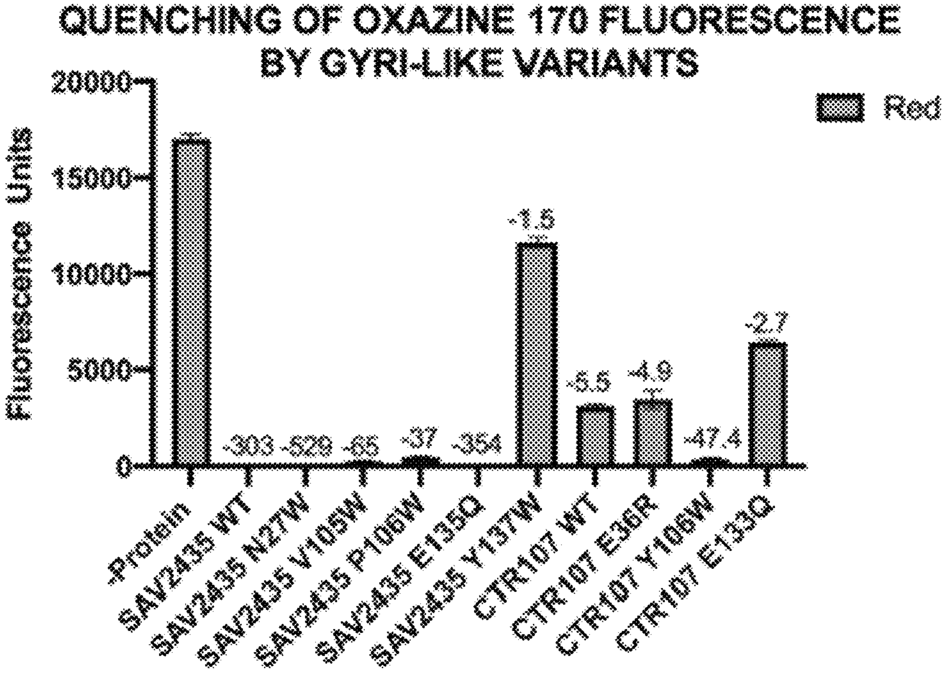
FIG. 13B Bar Graph comparing the Oxazine 170 fluorescence quenching by Gyrl-like protein variants. Black bars represent data collected under the green channel and grey bars represents data collected under the red channel. Each bar is the mean of data collected in duplicate experiments and error bars represent the standard deviation of averaged results. Fold changes in fluorescence by aptamers are displayed above each bar.

We explored additional variants of SAV2435 WT and CTR107 WT to identify aptamers with stronger quenching effects. In fluorescence assays, all SAV2435 variant aptamers showed strong quenching effects except SAV2435 Y137W which only showed a small decrease. Fluorescence enhancers SAV2345 V105W (−65-fold decrease) and SAV2435 P106W (−37-fold decrease) were around 10-20-fold weaker than SAV2435 WT (FIG. 13B). Non-enhancing mutants SAV2435 N27W and SAV2345 E135Q showed a 529-fold and 303-fold reduction in fluorescence, respectively, which is 1.5-2-fold more potent that SAV2435 wildtype (FIG. 13B). These aptamers also induced near 100% shut-off of Oxazine 170 fluorescence. In the case of CTR107 variants, only CTR107 Y106W induced strong quenching effects on Oxazine 170. This variant was 5-fold more potent than CTR107 WT and caused an overall 47-fold decrease in fluorescence. These results demonstrate that mutagenesis of the CTR107 and SAV2435 binding pocket, in accordance with the present invention, can produce more potent quenchers of dye fluorescence.

Figure 13C:
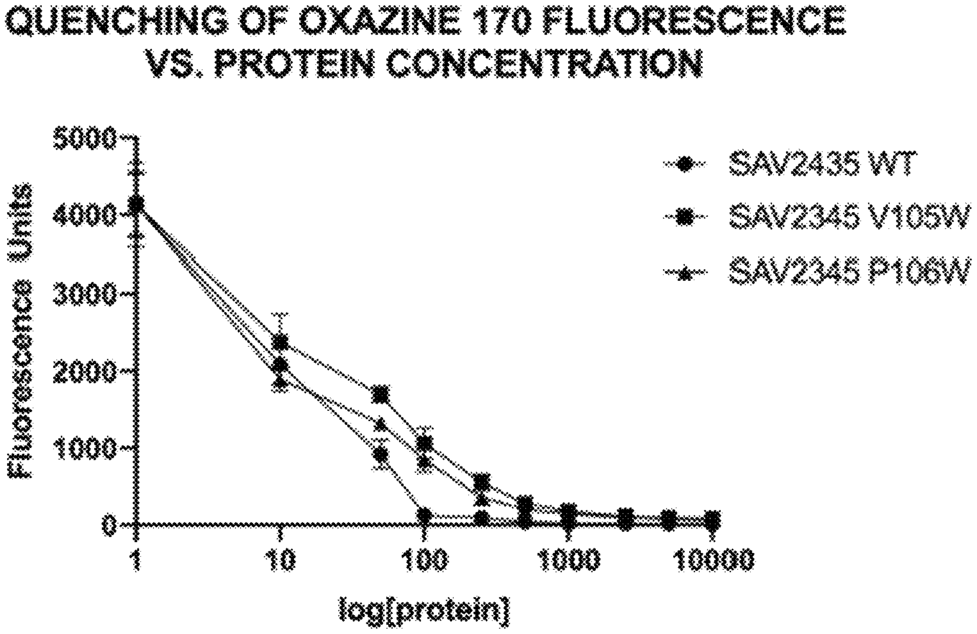
FIG. 13C Comparison of Oxazine 170 fluorescence quenching as a function of protein concentration for SAV2435 variants. Each point is the mean of data collected in duplicate experiments and error bars represent the standard deviation of averaged results.

We also analyzed the effects of SAV2345 WT on the absorbance spectrum of Oxazine. When no protein is present, Oxazine shows a broad excitation peak at 615-625 nm. When SAV2435 is present the excitation peak doubles and is red shifted to a sharper peak from 640-645 nm. These changes in excitation properties induced by SAV2435 when bound to oxazine 170 contribute to the observed quenching mechanism. We further compared the concentration dependence of SAV2435 variant aptamers on quenching. In this experiment, we compared SAV2435 WT to weaker quenchers SAV2435 V105W and SAV2435 P106W to analyze the sensitivity of fluorescence quenching of 100 nM Oxazine 170 (FIG. 13C). For all three SAV2435 variants, 50% quenching is achieved at 10-50 nM. However, at 100 nM SAV2435 WT is able to induce near 100% fluorescence shut-off while both mutants only induced 60% decrease at this concentration. Even at saturation, mutants were less effective than SAV2435 WT at shutting off fluorescence.

Figure 13D:
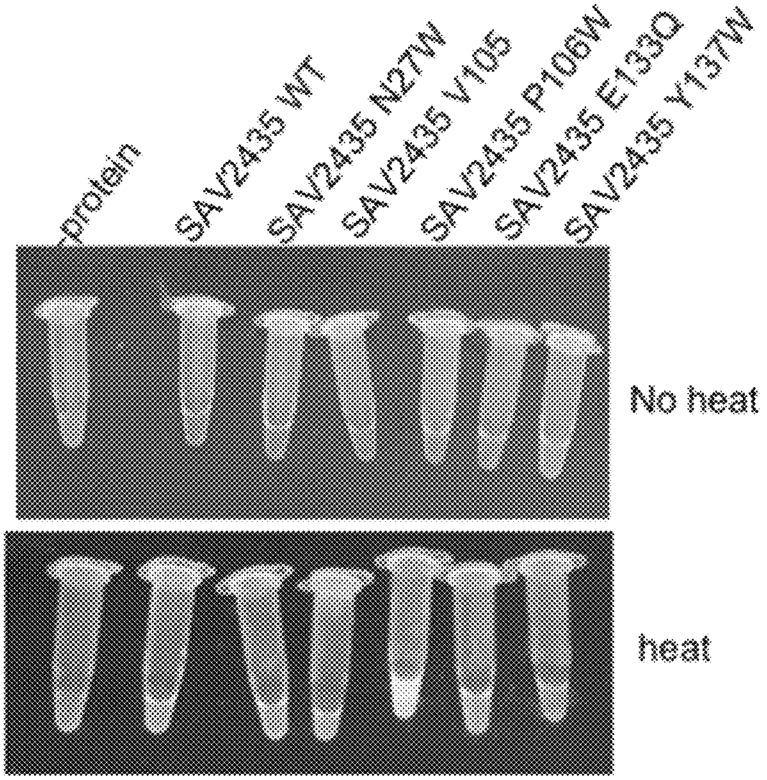
FIG. 13D Reversibility of Oxazine 170 UV fluorescence quenching by SAV2435 variants. Heated samples were incubated at 95° C. for 10 minutes then rapidly imaged.

Oxazine 170 (blue dye by eye) displays bright red fluorescence when illuminated with UV light. We compared the UV fluorescence of unbound dye with dye bound by SAV2435 variants. Under UV light all SAV2435 variant aptamers completely shut-off the red fluorescence seen with unbound dye except the non-quencher SAV2435 Y137W (FIG. 13D). When samples are heated to 95° C. followed by imaging under UV light a complete restoration of fluorescence is observed by all SAV2435 variant aptamers, meaning that the fluorescence quenching mechanism is reversible and unlike the irreversible quenching observed in example 10 with the GYRYZME LIN2189 DUB. These reversible properties prove that SAV2435 and its variant aptamers cause fluorescence decrease through a ligand-binding mechanism and not catalysis.

In accordance with the present invention, we have developed a series of potent fluorescence quenching aptamers from the Gyrl-like family of proteins. These aptamers are able to completely shut-off the far-red fluorescence of Oxazine 170. In particular embodiments, the switch and sensor properties of invention aptamers can be utilized in a wide range of biotechnology tools. The invention method provides a protocol for identifying potent fluorescence quenchers from the Gyrl-like family. Those of skill in the art will recognize that by using the invention methods with mutant libraries of Gyrl-like proteins, numerous binding aptamers that function as potent fluorescence quenchers can be identified.

Example 12: Development of a Protocol for Identifying Gyrl-Like Dye Binding Aptamers that do not Induce Changes in Fluorescence In example 9 we designed rational mutants of CTR107 WT that improved FAM dye binding but did not cause a significant decrease in fluorescence at saturations (FIG. 11B). These aptamers may still bind with high affinity but cannot be monitored by fluorescence. Because of their non-quenching ability these aptamers are suitable for particular bioswitch applications.

Figure 14A:
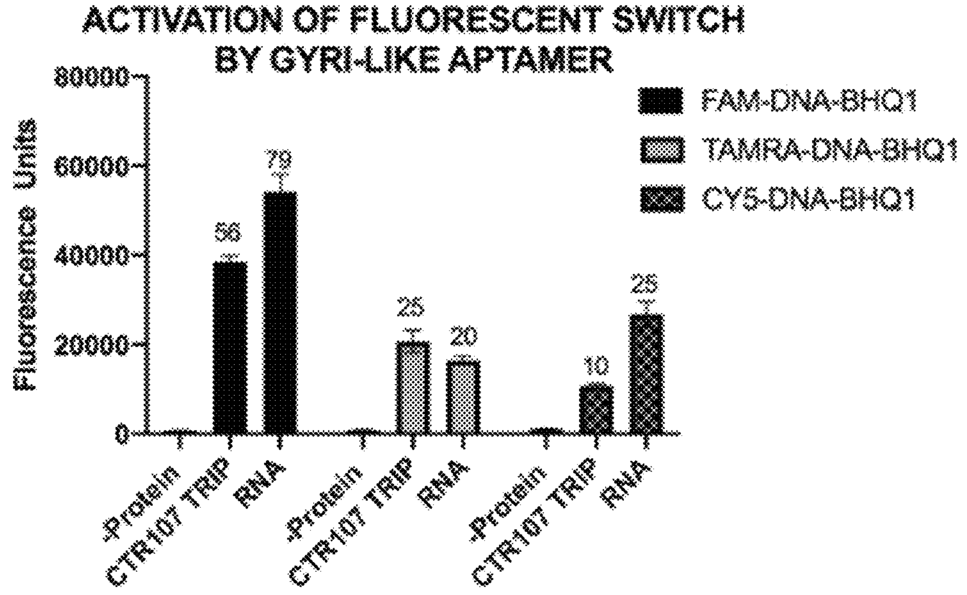
FIG. 14A Activation of fluorescent switches by rationally designed CTR107 high affinity aptamer.

To test the binding of non-quenching or non-enhancing aptamers, we developed a fluorescence switch assay similar to example 8 (FIG. 10A). In this assay, a DNA that is labeled at the 5'-end with fluorophore and at the 3'-end with a BHQ1 quencher is in an off-state due to ground state contact quenching. When a complementary nucleic acid or competitive-binder binds to the labeled DNA, (see example 9) fluorescence is activated due to disruption of contact quenching. We tested whether the CTR107 E36R H40Y Y106W triple mutant (CTR107 TRIP) could activate three bioswitches FAM-DNA-BHQ1, TAMRA-DNA-BHQ1, CY5-DNA-BHQ1 (FIG. 14A). In this experiment we observed that CTR107 was able to activate the FAM-DNA-BHQ1, TAMRA-DNA-BHQ1, CY5-DNA-BHQ1 by 56-fold, 25-fold and 10-fold, respectively. This protocol demonstrates that binding of aptamers that do not affect fluorescence can be studied by this approach. We included bioswitch activation by a complementary RNA to compare the potency of CTR107 TRIP. In the case of FAM-DNA-BHQ1 and TAMRA-DNA-BHQ1 bioswitch activation was comparable, but with CY5-DNA-BHQ1 CTR107 TRIP was 50% weaker than complementary RNA. This result is expected because FAM and TAMRA are similar in structure and charge, in comparison to CY5 (FIG. 4). This result emphasizes that rationally designed CTR107 TRIP aptamers are more selective for FAM and its analogs compared to other unrelated compounds. In accordance with the present invention, rapid and accurate methods are provided to analyze binding of Gyrl-like variant aptamers using a DNA-based fluorescent bioswitch. DNA bioswitches of this kind can be used as biosensors, bioswitches or in molecular diagnostic technologies.

Example 13: Design of a Dual Fluorescence-on/Fluorescence-Off (i.e., on/Off) Bioswitch Using Gyrl-Like Proteins In Example 9 we isolated a GYRYZYME LIN2189 DUB that efficiently shut off fluorescence of FAM and TAMRA dyes. We next assessed whether coupling aptamers that could turn on fluorescence in Example 12 with fluorescence quenching aptamers from Example 9 could create a bidirectional fluorescence on/off bioswitch. In this particular embodiment, a dual fluorescence bioswitching module was designed that can be turned on by CTR107 TRIP or complementary RNA and subsequently shut off (e.g., quenched) by the addition of LIN2189 DUB (FIG. 10A).

Figure 14B:
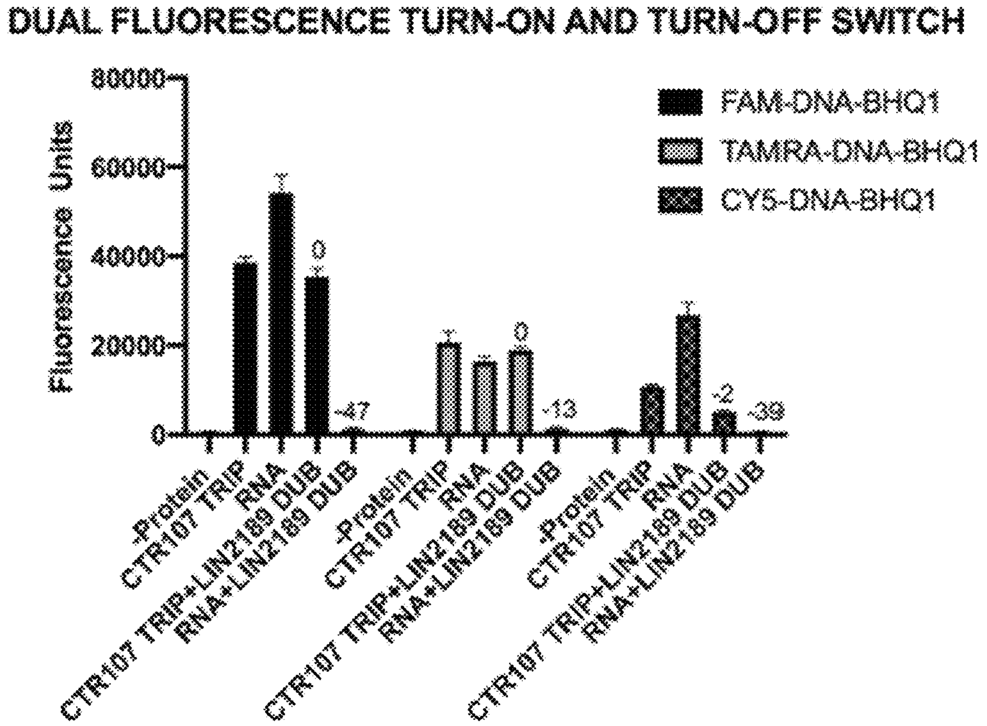
FIG. 14B Design of a dual fluorescence turn-on and turn-off switch using complementary RNA and LIN2189 enzymatic quencher. FAM data were collected under the green channel while TAMRA and CY5 data were collected under the red channel. Bars are colored according to switches in figure legend. Each bar is the mean of data collected in duplicate experiments and error bars represent the standard deviation of averaged results. Fold changes in fluorescence by aptamers are displayed above each bar.

In this embodiment, we compared the ability of the LIN2189 GYRYZYME to shut-off fluorescence from FAM-DNA-BHQ1, TAMRA-DNA-BHQ1, and CY5-DNA-BHQ1 that were pre-activated with CTR107 TRIP or complementary RNA (FIG. 14B). LIN2189 DUB was able to cause a 47-fold reduction with FAM-DNA-BHQ1-RNA activated complex but had no effect on FAM-DNA-BHQ1 activated CTR107 TRIP. A similar result was obtained with TAMRA-DNA-BHQ1 where LIN2189 DUB was able cause a 13-fold decrease in fluorescence when the switch was activated by RNA but had no effect when activated by CTR107 TRIP (FIG. 14B). With CY5-DNA-BHQ1, LIN2189 DUB causes a 39-fold reduction in fluorescence when activated by and complementary RNA, but only a 2-fold reduction when activated by CTR107 TRIP.

These results show that CTR107 TRIP is able to competitively protect fluorophores from enzymatic modification by LIN2189. Moreover, these results strongly show that binding of similar compounds FAM and TAMRA by CTR107 TRIP is tighter than binding with the GYRYZYME LIN2189 DUB. The −2 fold reduction in CY5-DNA-BHQ1 activated by CTR107 TRIP suggests that CY5 does not bind tightly. The weaker activation of CY5-DNA-BHQ1 by CTR107 TRIP compared to activation by complementary RNA also suggests that CY5 is a weaker ligand for CTR107 TRIP. The sharp fluorescence decrease caused by LIN2189 DUB when mixed with the CY5-DNA-BHQ1 template provides evidence that CY5 is a substrate for GYRYZMES.

Accordingly, provided herein is an invention dual fluorescence on/off bioswitch system using a molecule (e.g., DNA, RNA, protein, linker, and the like) that is labeled with a fluorophore at one end, and a quencher at the other end, wherein the fluorophore or quencher can be modulated by an invention variant aptamer. In one embodiment, the invention bioswitch system achieves the fluorescence activation using a complementary RNA that can be subsequently shut off by the GYRYZYME LIN2189 DUB. When both the fluorophore and quencher are combined on respective ends of a particular molecule (e.g., RNA molecule, DNA molecule, and the like), the invention dual on/off bioswitch systems represent a general prototype for designing a multitude of invention dual fluorescent bioswitches that incorporate at least one of the invention variant aptamers. Using the invention methods provided herein, numerous other fluorescence on/off dual bioswitch systems can be designed by mutagenesis and screening of Gyrl-like proteins. These invention bioswitch systems can be used in multiplexed applications to simultaneously detect nucleic acids and proteins. These tools can be used in a wide range of biotechnological applications such as biosensors, bioswitches, and molecular diagnostic technologies.

Figure 15A:
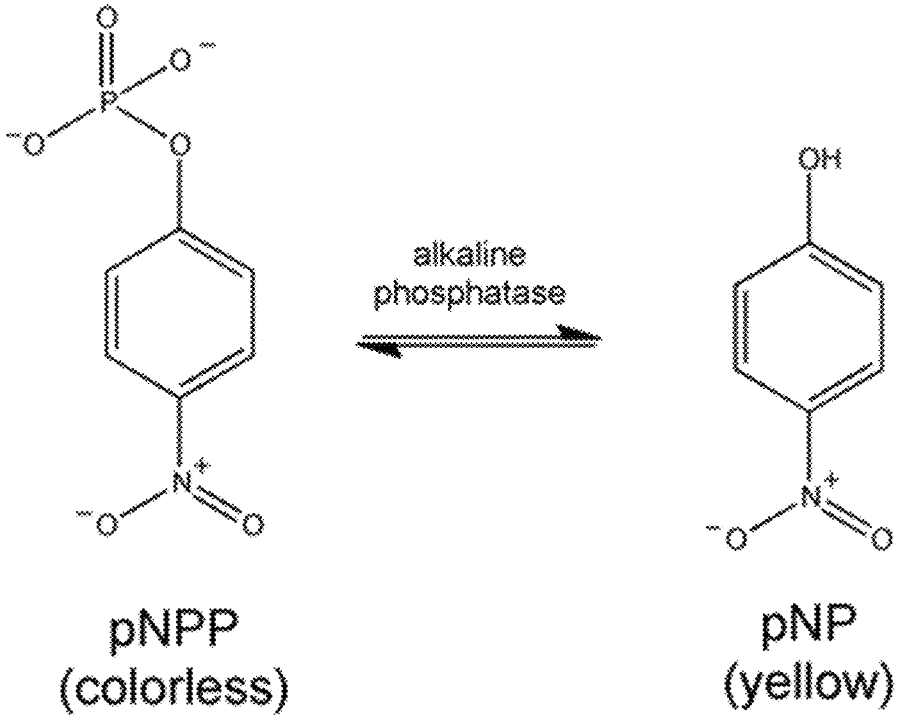
FIG. 15A Chemical reaction of the catalytic conversion of p-Nitrophenylphosphate to p-Nitrophenol by alkaline phosphatase.
Figure 15B:
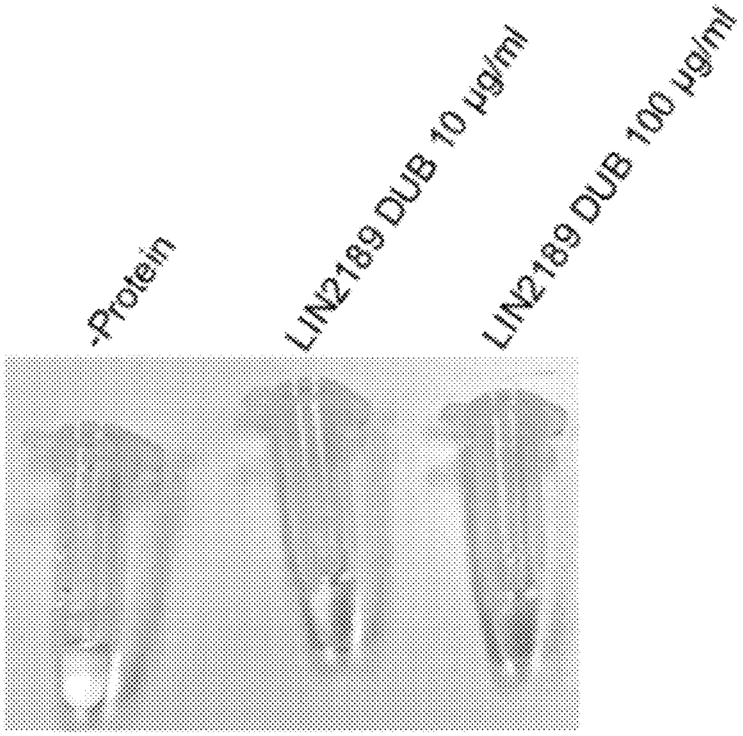
FIG. 15B Catalytic conversion of p-Nitrophenylphosphate to p-Nitrophenol by the GYRYZYME LIN2189 DUB.

Example 14: Design of Additional Versatile GYRYZYMES from the Gyrl-Like Family of Proteins In example 9, we engineered a novel enzymatic Gyrl-like aptamer LIN2189 DUB that is capable of modifying unrelated fluorescence dyes thereby quenching their fluorescence. Using the invention methods provided herein, those of skill in the art recognize that several other enzymatic Gyrl-like proteins can be selected for numerous chemical substrates. We examined whether LIN2189 DUB and other Gyrl-like variant aptamers function to catalyze other important chemical reactions used in biotechnology. Alkaline phosphatase is an important enzyme used in biotechnology for dephosphorylating chemical and biological substrates. In simple colorimetric reactions, alkaline phosphatase is able to dephosphorylate its colorless substrate p-Nitrophenyl Phosphate (pNPP) producing the yellow product p-Nitrophenol (pNP) (FIG. 15A). Because LIN2189 WT is categorized as a hydrolase like alkaline phosphatase, we assessed whether the promiscuous GYRYZYME LIN2189 DUB could hydrolyze pNPP to produce pNP. We mixed 100 μl of pNPP substrate in samples with no protein or with 10 μg/ml or 100 μg/ml LIN2189 DUB. In 3 hours incubation time we were able to detect strong colorimetric changes in samples that contain LIN2189 DUB indicating a conversion of pNPP to pNP (FIG. 15B). These results establish that our invention LIN2189 DUB variant aptamer displays partial phosphatase activity.

Figure 15C:
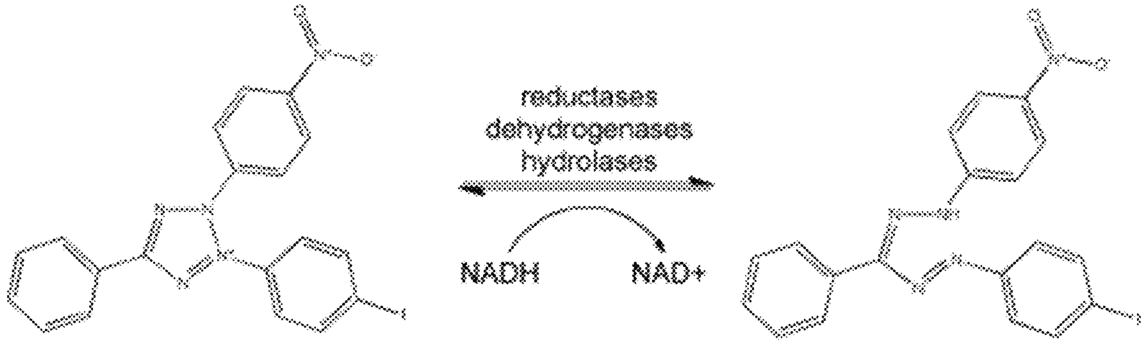
FIG. 15C Colorimetric reaction for the NADPH-dependent catalytic conversion of iodonitrotetrazolium to iodonitroformazan.
Figure 15D:
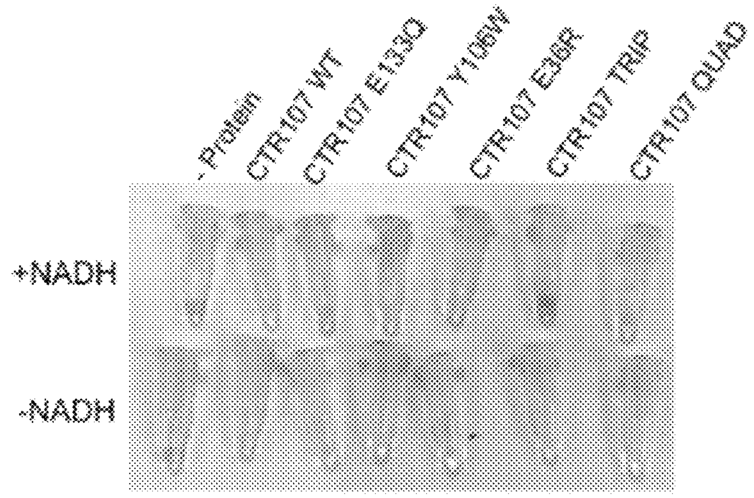
FIG. 15D NADPH-dependent conversion of iodonitrotetrazolium to iodonitroformazan by Gyri-like aptamers after 5-minute incubation.
Figure 15E:
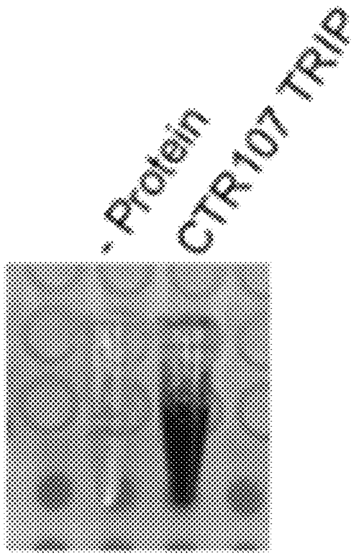
FIG. 15E NADPH-dependent conversion of iodonitrotetrazolium to iodonitroformazan by CTR107 TRIP aptamer after 2-hour incubation.

We further explored the enzymatic functions of other invention Gyrl-like variant aptamers in more complex electron transfer reactions by assessing their ability act on Tetrazolium substrates. Tetrazolium dyes are commonly used as colorimetric indicators in many biotechnological applications. Their ability to act as a final electron acceptor or proton acceptor in multistep reactions allows for the detection of various enzymatic activities (FIG. 15C). A colorimetric signal is observed after protonation of a usually colorless Tetrazolium dye, which converts it to a colored insoluble Formazan product. We assessed whether invention CTR107 variant aptamers could enzymatically convert colorless lodonitrotetrazolium to its red Formazan product in the presence of Nicotinamide Adenine Dinucleotide Hydrate (NADH) (FIG. 15C). In experiments without NADH, no color change is observed with all variants of CTR107 mixed with 500 μM lodonitrotetrazolium at 37° C. for 5 minutes (FIG. 15D). When 100 μM NADH cofactor is added to 500 μM lodonitrotetrazolium in the presence CTR107 E133Q and CTR107 QUAD (E36R, H40Y, Y106W, E133Q quadruple mutant) a faint red signal is observed. CTR107 TRIP showed a much stronger red colorimetric change in comparison to all variants at 5 minutes (FIG. 15D). When reactions are allowed to proceed for 2 hr a dark burgundy color change is observed in samples with CTR107 TRIP and NAPH cofactor present with substrate (FIG. 15E). These results provide evidence that CTR107 TRIP can enzymatically convert lodonitrotetrazolium to its Formazan product.

In accordance with the present invention methods, two unrelated GYRYZYMEs, LIN2189 DUB and CTR107 TRIP have been identified, that can catalyze hydrolysis of biotechnological important reagents. Those of skill in the art will realize that the invention methods can be used to identify other invention enzymatic Gyrl-like variant aptamers that can function as catalysts in a wide range of biochemical reactions. The invention mutagenesis libraries of Gyrl-like proteins have provided various biotechnologically important novel GYRYZYMEs.

Example 15: Design of a Novel Ampicillin Aptamer from the Gyrl-Like Proteins

Some Gyrl-like proteins have the natural ability to bind or modify the structure of drugs by catalysis. We assessed whether high affinity drug-binding variant aptamers could be identified using the invention methods. The first step was screening the three selected Gyrl-like proteins SAV2435, CTR107 and LIN2189 and using the toxicity of drugs as an indirect readout of aptamer binding. We next determined whether expression of selected Gyrl-like proteins in vivo would induce *E. coli* drug resistance through binding and sequestering drugs, or by enzymatic modification, thereby preventing them from reaching their targets and reducing cytotoxicity (FIG. 16 A, B).

Figure 16A:
FIG. 16A Schematic of hypothesis for screening in vivo drug-binding Gyrl-like aptamers using drug sequestration and resistance. Bacteria expressing high-affinity Gyrl-like aptamers will induce resistance by preventing drugs from accessing their natural target site.
Figure 16B:
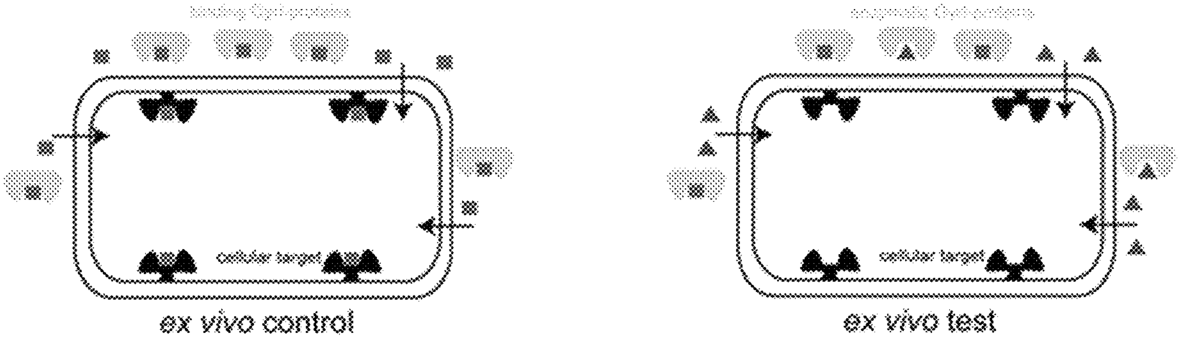
FIG. 16B Schematic of hypothesis for testing for enzymatic Gyrl-like proteins. Ex vivo inactivation of drugs will induce resistance when non-resistant bacteria are grown in the presence of inactivated drugs.
Figure 16C:
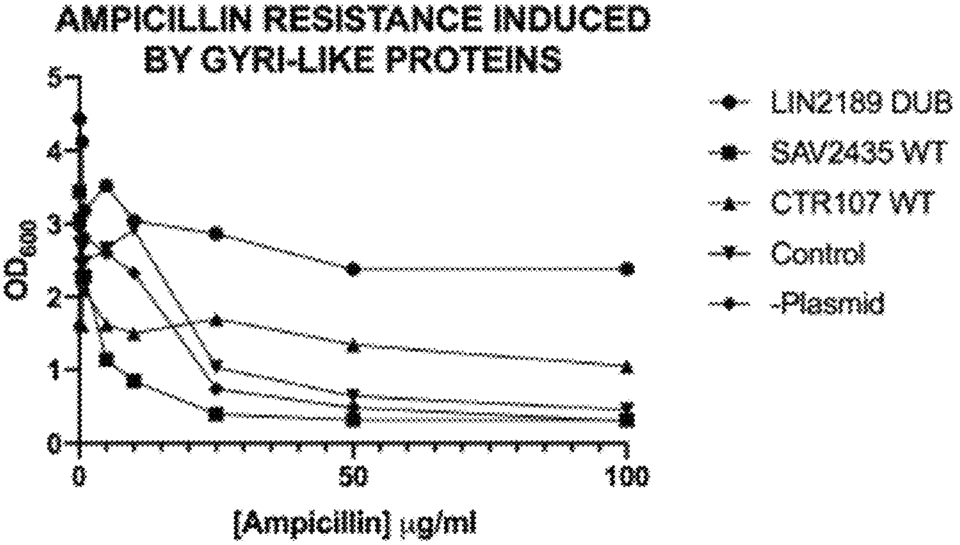
FIG. 16C Plot of *E. coli* growth as a function of ampicillin concentration after protein expression. Figure legend displays plasmid-expressed proteins for each experiment.
Figure 16D:
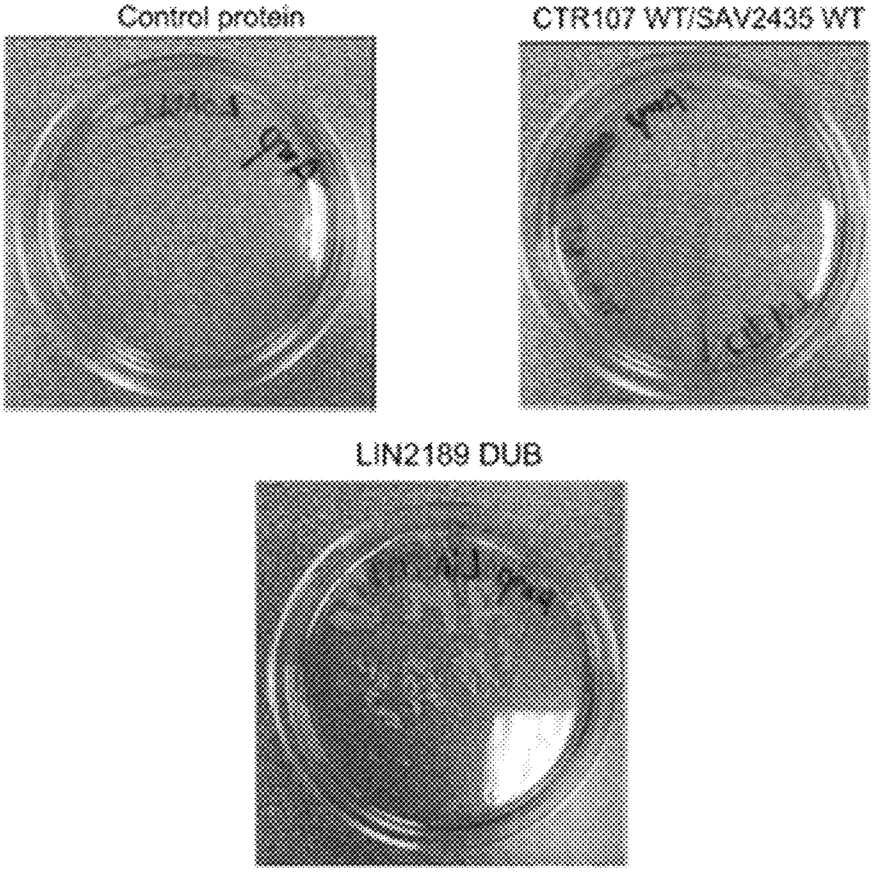
FIG. 16D *E. coli* growth ampicillin plates with Gyrl-like protein induction after 24 hours. Plates contain 50 μg/ml ampicillin and 1 mM IPTG.
Figure 16E:
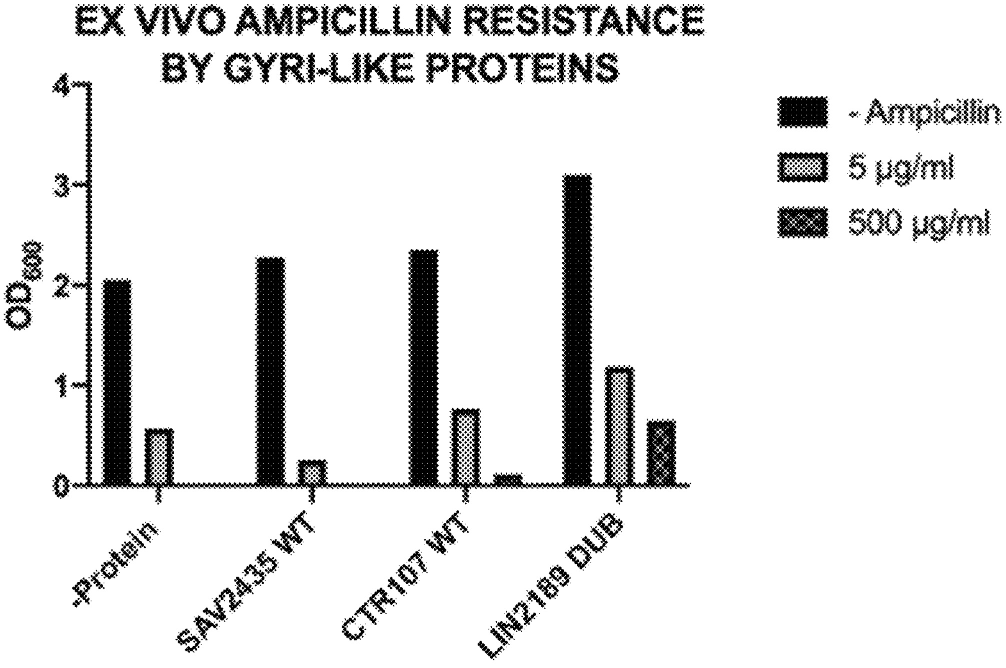
FIG. 16E *E. coli* growth in ampicillin inactivated with Gyrl-like protein ex vivo. Ampicillin was inactivated by 80 ug/ml prior to bacterial growth.

We developed both in vivo and ex vivo protocols to identify aptamers that can bind to the antibiotic Ampicillin or inactivate Ampicillin through enzymatic modification as a proof-of-principle of our hypothesis. In vivo expression of Gyrl-like proteins showed mixed results. SAV2435WT was susceptible to ampicillin similarly to control protein expression or bacterial growth with plasmid absent. Gyrl-like resistant proteins CTR107 WT showed partial resistance up to 100 μg/ml while enzymatic LIN2189 DUB showed the highest resistance at 100 μg/ml concentrations of ampicillin. To further assay aptamer binding via drug resistance we plated *E. coli* cells harboring plasmids that expressed Gyrl-like proteins or control protein on LB agar plates containing ampicillin and IPTG to induce protein expression (FIG. 16D). These plates were allowed to grow overnight to determine whether Gyrl-like proteins can induce ampicillin resistance. In control experiments no bacterial colonies are observed after 24-hour incubation at 37° C. Similarly, experiments where CTR107 WT or SAV2435 WT were expressed in bacteria produced no bacterial colonies on plates. Only expression of LIN2189 DUB showed bacterial growth after 24 hours (FIG. 16B). This example provides an invention method for identifying drug-modifying aptamers from the Gyrl-like proteins. Moreover, this example shows that LIN2189 DUB is an ampicillin aptamer that can induce resistance when expressed in bacteria.

LIN2189 DUB is an invention GYRYZYME that can act on a wide range of substrates. It is likely that the mechanism of ampicillin resistance can occur through binding and sequestering or through enzymatic modification to a non-toxic product. To determine if LIN2189 functions as a GYRYZYME in ampicillin resistance we assessed the ex vivo inactivation of ampicillin on bacterial growth. In this experiment enzymatic LIN2189 or non-enzymatic control proteins SAV2435 and CTR107 were mixed with various concentration of ampicillin in vitro to inactivate ampicillin prior to testing for bacterial growth (FIG. 16B). We assessed whether ampicillin incubated with LIN2189 GYRYZYME will be inactivated by catalysis; therefore, no toxic effects on bacterial growth will be observed when added to media. For control experiments that cause no enzymatic modification no growth will be observed because ampicillin is still in its active state. Addition of 5 μg/ml or 500 μg/ml ampicillin to cells substantially inhibited growth in SAV2435 an CTR107 experiments. However, LIN2189 was able to induce resistance up to 500 μg/ml ampicillin. These results confirm the enzymatic inactivation of ampicillin by LIN2189 DUB.

In accordance with the present invention, we have identified a GYRYZYME aptamer LIN2189 DUB that can bind and inactivate ampicillin. Those of skill in the art will understand the other modifications of LIN2189 wt using the invention methods provided herein will produce other invention LIN2189 variant aptamers that display broad catalytic activity. Those of skill in the art will understand that other modifications of LIN2189 wt can produce additional high affinity invention aptamers that lack catalytic activity (e.g., invention GYRYAPTS). Our protocol establishes a general approach to identify drug-binding aptamers or drug metabolizing aptamers form the Gyrl-like family of proteins.

Example 16: Design of a Novel Daunorubicin Aptamer from the Gyrl-Like Proteins

Our experimental results have demonstrated that the Gyrl-like family can be engineered to bind a wide variety of organic molecules regardless of chemical structure. This family can be a powerful tool for designing aptamers that bind to target drug molecules that can be designed for drug enhancement modules or drug delivery technology. To design drug-binding aptamers, both a method of selection and a mutagenesis strategy are required. The invention methods provided herein can be used for identifying drug-binding aptamers from the Gyrl-like family for the chemotherapeutic daunorubicin. This method of screening and subsequent mutagenesis permits the isolation of Gyrl-like aptamers that can be used for biopharmaceutical applications.

Figure 17A:
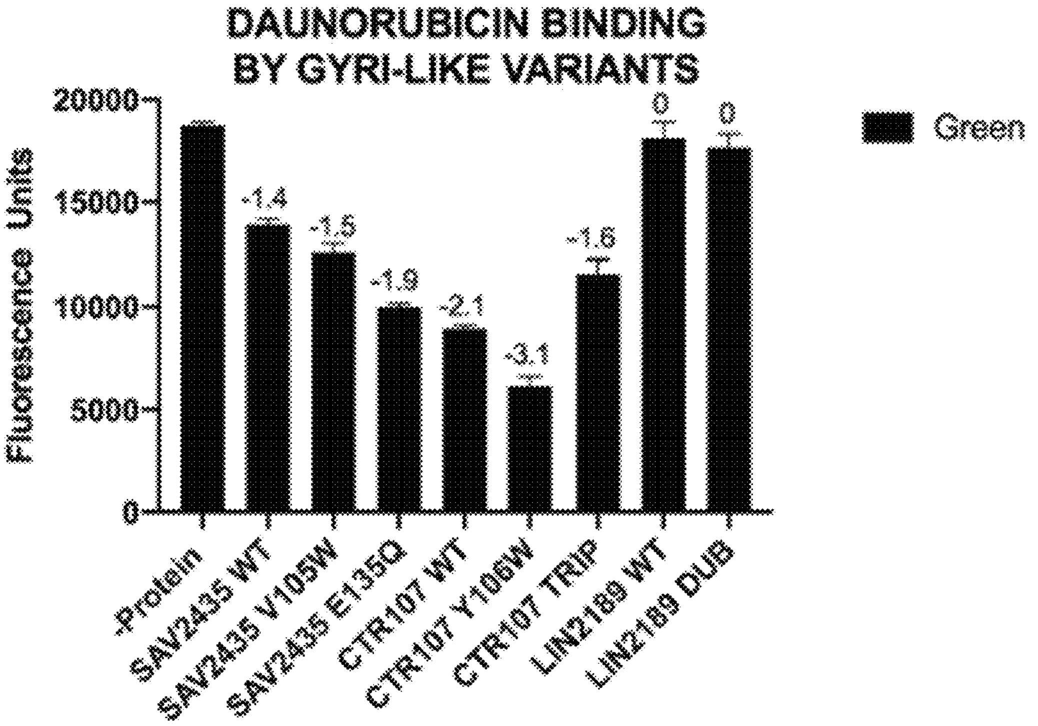
FIG. 17A Bar graph showing the fluorescence decrease induced by Gyrl-like aptamers binding to Daunorubicin. Black bars represent data collected under the green channel and grey bars represents data collected under the red channel. Each bar is the mean of data collected in duplicate experiments and error bars represent the standard deviation of averaged results. Fold changes in fluorescence by aptamers are displayed above each bar.
Figure 17B:
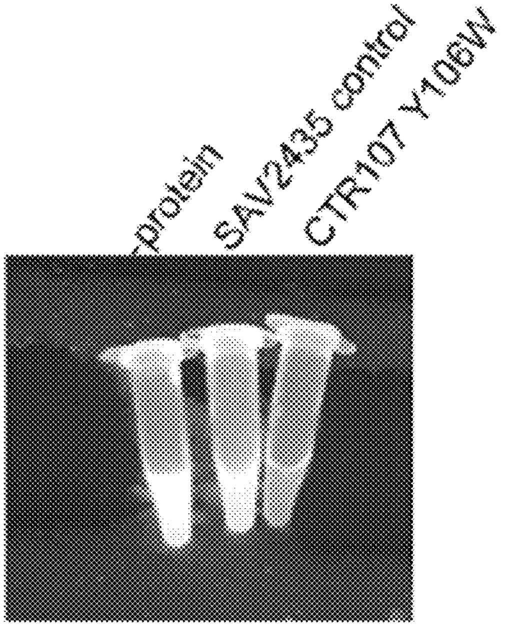
FIG. 17B UV fluorescence quenching by Daunorubicin-binding aptamer.

Because of its fluorescent properties, daunorubicin binding by Gyrl-like proteins can be screened using our fluorescence assay. Daunorubicin has excitation and emission peaks at 480 nm and 590 nm, respectively. This allows for changes in fluorescence properties to be monitored under the green channel. It is believed that aptamers that bind tightly will cause a fluorescence decrease when bound to daunorubicin. At 50 μM concentration, daunorubicin displays high fluorescence intensities under the green channel (FIG. 17A). Screening Gyrl-like variants for binding revealed that most variant aptamers slightly affected the intrinsic daunorubicin fluorescence, however, variants CTR107 WT and CTR107 Y106W showed a fluorescence decrease greater than 2-fold. Single mutant CTR107 Y106W was the strongest quencher inducing a 3-fold decrease in fluorescence. Overall LIN2189 variants had no effect on Daunorubicin fluorescence. We further UV analyzed the in vitro quenching of Daunorubicin fluorescence using ultraviolet light (FIG. 17A). In these experiments, samples with 5 μM daunorubicin in the absence of Gryl-like proteins or with saturating amounts of non-quenching SAV2435 control protein or CTR107 Y106W were illuminated with UV light. As expected, samples with no Gyrl-like protein or SAV2435 control displayed bright UV fluorescence. When CTR107 Y106W is added a complete shut off of fluorescence is observed.

Figure 17C:
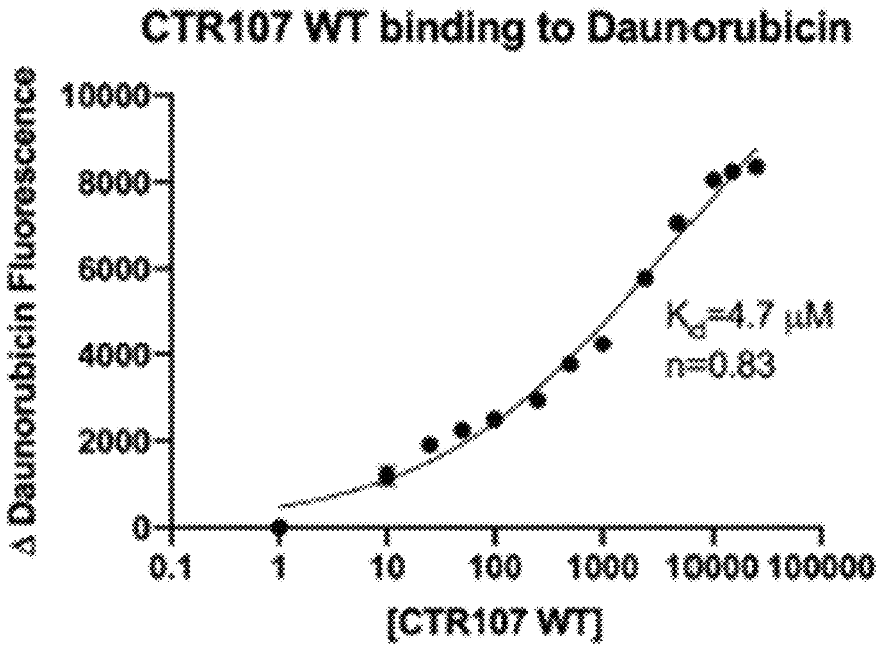
FIG. 17C Nonlinear regression analysis of fluorescence-binding data for CTR107 wildtype binding to the drug Daunorubicin.
Figure 17D:
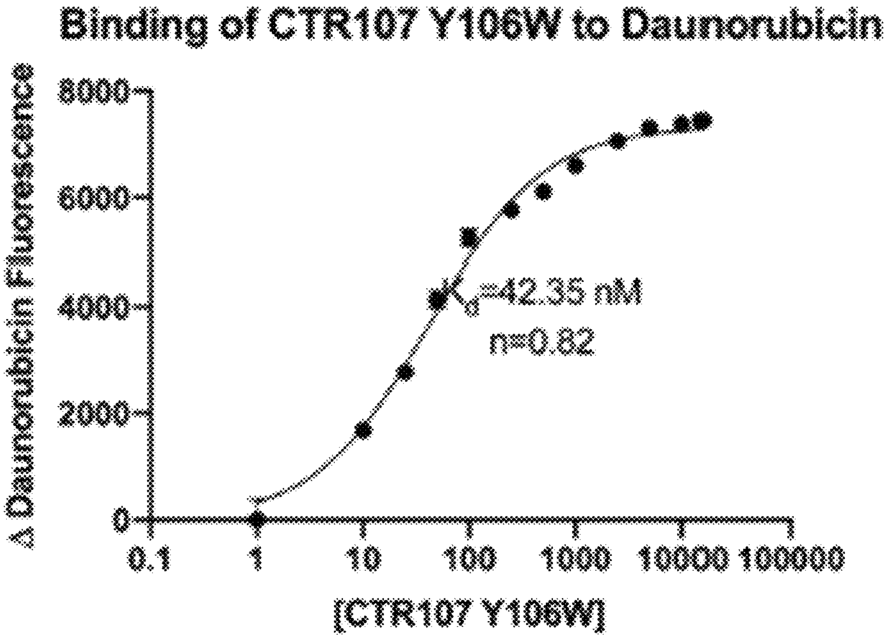
FIG. 17D Nonlinear regression analysis of fluorescence-binding data for CTR107 Y106W variant binding to the drug Daunorubicin. Dissociation constant and Hill coefficient are shown on each graph. Data represents the mean of duplicate measurements.

The visual changes in Daunorubicin fluorescence is a rapid and high-throughput method that can be used to analyze drug binding by Gyrl-like protein variants. We used our fluorescence-binding assay to determine the affinity of CTR107 Y106W for Daunorubicin compared to wildtype CTR107. Nonlinear regression Model fitting to Hill Equation produced a dissociation constant of 42 nM for CTR107 Y106W and 4 μM for CTR107 wildtype (FIG. 17C, D). The CTR107 Y106W daunorubicin-binding aptamer displays approximately 100-fold increase in binding affinity for daunorubicin compared to the multispecific wildtype CTR107. This result highlights that minimal mutations of Gyrl-like proteins can produce large increases in ligand-binding affinity.

Overall, this example provides an invention method of identifying drug-binding aptamers from the Gyrl-like family of proteins. Using both mutagenesis and screening, aptamers can be isolated for binding to numerous therapeutic small molecules of interest. Our invention methods provide a versatile protocol for creating drug-specific aptamers that can improve drug function and drug action. These aptamers can be used in drug delivery technologies for the creation of high efficacy biotherapeutics.

Example 17: Design of High-Affinity Gyrl-Like Aptamers for FAM-Binding Using Combinatorial Mutant Libraries and Selection by Phage Display In examples 1-15 we demonstrated that Gyrl-like proteins can be rationally engineered to create aptamers that bind with moderate affinities to target organic molecules. In several cases high affinity aptamers will be required for various applications. Provided herein is an invention method for engineering Gyrl-like proteins to create specific and high-affinity aptamers through combinatorial mutagenesis followed by selection with phage display (FIG. 18). In accordance with the present invention, high-affinity aptamers are created using mutant libraries of Gyrl-like protein SAV2435, CTR107, LIN2189 or through rational in silico design.

For mutant library creation, we identified residues in the binding site of our selected Gyrl-like template proteins that are involved in ligand binding (FIG. 20, 21). Next, an NNK mutagenesis scheme was used to randomize binding site residues to create a mutant library that contained 1320-1820 possible variants. Diversity of the NNK mutagenesis libraries was confirmed by Sanger sequencing of 100 variants. We cloned mutant DNA libraries into capsid protein 10 to display variants on the T7 phage exterior. Our phage display libraries contain between $10^{8}$-$10^{10}$ variants. Using 4 rounds of biopanning with target ligands immobilized onto a surface, our phage display libraries of Gyrl-like protein produced high-affinity target-binding aptamers; which were identified from sequencing positive recombinants from phage plaque assays. Variants can be expressed, purified and analyzed for binding using various techniques. As a proof-of-principle, we have probed our mutant library for aptamers that bind to FAM (6-Carboxyfluorescein; FIG. 4). Using the protocol described above, we identified 7 unique FAM-binding aptamers from biopanning experiments using the CTR107 library (FIG. 22).

Figure 23A:
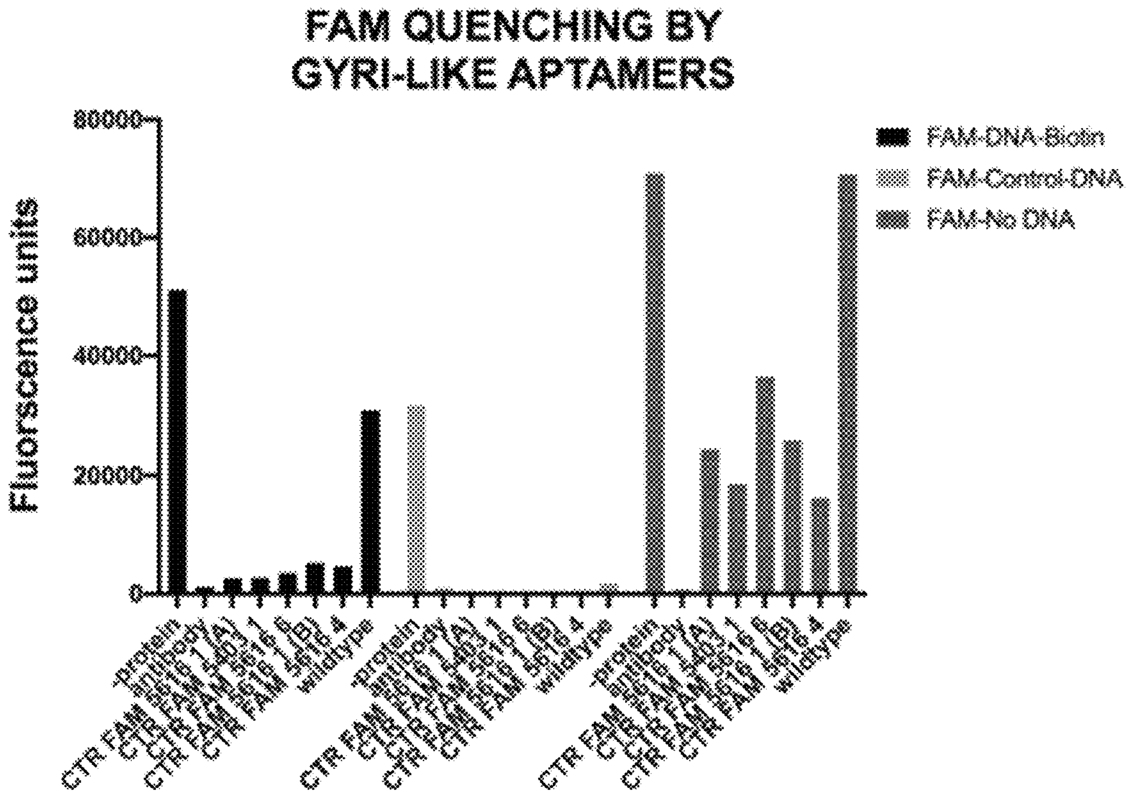
FIG. 23A FAM fluorescence quenching by Gyrl-like aptamers identified phage display mutant library protocol. Experiments were conducted in duplicates and the mean values depicted as bar graphs. FAM template is shown to the right in legend.
Figure 23B:
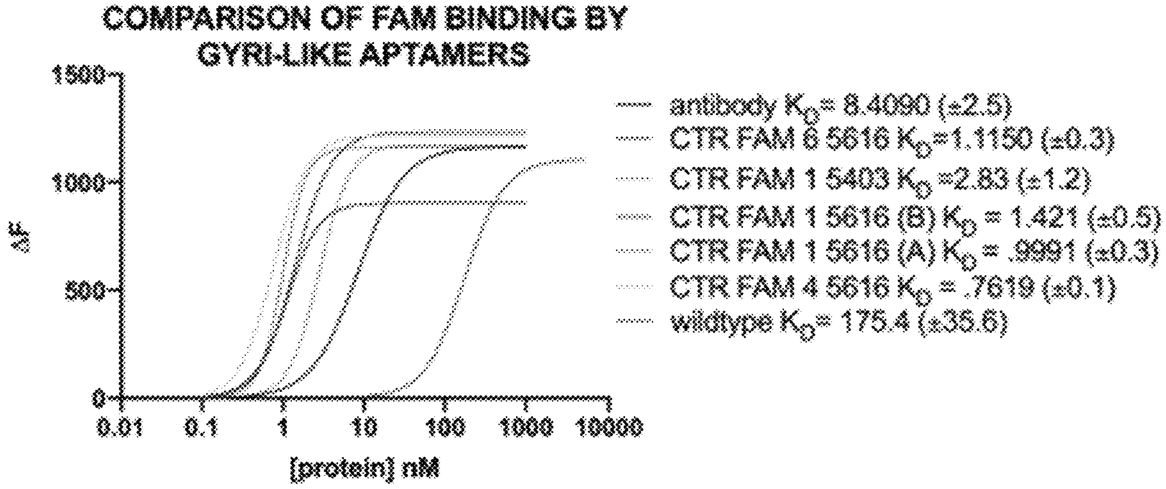
FIG. 23B Comparison of FAM affinities for Gyrl-like aptamers to FAM antibody and wildtype CTR107. Experiments were conducted in duplicates and the mean values depicted as bar graphs. Kd values are shown next to legend for each protein in nanomolar. Graphs are colored according to protein identity in legend.

In fluorescence binding experiments we observed that aptamers induce a strong quenching of FAM-DNA fluorescence at saturating concentrations (FIG. 23A). Our Gyrl-like aptamers showed no preference for DNA sequence as purified FAM-control DNA (not used in biopanning) showed stronger quenching than biopanning template (FIG. 23A). Our aptamers showed weaker quenching for unlabeled FAM relative to the antibody which suggest that FAM-DNA is the preferred high-affinity ligand (FIG. 23B). Using our fluorescence-binding assay, we determined the dissociation constants for FAM antibody and our Gyrl-like aptamer variants (FIG. 23B). Using nonlinear regression fits to the hill equation we observe that all aptamers display low nanomolar affinity (FIG. 23B). FAM antibody bound with a Kd of 8 nM, whereas our weakest aptamer bound with a Kd of 3 nM (FIG. 23B). Our highest affinity aptamer bound with a Kd affinity of 760 picomolar which is 11-fold stronger than FAM. Overall, our FAM-binding aptamers display 50-700 fold increase in affinity compared to wildtype CTR107. These data demonstrate Gyrl-like proteins can be engineered to create high-affinity aptamers for ligands. Our schematic protocol allows for the creation of aptamers either through large mutagenesis libraries or through in silico design and rational mutagenesis. Our invention methods allow for the creation of high-affinity aptamers for any ligand of interest.

Example 18: Design of High-Affinity Gyrl-Like Aptamers for Various Small Molecules Using Combinatorial Mutant Libraries and Selection by Phage Display In example 17 we demonstrated an efficient invention protocol for the engineering of high-affinity aptamers from Gyrl-like proteins using phage display mutagenesis libraries. Our proof-of-principle protocol allowed us to successfully identify several aptamer candidates for ligands FAM, CY5, T01, Cytarabine and SARS-COV2 spike protein receptor binding domain (RBD) from Gyrl-like protein libraries of SAV2435, CTR107, LIN2189 (FIG. 24). Using our broad strategy described in our invention protocol we were able to find aptamers using phage display combined with our mutagenesis libraries after 4 rounds of biopanning (FIG. 18). Sequencing of positive recombinants shows that variants are diverse and show little similarity to wildtype proteins (FIG. 24). Biophysical analysis can further identify the highest affinity candidates from our invention library collection. In other embodiments, our Gyrl-like aptamers can be further engineered to create important biotechnology tools for medicine.

In particular embodiments for example, invention Cytarabine aptamers can be used to deliver this important chemotherapeutic to target cancer cells to improve drug efficacy. In additional embodiments, invention spike protein aptamers can be used as drug candidates to treat diseases related to the novel SARS coronavirus pandemic. These results further confirm the versatility of our invention mutagenesis libraries and phage display methodologies. In additional embodiments, the invention protocols can be modified herein to screen for Gyrl-like aptamers to identify high-affinity aptamers for any target molecule of interest. The invention methods and libraries provided herein can be used to design a plethora of diverse and innovative tools for natural and life science research, nanotechnology, biotechnology and medicine.

The invention claimed is:

1. A non-native variant aptamer comprising any combination of one up to all 13 of variant amino acids, relative to wild-type SAV2435, among all variant-positions in the polypeptide set forth in FIG. 20/SEQ ID NO:2; wherein the variant positions correspond to amino acid positions 27, 30, 31, 34, 38, 105, 106, 109, 110, 113, 135, 137 and 142 of SEQ ID NO: 2.

2. The non-native variant aptamer of claim 1, wherein the variant aptamer comprises a variant amino acid at a number of variant-positions set forth in FIG. 20/SEQ ID NO:2 compared to wild-type SAV2435, wherein the number of variant-positions is selected from the group consisting of: 1, 2, 3, 4, 5, 6, 7, 8, 9, 10, 11, 12, and 13.

3. The non-native variant aptamer of claim 1, wherein the variant aptamer is capable of one or more functions selected from: fluorescence enhancement of a dye; or fluorescence quenching of a dye; binding to a target-molecule; or enzymatic activity.

4. The non-native variant aptamer of claim 1, wherein the variant aptamer is capable of fluorescence enhancement of a dye, and wherein the dye is selected from the group consisting of: SYTO9, DHMBI, Malachite Green, Thiazole Orange, Thioflavin T, Atto495, and Acridine Orange.

5. The non-native variant aptamer of claim 1, wherein the variant aptamer is capable of fluorescence quenching of a dye, wherein the dye is selected from the group consisting of 5(6)-Carboxfluorescein, 5-Carboxytetramethylrhodamine, and oxazine.

6. The non-native variant aptamer of claim 1, wherein the variant aptamer is capable of binding to a target-molecule selected from the group consisting of: small-molecules, proteins, oligonucleotides, oligosaccharides, lipids, peptides, and polymers.

7. The non-native variant aptamer of claim 1, wherein the variant aptamer is capable of binding to a molecule selected from the group consisting of: FAM, CY5, Thiazole-orange, Cytarabine, SARS-Cov-2 spike protein, SYTO9, DHMBI, Malachite Green, Thiazole Orange, Thioflavin T, Atto495, Acridine Orange, 5(6)-Carboxfluorescein, 5-Carboxytetramethylrhodamine, and oxazine.

8. The non-native variant aptamer of claim 1, wherein the variant aptamer is selected from the group consisting of: SAV2435 N27W (SEQ ID NO:8); SAV2435 V105W (SEQ ID NO:10); SAV2435 P106W (SEQ ID NO:12); SAV2435 E135Q (SEQ ID NO:14); SAV2435 Y137W (SEQ ID NO:16); and SEQ ID NOs:40-45 and SEQ ID NOs:58-59.

9. A non-native variant aptamer comprising any combination of one up to all 12 of variant amino acids, relative to wild-type CTR107, among all variant-positions in the polypeptide set forth in FIG. 20/SEQ ID NO:4; wherein the variant positions correspond to amino acid positions 31, 32, 35, 36, 39, 40, 43, 75, 106, 133, 135 and 138 of SEQ ID NO:4.

10. The non-native variant aptamer of claim 9, wherein the variant aptamer comprises a variant amino acid at a number of variant-positions set forth in FIG. 20/SEQ ID NO:4 compared to wild-type CTR107, wherein the number of variant-positions is selected from the group consisting of: 1, 2, 3, 4, 5, 6, 7, 8, 9, 10, 11, and 12.

11. The non-native variant aptamer of claim 9, wherein the variant aptamer is capable of one or more functions selected from: fluorescence enhancement of a dye; or fluorescence quenching of a dye; binding to an organic molecule; or enzymatic activity.

12. The non-native variant aptamer of claim 9, wherein the variant aptamer is capable of fluorescence enhancement of a dye, and wherein the dye is selected from the group consisting of: SYTO9, DHMBI, Malachite Green, Thiazole Orange, Thioflavin T, Atto495, and Acridine Orange.

13. The non-native variant aptamer of claim 9, wherein the variant aptamer is capable of fluorescence quenching of a dye, wherein the dye is selected from the group consisting of 5(6)-Carboxfluorescein, 5-Carboxytetramethylrhodamine, and oxazine.

14. The non-native variant aptamer of claim 9, wherein the variant aptamer is capable of binding to an organic molecule selected from the group consisting of: small-molecules, proteins, oligonucleotides, oligosaccharides, lipids, peptides, and polymers.

15. The non-native variant aptamer of claim 9, wherein the variant aptamer is capable of binding to a molecule selected from the group consisting of: FAM, CY5, Thiazole-orange, Cytarabine, SARS-Cov-2 spike protein, SYTO9, DHMBI, Malachite Green, Thiazole Orange, Thioflavin T, Atto495, Acridine Orange, 5(6)-Carboxfluorescein, 5-Carboxytetramethylrhodamine, and oxazin.

16. The non-native variant aptamer of claim 9, wherein the variant aptamer is selected from the group consisting of: CTR107 E36R (SEQ ID NO:18); CTR107 Y106W (SEQ ID NO:20); CTR107 E133Q (SEQ ID NO:22); CTR107 E36R (SEQ ID NO:18); CTR107 TRIP E36R H40Y Y106W (SEQ ID NO:24); CTR107 QUAD E36R H40Y Y106W E133Q (SEQ ID NO:26); and SEQ ID NOs:33-39 and SEQ ID NOs:46-50.

17. A non-native variant aptamer comprising any combination of one up to all 17 of variant amino acids, relative to wild-type LIN2189, among all variant-positions in the polypeptide set forth in FIG. 20/SEQ ID NO:6; wherein the variant positions correspond to amino acid positions 41, 42, 46, 50, 54, 58, 81, 85, 93, 99, 154, 157, 185, 187, 190, 191 and 192 of SEQ ID NO:6.

18. The non-native variant aptamer of claim 17, wherein the variant aptamer comprises a variant amino acid at a number of variant-positions set forth in FIG. 20/SEQ ID NO:6 compared to wild-type LIN2189, wherein the number of variant-positions is selected from the group consisting of: 1, 2, 3, 4, 5, 6, 7, 8, 9, 10, 11, 12, 13, 14, 15, 16 and 17.

19. The non-native variant aptamer of claim 17, wherein the variant aptamer is capable of one or more functions selected from: fluorescence enhancement of a dye; or fluorescence quenching of a dye; binding to an organic molecule; or enzymatic activity.

20. The non-native variant aptamer of claim 17, wherein the variant aptamer is capable of fluorescence enhancement of a dye, and wherein the dye is selected from the group consisting of: SYTO9, DHMBI, Malachite Green, Thiazole Orange, Thioflavin T, Atto495, and Acridine Orange.

21. The non-native variant aptamer of claim 17, wherein the variant aptamer is capable of fluorescence quenching of a dye, wherein the dye is selected from the group consisting of 5(6)-Carboxfluorescein, 5-Carboxytetramethylrhodamine, and oxazine.

22. The non-native variant aptamer of claim 19, wherein the variant aptamer is capable of binding to an organic molecule selected from the group consisting of: small-molecules, proteins, oligonucleotides, oligosaccharides, lipids, peptides, and polymers.

23. The non-native variant aptamer of claim 17, wherein the variant aptamer is capable of binding to a molecule selected fem from the group consisting of: FAM, CY5, Thiazole-orange, Cytarabine, SARS-Cov-2 spike protein, SYTO9, DHMBI, Malachite Green, Thiazole Orange, Thioflavin T, Atto495, Acridine Orange, 5(6)-Carboxfluorescein, 5-Carboxytetramethylrhodamine, and oxazine.

24. The non-native variant aptamer of claim 17, wherein the variant aptamer is selected from the group consisting of: LIN2189 E157A (SEQ ID NO:28); LIN2189 E185L (SEQ ID NO:30); and LIN2189 DUB E157A, E185L (SEQ ID NO:32); and SEQ ID NOs:52-57.

25. An engineered non-native aptamer selected from the group consisting of:

SAV2435 N27W (SEQ ID NO:8); SAV2435 V105W (SEQ ID NO:10); SAV2435 P106W (SEQ ID NO:12); SAV2435 E135Q (SEQ ID NO:14); SAV2435 Y137W (SEQ ID NO:16); CTR107 E36R (SEQ ID NO:18); CTR107 Y106W (SEQ ID NO:20); CTR107 E133Q (SEQ ID NO:22); CTR107 TRIP (E36R, H40Y, Y106W)(SEQ ID NO:24); CTR107 QUAD (E36R, H40Y, Y106W, E133Q)(SEQ ID NO:26); LIN2189 E157A (SEQ ID NO:28); LIN2189 E185L (SEQ ID NO:30); and LIN2189 DUB (E157A, E185L)(SEQ ID NO:32); and SEQ ID NOs:33-59.

26. A fluorescence-on/off bioswitch system comprising:

a first Gyrl-like aptamer; and a fluorogenic dye, wherein the first Gyrl-like apatamer is selected from:

(a) a non-native variant aptamer comprising any combination of one up to all 13 of variant amino acids, relative to wild-type SAV2435, among all variant-positions in the polypeptide set forth in FIG. 20/SEQ ID NO:2; wherein the variant positions correspond to amino acid positions 27, 30, 31, 34, 38, 105, 106, 109, 110, 113, 135, 137 and 142 of SEQ ID NO:2;

(b) a non-native variant aptamer comprising any combination of one up to all 12 of variant amino acids, relative to wild-type CTR107, among all variant-positions in the polypeptide set forth in FIG. 20/SEQ ID NO:4; wherein the variant positions correspond to amino acid positions 31, 32, 35, 36, 39, 40, 43, 75, 106, 133, 135 and 138 of SEQ ID NO:4; and (c) a non-native variant aptamer comprising any combination of one up to all 17 of variant amino acids, relative to wild-type LIN2189, among all variant-positions in the polypeptide set forth in FIG. 20/SEQ ID NO:6; wherein the variant positions correspond to amino acid positions 41, 42, 46, 50, 54, 58, 81, 85, 93, 99, 154, 157, 185, 187, 190, 191 and 192 of SEQ ID NO:6.

27. The bioswitch system of claim 26, wherein the dye is selected from the group consisting of: 5(6)-Carboxfluorescein (FAM), 5-Carboxytetramethylrhodamine (TAMRA), oxazine, SYTO9, DHMBI, Malachite Green, Thiazole Orange, Thioflavin T, Atto495, and Acridine Orange.

28. The bioswitch system of claim 26, wherein the Gyrl-like aptamer is a non-native variant Gyrl-like aptamer that is thermostable and/or pH-stable.

29. The bioswitch system of claim 26, further comprising a second Gyrl-like aptamer.

30. The bioswitch system of claim 29, wherein the dye is Atto495; and the first and second aptamers are selected from the group consisting of: CTR107 E1330 and SAV2435 N27W; CTR107 E1330 and SAV2435 Y137W; CTR107 E1330 and CTR107 Y106W; CTR107 E1330 and LIN2189 E157A-E185L double mutant; SAV2435 E1350 and SAV2435 N27W; SAV2435 E1350 and SAV2435 Y137W; SAV2435 E1350 and CTR107 Y106W; and SAV2435 E1350 and LIN2189 E157A-E185L double mutant.

31. The bioswitch system of claim 29, wherein the dye is Acridine Orange; and the first aptamer is selected from the group consisting of any one or more of: SAV2435 E1350, SAV2435 V105W, SAV2435 P106W, CTR107 WT and CTR107 E1330; and the second aptamer is selected from the group consisting of any one or more of: SAV2435 WT, SAV2435 N27W, SAV2435 Y137W, and CTR107 Y106W.

32. The bioswitch system of claim 29, wherein the dye is Acridine Orange; and the first and second aptamers are selected from the group consisting of: SAV2435 E1350 and SAV2435 WT, SAV2435 E1350 and SAV2435 N27W, SAV2435 E1350 and SAV2435 Y137W, SAV2435 E1350 and CTR107 Y106W, SAV2435 V105W and SAV2435 WT, SAV2435 V105W and SAV2435 N27W, SAV2435 V105W and SAV2435 Y137W, SAV2435 V105W and CTR107 Y106W, SAV2435 P106W and SAV2435 WT, SAV2435 P106W and SAV2435 N27W, SAV2435 P106W and SAV2435 Y137W, SAV2435 P106W and CTR107 Y106W, CTR107 WT and SAV2435 WT, CTR107 WT and SAV2435 N27W, CTR107 WT and SAV2435 Y137W, CTR107 WT and CTR107 Y106W, CTR107 E133Q and SAV2435 WT, CTR107 E133Q and SAV2435 N27W, CTR107 E133Q and SAV2435 Y137W, and CTR107 E133Q and CTR107 Y106W.

33. A library of non-native SAV2435 variant aptamers comprising non-native variant aptamers having any combination of one up to all 13 of variant amino acids, relative to wild-type SAV2435, among all variant-positions in the polypeptide set forth in FIG. 20/SEQ ID NO: 2; wherein the variant positions correspond to amino acid positions 27, 30, 31, 34, 38, 105, 106, 109, 110, 113, 135, 137 and 142 of SEQ ID NO: 2.

34. A library of non-native CTR107 variant aptamers comprising non-native variant aptamers having any combination of one up to all 12 of variant amino acids, relative to wild-type CTR107, among all variant-positions in the polypeptide set forth in FIG. 20/SEQ ID NO: 4; wherein the variant positions correspond to amino acid positions 31, 32, 35, 36, 39, 40, 43, 75, 106, 133, 135 and 138 of SEQ ID NO: 4.

35. A library of non-native LIN2189 variant aptamers comprising non-native variant aptamers having any combination of one up to all 17 of variant amino acids, relative to wild-type LIN2189, among all variant-positions in the polypeptide set forth in FIG. 20/SEQ ID NO: 6; wherein the variant positions correspond to amino acid positions 41, 42, 46, 50, 54, 58, 81, 85, 93, 99, 154, 157, 185, 187, 190, 191 and 192 of SEQ ID NO: 6.

36. The non-native variant aptamer of claim 26, wherein the variant aptamer comprises a variant amino acid at a number of variant-positions set forth in FIG. 20/SEQ ID NO:2 compared to wild-type SAV2435, wherein the number of variant-positions is selected from the group consisting of: 1, 2, 3, 4, 5, 6, 7, 8, 9, 10, 11, 12, and 13.

37. The non-native variant aptamer of claim 26, wherein the variant aptamer is capable of one or more functions selected from: fluorescence enhancement of a dye; or fluorescence quenching of a dye; binding to a target-molecule; or enzymatic activity.

38. The non-native variant aptamer of claim 26, wherein the variant aptamer is capable of fluorescence enhancement of a dye, and wherein the dye is selected from the group consisting of: SYTO9, DHMBI, Malachite Green, Thiazole Orange, Thioflavin T, Atto495, and Acridine Orange.

39. The non-native variant aptamer of claim 26, wherein the variant aptamer is capable of fluorescence quenching of a dye, wherein the dye is selected from the group consisting of 5(6)-Carboxfluorescein, 5-Carboxytetramethylrhodamine, and oxazine.

40. The non-native variant aptamer of claim 26, wherein the variant aptamer is capable of binding to a target-molecule selected from the group consisting of: small-molecules, proteins, oligonucleotides, oligosaccharides, lipids, peptides, and polymers.

41. The non-native variant aptamer of claim 26, wherein the variant aptamer is capable of binding to a molecule selected from the group consisting of: FAM, CY5, Thiazole-orange, Cytarabine, SARS-Cov-2 spike protein, SYTO9, DHMBI, Malachite Green, Thiazole Orange, Thioflavin T, Atto495, Acridine Orange, 5(6)-Carboxfluorescein, 5-Carboxytetramethylrhodamine, and oxazine.

42. The non-native variant aptamer of claim 26, wherein the variant aptamer is selected from the group consisting of:

(a) SAV2435 N27W (SEQ ID NO:8); SAV2435 V105W (SEQ ID NO:10); SAV2435 P106W (SEQ ID NO:12); SAV2435 E135Q (SEQ ID NO:14); SAV2435 Y137W (SEQ ID NO:16); and SEQ ID NOs:40-45 and SEQ ID NOs:58-59;

(b) CTR107 E36R (SEQ ID NO:18); CTR107 Y106W (SEQ ID NO:20); CTR107 E133Q (SEQ ID NO:22); CTR107 E36R (SEQ ID NO:18); CTR107 TRIP E36R H40Y Y106W (SEQ ID NO:24); CTR107 QUAD E36R H40Y Y106W E133Q (SEQ ID NO:26); and SEQ ID NOs:33-39 and SEQ ID NOs:46-50; and (c) LIN2189 E157A (SEQ ID NO:28); LIN2189 E185L (SEQ ID NO:30); and LIN2189 DUB E157A, E185L (SEQ ID NO:32); and SEQ ID NOs:52-57.

* * * * *